(12) United States Patent
Wilk

(10) Patent No.: US 7,294,115 B1
(45) Date of Patent: *Nov. 13, 2007

(54) METHODS OF PROVIDING DIRECT BLOOD FLOW BETWEEN A HEART CHAMBER AND A CORONARY VESSEL

(75) Inventor: Peter J. Wilk, New York, NY (US)

(73) Assignee: Percardia, Inc., Merrimack, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/534,038

(22) Filed: Mar. 24, 2000

Related U.S. Application Data

(63) Continuation-in-part of application No. PCT/US99/03484, filed on Feb. 17, 1999, which is a continuation of application No. 09/369,039, filed on Aug. 4, 1999, now abandoned, and a continuation-in-part of application No. 09/016,485, filed on Jan. 30, 1998, now abandoned.

(60) Provisional application No. 60/099,691, filed on Sep. 10, 1998, provisional application No. 60/099,767, filed on Sep. 10, 1998, provisional application No. 60/099,720, filed on Sep. 10, 1998, provisional application No. 60/104,397, filed on Oct. 15, 1998.

(51) Int. Cl.
| | |
|---|---|
| A61M 5/00 | (2006.01) |
| A61M 29/00 | (2006.01) |
| A61B 19/00 | (2006.01) |
| A61F 11/00 | (2006.01) |
| A61F 2/06 | (2006.01) |

(52) U.S. Cl. ............... 604/8; 128/898; 606/108; 606/194; 623/1.11; 623/1.13

(58) Field of Classification Search ............ 604/8, 604/22, 500, 506–8, 510, 96.01, 158–59, 604/164.01–164.02, 164, 164.06, 164.09, 604/164.12, 165, 171, 165.01–165.04, 528, 604/107, 108, 264, 523; 607/88, 89; 606/7, 606/12–18, 33, 41, 45–48, 50, 108, 119, 120, 606/139–144, 148, 151, 153, 155, 157–59, 606/170, 171, 180, 185, 190, 192, 194–95, 606/198, 213, 220; 128/898; 623/1.1, 1.11, 623/3.11, 3.26, 8

See application file for complete search history.

(56) References Cited

U.S. PATENT DOCUMENTS

| | | | |
|---|---|---|---|
| 4,503,568 | A | 3/1985 | Madras |
| 4,531,936 | A | 7/1985 | Gordon |
| 4,733,665 | A | 3/1988 | Palmaz |
| 4,769,029 | A | 9/1988 | Patel |
| 4,953,553 | A | 9/1990 | Tremulis |
| 4,995,857 | A | 2/1991 | Arnold |
| 5,035,702 | A | 7/1991 | Taheri |
| 5,071,407 | A | 12/1991 | Termin et al. |
| 5,135,467 | A | 8/1992 | Citron |
| 5,180,366 | A | 1/1993 | Woods |
| 5,190,058 | A | 3/1993 | Jones et al. |
| 5,193,546 | A | 3/1993 | Shaknovich |
| 5,226,889 | A | 7/1993 | Sheiban |
| 5,258,008 | A | 11/1993 | Wilk |
| 5,287,861 | A | 2/1994 | Wilk |
| 5,330,486 | A | 7/1994 | Wilk |
| 5,342,348 | A | 8/1994 | Kaplan |
| 5,344,426 | A | 9/1994 | Lau et al. |
| 5,385,541 | A | 1/1995 | Kirsch et al. |
| 5,389,096 | A | 2/1995 | Aita et al. |
| 5,409,019 | A | 4/1995 | Wilk |
| 5,411,552 | A | 5/1995 | Andersen et al. |
| 5,423,744 | A | 6/1995 | Gencheff et al. |
| 5,423,851 | A | 6/1995 | Samuels |
| 5,429,144 | A | 7/1995 | Wilk |
| 5,443,497 | A | 8/1995 | Venbrux |
| 5,456,694 | A | 10/1995 | Marin et al. |
| 5,456,712 | A | 10/1995 | Maginot |
| 5,456,714 | A | 10/1995 | Owen |
| 5,470,320 | A | 11/1995 | Tiefenbrun et al. |
| 5,527,337 | A | 6/1996 | Stack et al. |
| 5,554,119 | A | 9/1996 | Harrison et al. |

| | | | | | | |
|---|---|---|---|---|---|---|
| 5,578,075 A | 11/1996 | Dayton | | 6,001,123 A | 12/1999 | Lau |
| 5,593,434 A | 1/1997 | Williams | | 6,004,261 A | 12/1999 | Sinofsky et al. |
| 5,609,626 A | 3/1997 | Quijano et al. | | 6,004,347 A | 12/1999 | McNamara et al. |
| 5,618,299 A | 4/1997 | Khosravi et al. | | 6,004,348 A | 12/1999 | Banas et al. |
| 5,643,278 A | 7/1997 | Wijay | | 6,005,020 A | 12/1999 | Loomis |
| 5,655,548 A | 8/1997 | Nelson et al. | | 6,007,543 A | 12/1999 | Ellis et al. |
| 5,662,124 A | 9/1997 | Wilk | | 6,007,544 A | 12/1999 | Kim |
| 5,676,670 A | 10/1997 | Kim | | 6,007,575 A | 12/1999 | Samuels |
| 5,733,267 A | 3/1998 | Del Toro | | 6,007,576 A | 12/1999 | McClellan |
| 5,755,682 A | 5/1998 | Knudson et al. | | 6,010,449 A | 1/2000 | Selmon et al. |
| 5,758,663 A | 6/1998 | Wilk et al. | | 6,010,530 A | 1/2000 | Goicoechea |
| 5,797,920 A | 8/1998 | Kim | | 6,017,365 A | 1/2000 | Von Oepen |
| 5,797,933 A | 8/1998 | Snow et al. | | 6,026,814 A | 2/2000 | LaFontaine et al. |
| 5,807,384 A | 9/1998 | Mueller | | 6,029,672 A | 2/2000 | Vanney et al. |
| 5,810,836 A | 9/1998 | Hussein et al. | | 6,035,856 A | 3/2000 | LaFontaine et al. |
| 5,810,871 A | 9/1998 | Tuckey et al. | | 6,036,677 A | 3/2000 | Javier, Jr. et al. |
| 5,824,038 A | 10/1998 | Wall | | 6,036,697 A | 3/2000 | DiCaprio |
| 5,824,071 A | 10/1998 | Nelson et al. | | 6,039,721 A | 3/2000 | Johnson et al. |
| 5,830,222 A | 11/1998 | Makower et al. | | 6,042,581 A | 3/2000 | Ryan et al. |
| 5,840,059 A | 11/1998 | March et al. | | 6,045,565 A | 4/2000 | Ellis et al. |
| 5,840,081 A | 11/1998 | Andersen et al. | | 6,053,911 A | 4/2000 | Ryan et al. |
| 5,843,163 A | 12/1998 | Wall | | 6,053,924 A | 4/2000 | Hussein |
| 5,851,232 A | 12/1998 | Lois | | 6,053,942 A | 4/2000 | Eno et al. |
| 5,855,597 A | 1/1999 | Jayaraman | | 6,056,743 A | 5/2000 | Ellis et al. |
| 5,865,723 A | 2/1999 | Love | | 6,067,988 A | 5/2000 | Mueller |
| 5,876,373 A | 3/1999 | Giba et al. | | 6,068,638 A | 5/2000 | Makower et al. |
| 5,876,419 A | 3/1999 | Carpenter et al. | | 6,071,292 A | 6/2000 | Makower et al. |
| 5,878,751 A | 3/1999 | Hussein et al. | | 6,076,529 A | 6/2000 | Vanney et al. |
| 5,885,259 A | 3/1999 | Berg | | 6,080,163 A | 6/2000 | Hussein et al. |
| 5,908,028 A | 6/1999 | Wilk | | 6,080,170 A | 6/2000 | Nash et al. |
| 5,908,029 A | 6/1999 | Knudson et al. | | 6,092,526 A * | 7/2000 | LaFontaine et al. ........ 128/898 |
| 5,922,022 A | 7/1999 | Nash et al. | | 6,093,166 A | 7/2000 | Knudson et al. |
| 5,925,012 A | 7/1999 | Murphy-Chutorian et al. | | 6,093,177 A | 7/2000 | Javier, Jr. et al. |
| 5,931,848 A | 8/1999 | Saadat | | 6,093,185 A | 7/2000 | Ellis et al. |
| 5,935,119 A | 8/1999 | Guy et al. | | 6,095,997 A | 8/2000 | French et al. |
| 5,935,161 A | 8/1999 | Robinson et al. | | 6,102,941 A | 8/2000 | Tweden et al. |
| 5,935,162 A | 8/1999 | Dang | | 6,106,538 A | 8/2000 | Shiber |
| 5,938,632 A | 8/1999 | Ellis | | 6,110,201 A | 8/2000 | Quijano et al. |
| 5,944,019 A * | 8/1999 | Knudson et al. ............ 128/898 | | 6,113,823 A | 9/2000 | Eno |
| 5,961,548 A | 10/1999 | Schmulewitz | | 6,117,165 A | 9/2000 | Becker |
| 5,968,064 A | 10/1999 | Selmon et al. | | 6,120,520 A | 9/2000 | Saadat et al. |
| 5,968,093 A | 10/1999 | Kranz | | 6,123,682 A | 9/2000 | Knudson et al. |
| 5,971,993 A | 10/1999 | Hussein et al. | | 6,126,649 A | 10/2000 | Van Tassel et al. |
| 5,976,153 A | 11/1999 | Fischell et al. | | 6,126,654 A | 10/2000 | Giba et al. |
| 5,976,155 A | 11/1999 | Foreman et al. | | 6,132,451 A | 10/2000 | Payne et al. |
| 5,976,159 A | 11/1999 | Bolduc et al. | | 6,139,541 A | 10/2000 | Vanney et al. |
| 5,976,169 A | 11/1999 | Imran | | 6,152,141 A | 11/2000 | Stevens et al. |
| 5,976,181 A | 11/1999 | Whelan et al. | | 6,155,264 A | 12/2000 | Ressemann et al. |
| 5,976,182 A | 11/1999 | Cox | | 6,156,031 A | 12/2000 | Aita et al. |
| 5,976,192 A | 11/1999 | McIntyre et al. | | 6,157,852 A | 12/2000 | Selmon et al. |
| 5,976,650 A | 11/1999 | Campbell et al. | | 6,159,196 A | 12/2000 | Ruiz |
| 5,979,455 A | 11/1999 | Maginot | | 6,159,225 A | 12/2000 | Makower |
| 5,980,530 A | 11/1999 | Willard et al. | | 6,162,245 A | 12/2000 | Jayaraman |
| 5,980,533 A | 11/1999 | Holman | | 6,165,185 A | 12/2000 | Shennib et al. |
| 5,980,548 A * | 11/1999 | Evans et al. ................. 606/185 | | 6,165,188 A | 12/2000 | Saadat et al. |
| 5,980,551 A | 11/1999 | Summers et al. | | 6,168,614 B1 | 1/2001 | Andersen et al. |
| 5,980,552 A | 11/1999 | Pinchasik et al. | | 6,171,251 B1 | 1/2001 | Mueller et al. |
| 5,980,553 A | 11/1999 | Gray et al. | | 6,182,668 B1 | 2/2001 | Tweden et al. |
| 5,980,566 A | 11/1999 | Alt et al. | | 6,186,972 B1 | 2/2001 | Nelson et al. |
| 5,984,955 A | 11/1999 | Wisselink | | 6,187,034 B1 | 2/2001 | Frantzen |
| 5,984,956 A | 11/1999 | Tweden et al. | | 6,190,353 B1 | 2/2001 | Makower et al. |
| 5,984,963 A | 11/1999 | Ryan et al. | | 6,193,726 B1 | 2/2001 | Vanney |
| 5,984,965 A | 11/1999 | Knapp et al. | | 6,193,734 B1 | 2/2001 | Bolduc et al. |
| 5,985,307 A | 11/1999 | Hanson et al. | | 6,196,230 B1 | 3/2001 | Hall et al. |
| 5,989,207 A | 11/1999 | Hughes | | 6,197,050 B1 | 3/2001 | Eno et al. |
| 5,989,263 A | 11/1999 | Shmulewitz | | 6,197,324 B1 | 3/2001 | Crittenden |
| 5,989,287 A | 11/1999 | Yang et al. | | 6,200,311 B1 | 3/2001 | Danek et al. |
| 5,993,481 A | 11/1999 | Marcade et al. | | 6,203,556 B1 | 3/2001 | Evans et al. |
| 5,993,482 A | 11/1999 | Chuter | | 6,213,126 B1 | 4/2001 | LaFontaine et al. |
| 5,997,525 A | 12/1999 | March et al. | | 6,214,041 B1 | 4/2001 | Tweden et al. |
| 5,997,563 A | 12/1999 | Kretzers | | 6,217,527 B1 | 4/2001 | Selmon et al. |
| 5,997,573 A | 12/1999 | Quijano et al. | | 6,217,549 B1 | 4/2001 | Selmon et al. |
| 5,999,678 A | 12/1999 | Murphy-Chutorian et al. | | 6,217,575 B1 | 4/2001 | DeVore et al. |

| | | |
|---|---|---|
| 6,221,049 B1 | 4/2001 | Selmon et al. |
| 6,223,752 B1 | 5/2001 | Vanney et al. |
| 6,224,584 B1 | 5/2001 | March et al. |
| 6,231,546 B1 | 5/2001 | Milo et al. |
| 6,231,551 B1 | 5/2001 | Barbut |
| 6,231,568 B1 | 5/2001 | Loeb et al. |
| 6,231,587 B1 | 5/2001 | Makower |
| 6,235,000 B1 | 5/2001 | Milo et al. |
| 6,237,607 B1 * | 5/2001 | Vanney et al. .............. 128/898 |
| 6,238,406 B1 | 5/2001 | Ellis et al. |
| 6,241,667 B1 | 6/2001 | Vetter et al. |
| 6,245,102 B1 | 6/2001 | Jayaraman |
| 6,248,112 B1 | 6/2001 | Gambale et al. |
| 6,250,305 B1 | 6/2001 | Tweden |
| 6,251,079 B1 | 6/2001 | Gambale et al. |
| 6,251,104 B1 | 6/2001 | Kesten et al. |
| 6,251,116 B1 | 6/2001 | Shennib et al. |
| 6,251,418 B1 | 6/2001 | Ahern et al. |
| 6,253,768 B1 | 7/2001 | Wilk |
| 6,253,769 B1 | 7/2001 | LaFontaine et al. |
| 6,254,564 B1 | 7/2001 | Wilk et al. |
| 6,258,052 B1 | 7/2001 | Milo |
| 6,258,119 B1 | 7/2001 | Hussein et al. |
| 6,261,304 B1 | 7/2001 | Hall et al. |
| 6,283,951 B1 | 9/2001 | Flaherty et al. |
| 6,283,983 B1 | 9/2001 | Makower et al. |
| 6,285,903 B1 | 9/2001 | Rosenthal et al. |
| 6,287,317 B1 | 9/2001 | Makower et al. |
| 6,290,709 B1 | 9/2001 | Ellis et al. |
| 6,290,719 B1 | 9/2001 | Garberoglio |
| 6,290,728 B1 * | 9/2001 | Phelps et al. |
| 6,293,955 B1 | 9/2001 | Houser et al. |
| 6,302,875 B1 | 10/2001 | Makower |
| 6,302,892 B1 | 10/2001 | Wilk |
| 6,306,125 B1 | 10/2001 | Parker et al. |
| 6,309,370 B1 | 10/2001 | Haim et al. |
| 6,322,548 B1 | 11/2001 | Payne et al. |
| RE37,463 E | 12/2001 | Altman |
| 6,329,348 B1 | 12/2001 | Crystal et al. |
| 6,330,884 B1 | 12/2001 | Kim |
| 6,331,527 B1 | 12/2001 | Parmacek et al. |
| 6,350,248 B1 | 2/2002 | Knudson et al. |
| 6,361,519 B1 | 3/2002 | Knudson et al. |
| 6,363,938 B2 | 4/2002 | Saadat et al. |
| 6,363,939 B1 | 4/2002 | Wilk |
| 6,375,615 B1 | 4/2002 | Flaherty et al. |
| 6,379,319 B1 | 4/2002 | Garibotto et al. |
| 6,387,119 B2 | 5/2002 | Wolf et al. |
| 6,390,098 B1 | 5/2002 | LaFontaine et al. |
| 6,395,208 B1 | 5/2002 | Herweck et al. |
| 6,402,719 B1 | 6/2002 | Ponzi et al. |
| 6,402,740 B1 | 6/2002 | Ellis et al. |
| 6,406,488 B1 | 6/2002 | Tweden et al. |
| 6,406,491 B1 | 6/2002 | Vanney |
| 6,409,697 B2 | 6/2002 | Eno et al. |
| 6,409,751 B1 | 6/2002 | Hall et al. |
| 6,416,490 B1 | 7/2002 | Ellis et al. |
| 6,416,510 B1 | 7/2002 | Altman et al. |
| 6,423,089 B1 | 7/2002 | Gingras et al. |
| 6,432,119 B1 | 8/2002 | Saadat |
| 6,432,126 B1 | 8/2002 | Gambale et al. |
| 6,432,127 B1 | 8/2002 | Kim et al. |
| 6,432,132 B1 | 8/2002 | Cottone et al. |
| 6,443,158 B1 | 9/2002 | LaFontaine et al. |
| 6,443,949 B2 | 9/2002 | Altman |
| 6,447,522 B2 | 9/2002 | Gambale et al. |
| 6,447,539 B1 | 9/2002 | Nelson et al. |
| 6,454,760 B2 | 9/2002 | Vanney |
| 6,454,794 B1 | 9/2002 | Knudson et al. |
| 6,458,092 B1 | 10/2002 | Gambale et al. |
| 6,458,140 B2 | 10/2002 | Akin et al. |
| 6,458,323 B1 | 10/2002 | Boekstegers |
| 6,464,709 B1 | 10/2002 | Shennib et al. |
| 6,475,226 B1 | 11/2002 | Belef et al. |
| 6,475,244 B2 | 11/2002 | Herweck et al. |
| 6,482,220 B1 | 11/2002 | Mueller |
| 6,491,689 B1 | 12/2002 | Ellis et al. |
| 6,491,707 B2 | 12/2002 | Makower et al. |
| 6,508,825 B1 | 1/2003 | Selmon et al. |
| 6,511,458 B2 | 1/2003 | Milo et al. |
| 6,514,217 B1 | 2/2003 | Selmon et al. |
| 6,514,271 B2 | 2/2003 | Evans et al. |
| 6,517,527 B2 | 2/2003 | Gambale et al. |
| 6,517,558 B2 | 2/2003 | Gittings et al. |
| 6,524,323 B1 | 2/2003 | Nash et al. |
| 6,544,230 B1 | 4/2003 | Flaherty et al. |
| 6,559,132 B1 | 5/2003 | Holmer |
| 6,561,998 B1 | 5/2003 | Roth et al. |
| 6,565,528 B1 | 5/2003 | Mueller |
| 6,565,555 B1 | 5/2003 | Ryan et al. |
| 6,565,594 B1 | 5/2003 | Herweck et al. |
| 6,569,145 B1 | 5/2003 | Shmulewitz et al. |
| 6,569,147 B1 | 5/2003 | Evans et al. |
| 6,575,168 B2 | 6/2003 | LaFontaine et al. |
| 6,579,311 B1 | 6/2003 | Makower |
| 6,582,444 B2 | 6/2003 | Wilk |
| 6,599,304 B1 | 7/2003 | Selmon et al. |
| 6,605,053 B1 | 8/2003 | Kamm et al. |
| 6,605,113 B2 | 8/2003 | Wilk |
| 6,610,100 B2 | 8/2003 | Phelps et al. |
| 6,613,081 B2 | 9/2003 | Kim et al. |
| 6,616,675 B1 | 9/2003 | Evard et al. |
| 6,638,237 B1 * | 10/2003 | Guiles et al. .................. 604/8 |
| 6,638,247 B1 | 10/2003 | Selmon et al. |
| 6,638,293 B1 | 10/2003 | Makower et al. |
| 6,641,610 B2 | 11/2003 | Wolf et al. |
| 6,651,670 B2 * | 11/2003 | Rapacki et al. .............. 128/898 |
| 6,652,540 B1 | 11/2003 | Cole et al. |
| 6,652,546 B1 | 11/2003 | Nash et al. |
| 6,655,386 B1 | 12/2003 | Makower et al. |
| 6,660,003 B1 | 12/2003 | DeVore et al. |
| 6,660,024 B1 | 12/2003 | Flaherty et al. |
| 6,669,709 B1 | 12/2003 | Cohn et al. |
| 6,685,648 B2 | 2/2004 | Flaherty et al. |
| 6,694,983 B2 | 2/2004 | Wolf et al. |
| 6,709,425 B2 | 3/2004 | Gambale et al. |
| 6,709,444 B1 | 3/2004 | Makower |
| 6,719,770 B2 | 4/2004 | Laufer et al. |
| 6,726,677 B1 | 4/2004 | Flaherty et al. |
| 6,746,464 B1 | 6/2004 | Makower |
| 6,774,278 B1 | 8/2004 | Ragheb et al. |
| 6,786,929 B2 | 9/2004 | Gambale et al. |
| 6,802,858 B2 | 10/2004 | Gambale et al. |
| 6,808,498 B2 | 10/2004 | Laroya et al. |
| 6,830,568 B1 | 12/2004 | Kesten et al. |
| 6,863,684 B2 | 3/2005 | Kim et al. |
| 6,881,199 B2 | 4/2005 | Wilk et al. |
| 2001/0000041 A1 | 3/2001 | Selmon et al. |
| 2001/0004683 A1 | 6/2001 | Gambale et al. |
| 2001/0004690 A1 | 6/2001 | Gambale et al. |
| 2001/0004699 A1 | 6/2001 | Gittings et al. |
| 2001/0008969 A1 | 7/2001 | Evans et al. |
| 2001/0012948 A1 | 8/2001 | Vanney |
| 2001/0014813 A1 | 8/2001 | Saadat et al. |
| 2001/0016700 A1 | 8/2001 | Eno et al. |
| 2001/0018596 A1 | 8/2001 | Selmon et al. |
| 2001/0020172 A1 | 9/2001 | Selmon et al. |
| 2001/0025643 A1 * | 10/2001 | Foley ....................... 128/898 |
| 2001/0027287 A1 | 10/2001 | Shmulewitz et al. |
| 2001/0029385 A1 | 10/2001 | Shennib et al. |
| 2001/0034547 A1 | 10/2001 | Hall et al. |
| 2001/0037086 A1 | 11/2001 | Gambale et al. |
| 2001/0037117 A1 | 11/2001 | Gambale et al. |
| 2001/0037149 A1 | 11/2001 | Wilk |
| 2001/0039426 A1 | 11/2001 | Makower et al. |
| 2001/0039445 A1 | 11/2001 | Hall et al. |

| | | | | | | |
|---|---|---|---|---|---|---|
| 2001/0041902 A1 | 11/2001 | Lepulu et al. | | 2004/0122318 A1 | 6/2004 | Flaherty et al. |
| 2001/0044631 A1 | 11/2001 | Akin et al. | | 2004/0122347 A1 | 6/2004 | Knudson et al. |
| 2001/0047165 A1 | 11/2001 | Makower et al. | | 2004/0133154 A1 | 7/2004 | Flaherty et al. |
| 2001/0049523 A1 | 12/2001 | DeVore et al. | | 2004/0133225 A1 | 7/2004 | Makower |
| 2001/0053932 A1 | 12/2001 | Phelps et al. | | 2004/0147869 A1* | 7/2004 | Wolf et al. ............... 604/8 |
| 2002/0002349 A1 | 1/2002 | Flaherty et al. | | 2004/0158143 A1 | 8/2004 | Flaherty et al. |
| 2002/0004662 A1 | 1/2002 | Wilk | | 2004/0167444 A1 | 8/2004 | Laroya et al. |
| 2002/0004663 A1 | 1/2002 | Gittings et al. | | 2004/0168691 A1 | 9/2004 | Sharkawy et al. |
| 2002/0007138 A1 | 1/2002 | Wilk et al. | | 2004/0186507 A1 | 9/2004 | Hall et al. |
| 2002/0019629 A1 | 2/2002 | Dietz et al. | | 2004/0186557 A1 | 9/2004 | Gambale et al. |
| 2002/0029079 A1 | 3/2002 | Kim et al. | | 2004/0186587 A1 | 9/2004 | Ahern |
| 2002/0032476 A1 | 3/2002 | Gambale et al. | | 2004/0219180 A1 | 11/2004 | Gambale et al. |
| 2002/0049486 A1 | 4/2002 | Knudson et al. | | 2004/0220598 A1 | 11/2004 | Bolduc et al. |
| 2002/0058897 A1 | 5/2002 | Renati | | 2004/0225355 A1 | 11/2004 | Stevens |
| 2002/0062146 A1 | 5/2002 | Makower et al. | | 2004/0236418 A1 | 11/2004 | Stevens |
| 2002/0065478 A1 | 5/2002 | Knudson et al. | | 2005/0004505 A1 | 1/2005 | Phelps et al. |
| 2002/0072699 A1 | 6/2002 | Knudson et al. | | 2005/0004558 A1 | 1/2005 | Gambale et al. |
| 2002/0077566 A1 | 6/2002 | Laroya et al. | | 2005/0033220 A1 | 2/2005 | Wilk et al. |
| 2002/0077654 A1 | 6/2002 | Javier, Jr. et al. | | | | |
| 2002/0092535 A1 | 7/2002 | Wilk | | FOREIGN PATENT DOCUMENTS | | |
| 2002/0092536 A1 | 7/2002 | LaFontaine et al. | | | | |
| 2002/0095111 A1 | 7/2002 | Tweden et al. | | AU | 757647 B2 | 2/2003 |
| 2002/0095206 A1 | 7/2002 | Addonizio et al. | | EP | 0 592 410 B1 | 10/1995 |
| 2002/0100484 A1 | 8/2002 | Wolf et al. | | EP | 0 732 088 A2 | 9/1996 |
| 2002/0111669 A1 | 8/2002 | Pazienza et al. | | EP | 0 792 624 A1 | 9/1997 |
| 2002/0111672 A1 | 8/2002 | Kim et al. | | EP | 0 797 957 A1 | 10/1997 |
| 2002/0123698 A1 | 9/2002 | Garibotto et al. | | EP | 0 797 958 A1 | 10/1997 |
| 2002/0138087 A1 | 9/2002 | Shennib et al. | | EP | 0 799 604 A1 | 10/1997 |
| 2002/0143285 A1 | 10/2002 | Eno et al. | | EP | 0 801 928 A1 | 10/1997 |
| 2002/0143289 A1 | 10/2002 | Ellis et al. | | EP | 0 815 798 A2 | 1/1998 |
| 2002/0144696 A1 | 10/2002 | Sharkawy et al. | | EP | 0 824 903 A1 | 2/1998 |
| 2002/0161383 A1 | 10/2002 | Akin et al. | | EP | 0 829 239 A1 | 3/1998 |
| 2002/0161424 A1 | 10/2002 | Rapacki et al. | | EP | 0 836 834 A2 | 4/1998 |
| 2002/0165479 A1 | 11/2002 | Wilk | | EP | 0 858 779 A1 | 8/1998 |
| 2002/0165606 A1 | 11/2002 | Wolf et al. | | EP | 0 876 796 A2 | 11/1998 |
| 2002/0177772 A1 | 11/2002 | Altman et al. | | EP | 0 876 803 A2 | 11/1998 |
| 2002/0179098 A1 | 12/2002 | Makower et al. | | EP | 0 888 750 A1 | 1/1999 |
| 2002/0183716 A1 | 12/2002 | Herweck et al. | | EP | 0 895 752 A1 | 2/1999 |
| 2002/0193782 A1 | 12/2002 | Ellis et al. | | EP | 0 903 123 A1 | 3/1999 |
| 2003/0018379 A1 | 1/2003 | Knudson et al. | | EP | 0 904 745 A2 | 3/1999 |
| 2003/0044315 A1 | 3/2003 | Boekstegers | | EP | 0 934 728 A2 | 8/1999 |
| 2003/0045828 A1 | 3/2003 | Wilk | | EP | 0 955 017 A2 | 11/1999 |
| 2003/0055371 A1 | 3/2003 | Wolf et al. | | EP | 0 955 019 A2 | 11/1999 |
| 2003/0073973 A1 | 4/2003 | Evans et al. | | EP | 0 962 194 A2 | 12/1999 |
| 2003/0078561 A1 | 4/2003 | Gambale et al. | | EP | 1 020 166 A1 | 7/2000 |
| 2003/0100920 A1 | 5/2003 | Akin et al. | | EP | 1 027 870 A1 | 8/2000 |
| 2003/0105514 A1 | 6/2003 | Phelps et al. | | EP | 1 029 511 A1 | 8/2000 |
| 2003/0120195 A1 | 6/2003 | Milo et al. | | EP | 1 166 721 A2 | 1/2002 |
| 2003/0149474 A1 | 8/2003 | Becker | | EP | 0 959 815 B1 | 12/2002 |
| 2003/0158573 A1 | 8/2003 | Gittings et al. | | EP | 1 112 097 A1 | 6/2003 |
| 2003/0181938 A1 | 9/2003 | Roth et al. | | EP | 0 954 248 B1 | 9/2004 |
| 2003/0191449 A1 | 10/2003 | Nash et al. | | EP | 1 115 452 B1 | 11/2004 |
| 2003/0195457 A1 | 10/2003 | LaFontaine et al. | | EP | 1 477 202 A2 | 11/2004 |
| 2003/0195458 A1 | 10/2003 | Phelps et al. | | EP | 1 107 710 B1 | 12/2004 |
| 2003/0212413 A1 | 11/2003 | Wilk | | EP | 1 484 081 A1 | 12/2004 |
| 2003/0216679 A1 | 11/2003 | Wolf et al. | | EP | 1 516 599 A2 | 3/2005 |
| 2003/0229366 A1 | 12/2003 | Reggie et al. | | GB | 2316322 | 10/1998 |
| 2003/0236542 A1 | 12/2003 | Makower | | WO | WO94/16629 | 8/1994 |
| 2004/0006298 A1 | 1/2004 | Wilk | | WO | WO96/32972 | 10/1996 |
| 2004/0015225 A1 | 1/2004 | Kim et al. | | WO | WO96/35469 | 11/1996 |
| 2004/0019348 A1 | 1/2004 | Stevens et al. | | WO | WO96/39962 A1 | 12/1996 |
| 2004/0044392 A1 | 3/2004 | Von Oepen | | WO | WO96-39964 A1 | 12/1996 |
| 2004/0058097 A1 | 3/2004 | Weder | | WO | WO96-39965 A1 | 12/1996 |
| 2004/0059280 A1 | 3/2004 | Makower et al. | | WO | WO97/13463 | 4/1997 |
| 2004/0073157 A1 | 4/2004 | Knudson et al. | | WO | WO97/13471 | 4/1997 |
| 2004/0073238 A1 | 4/2004 | Makower | | WO | WO97/18768 | 5/1997 |
| 2004/0077987 A1 | 4/2004 | Rapacki et al. | | WO | WO97/27893 | 8/1997 |
| 2004/0077988 A1 | 4/2004 | Tweden et al. | | WO | WO97/27897 | 8/1997 |
| 2004/0077990 A1 | 4/2004 | Knudson et al. | | WO | WO97/27898 | 8/1997 |
| 2004/0088042 A1 | 5/2004 | Kim et al. | | WO | WO97/32551 | 9/1997 |
| 2004/0106931 A1* | 6/2004 | Guiles et al. ............... 606/108 | | WO | WO97/41916 | 11/1997 |
| 2004/0113306 A1 | 6/2004 | Rapacki et al. | | WO | WO97/43961 | 11/1997 |
| 2004/0118415 A1 | 6/2004 | Hall et al. | | WO | WO98/02099 | 1/1998 |

| | | |
|---|---|---|
| WO | WO98-03118 A1 | 1/1998 |
| WO | WO98/06356 | 2/1998 |
| WO | WO98/08456 | 3/1998 |
| WO | WO98/10714 | 3/1998 |
| WO | WO98/16161 | 4/1998 |
| WO | WO98/19607 | 5/1998 |
| WO | WO98/19614 | 5/1998 |
| WO | WO98-24373 A1 | 6/1998 |
| WO | WO98-25533 A1 | 6/1998 |
| WO | EP 0 853 921 A2 | 7/1998 |
| WO | WO98-38916 A1 | 9/1998 |
| WO | WO98-38925 A1 | 9/1998 |
| WO | WO98-38939 A1 | 9/1998 |
| WO | WO98-38941 A1 | 9/1998 |
| WO | WO98-39038 A1 | 9/1998 |
| WO | WO98/44869 | 10/1998 |
| WO | WO98/46115 | 10/1998 |
| WO | WO98/46119 | 10/1998 |
| WO | WO98/49964 | 11/1998 |
| WO | WO98/53759 | 12/1998 |
| WO | WO98/55027 | 12/1998 |
| WO | WO98-57590 A1 | 12/1998 |
| WO | WO98/57591 | 12/1998 |
| WO | WO98-57592 A1 | 12/1998 |
| WO | WO99-07296 A1 | 2/1999 |
| WO | WO99/08624 | 2/1999 |
| WO | WO99-15220 A1 | 4/1999 |
| WO | WO99-17671 A1 | 4/1999 |
| WO | WO99/17683 | 4/1999 |
| WO | WO99/21490 | 5/1999 |
| WO | WO99/21510 | 5/1999 |
| WO | WO99/22655 | 5/1999 |
| WO | WO99-22658 A1 | 5/1999 |
| WO | WO99/25273 | 5/1999 |
| WO | WO99-27985 A1 | 6/1999 |
| WO | WO99/29251 | 6/1999 |
| WO | WO99/32051 | 7/1999 |
| WO | WO99/33407 | 7/1999 |
| WO | WO99-35977 A1 | 7/1999 |
| WO | WO99-35979 A1 | 7/1999 |
| WO | WO99-35980 A1 | 7/1999 |
| WO | WO99/36000 | 7/1999 |
| WO | WO99/36001 | 7/1999 |
| WO | WO99/37218 | 7/1999 |
| WO | WO99/38459 | 8/1999 |
| WO | WO99-40853 A1 | 8/1999 |
| WO | WO99/40868 | 8/1999 |
| WO | WO99-40963 A1 | 8/1999 |
| WO | WO99-44524 A2 | 9/1999 |
| WO | WO99/47071 | 9/1999 |
| WO | WO99/47078 | 9/1999 |
| WO | WO99/48427 | 9/1999 |
| WO | WO99/48545 | 9/1999 |
| WO | WO99-48549 A2 | 9/1999 |
| WO | WO99/49790 | 10/1999 |
| WO | WO99/49793 | 10/1999 |
| WO | WO99/49910 | 10/1999 |
| WO | WO99/51162 | 10/1999 |
| WO | WO99/52481 | 10/1999 |
| WO | WO99/53863 | 10/1999 |
| WO | WO99-53863 A1 | 10/1999 |
| WO | WO99/55406 | 11/1999 |
| WO | WO99/60941 | 12/1999 |
| WO | WO99/62430 | 12/1999 |
| WO | WO 00/09195 | 2/2000 |
| WO | WO 00/10623 | 3/2000 |
| WO | WO 00/12029 | 3/2000 |
| WO | WO 00-13722 A1 | 3/2000 |
| WO | WO 00/15146 | 3/2000 |
| WO | WO 00/15147 | 3/2000 |
| WO | WO 00/15148 | 3/2000 |
| WO | WO 00/15149 | 3/2000 |
| WO | WO 00/15275 | 3/2000 |
| WO | WO 00-16848 A1 | 3/2000 |
| WO | WO 00/18302 | 4/2000 |
| WO | WO 00-18323 A2 | 4/2000 |
| WO | WO 00/18325 | 4/2000 |
| WO | WO 00/18326 | 4/2000 |
| WO | WO 00/18331 | 4/2000 |
| WO | WO 00/18462 | 4/2000 |
| WO | WO 00/21436 | 4/2000 |
| WO | WO 00/21461 | 4/2000 |
| WO | WO 00/21463 | 4/2000 |
| WO | WO 00/24449 | 5/2000 |
| WO | WO 00/24452 | 5/2000 |
| WO | WO 00/33725 | 6/2000 |
| WO | WO 00/35376 | 6/2000 |
| WO | WO 00/36997 | 6/2000 |
| WO | WO 00/41632 | 7/2000 |
| WO | WO 00/41633 | 7/2000 |
| WO | WO 00/43051 | 7/2000 |
| WO | WO 00/45711 | 8/2000 |
| WO | WO 00-45886 A2 | 8/2000 |
| WO | WO 00-49952 A1 | 8/2000 |
| WO | WO 00-49954 A2 | 8/2000 |
| WO | WO 00-49956 A1 | 8/2000 |
| WO | WO 00/54660 | 9/2000 |
| WO | WO 00-54661 A1 | 9/2000 |
| WO | WO 00-56224 A1 | 9/2000 |
| WO | WO 00-56225 A1 | 9/2000 |
| WO | WO 00/56387 | 9/2000 |
| WO | WO 00/66007 | 11/2000 |
| WO | WO 00/66009 | 11/2000 |
| WO | WO 00/66035 | 11/2000 |
| WO | WO 00/69345 | 11/2000 |
| WO | WO 00/69504 | 11/2000 |
| WO | WO 00/71195 | 11/2000 |
| WO | WO 01-08566 A1 | 2/2001 |
| WO | WO 01/08602 A1 | 2/2001 |
| WO | WO 01/10340 | 2/2001 |
| WO | WO 01/10341 | 2/2001 |
| WO | WO 01/10347 | 2/2001 |
| WO | WO 01/10348 | 2/2001 |
| WO | WO 01/10349 | 2/2001 |
| WO | WO 01/10350 A1 | 2/2001 |

OTHER PUBLICATIONS

Tweden et al., "Ventriculocoronary Artery Bypass (VCAB), a Novel Approach to Myocardial Revascularization".

*American Medical Association Publication*; International Cardiovascular Society, "Myocardial Boring for the Ischemic Heart," A. Wakabayashi, M.D., et al.; Fifteenth Scientific Meeting, Atlantic City, NJ, Jun. 16 and 17, 1967; *Archives of Surgery*, pp. 743-752, vol. 95, No. 5, Nov. 1967.

*American Medical Association Publication*; "Myocardial Revascularization Experiments Using the Epicardium," B. G. Lary, M.D., et al.; *Archives of Surgery*, pp. 69-72, vol. 98, No. 1, Jan. 1969.

*The Journal of Thoracic and Cardiovascular Surgery*, "Experimental Evaluation of Direct Transventricular Revascularization," L. Kuzela, M.D., et al., pp. 770-773, vol. 57, Jan.-Jun. 1969, The C.V. Mosby Co., St. Louis, MO.

*The Journal of Thoracic and Cardiovascular Surgery*, "Myocardial Revascularization by a New Method of Carrying Blood Directly from the Left Ventricular Cavity into the Coronary Circulation," C Massimo, M.D., et al., pp. 257-264, Aug. 1957.

*The Journal of Thoracic and Cardiovascular Surgery*, "Experimental Evaluation of Myocardial Tunnelization as a Method of Myocardial Revascularization," I. Anabtawi, M.D., et al., pp. 638-646., Nov. 1969.

*The Journal of Thoracic and Cardiovascular Surgery*, "The Possibility of Myocardial Revascularization by Creation of a Left Ventriculocoronary Artery Fistula," I. Munro, M.D., et al., pp. 25-32., vol. 58, 1969.

*AJR*, "Expandable Inrahepatic Portacaval Shunt Stents in Dogs with Chronic Portal Hypertension," J. Palmaz, et al., pp. 1251-1256, Dec. 1988.
*AJR*, "Expandable Intrahepatic Portacaval Shunt Stents: Early Experience in the Dog," J. Palmaz, et al., pp. 821-825.
*Journal of Surgical Research*, "An Experimental Anatomic Study of Indirect Myocardial Revascularization," Gardner, M.D. et al., May 1971, vol. 11, No. 5, pp. 243-247.
*Surgery*, A method for creating a coronary-myocardial artery, Lary, B. et al., Jun. 1966, vol. 59, No. 6, pp. 1061-1064.
*Am. Heart J.*, "Silent left coronary artery-cameral fistula: Probable cause of myocardial ischemia," Ahmed, S. et al., Oct. 1982, vol. 104, No. 4, pp. 869-870.
*JAMA*, "Percutaneous Transjugular Portosystemic Shunt," Zemel, G. et al., Jul. 1991, vol. 266, No. 3, pp. 390-393.
*Radiology*, "Transjugular Intrahepatic Portacaval Stent Shunt: Preliminary Clinical Results," Richter, G. et al., Mar. 1990, vol. 174, No. 3, pp. 1027-1030.
Alfred Goldman, Seymour M. Greenstone, Fred S. Preuss, Sherman H. Strauss & En-Shu Chang; "Experimental Methods for Producing a Collateral Circulation to the Heart Directly from the Left Ventricle"; Journal of Thoracic Surgery; Mar. 1956; pp. 364-374; vol. 31, No. 3; U.S.A.
Akio Wakayabashi, Solomon T. Little, Jr. & John E. Connolly; "Myocardial Boring for the Ischemic Heart"; Archives of Surgery; Nov. 1967; pp. 743-752; vol. 95; American Medical Asssociation; U.S.A.
Frank M. Galioto, Milton J. Reitman, Arnold J. Slovis & Irving A. Sarot; "Right coronary artery to left ventricle fistula: A case report and discussion"; American Heart Journal; Jul. 1971; pp. 93-97; vol. 82, No. 1; The C.V. Mosby Company; St. Louis, MO.
Joseph P. Archie Jr.; "Intramyocardial Pressure: Effect of Preload on Transmural Distribution of Systolic Coronary Blood Flow"; The American Journal of Cardiology; Jun. 1975; pp. 904-911; vol. 35; U.S.A.
L. Levinsky, T.Z. Lajos, A.B. Lee, Jr., C. Espersen, & G. Schimert; "The Revival of the Horseshoe Graft (Side-toSide Saphenous-Vein-to-Aorta Anastomosis"; The Thoracic and Cardiovascular Surgeon; Oct. 1979; pp. 322-324; vol. 27, No. 5; Georg Thieme Publishers; Stuttgart, Germany.
Garrett Lee, Richard M. Ikeda, Jerold Theis, Daniel Stobbe, Claire Ogata, Henry Lui, Robert L. Reis, & Dean T. Mason; "Effects of laser Irradiation delivered by flexible fiberoptic system on the left ventricular internal myocardium"; American Heart Journal; Sep. 1983; pp. 587-590; vol. 106, No. 3; The C.V. Mosby Company; St. Louis, MO.
Medical Industry Today Headline News; "Eclipse Gets OK to Pump Catheter Marketing in Europe"; Jul. 17, 1998; pp. 1-2; Article #07179802, Article is 349 words long; Medical Data International, Inc.; Santa Ana, CA.
Medical Industry Today Headline News; "Sales Dive, Losses Soar in 2Q for CardioGenesis"; Jul. 17, 1998; pp. 1-2; Article #07179808, Article is 560 words long; Medical Data International, Inc.; U.S.A.
Howard A. Cohen & Marco Zenati; "Alternative Approaches to Coronary Revascularization"; Current International Cardiology Reports; 1999; pp. 138-146; vol. 1; Current Science, Inc.; U.S.A.
Stephen N. Oesterle, Nicolaus Reifart, Motoya Hayase, Eugen Haputmann, Reginald Low, Raimund Erbel, Michael Hause, Olaf Dirsch, Gerhard C. Schuler, Renu Virmani & Alan C. Yeung; "Catheter-Based Coronary Bypass: A Development Update"; Catheterization and Cardiovascular Interventions; 2003; pp. 212. 218; vol. 58; Wiley-Liss, Inc.; U.S.A.

US 6,331,185, 12/2001, Gambale et al. (withdrawn)

* cited by examiner

*Primary Examiner*—Patricia Bianco
(74) *Attorney, Agent, or Firm*—Finnegan, Henderson, Farabow, Garrett & Dunner LLP

(57) ABSTRACT

Methodology and related medical devices for effectively bypassing a blocked or partially blocked coronary artery and providing oxygenated blood to the myocardium. A coronary artery bypass method utilizes a shunt member. An upstream end portion of the shunt member is disposed in the myocardium of a patient's heart so that the upstream end portion communicates with the left ventricle of the patient's heart. An opposite or downstream end portion of the shunt member is placed in communication with a coronary artery of the patient downstream of a blockage in the coronary artery. The shunt member extends into the coronary artery from the myocardium either directly or indirectly with an intermediate or middle portion of the shunt member being disposed in an intrapericardial space of the patient, outside of the myocardium and outside of the coronary artery. In a method for performing a myocardial revascularization a passageway is formed at least partially through a myocardium of a patient from an outer surface of the patient's heart, with a surgical operation being performed at an outer end of the passageway to permanently close the passageway at the outer end. The passageway may extend though a posterior wall of a coronary artery and is produced by forming an aperture in an anterior wall of the coronary artery and forming the passageway in substantial alignment with the aperture. The closure of the passageway is effectuated particularly by closing the aperture in the anterior wall of the coronary artery.

14 Claims, 94 Drawing Sheets

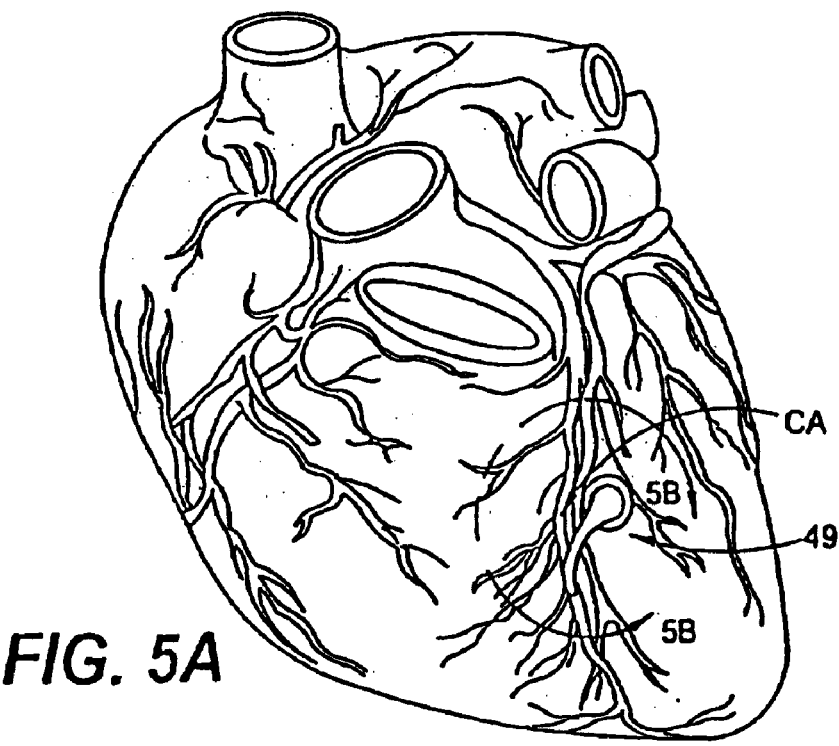
FIG. 5A
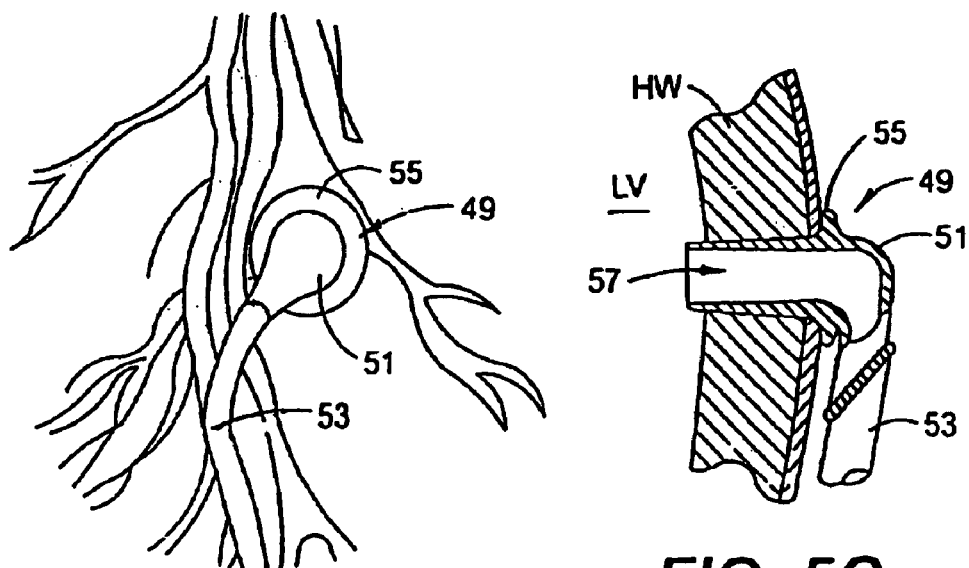
FIG. 5B
FIG. 5C

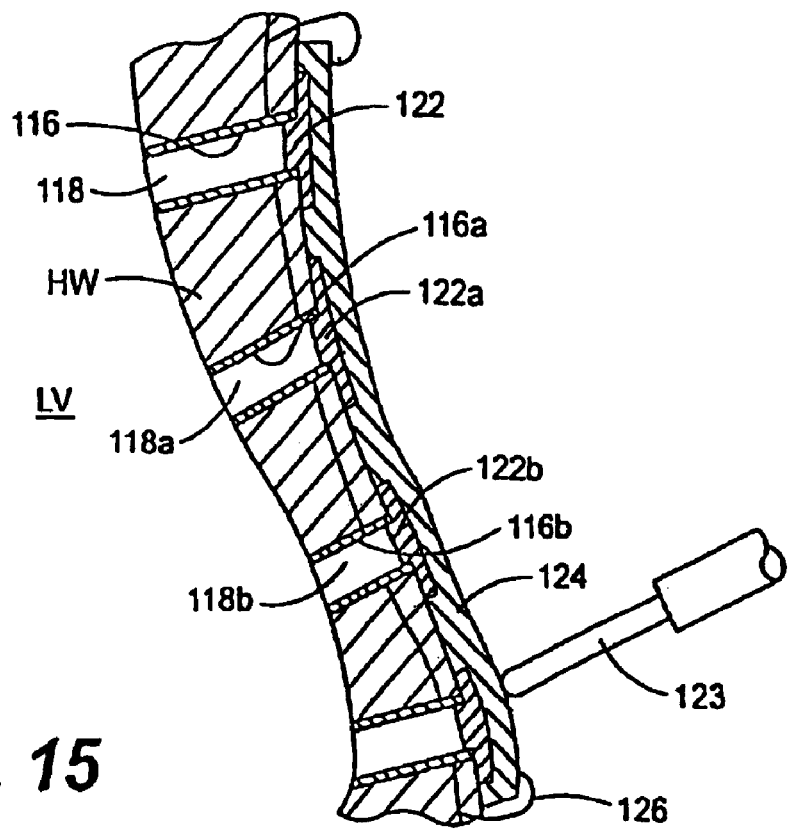
FIG. 15
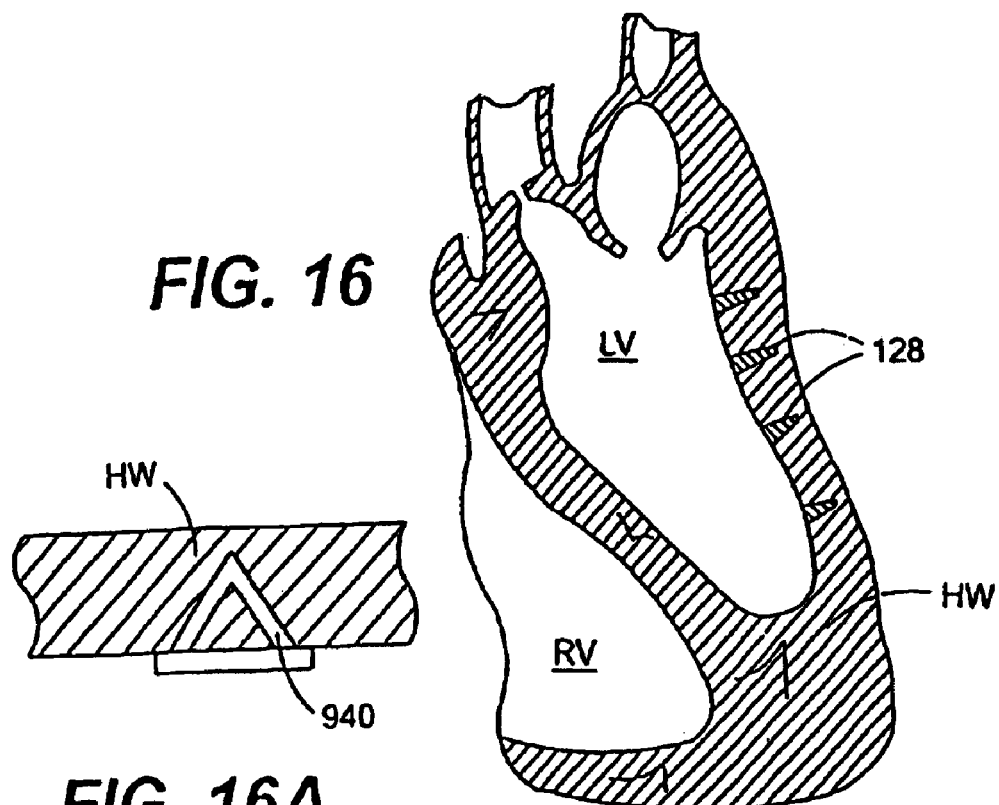
FIG. 16
FIG. 16A

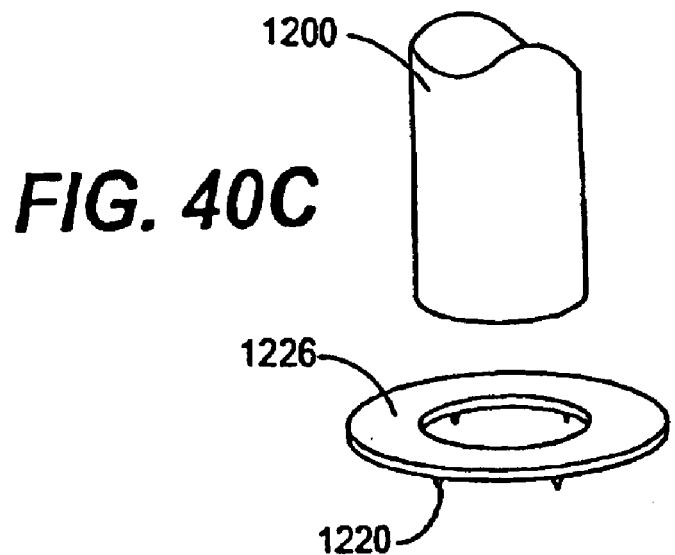
FIG. 40C
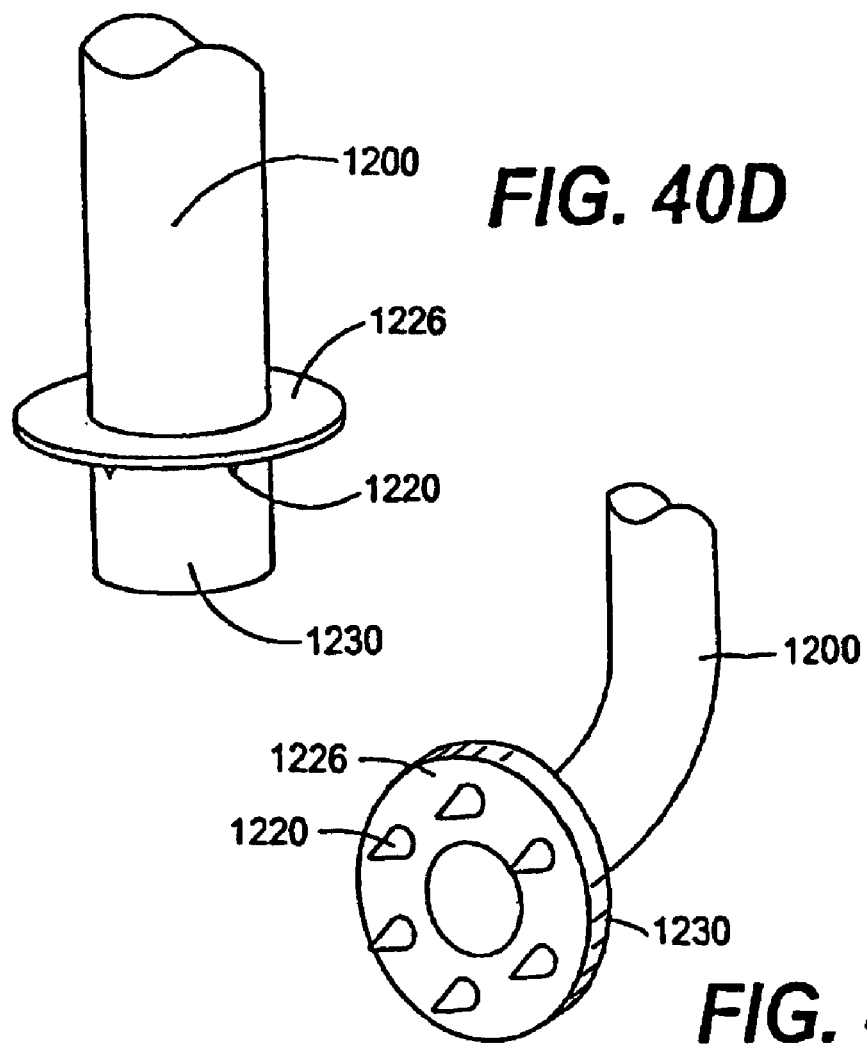
FIG. 40D
FIG. 40E

INSERTION STEPS

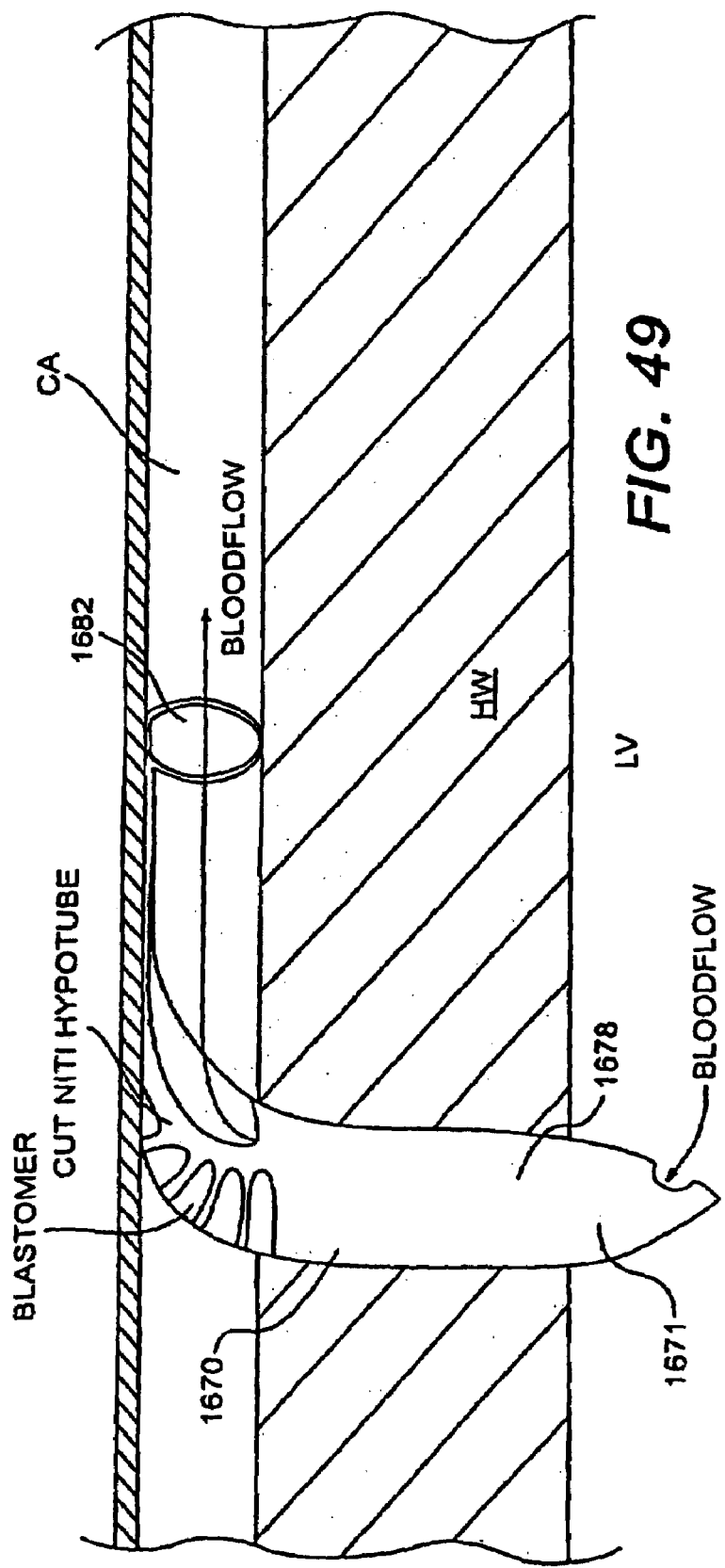

METHODS OF PROVIDING DIRECT BLOOD FLOW BETWEEN A HEART CHAMBER AND A CORONARY VESSEL

CROSS-REFERENCE TO RELATED APPLICATIONS

This is a continuation of application Ser. No. 09/369,039, filed Aug. 4, 1999, now abandoned and a continuation-in-part of application Ser. No. 09/016,485, filed Jan. 30, 1998 now abandoned and a continuation-in-part of PCT application Ser. No. PCT/US99/03484, filed Feb. 17, 1999, and which claims the benefit of U.S. provisional application Nos. 60/099,691 and 60/099,720, each filed Sep. 10, 1998; U.S. provisional application no. 60/099,767, filed Sep. 10, 1998; and U.S. provisional application no. 60/104,397, filed Oct. 15, 1998, all of which are incorporated herein by reference.

BACKGROUND OF THE INVENTION

1. Field of the Invention

This invention relates to an apparatus and method for implanting a conduit to allow communication of fluids from one portion of a patient's body to another; and, more particularly, to a blood flow conduit to allow communication from a heart chamber to a vessel or vice versa, and/or vessel to vessel. Even more particularly, the invention relates to a left ventricular conduit and related conduit configurations for controlling the flow of blood through the conduit to achieve bypass of an occluded coronary artery.

2. Description of Related Art

Coronary artery disease is a major problem in the U.S. and throughout the world. In fact, about 1.1 million "open heart" procedures are performed each year, and current estimates are that approximately 4.8 million people suffer from some degree of congestive heart failure.

When coronary arteries or other blood vessels become clogged with plaque, the results are at the very least impairment of the efficiency of the heart's pumping action. On the more severe side of the scale are heart attack and death. In some cases, clogged arteries can be unblocked through minimally invasive techniques such as balloon angioplasty. In more difficult cases, a surgical bypass of the blocked vessel is necessary.

In a bypass operation, one or more arterial or venous segments are harvested from the body and then surgically inserted between the aorta and the coronary artery. The inserted vessel segments, or transplants, act as a bypass of the blocked portion of the coronary artery and thus provide for a free or unobstructed flow of blood to the heart. More than 500,000 bypass procedures are performed in the U.S. every year.

Coronary artery bypass grafting (CABG) has been used for more than 30 years. Initially, the saphenous vein (SV) served as the principal conduit for coronary bypass, but studies over the last dozen years have shown a 35–40% increase in 10-year patency rate for the internal thoracic artery (ITA) compared with the SV. The SV, in fact, has only been shown to have a 10-year patency rate of 50%. Since the mid 1980's, not only the ITA, but also the alternative arterial conduits have been increasingly used. These conduits include the grastroepiploic artery (GEA), inferior epigastric artery (IEA), and radial artery (RA), which have been used primarily as supplements to both the right and left ITA.

Although the use of arterial conduits results in demonstrably better long-term patency, use of arteries in place of the SV often requires complex technical challenges, such as free grafts, sequential anastomosis, and conduit-to-conduit anastomosis. Some of the reasons for the difficulty in using arterial conduits reside in the fact that they are much more fragile than the SV and therefore easier to damage, and due to their smaller size, easier to occlude completely or partially through technical error during grafting.

Such coronary artery bypass surgery, however, is a very intrusive procedure that is expensive, time-consuming and traumatic to the patient. The operation requires an incision through the patient's sternum (sternotomy), and the patient be placed on a bypass pump so that the heart can be operated on while not beating. A vein graft is harvested from the patient's leg, another highly invasive procedure, and a delicate surgical procedure is required to piece the bypass graft to the coronary artery (anastomosis). Hospital stays subsequent to the surgery and convalescence periods are prolonged.

As mentioned above, another conventional treatment is percutaneous transluminal coronary angioplasty (PTCA) or other types of angioplasty. However, such vascular treatments are not always indicated due to the type or location of the blockage, or due to the risk of the emboli formation.

One bypass technique employed in the prior art is taught by Wilk (U.S. Pat. Nos. 5,287,861, 5,409,019, 5,662,124, and 5,429,144, the entirety of each of which is hereby incorporated herein by this reference). These Wilk references teach the use of a stent which is introduced through the myocardial wall from an adjacent coronary artery to provide a bypass conduit between the left ventricle and the adjacent coronary artery. In one embodiment, this technique teaches the delivery of a transmyocardial bypass shunt in a collapsed, reduced-profile configuration, which requires radial expansion subsequent to delivery in a bore preformed in the myocardial wall. The bore is formed, for example, by a drill, needle, Seldinger wire, dilating wires or catheters, or other devices prior to stent placement and expansion.

In another embodiment, Wilk discloses the disposition of a stent in the myocardium so that the stent extends only in the myocardium. The stent may extend only partially through the myocardium, from the left ventricle of the heart or from a coronary artery, upstream of a vascular obstruction. Alternatively, the stent may extend completely through the myocardium to establish a blood flow path or conduit from the left ventricle to a coronary artery, downstream of a vascular obstruction.

Where stents are used in the Wilk cardiac revascularization techniques to guide blood from the left ventricle, the stents may be designed to lock upon opening from collapsed insertion configurations. Such stents enable the infusion of blood into the myocardium during systole. The stents may be provided with one-way valves to regulate or control the backflow of blood during diastole.

Thus, there is a continuing need for improved bypass methods and apparatus that allow for the realization of increased long-term patency rates, and that are less physically traumatic to the patient.

SUMMARY OF THE INVENTION

Thus, in one preferred embodiment there is provided a new apparatus and method for performing a coronary artery by-pass operation which is less invasive and less traumatic to the patient than conventional by-pass surgery. Another advantage of this embodiment is that it requires no incision through the chest wall. In another embodiment there is provided a catheter assembly for use in performing the method of the invention.

Conduit Utilizing Intrapericardial Space

In another embodiment, there is provided methodology and related medical devices for effectively bypassing a blocked or partially blocked coronary artery and providing oxygenated blood to the myocardium. In accordance with this embodiment, a coronary artery bypass method utilizes a fluid communication conduit or shunt member. An upstream end portion of the shunt member is disposed in the myocardium of a patient's heart so that the upstream end portion communicates with the left ventricle of the patient's heart. An opposite downstream end portion of the shunt member is placed in communication with a coronary artery of the patient downstream of a blockage in the coronary artery, so that an intermediate or middle portion of the shunt member is disposed in an intrapericardial space of the patient, outside of the myocardium and outside of the coronary artery. The downstream end portion of the shunt is inserted into the coronary artery or, alternatively, attached to a generally anterior wall of the coronary artery.

Where the downstream end portion of the shunt is attached to the anterior wall of the coronary artery, the method further comprises forming an aperture in the anterior wall of the coronary artery after attaching the downstream end portion of the shunt member to the anterior wall, thereby opening communication between the shunt member and the coronary artery. The shunt member is preferably delivered intravascularly into the left ventricle of the patient's heart. The downstream end portion of the shunt member is then passed completely through the myocardium and the intrapericardial space to the anterior wall of the coronary artery. The aperture in the coronary artery is formed by inserting a free end portion of an incising instrument intravascularly and through the shunt member after disposition of the upstream end portion of the shunt member in the myocardium and after attaching of the downstream end portion of the shunt member to the coronary artery. The incising instrument is operated, after inserting thereof, to perforate the anterior wall of the coronary artery.

The incising instrument may be a laser instrument including an optical fiber. The incising instrument is operated in part by transmitting monochromatic or laser radiation through the optical fiber to the anterior wall of the coronary artery.

The method utilizing the shunt member further comprises forming a passageway through the myocardium prior to the disposing of the upstream end portion of the shunt member in the myocardium. The passageway is formed by inserting a surgical instrument intravascularly into the left ventricle of the patient and operating the instrument from outside the patient to bore or tunnel through the myocardium. The upstream end portion of the shunt member is disposed in the passageway and subsequently the downstream end portion of the shunt member is placed in communication with the coronary artery of the patient.

The shunt member may be deployed in a pericardioscopic operation wherein pericardioscopic surgical instruments are operated from outside the patient to manipulate the downstream end portion of the shunt member and to place the downstream end portion of the shunt member into communication with the coronary artery of the patient after passing of the downstream end portion of the shunt member through the passageway in the myocardium.

Where the downstream end portion of the shunt member is inserted into the coronary artery, the sequence of operations is similar to the case where the shunt member is attached to the anterior wall of the coronary artery. The shunt member is delivered intravascularly into the left ventricle of the patient's heart and subsequently the downstream end portion of the shunt member is passed through the myocardium; the downstream end portion of the shunt member is then inserted into the coronary artery. In this case, as well, the shunt member may be deployed in a pericardioscopic operation wherein pericardioscopic surgical instruments are operated from outside the patient to place the downstream end portion of the shunt member in communication with the coronary artery.

Generally, in the above-described procedure, the downstream end portion of the shunt member communicates with the coronary artery downstream of a blockage. During systole, blood travels from the patient's left ventricle through the shunt member to the coronary artery and then to the myocardium along natural vessels. It may be necessary, in some patients, to provide two or more shunt members, depending on the number of blockages and their locations along the coronary artery.

Conduit Construction

The shunt or conduit member comprises a generally tubular, rounded or circumferential member having a length greater than a width of the myocardium. The shunt member is made of a biocompatible material such as polyethylene or GORTEX™ and is flexible at least along the middle or intermediate portion thereof. Accordingly, the intermediate or middle portion of the shunt member may be bent into an arc to facilitate the formation of a proper junction between the downstream end portion of the shunt member and the coronary artery of the patient. The tubular shunt member may be provided with a one-way valve preventing back flow of blood from the coronary artery into the ventricle. In a specific embodiment of the invention, the upstream end portion of the tubular shunt member is wider than the downstream end portion.

As discussed above, an upstream end portion of a generally tubular shunt member may be disposed in a myocardium of a patient's heart so that the upstream end portion communicates with a left ventricle of the patient's heart, while a downstream end portion of the shunt member is inserted into a coronary artery of the patient downstream of a blockage in the coronary artery so that the downstream end portion is disposed inside the coronary artery. In a variation of the present invention, the shunt member is deployed so as to be disposed only inside the myocardium and the coronary artery. In contrast to the above-described methodology, no portion of the shunt member lies in the intrapericardial space. In this variation of the method, the shunt member is again delivered intravascularly into the left ventricle of the patient's heart, with the downstream end portion being passed through the myocardium. However, in this variation, the downstream end portion is inserted directly into the coronary artery through a posterior wall thereof in contact with the myocardium.

Posterior Wall Access

A method for performing a myocardial revascularization comprises, in accordance with another embodiment of the present invention, forming a passageway at least partially through a myocardium of a patient from an outer surface of the patient's heart, and performing a surgical operation at an outer end of the passageway to permanently close the passageway at the outer end. In a particular implementation of this embodiment of the invention, the passageway includes a portion extending though a posterior wall of a coronary artery and is produced by forming an aperture in an anterior wall of the coronary artery and forming the passageway in substantial alignment with the aperture. In this case, the closure of the passageway is effectuated particularly by closing the aperture in the anterior wall of the coronary artery. The closing of the aperture in the anterior wall of the coronary artery may be effectuated by one or more of several techniques, including suturing, plugging, and laser coagulation. To reinforce the closure of the artery wall, a brace may be placed over the closure. The brace may take the form of a biocompatible patch attached to the heart via suturing or laser welding.

Conduit Configurations

Pursuant to another feature of a myocardial revascularization technique, in accordance with yet another embodiment of the present invention, a stent is inserted into the passageway formed at least partially through the patient's myocardium. The inserting of the stent is preferably performed prior to the performing of the surgical operation to close the passageway at the outer end. The myocardial revascularization technique, including the insertion of the stent, may be performed in open heart surgery or in a pericardioscopic operation. In either case, the aperture in the anterior wall of the coronary artery and the passageway in the myocardium are formed by operating an instrument taken from the group consisting of a surgical drill and a surgical laser.

The passageway formed to communicate at an inner end with a left ventricle of the patient may communicate at an outer end with a coronary artery or, alternatively, may terminate in the myocardium after closure of the outer end of the passageway. In the former case, blood flows from the left ventricle through the passageway, the coronary artery and blood vessels communicating with the coronary artery. In the latter case, the myocardium is revascularized directly by the passageway, rater than indirectly through the coronary artery and its tributaries.

In a myocardial revascularization technique in accordance with another embodiment of the present invention, the passageway may be one of a plurality of similarly formed passageways extending from the coronary artery into the myocardium of the patient. Each passageway is produced by forming a plurality of openings in the anterior wall of the coronary artery and forming the passageways in alignment with respective ones of the openings. The passageways are effectively closed from the external environment (the intrapericardial space) by closing the openings in the anterior wall of the coronary artery. Where a myocardial passageway formed in accordance with this embodiment does not extend through or into a coronary artery, the closure of the passageway is effectuated on an epicardium of the patient.

A stent for a coronary artery bypass or myocardium revascularization procedure in accordance with another embodiment of the present invention has a collapsed configuration and an expanded configuration. The expanded configuration may have an arcuate form, to provide a curved flow path for blood upon implantation of the stent into a myocardium of a patient. This curved flow path smoothly redirects blood flow and minimizes possible adverse effects that the impulsive force of the blood might have on the patient's coronary artery and other layers of heart tissue. The stent may have a one-way valve for preventing retrograde flow of blood.

Another stent in accordance with another embodiment has a collapsed configuration and an expanded configuration and is provided with a sensor and means for transmitting signals from the sensor to a receiver external to the stent. The sensor is taken from the group consisting of a pressure sensor and a flow sensor.

Self-Inserting Conduits

In yet another embodiment of the present bypass apparatus there is provided a self-inserting conduit for diverting blood directly from the left ventricle of the heart to the coronary artery at a point distal to the blockage, therefore bypassing the blocked portion of the vessel. The shunt comprises a stent in the form of a single conduit having an opening at either end, and adapted to be positioned in the myocardium. The coronary artery, the myocardium and the wall of the left ventricle of the heart are pierced by the conduit from an outside space or tissue in a transverse manner to provide a channel completely through from the coronary artery to the left ventricle of the heart. An opening located on the distal end of the conduit is positioned in the coronary artery. Oxygenated blood is pumped from the left ventricle, through the distal opening, through the hollow central portion of the conduit, out of the proximal opening and into the coronary artery distal to the blockage. The conduit is anchored in the myocardium to provide a permanent passage for blood to flow between the left ventricle of the heart and the coronary artery, distal to the blockage.

The apparatus of the present invention is preferably implanted in a minimally invasive manner using thoroscopy or another endoscopic procedure, although open surgery or other means of vascular access are also possible.

Coronary Bypass

The present system preferably utilizes a combination conduit comprising an access and shunt device for forming a diversion of the blood from the coronary and proximally to the stenosis. A similar access and shunt device is located in the vessel distal of the stenosis to receive the diverted blood and allow it to continue on its course downstream. The combination access/shunt device comprises a conduit element for providing access to the vessel and anchoring the system in place. The conduit pierces the artery from the outside and travels completely through it and into the myocardium or other heart tissue adjacent the coronary artery. The conduit has a conduit or barb or series of barbs on its distal end and is otherwise designed so that it has substantial resistance to pull back or exit from the vessel. As noted, the conduit pierces through the vessel from an outside space or tissue in a transverse manner. Mounted on top of the conduit is a shunt device which comprises an aperture and a diversion conduit. With the conduit in its anchoring position, the shunt device is located partially in the vessel and partially outside of the vessel from the direction in which the conduit entered. The aperture resides in the vessel to allow blood to enter therein and from there to the diversion tube which is in fluid communication with the aperture. This provides the shunt of blood into the diversion tube of the combination access/shunt device. Mounted on top of the diversion tube is a connector piece which mates with a bypass conduit. These elements are also in fluid communication to allow the blood to bypass the blockage and to be shunted to a location distal thereof.

At such distal location, another similar combination access/shunt device is placed to allow the shunted blood to re-enter the artery in a free-graft configuration, and continue on its path downstream. However, a single device can be used distal of the restriction and connected to an appropriate graft for revascularization.

The apparatus of the present invention is preferably implanted in a minimally invasive manner using thoroscopy or other endoscopic procedure, although open surgery or other means of vascular access are also possible. The apparatus can be implanted permanently, or can be used temporarily to provide a bypass system during various surgical procedures, including coronary bypass procedures.

Thus, the present system is used to direct the flow of blood around the blocked portion of the vessel. In one embodiment, a shunt is used to direct blood directly from the left ventricle of the heart to the coronary artery at a point distal to the blockage. According to one aspect of the invention, the shunt comprises a rigid, generally elongated stent in the form of a single conduit having an opening at either end, and adapted to be positioned in the myocardium. The coronary artery, the myocardium and the wall of the left ventricle of the heart are pierced by the conduit from an outside space or tissue in a transverse manner to provide a channel completely through from the coronary artery to the left ventricle of the heart. An opening located on the distal end of the conduit is positioned within the left ventricle. An opening on the proximal end of the conduit is positioned in the coronary artery. Oxygenated blood is pumped from the left ventricle, through the distal opening, through the hollow central portion of the conduit, out of the proximal opening and into the coronary artery distal to the blockage. The conduit is anchored in the myocardium to provide a permanent passage for blood to flow between the left ventricle of the heart and the coronary artery, distal to the blockage.

Alternatively, the conduit can be used temporarily to maintain blood flow through the coronary artery during therapeutic procedures, such as coronary bypass. The conduit can be used to deliver a vein graft, and to provide for the passage of blood around the blockage until the anastomosis of the graft is complete.

BRIEF DESCRIPTION OF THE DRAWINGS

FIG. 5A is a schematic view of a human heart showing a two piece conduit connecting the left ventricle to the left anterior descending coronary artery.

FIG. 5B is an enlarged view of the two piece conduit of FIG. 5A.

FIG. 5C is a schematic cross-sectional view of the two piece conduit of FIG. 5B.

FIG. 15 is a schematic partial cross-sectional view of a human heart, illustrating a modification to the artificial myocardial revascularization of FIG. 14B.

FIG. 16 is a schematic partial cross-sectional view of a human heart, illustrating a heart provided in a left ventricle with implants or plugs.

FIG. 16A is a schematic partial cross-sectional view of a conduit or plug, having therapeutic materials applied thereto.

[FIG. 26 is reserved]

[FIG. 36 is reserved]

FIGS. 46, 47A–47D, 48, 48A–48C, and 49 show curved conduits that direct blood flow downstream in a direction that is substantially parallel to the bloodstream in the vessel.

Figure 1A:
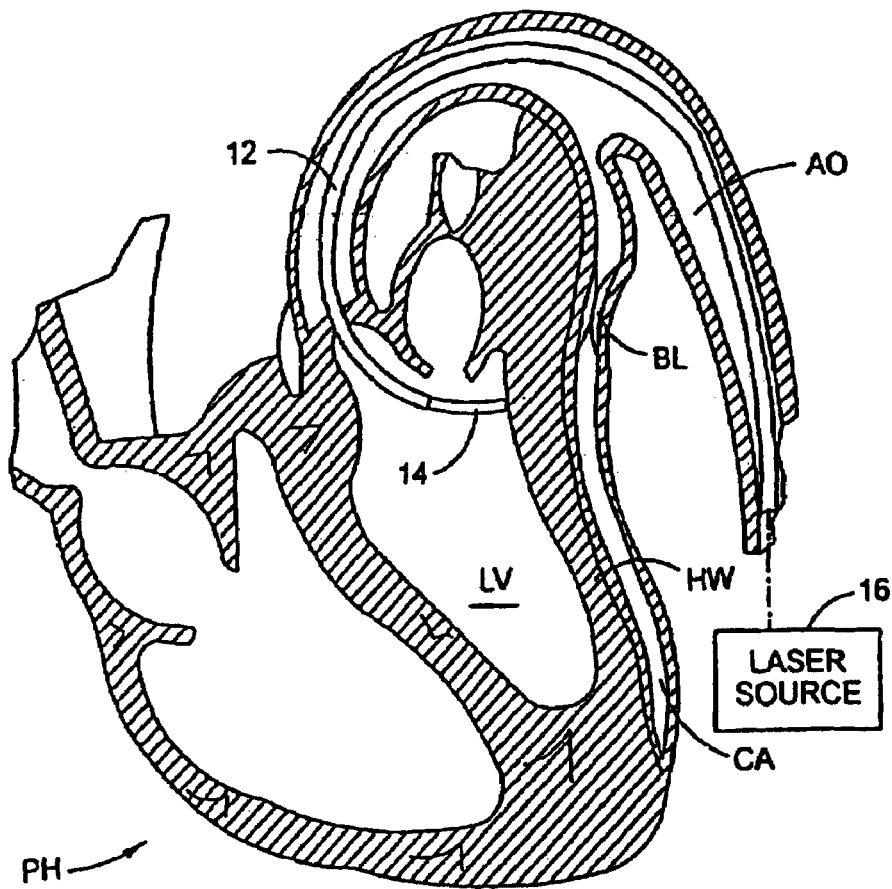
FIGS. 1A–1E are schematic cross-sectional views of a human heart, showing successive steps in a transmyocardial coronary artery bypass operation in accordance with one conduit embodiment of the present invention.

In the drawings, the same reference designations are used to designate the same objects. The word "distal" when used herein designates an instrument end which is spaced from the surgeon, radiologist or other operator. The physical relation of the instrument to the patient is not determinative.

DETAILED DESCRIPTION OF THE PREFERRED EMBODIMENTS

The principles of the present invention are not limited to left ventricular conduits, and apply to conduits for communicating bodily fluids from any space within a patient to another space within a patient, including any mammal. Furthermore, such fluid communication through the conduits is not limited to any particular direction of flow and can be antegrade or retrograde with respect to the normal flow of fluid. Moreover, the conduits may communicate between a bodily space and a vessel or from one vessel to another vessel (such as an artery to a vein or vice versa). Moreover, the conduits can reside in a single bodily space so as to communicate fluids from one portion of the space to another. For example, the conduits can be used to achieve a bypass within a single vessel, such as communicating blood from a proximal portion of an occluded coronary artery to a more distal portion of that same coronary artery.

In addition, the conduits and related methods can preferably traverse various intermediate destinations and are not limited to any particular flow sequence. For example, in one preferred embodiment of the present invention, the conduit communicates from the left ventricle, through the myocardium, into the intrapericardial space, and then into the coronary artery. However, other preferred embodiments are disclosed, including direct transmyocardial communication from a left ventricle, through the myocardium and into the coronary artery. Thus, as emphasized above, the term "transmyocardial" should not be narrowly construed in connection with the preferred fluid communication conduits, and other non-myocardial and even non-cardiac fluid communication are preferred as well. With respect to the walls of the heart (and more specifically the term "heart wall"), the preferred conduits and related methods are capable of fluid communication through all such walls including, without limitation, the pericardium, epicardium, myocardium, endocardium, septum, etc.

The bypass which is achieved with certain preferred embodiments and related methods is not limited to a complete bypass of bodily fluid flow, but can also include a partial bypass which advantageously supplements the normal bodily blood flow. Moreover, the occlusions which are bypassed may be of a partial or complete nature, and therefore the terminology "bypass" or "occlusion" should not be construed to be limited to a complete bypass or a complete occlusion but can include partial bypass and partial occlusion as described.

The preferred conduits and related methods disclosed herein can also provide complete passages or partial passages through bodily tissues. In this regard, the conduits can comprise stents, shunts, or the like, and therefore provide a passageway or opening for bodily fluid such as blood. Moreover, the conduits are not necessarily stented or lined with a device but can comprise mere tunnels or openings formed in the tissues of the patient.

The conduits of the present invention preferably comprise both integral or one-piece conduits as well as plural sections joined together to form a continuous conduit. In this regard, the anastomotic devices and methods utilized in connection with the various embodiments of the present invention are to be broadly construed to relate to connections of these various components. The present conduits can be deployed in a variety of methods consistent with sound medical practice including vascular or surgical deliveries, including minimally invasive techniques. For example, various preferred embodiments of delivery rods and associated methods are disclosed. In one embodiment, the delivery rod is solid and trocar like. It may be rigid or semi-rigid and capable of penetrating the tissues of the patient and thereby form the conduit, in whole or in part, for purposes of fluid communication. The delivery rod may be an incising instrument such as a laser or a drill. In other preferred embodiments, the delivery rods may be hollow so as to form the conduits themselves (e.g., the conduits are preferably self-implanting or self-inserting) or have a conduit mounted thereon (e.g., the delivery rod is preferably removed leaving the conduit installed). Thus, the preferred conduit device and method for installation is preferably determined by appropriate patient indications in accordance with sound medical practices.

Further details regarding conduits and conduit delivery systems are described in U.S. patent application Ser. No. 09/368,868, filed Aug. 4, 1999, now U.S. Pat. No. 6,261,304, entitled DELIVERY METHODS FOR LEFT VENTRICULAR CONDUIT, U.S. application Ser. No. 09/369,048 filed Aug. 4, 1999, now U.S. Pat. No. 6,290,728, entitled DESIGNS FOR LEFT VENTRICULAR CONDUIT, U.S. application Ser. No. 09/369,061, filed Aug. 4, 1999, now U.S. Pat. No. 6,254,564, entitled LEFT VENTRICULAR CONDUIT WITH BLOOD VESSEL GRAFT, U.S. application Ser. No. 09/368,393, filed Aug. 4, 1999, now pending, entitled VALVE DESIGNS FOR LEFT VENTRICULAR CONDUIT, and U.S. application Ser. No. 09/368,644, filed Aug. 4, 1999, now U.S. Pat. No. 6,302,892, entitled BLOOD FLOW CONDUIT DELIVERY SYSTEM AND METHOD OF USE and U.S. Pat. Nos. 5,429,144 and 5,662,124, the disclosures of which are all hereby incorporated by reference in their entirety.

Conduits Utilizing Intrapericardial Space

In a transmyocardial coronary artery bypass operation illustrated in FIGS. 1A–1E, a catheter 12 is inserted over a guidewire (not illustrated) through the vasculature of a patient and particularly through the aorta AO into the left ventricle LV of the patient's heart PH. (Although the embodiments described herein are discussed with respect to the left ventricle LV, they may also be applied to the right ventricle RV and the right and left atria.) Upon arrival of a distal end of catheter 12 in left ventricle LV, the guidewire is withdrawn and a surgical incising instrument 14 such as a light-transmitting optical fiber is inserted through catheter 12. The catheterization procedure is monitored via conventional radiographic techniques or, alternatively, via a CAT scanner or MRI machine.

Figure 1B:
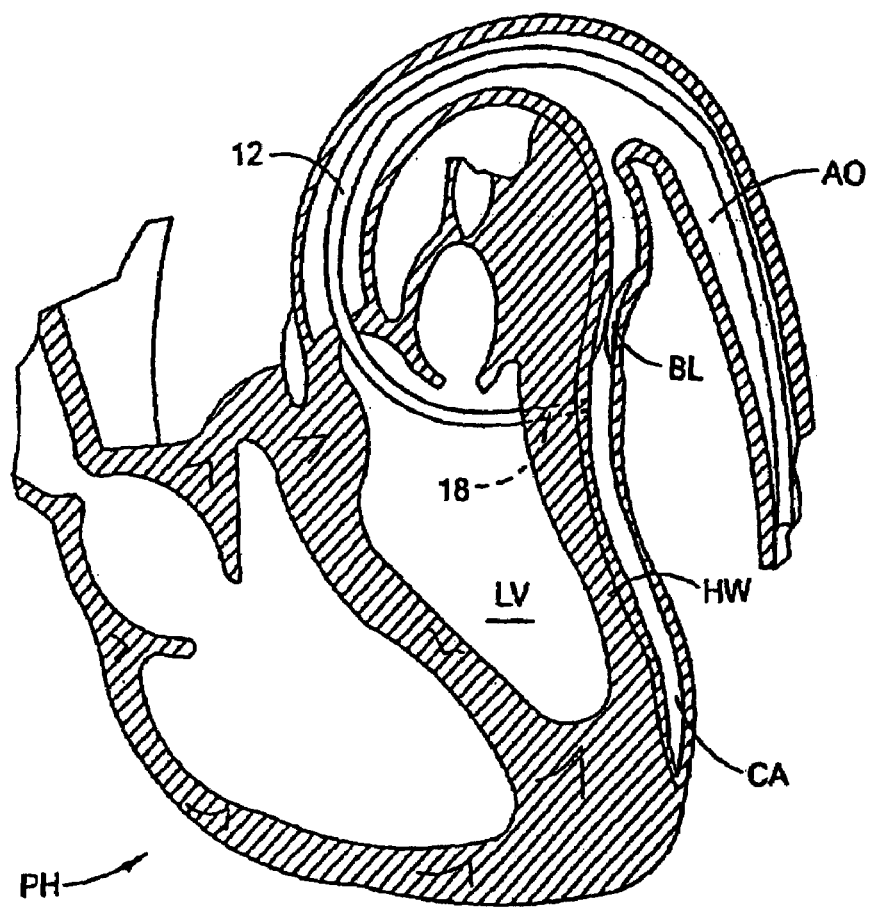

Upon ejection of a distal tip of optical fiber 14 from catheter 12 into left ventricle LV, the fiber tip is placed into contact with a heart wall HW of the patient at a predetermined location downstream of an arterial blockage BL in the coronary artery CA of the patient, as illustrated in FIG. 1A. A laser source 16 is then activated to transmit monochromatic electromagnetic radiation along optical fiber 14 to heart wall HW. The distal end of fiber 14 is pushed through heart wall HW, with the radiation being continuously or periodically transmitted through optical fiber 14, thereby forming a transmyocardial passageway 18 in heart wall HW (FIG. 1B).

Figure 1C:
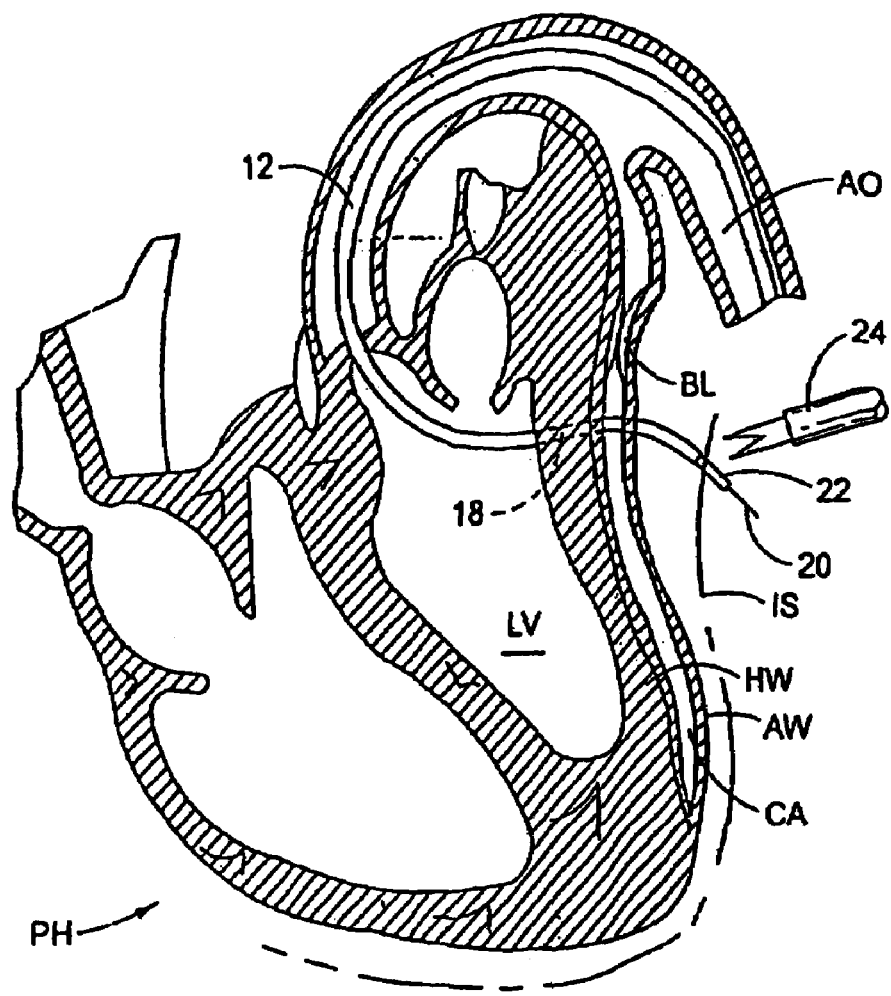
Figure 1D:
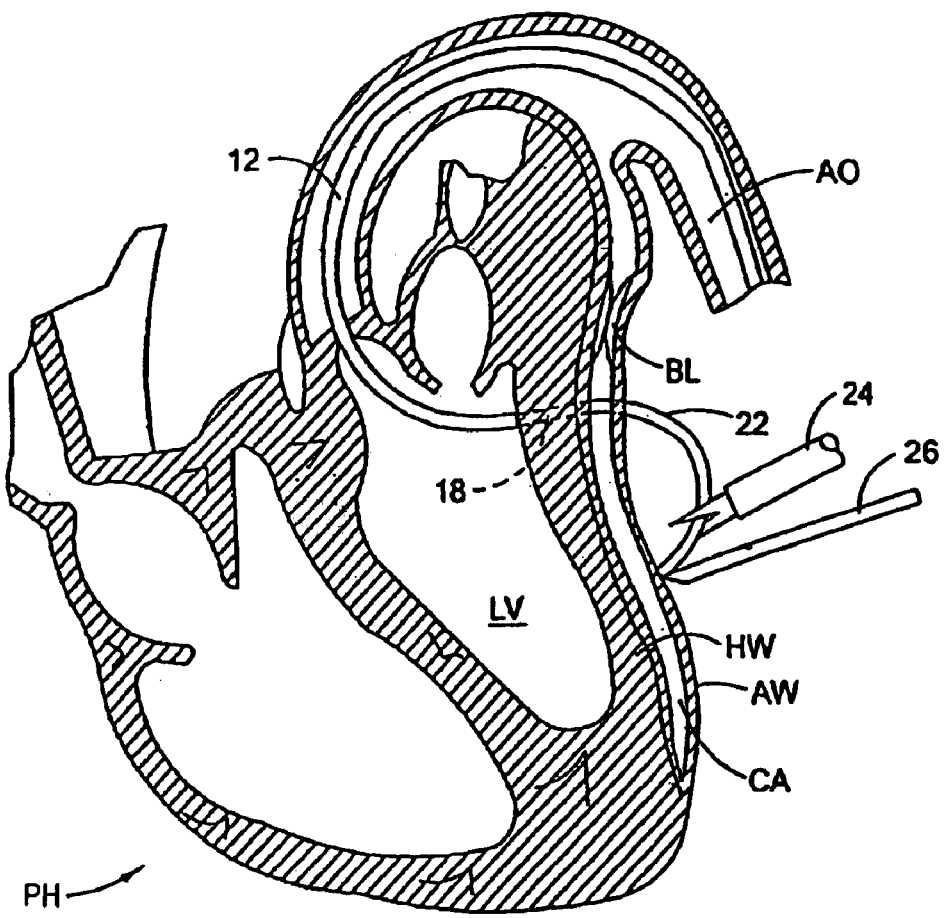

After the formation of passageway 18, optical fiber 14 is withdrawn from catheter 12 and replaced with a guidewire 20 (FIG. 1C). In addition, catheter 12 is pushed in a forward direction through passageway 18 so that a distal end portion of the catheter extends outwardly from passageway 18 into an intrapericardial space IS. A shunt 22 made of flexible biocompatible material such as polyethylene or GORTEX™ is then passed over guidewire 20 and through catheter 12. At this juncture, a forceps instrument 24 (FIGS. 1C and 1D) inserted into the patient via a pericardioscopic cannula or port (not shown) or through an open incision (not shown) is used to grasp shunt 22 and direct a free end of the shunt to an anterior wall AW of coronary artery CA, as illustrated in FIG. 1D. A laser instrument 26 is then used to attach the free end of shunt 22 to the anterior wall AW of coronary artery CA. At this point in the operation, there is no avenue of communication between left ventricle LV and coronary artery CA.

Figure 1E:
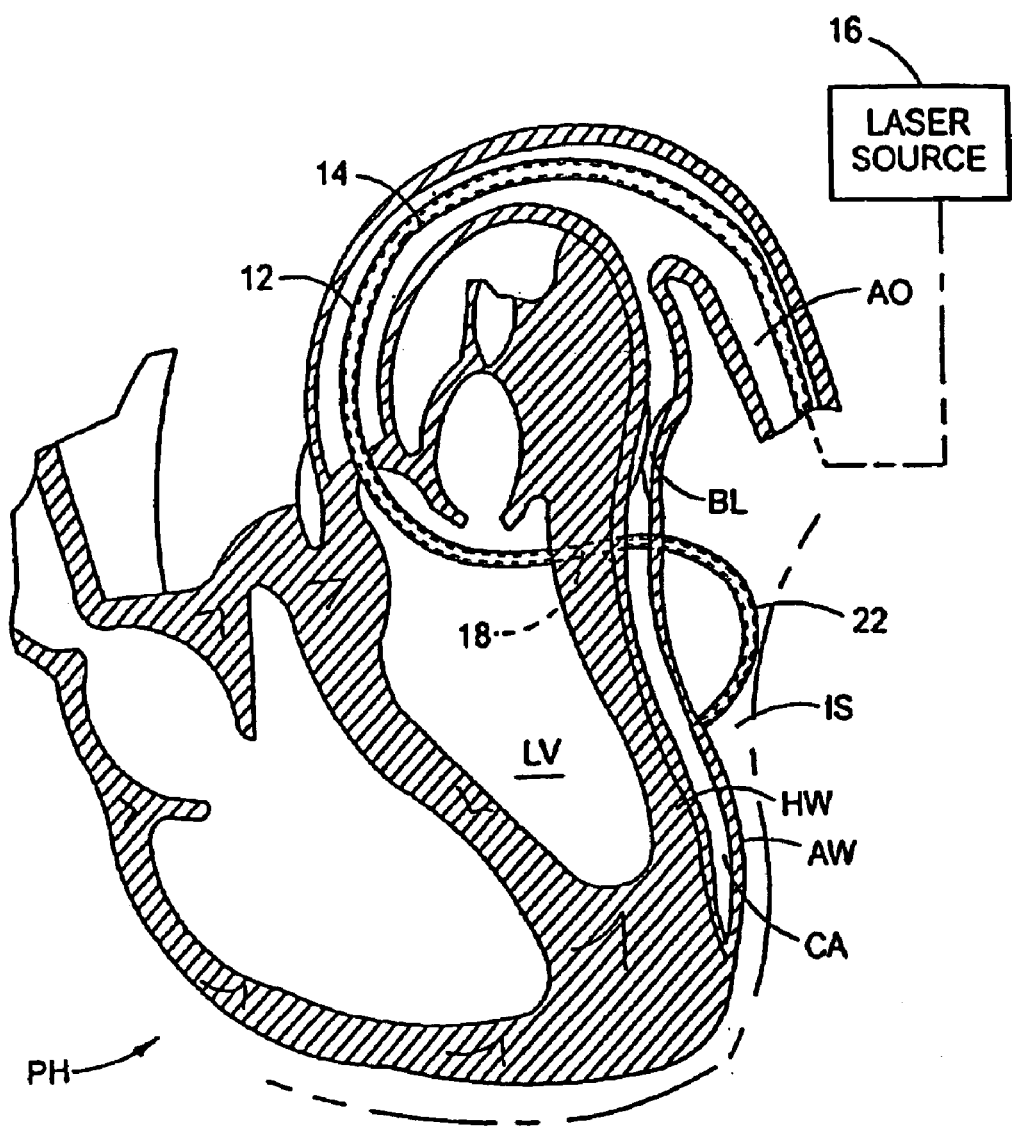

After the attachment of shunt 22 to anterior wall AW of coronary artery CA, optical fiber 14 is again inserted through catheter 12 and through shunt 22 to anterior wall AW of coronary artery CA. Laser source 16 is temporarily activated to form an aperture in anterior wall AW of coronary artery CA inside shunt 22, thereby establishing a transmyocardial coronary artery bypass path from left ventricle LV into the coronary artery downstream of blockage BL as illustrated in FIG. 1E. After the formation of the aperture in coronary artery CA, fiber 14 is withdrawn from shunt 22 and catheter 12 is withdrawn from heart wall HW. Optical fiber 14 may be used at that time (or previously) to attach an upstream end of shunt 22 to heart wall HW at left ventricle LV. The optical fiber 14 and catheter 12 are then extracted from the patient. The deployed shunt 22 extends from left ventricle LV through heart wall or myocardium HW to anterior wall AW of coronary artery CA, with a middle or intermediate portion (not separately designated) of shunt 22 being disposed in intrapericardial space IS.

Figure 2:
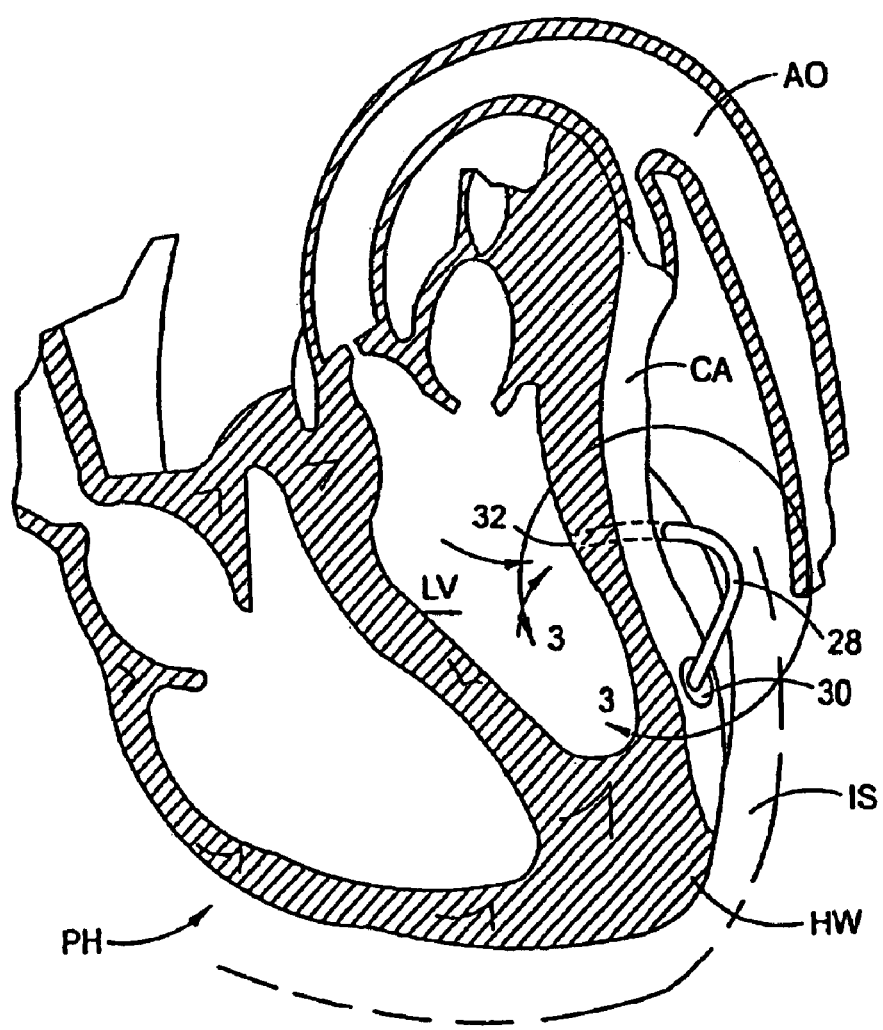
FIG. 2 is a schematic cross-sectional view of a human heart showing an alternative conduit to that used in the operation of FIGS. 1A–1E.

FIG. 2 depicts a transmyocardial coronary artery bypass similar to that shown in FIG. 1E, except that a different shunt 28 is used. Shunt 28 is provided at opposite ends with flanges 30 and 32 in the form of annular disks. These flanges 30 and 32 facilitate the attachment of shunt 28 to the heart wall HW at left ventricle LV and to anterior wall AW of coronary artery CA, respectively. The attachment of flanges 30 and 32 to heart wall HW and coronary artery CA may be effectuated by laser instrument 26 and/or by other techniques including gluing and suturing. Shunt 28 is installed in the manner described above with reference to FIGS. 1A–1E.

The structure of shunt 28, as well as different uses thereof, is described and illustrated in U.S. Pat. No. 5,470,320, the disclosure of which is hereby incorporated by reference.

Figure 3:
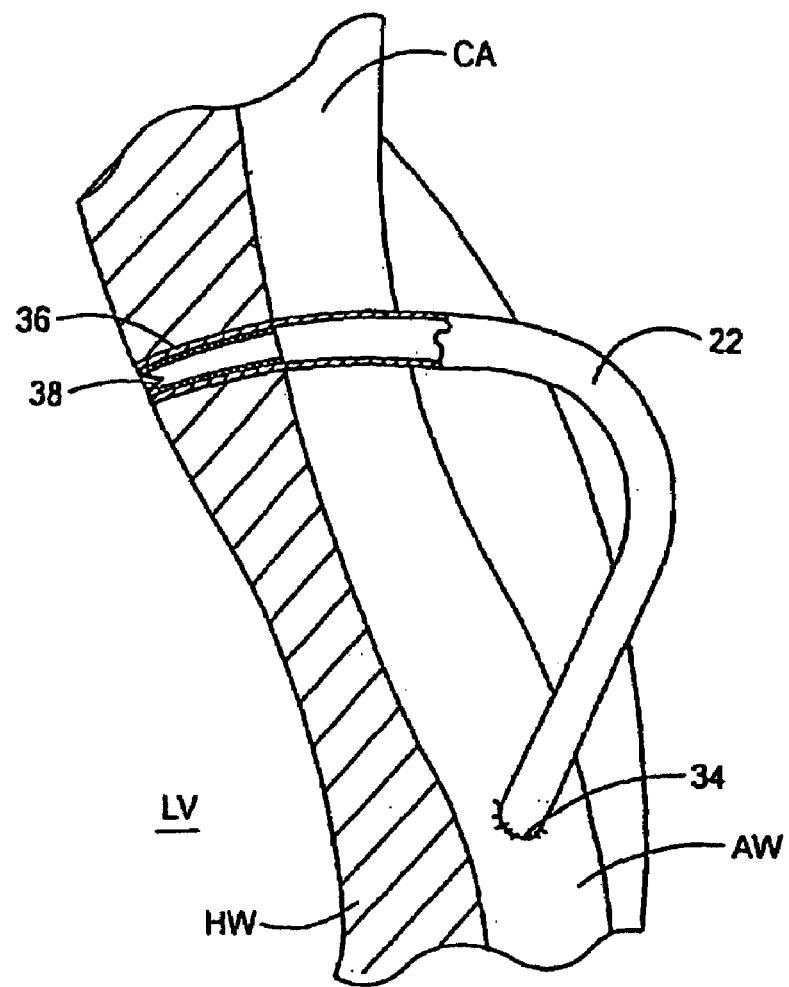
FIG. 3 is a schematic partial cross-sectional view, on a larger scale, showing a modification of the coronary artery bypass produced by the operation of FIGS. 1A–1E.

FIG. 3 shows a modification of the transmyocardial coronary artery bypass of FIG. 1E. The downstream end of shunt 22 is attached to anterior wall AW of coronary artery CA via sutures 34. A stent 36 with a one-way valve 38 is placed inside an upstream portion of shunt 22 located within heart wall or myocardium HW. Stent 36 functions to clamp the upstream end of shunt 22 to heart wall HW. One-way valve 38 permits blood to flow from ventricle LV to coronary artery CA during systole and prevents backflow to ventricle LV during diastole. Where shunt 22 is installed without stent 36, shunt 22 may be provided with an integral one-way valve (not illustrated). Stent 36 is generally introduced into heart PH in a collapsed configuration through a catheter. Stent 36 may be predisposed inside the upstream end portion of shunt 22 and inserted therewith into heart PH. Alternatively, stent 36 may be inserted into shunt 22 after the shunt has been passed through passageway 18 and before or after the attachment of the downstream end of shunt 22 to anterior wall AW of coronary artery CA. Stent 36, and other stents and shunts disclosed herein, may be provided with outwardly projecting barbs (not illustrated) for anchoring the stent or shunt to the myocardium.

In another variation (not illustrated) of the transmyocardial coronary artery bypass of FIG. 1E, shunt 22 has an upstream portion which is a stent. The stent is substantially coextensive with or smaller than passageway 18 and is accordingly lodged completely within passageway 18 upon installation of the shunt 22. The remainder of the shunt 22 is made of a continuous, essentially impermeable biocompatible film material, as in the embodiment discussed above.

Figure 4:
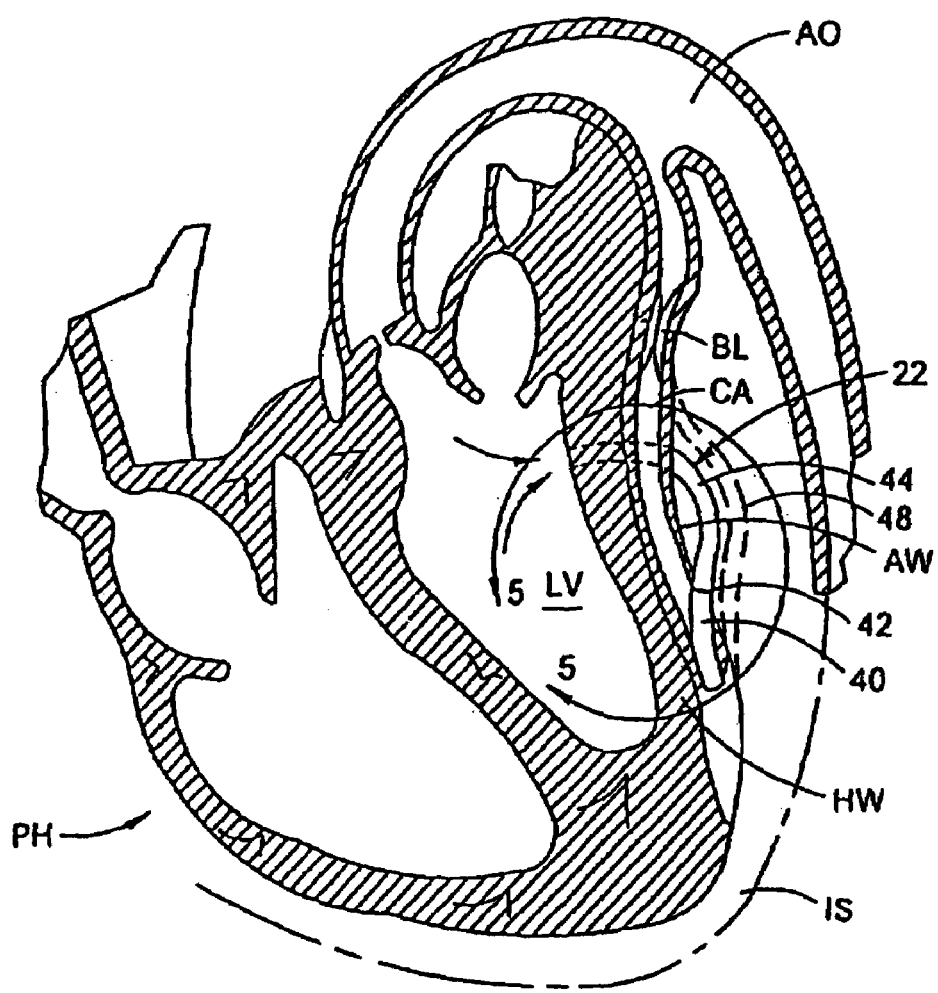
FIG. 4 is a schematic cross-sectional view of a human heart showing a modification of the coronary artery bypass operation depicted in FIGS. 1A–1E.

As illustrated in FIG. 4, another modification of the transmyocardial coronary artery bypass of FIG. 1E includes the insertion of a downstream end portion 40 of shunt 22 through an aperture 42 formed in anterior wall AW of coronary artery CA downstream of blockage BL. Clearly, in this bypass procedure, aperture 42 is formed in coronary artery CA prior to the joining of the downstream end portion 40 of shunt 22 and coronary artery CA. Aperture 42 is formed by an incising instrument (not shown) such as a laser or a scalpel blade which is inserted into intrapericardial space IS either through a pericardioscopic cannula or port (not shown) or through an open incision. Shunt 22 may be attached, by laser welding, glue or sutures, to coronary artery CA at aperture 42. As discussed hereinabove with respect to the embodiment of FIG. 1E, an intermediate or middle portion 44 of shunt 22 is disposed inside intrapericardial space IS upon deployment of shunt 22. A brace 48, for example, in the form of a patch (compare with FIG. 13), may be disposed over middle portion 44 of shunt 22 and attached to heart PH, to support the shunt 22 against possible dislodgment owing to the hydraulic forces of blood flow and the mechanical forces of myocardium contraction. Brace or patch 48, and similar braces or patches disclosed herein, is made of a strong biocompatible material such as KEVLAR™, polytetrafluoroethylene, silicone, etc.

Figure 5:
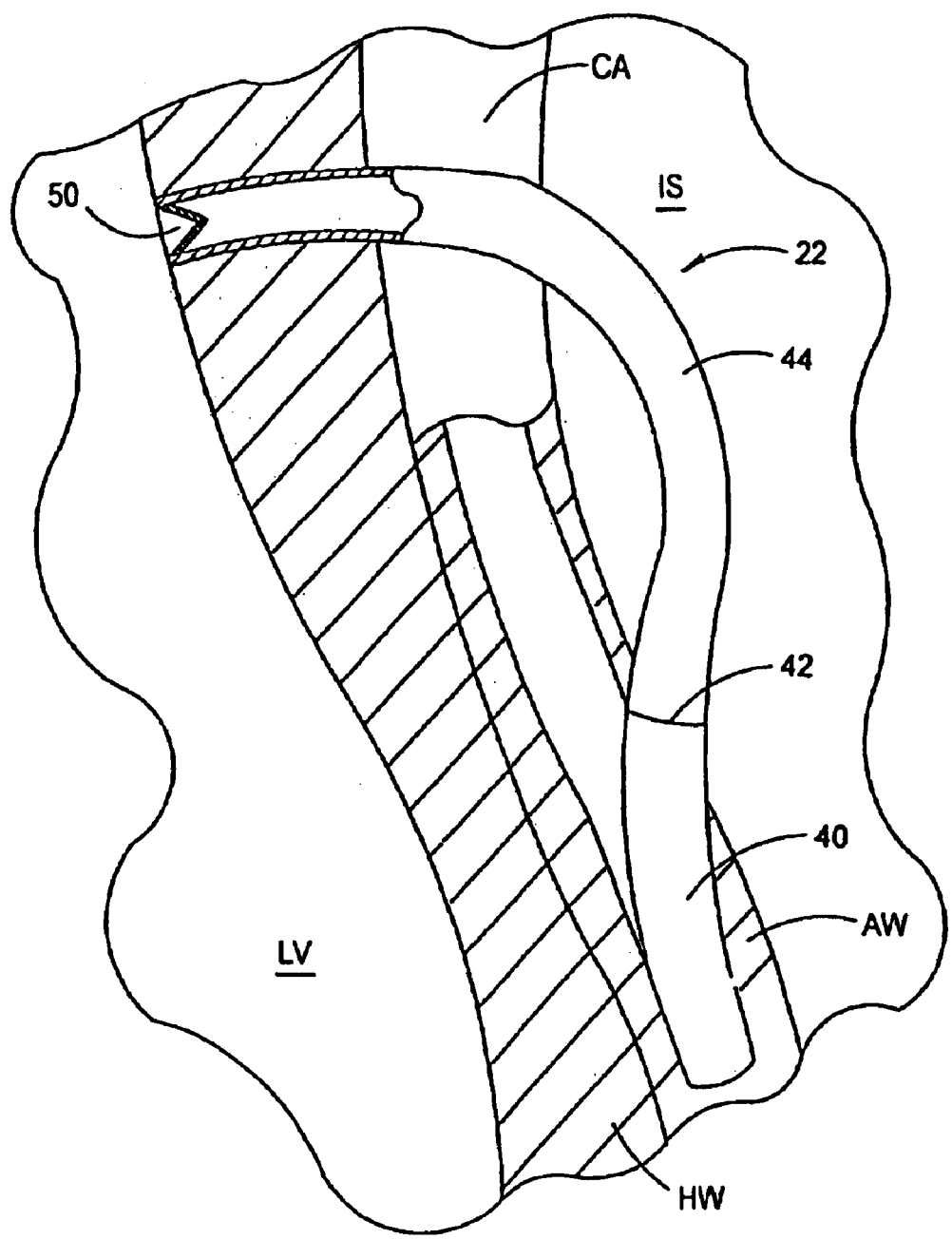
FIG. 5 is a schematic partial cross-sectional view, on a larger scale, showing a variation of the coronary artery bypass of FIG. 4.

FIG. 5 illustrates the shunt-implemented transmyocardial coronary artery bypass of FIG. 4, with a one-way valve 50 being provided at the upstream end of shunt 22 for permitting blood flow from ventricle LV into coronary artery CA during systole and for preventing blood flow from coronary artery CA toward ventricle LV during diastole.

Conduit Configurations

FIG. 5A illustrates a human heart PH, showing more particularly the left anterior descending coronary artery CA. The technical challenge presented herein is placing a conduit accurately and aligned properly between the left ventricle LV and the coronary artery CA. A conduit 49 is shown in FIGS. 5A–5C comprising two separate pieces, namely an access port 51 which punctures through the heart wall HW, including the myocardium, to the left ventricle LV, and an anastomosed segment 53. To place the conduit 49, the access port 51 is inserted into the heart wall HW from the outside of the heart PH, preferably adjacent but not necessarily through the coronary artery CA. Flange 55 determines the position of the port 51 by pressing against the outside of the heart PH, and the port extends into the left ventricle LV with a lumen 57 extending therethrough. The end of the port 51 on the outside of the heart wall HW may be curved as shown in FIG. 5C. After the port 51 is inserted, the port is connected to the artery CA preferably using a segment 53 which is more preferably an artificial graft. The location where the segment 53 is anastomosed to the coronary artery may preferably be downstream of a blockage (not shown) in the coronary artery CA.

The embodiment of FIGS. 5A–5C is advantageous in that it does not require extremely accurate placement of the port 51 into the heart PH. This is especially important because during a beating heart procedure placement of a device through the heart PH may be difficult. More specifically, as shown in FIGS. 5A–5C, the port 541 need not be positioned at a very precise position through or adjacent the coronary artery CA. Rather, the port 51 need only be placed near the coronary artery CA, and the graft segment 53 is used to connect the port 51 to the coronary artery CA. It will be appreciated that multiple conduits may be made to the artery CA.

Figure 6A:
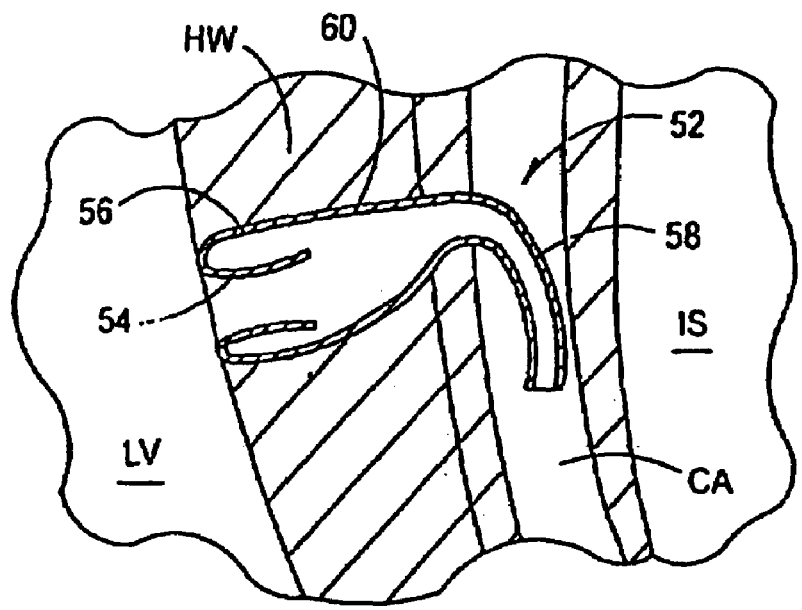
FIG. 6A is a schematic partial cross-sectional view of another coronary artery bypass showing a conduit or shunt with a one-way valve opened during systole.
Figure 6B:
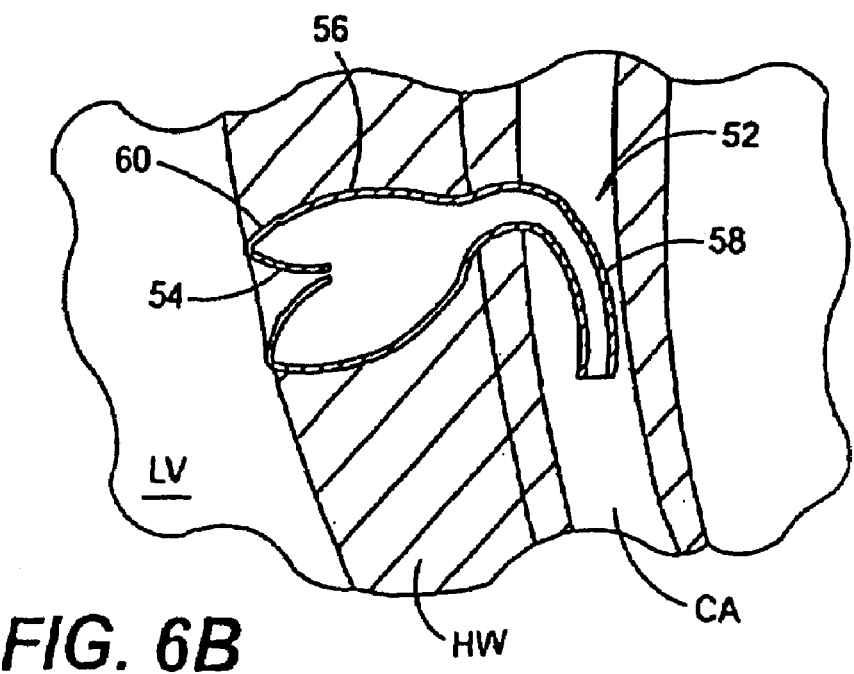
FIG. 6B is a schematic partial cross-sectional view similar to FIG. 6A, illustrating the shunt of FIG. 6A with the valve closed during diastole.

As depicted in FIGS. 6A and 6B, a transmyocardial coronary artery bypass is implemented by a conduit or shunt member 52 provided at an upstream end with a one-way valve 54. Shunt member 52 extends directly from left ventricle LV through heart wall HW into coronary artery CA and includes an upstream portion 56 disposed within heart wall or myocardium HW and a downstream portion 58 disposed in coronary artery CA. Shunt member 52 may have a tapered form which narrows down in a downstream direction so that downstream portion 58 is of smaller cross-section than upstream portion 56. Upstream portion 56 may take the form of a stent which is expanded from a collapsed insertion configuration to an expanded use configuration to lock or clamp shunt member 52 to a passageway 60 formed in heart wall or myocardium HW prior to the insertion of shunt member 52. Downstream portion 58 is made of a continuous, essentially impermeable biocompatible film material. In addition, upstream portion 56 may be flexible to an extent so as to expand, if necessary, during diastole (FIG. 6B) to accommodate some backflow. It will also be noted in connection with FIG. 6B, the upstream portion 56 also acts as a reservoir to accumulate blood during systole which is then passed into the coronary artery CA during diastole.

Shunt 52 is curved and bears the force of the blood ejected from left ventricle LV through passageway or channel 60 during systole.

Figure 6C:
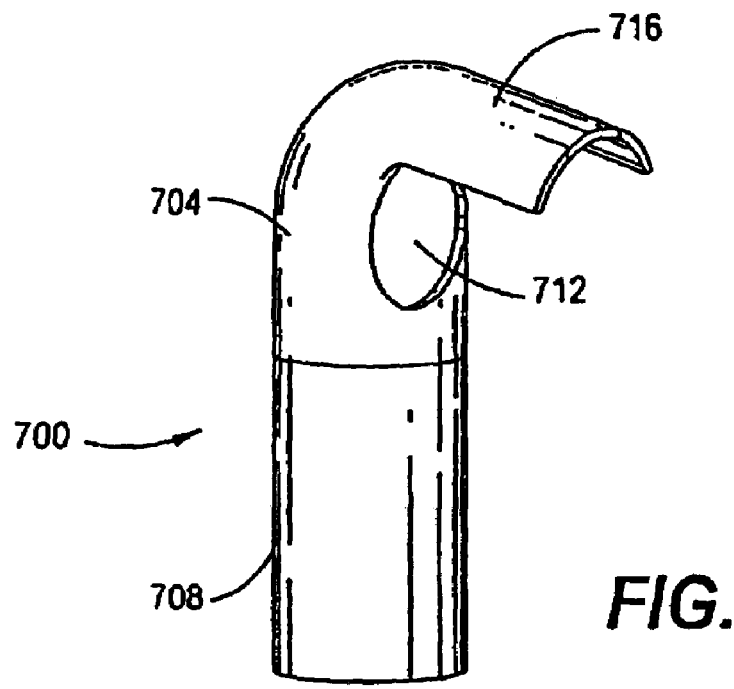
FIGS. 6C–6H are perspective views of conduits or stents with openings into the coronary artery having hoods, valves, or other flow direction/flow control devices.
Figure 6D:
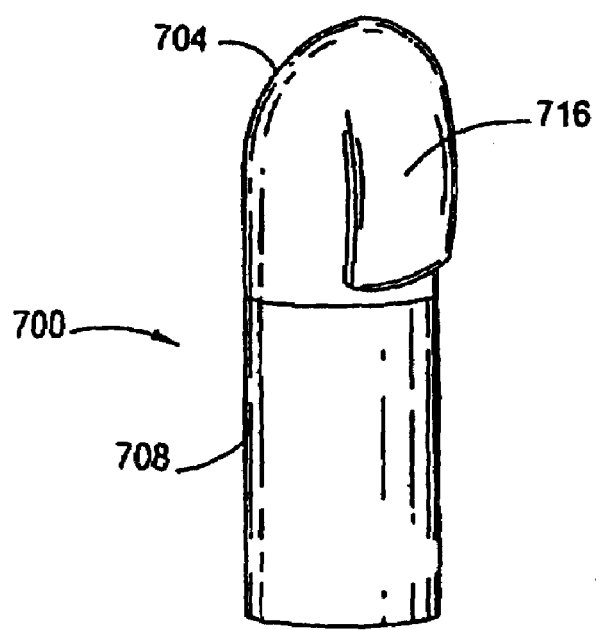

Other one way valve embodiments are shown in FIGS. 6C–6H and are particularly useful for directing laminar flow and controlling the flow of blood. FIGS. 6C and 6D show the open and closed positions, respectively, of a conduit 700. The conduit comprises a relatively soft, pliable portion 704 and a harder, firmer portion 708. In the open configuration (FIG. 6C), blood flows out of a hole 712 in the conduit 700 and into the left ventricle LV. The softer portion 704 has a resiliency such that a hood or flap portion 716 closes during diastole, thereby blocking the flow of blood.

Figure 6E:
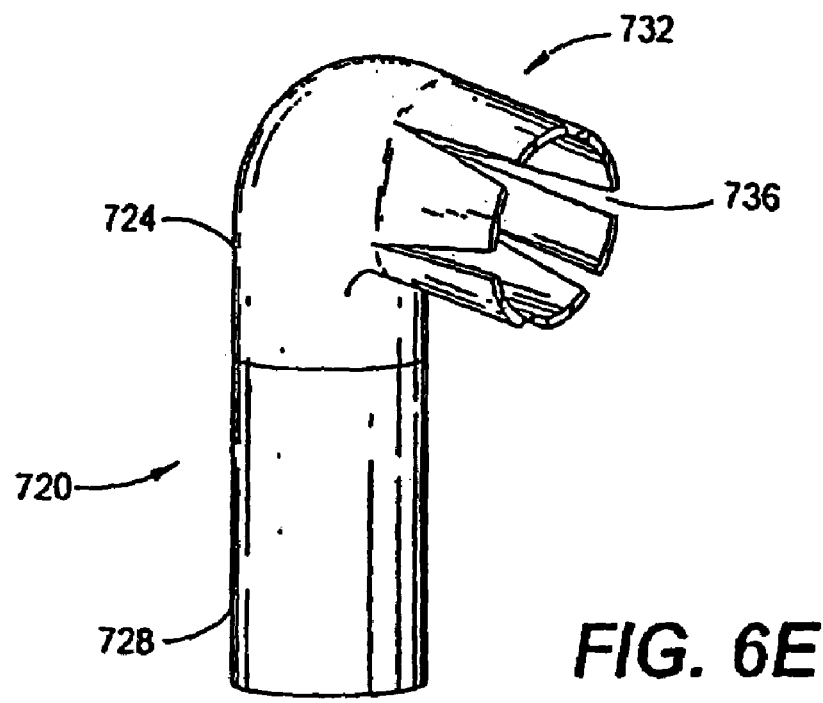
Figure 6F:
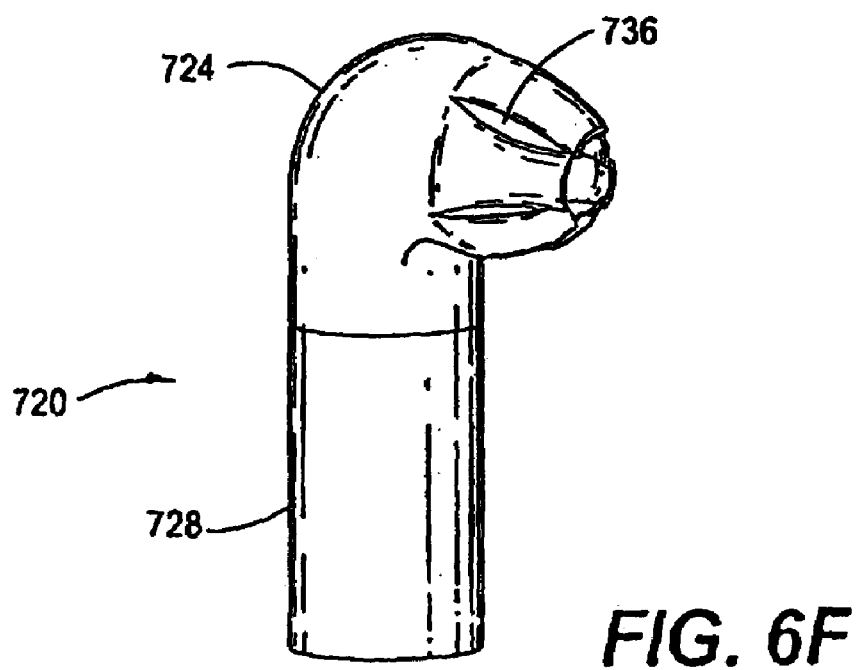

FIGS. 6E and 6F show another one way valve conduit embodiment 720 that comprises soft and hard portions 724 and 728, respectively. The soft portion 724 includes a flap portion 732 having a series of slits 736 therein which may be spaced equidistantly from each other as shown, or alternatively, the slits may be spaced unequally from each other. The resiliency of the conduit 720 is such that it is open during systole (FIG. 6F) but closes partially during diastole (FIG. 6F).

Figure 6G:
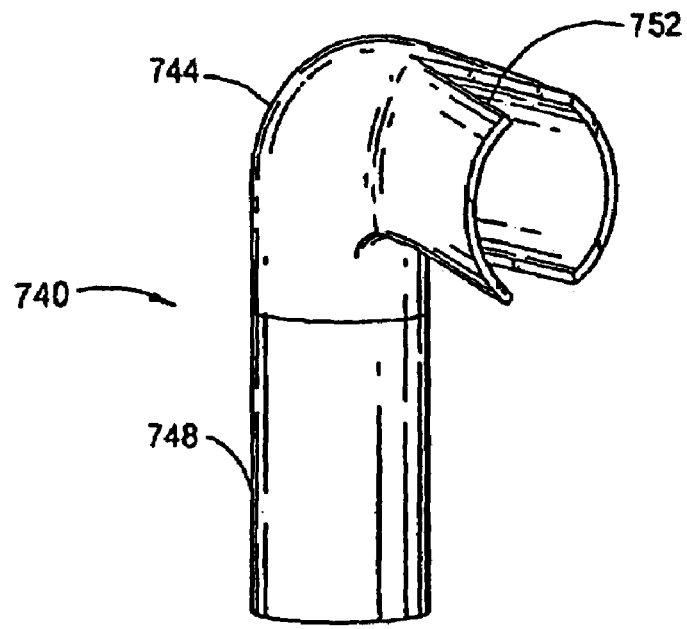
Figure 6H:
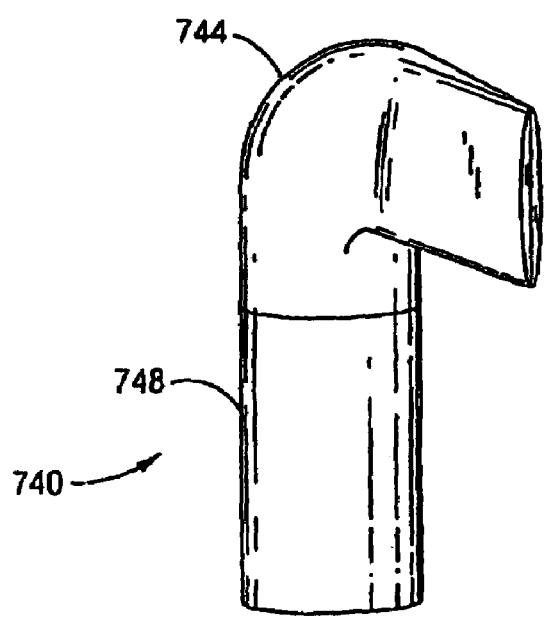

FIGS. 6G and 6H show another one way valve conduit embodiment 740 comprising soft and hard portions 744 and 748, in which a single slit 752 is formed in the soft portion 744. As in embodiments 6C–6D and 6E–6F, the resiliency of the soft portion is such that the conduit 740 acts as a one-way valve, with the conduit opening during systole and partially closing during diastole. Further, conduits (not shown) having an opening for blood flow, but no slits, may be used in which the portion of the conduit around the opening partially or completely collapses (closes) during diastole, but is at least partially open during systole.

Figure 7:
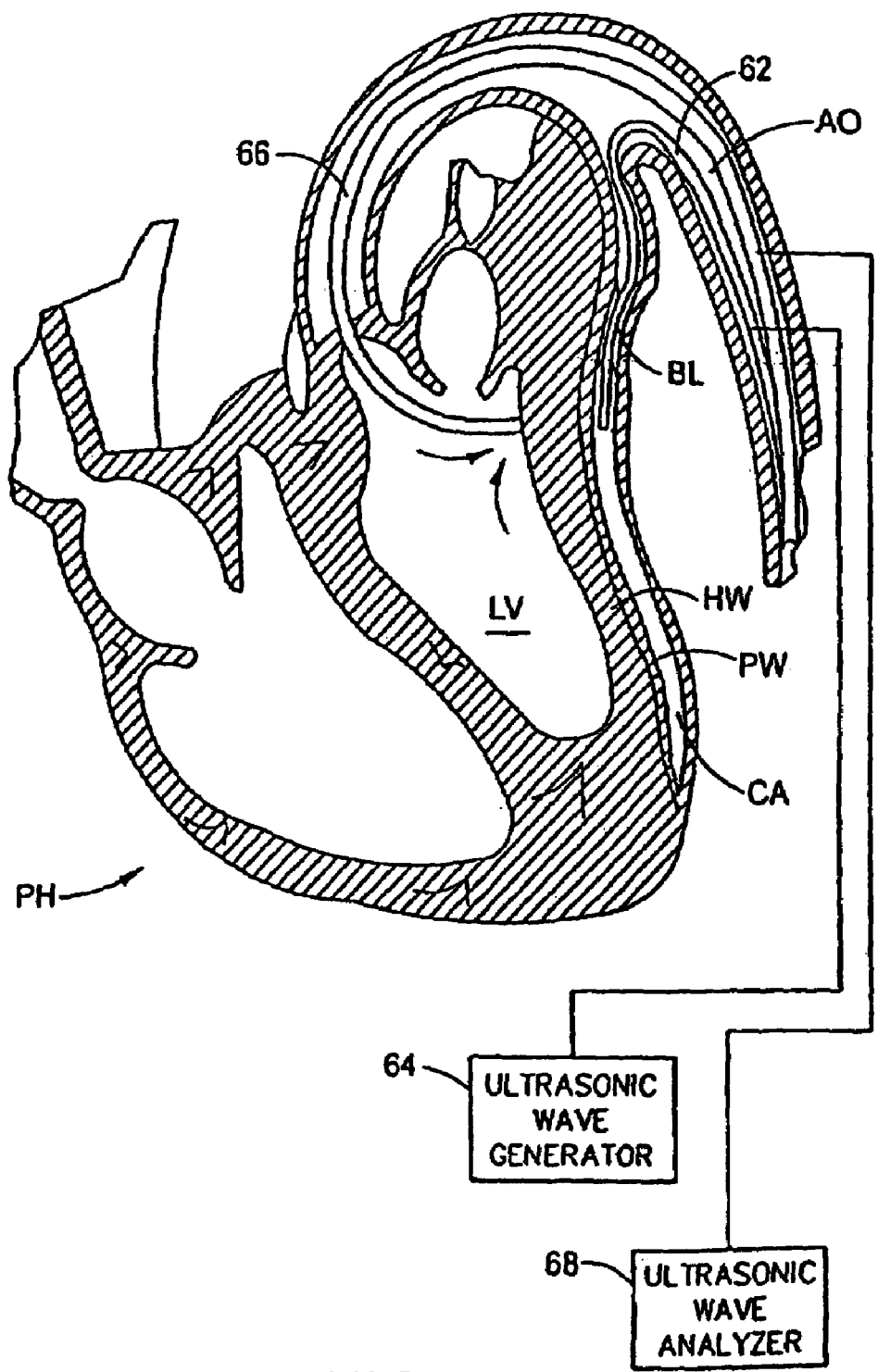
FIG. 7 is a schematic cross-sectional view of a human heart showing instrumentation used for implanting the shunt of FIGS. 6A and 6B.

As illustrated in FIG. 7, the deployment or installation of shunt 52 in an intravascular procedure requires instrumentation for enabling the precise locating of the coronary artery CA with respect to possible insertion points in left ventricle LV. To that end, a first catheter 62 is utilized which is provided at a distal end with an electroacoustic transducer (not illustrated) for converting an electrical signal of ultrasonic frequency to a mechanical pressure wave which is transmitted through a posterior wall PW of coronary artery CA and heart wall or myocardium HW. Catheter 62 and particularly the electroacoustic transducer (not shown) is operatively connected to an ultrasonic wave generator 64. Another catheter 66 is also inserted through aorta AO (and over a conventional guidewire, not illustrated). This second catheter 66 is introduced into left ventricle LV and is provided at a free end with an acoustoelectric transducer (not shown) for detecting pressure waves in an ultrasonic frequency range. Catheter 66 and its acoustoelectric transducer are operatively connected to an ultrasonic wave analyzer 68 which calculates the location of the distal tip of catheter 62 relative to the distal tip of catheter 66 and thus provides feedback to a surgeon or an insertion device for determining an insertion point and insertion angle for surgical incising instrument such as optical fiber 14 (FIG. 1A).

Several shunt members 22 or 52 may be necessary in cases of multiple coronary artery blockages. These multiple shunt members each tap into the coronary artery at a point downstream of a respective blockage.

Figure 8:
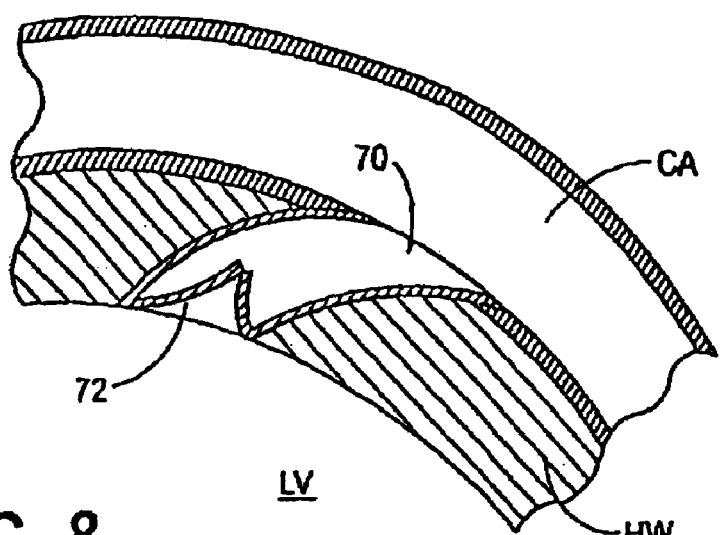
FIG. 8 is a schematic partial cross-sectional view of an arcuate conduit or stent with a one-way valve utilized in a further coronary artery technique.
Figure 8A:
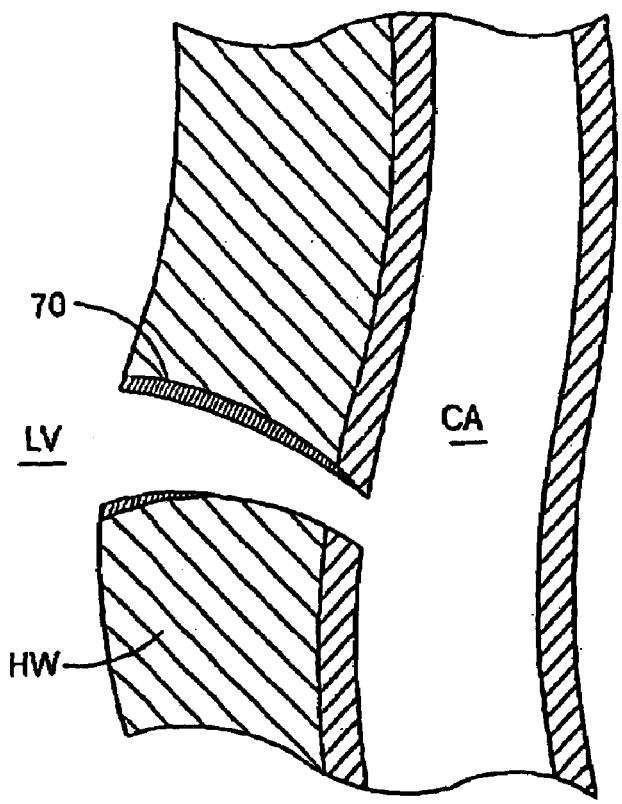
FIGS. 8A–8B are schematic partial cross-sectional views of arcuate conduits or stents having narrow openings into the coronary artery.
Figure 8B:
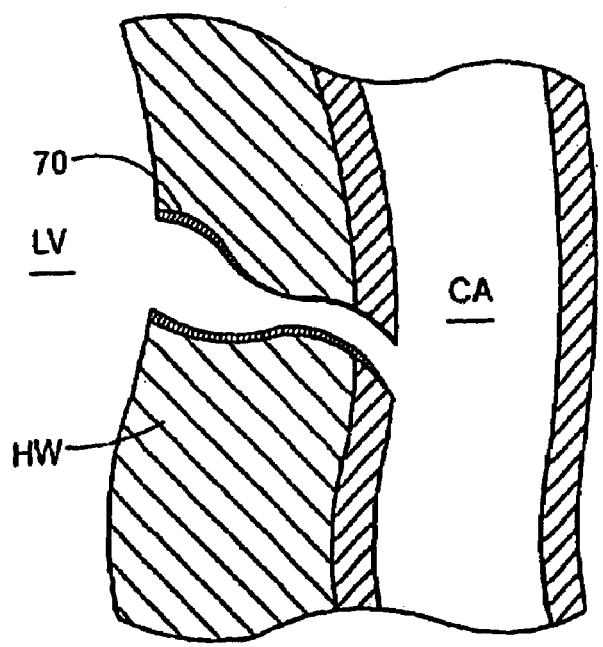

As depicted in FIG. 8, a transmyocardial stent 70 for maintaining a circulation path between left ventricle LV of patient's heart PH and coronary artery CA is curved in the longitudinal or flow direction to provide an arcuate flow path. This curvature serves to deflect the hydraulic forces from a direction substantially perpendicular to coronary artery CA to a direction substantially parallel to coronary artery CA. This deflection serves to prevent coronary artery dilatation and to protect anterior wall AW of artery CA from the substantial hydraulic forces generated during systole. Thus, this deflection serves to control the flow of the blood through the stent 70 during systole. Moreover, since the stent 70 narrows and curves towards the coronary artery CA, it serves to prevent or minimize backflow into the stent 70 during diastole, thus obviating the need for a valve 72. Stent 70 may be optionally provided with a one-way valve 72 and may be deployed as discussed above with reference to FIG. 7. Curved stent 70 may be used as upstream portion 56 of shunt member 52 or in place of stent 36 (FIG. 3) or as an upstream portion of shunt 22. FIGS. 8A and 8B illustrate further arcuate stent embodiments for maintaining circulation between the left ventricle LV and the coronary artery CA. As in FIG. 8, the embodiments of FIGS. 8A and 8B include a transmyocardial stent 70 that is curved in the longitudinal or flow direction to provide an arcuate flow path.

Figure 8C:
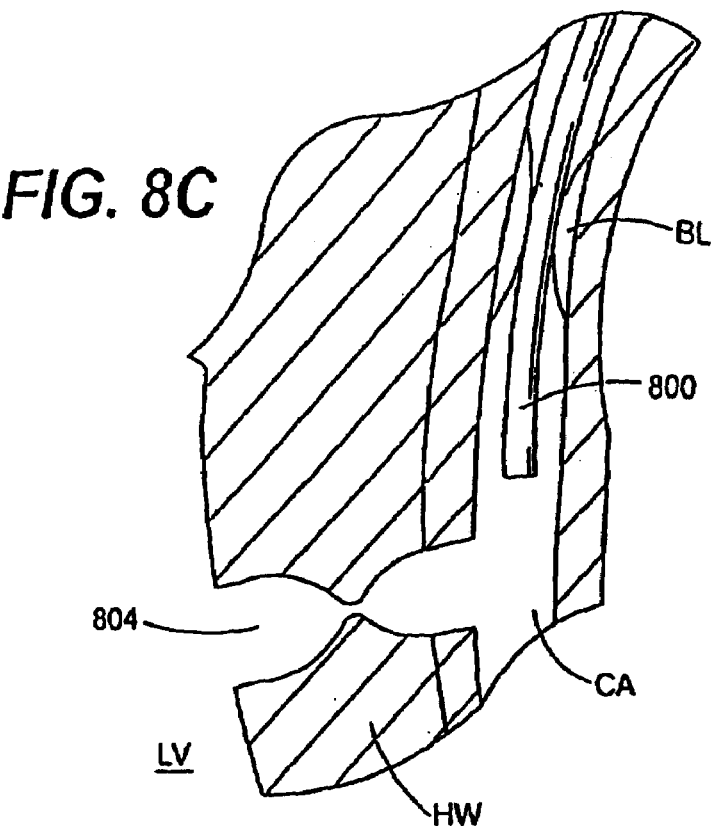
FIGS. 8C–8P are schematic partial cross-sectional views of conduits or stents having a variety of configurations to achieve flow control therethrough and to minimize backflow.
Figure 8D:
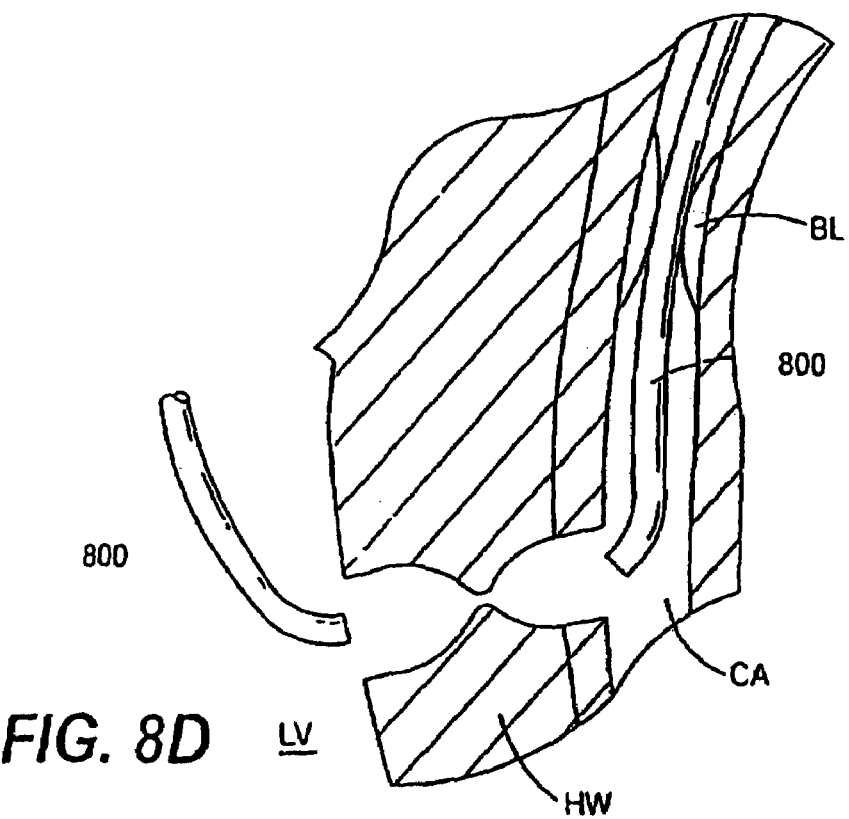

FIGS. 8C and 8D illustrate how a catheter 800 may be introduced into the coronary artery CA (FIG. 8C) or on both sides of the heart wall (FIG. 8D) for boring out a portion of the heart wall HW to form an hourglass-shaped portion 804 within the heart wall HW. The hourglass shaped portion 804 acts to create a valve effect so that blood is at least partially blocked during diastole.

Figure 8F:
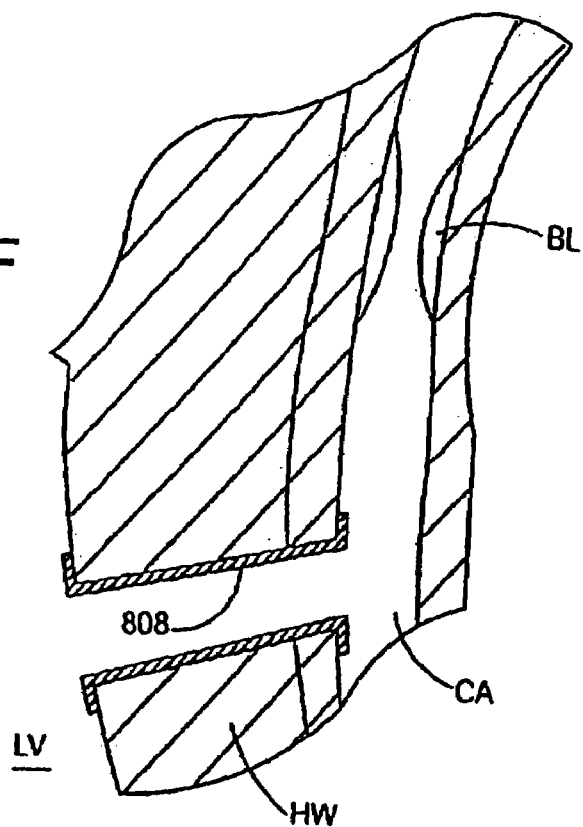
Figure 8E:
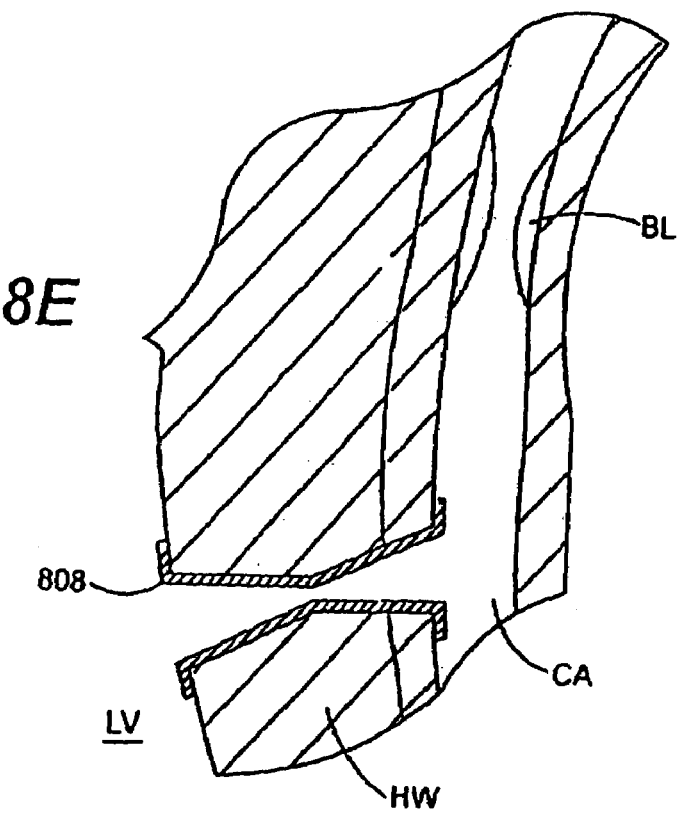
Figure 8G:
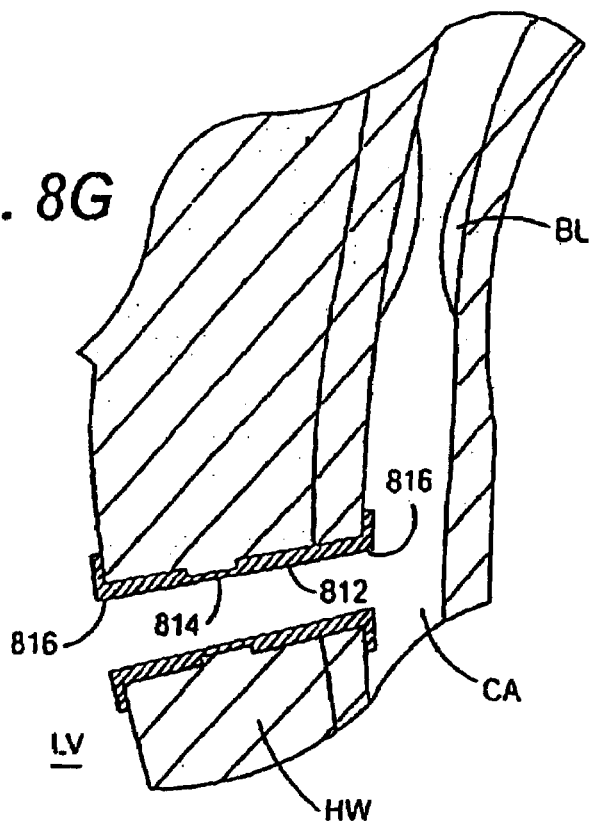
Figure 8H:
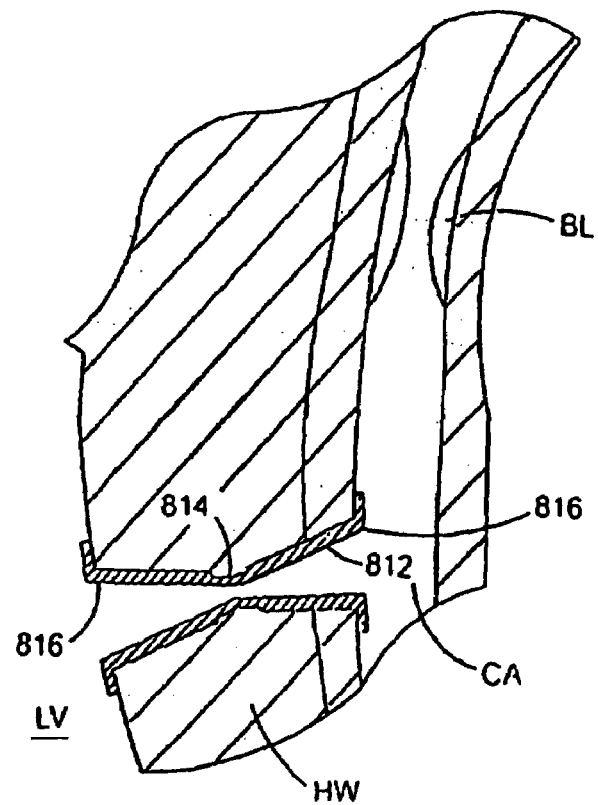
Figure 8I:
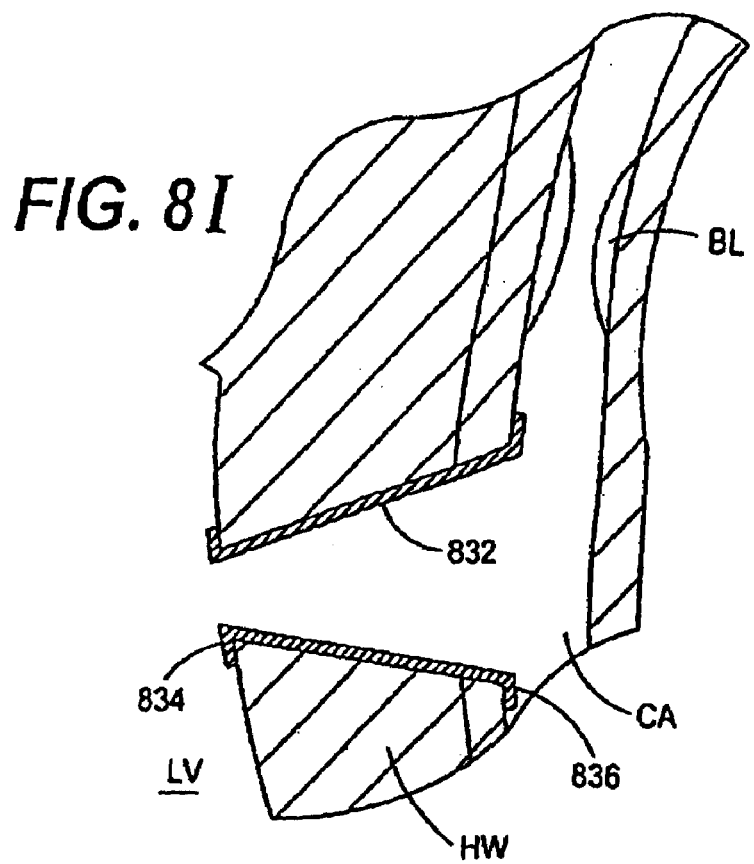

As seen in FIGS. 8E and 8F, a stent 808 may be positioned within the heart wall HW. As shown in FIG. 8E, the stent 808 is driven towards a closed position during diastole, whereas FIG. 8F shows the open position of the stent during systole. FIGS. 8G and 8H show an embodiment analogous to FIGS. 8E–F, except that a stent 812 is used that has a varying thickness. Using a stent 812 of nonconstant thickness has the effect of accentuating the deflection of the stent 812 at its central portion 814 relative to that at the outer portions 816 of the stent (at its ends).

Figures 8J, 8K:
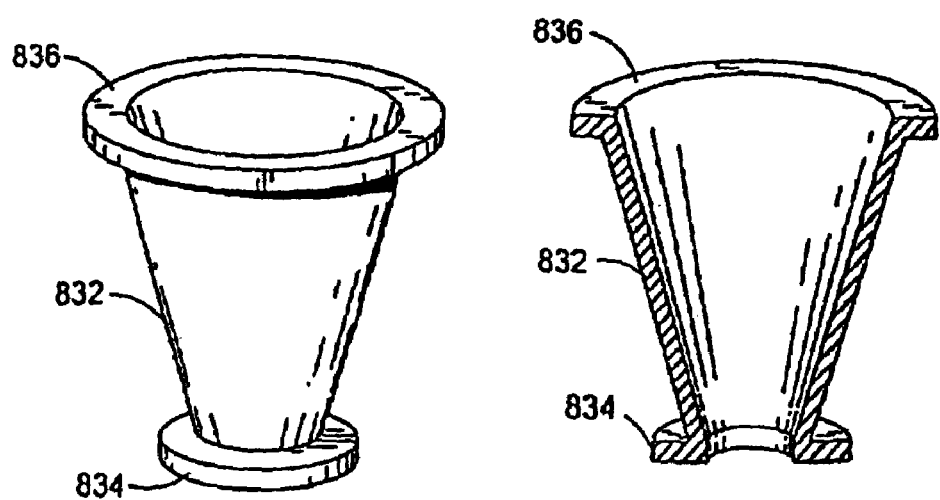
Figure 8L:
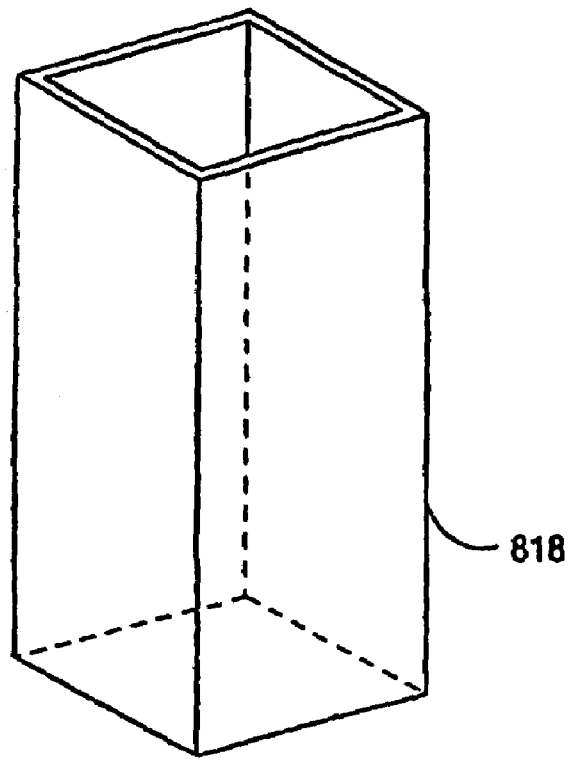
Figure 8M:
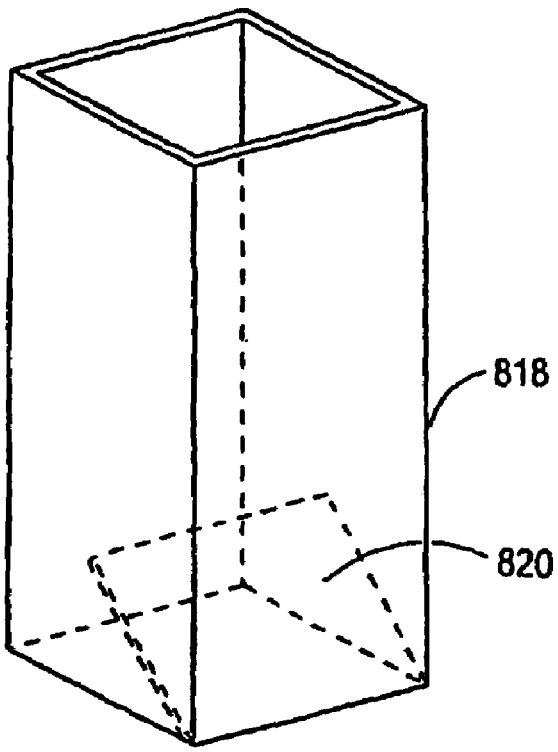
Figure 8N:
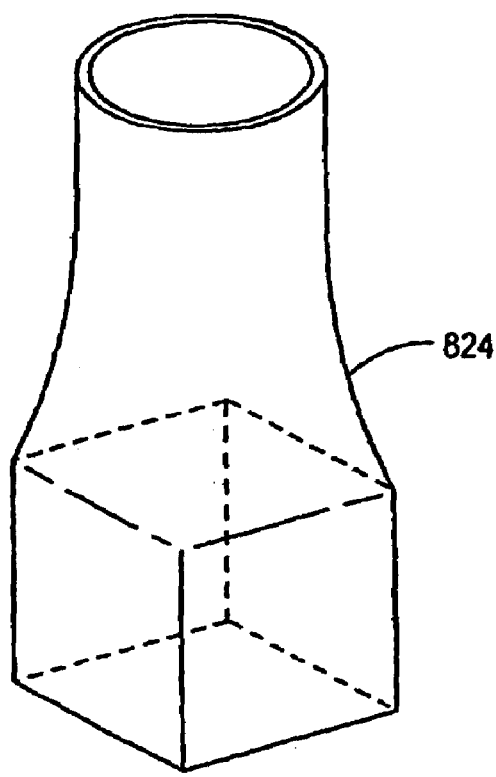
Figure 8O:
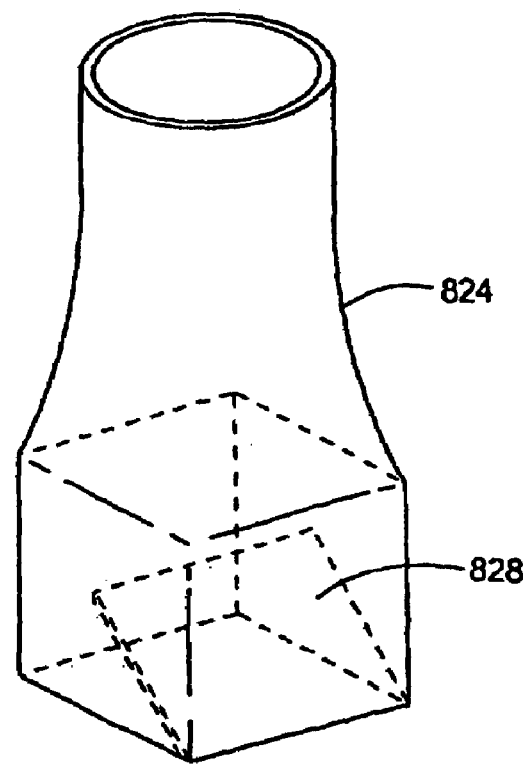

Other stent designs may be used like the parallelpiped shaped stents 818 of FIGS. 8L–M (which may include a movable flap portion 820 for controlling the flow of blood) or the stents 824 illustrated in FIGS. 8N–O (which likewise may include a movable flap 828 for controlling the flow). FIGS. 8–8K show another embodiment which includes a conically-shaped stent 832 whose base is located on the coronary artery side. The stent 832 includes rims 834 and 836 for securing the stent 832 to the heart wall HW.

Figure 8P:
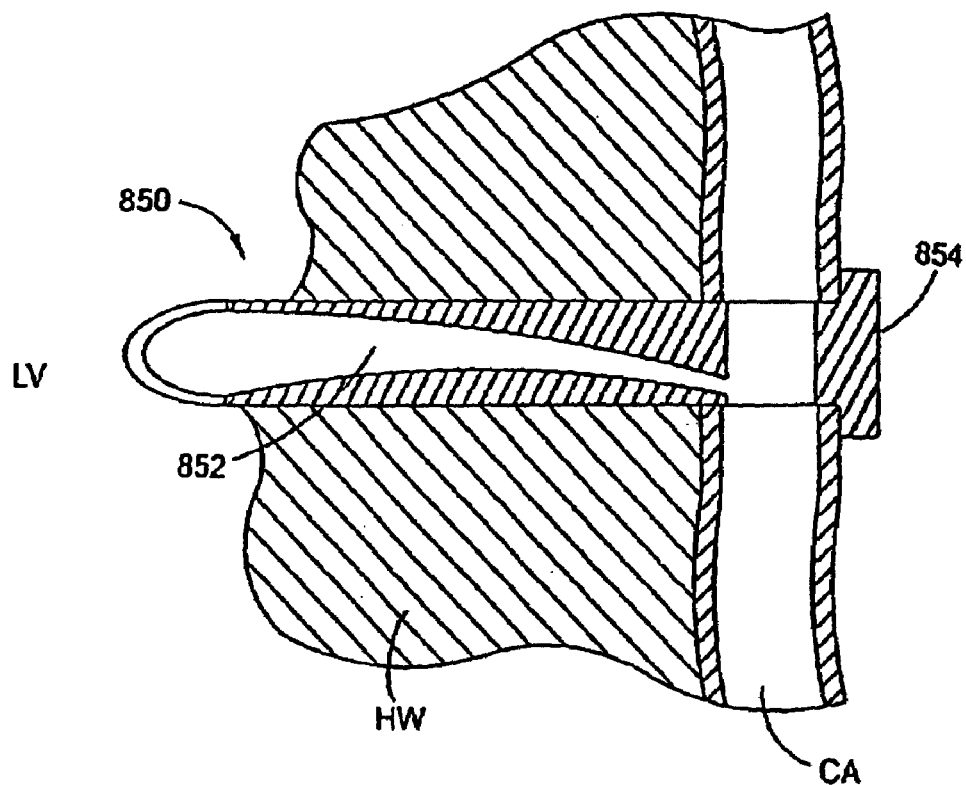

FIG. 8P illustrates an embodiment of a stent 850 which, like the embodiment of FIG. 8, maintains a circulation path between the left ventricle LV of patient's heart PH and coronary artery CA. The stent 850 has a lumen 852 therein which is curved, thereby deflecting hydraulic forces to control the flow of the blood through the stent 850 during systole. Further, the lumen 852 narrows and curves towards the coronary artery CA, which reduces backflow into the stent 850 during diastole and reduces the need for a valve. Nevertheless, the stent 850 may be optionally provided with a one-way valve 72 and may be deployed as discussed above with reference to FIG. 7. Further, the stent 850 may be used as upstream portion 56 of shunt member 52 or in place of stent 36 (FIG. 3) or as an upstream portion of shunt 22. Unlike its counterpart in FIG. 8, however, the lumen 852 of FIG. 8P is oriented within the stent 850 such that the lumen 852 joins the coronary artery CA at an oblique angle when the stent 850 is oriented perpendicular to the coronary artery CA. This aids the practitioner in the proper positioning of the lumen 852, and insures that the lumen 852 will be oriented with respect to the coronary artery CA as shown in FIG. 8P when a flange 854 of the stent 850 is positioned against the coronary artery CA. Further, the stent 850 of FIG. 8P may advantageously have an outer dimension that is substantially constant in cross section.

Figure 9:
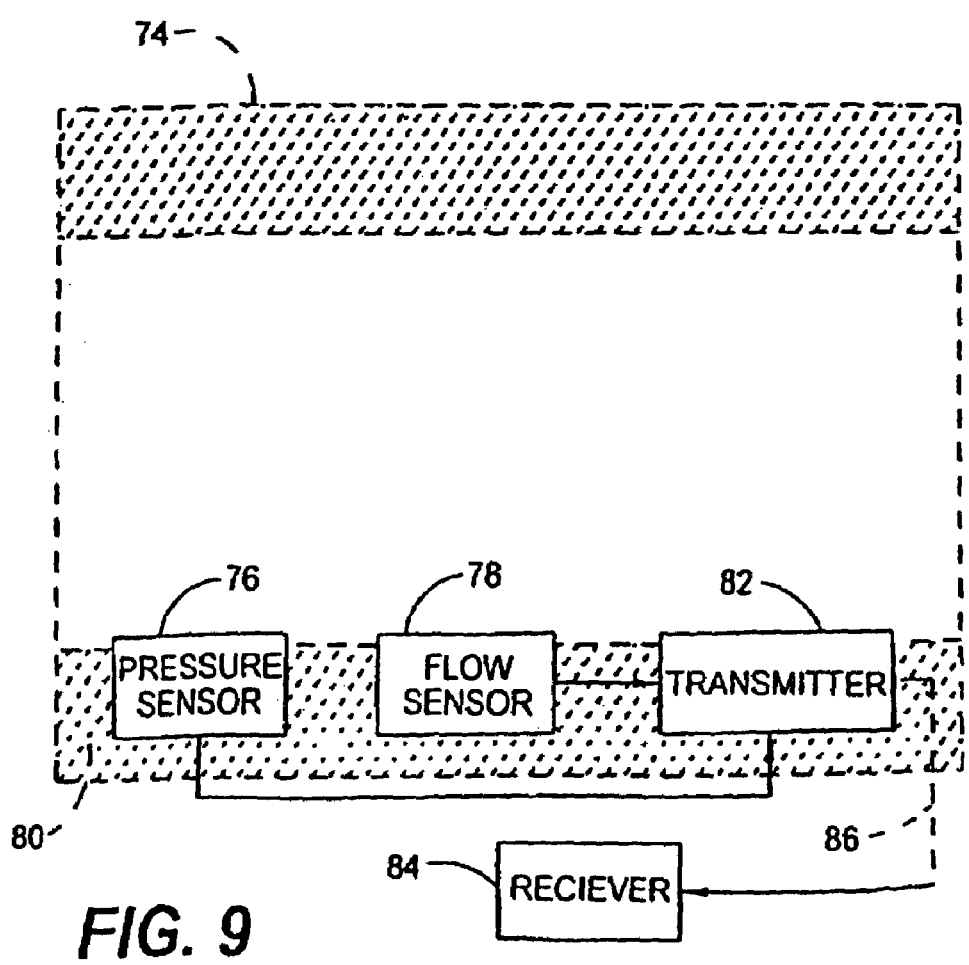
FIG. 9 is a block diagram of operational components with feedback as to operational parameters.

A shunt or stent 74 may be provided with a pressure sensor 76 and/or a flow sensor 78, as illustrated in FIG. 9. Sensors 76 and 78 are attached to or incorporated into a wall 80 of shunt or stent 74 and have outputs operatively connected to a transmitter 82 which is also attached to or incorporated into shunt or stent wall 80. Output signals from sensors 76 and 78 which encode data pertaining to pressures and flow rates are relayed to a receiver 84 via transmitter 82. Transmitter 82 may be wireless or connected by a wire 86 to receiver 84. The pressure and flow rate data collected via sensors 76 and 78 are useful for monitoring the effectiveness of the implanted stents or shunts for any particular patient and thereby determining whether additional stents or shunts may be necessary for that patient. Receiver 84 may be physically located on a chest of the patient or otherwise nearby.

Figure 9A:
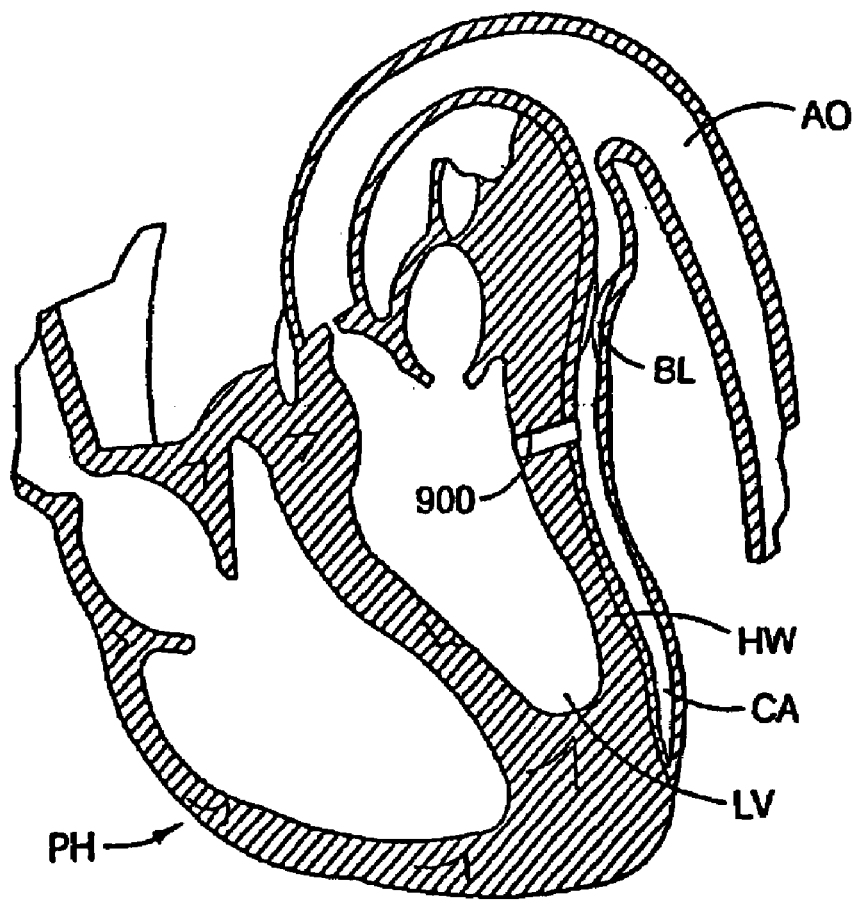
FIGS. 9A–9B illustrate a conduit having a flow sensor for measuring various blood flow parameters incorporated therein.
Figure 9B:
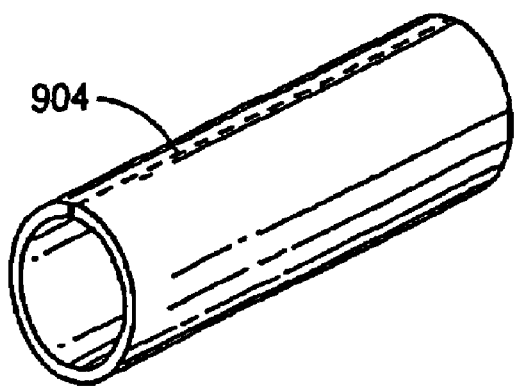
Figure 9C:
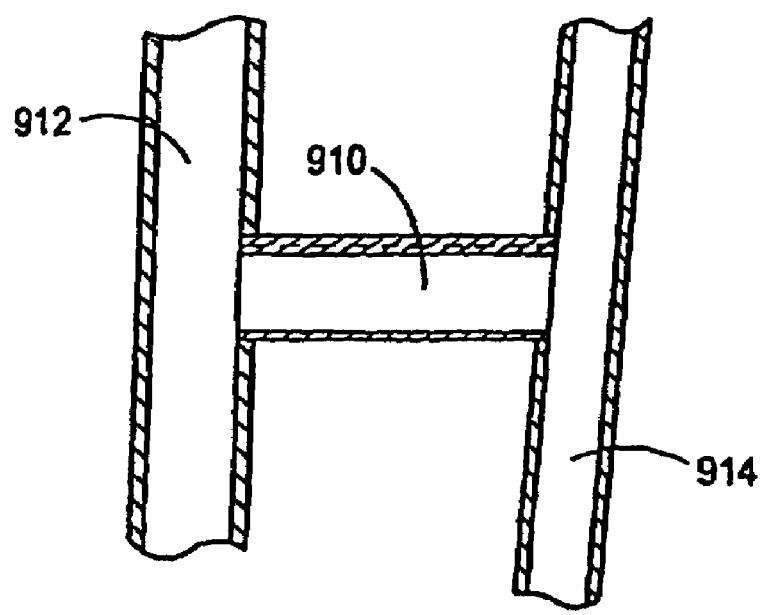
FIG. 9C is a schematic partial cross-sectional view of a conduit having the flow sensor FIG. 9B as installed between two vessels.

FIG. 9A illustrates a cross-section of the heart illustrating a stent 900 having incorporated therein a sensor 904 (shown in FIG. 9B) similar to the sensors described above in connection with FIG. 9. The sensor may be incorporated into the wall of the stent 900 as illustrated in FIG. 9B or may be associated with a stent in some other fashion. The sensor 904 may advantageously transmit an output signal which encodes data with respect to pressures and flow rates. For example, blood pressure during both systole and diastole may be monitored, and the sensor 904 may be used to indicate when the blood flow (or pressure) is decreasing or when the blood flow (or pressure) falls beneath a certain level. As shown in FIG. 9C, a conduit 910 having a sensor therein may be used between two vessels, such as an aorta 912 and a vein 914.

Posterior Wall Access

Figure 10A:
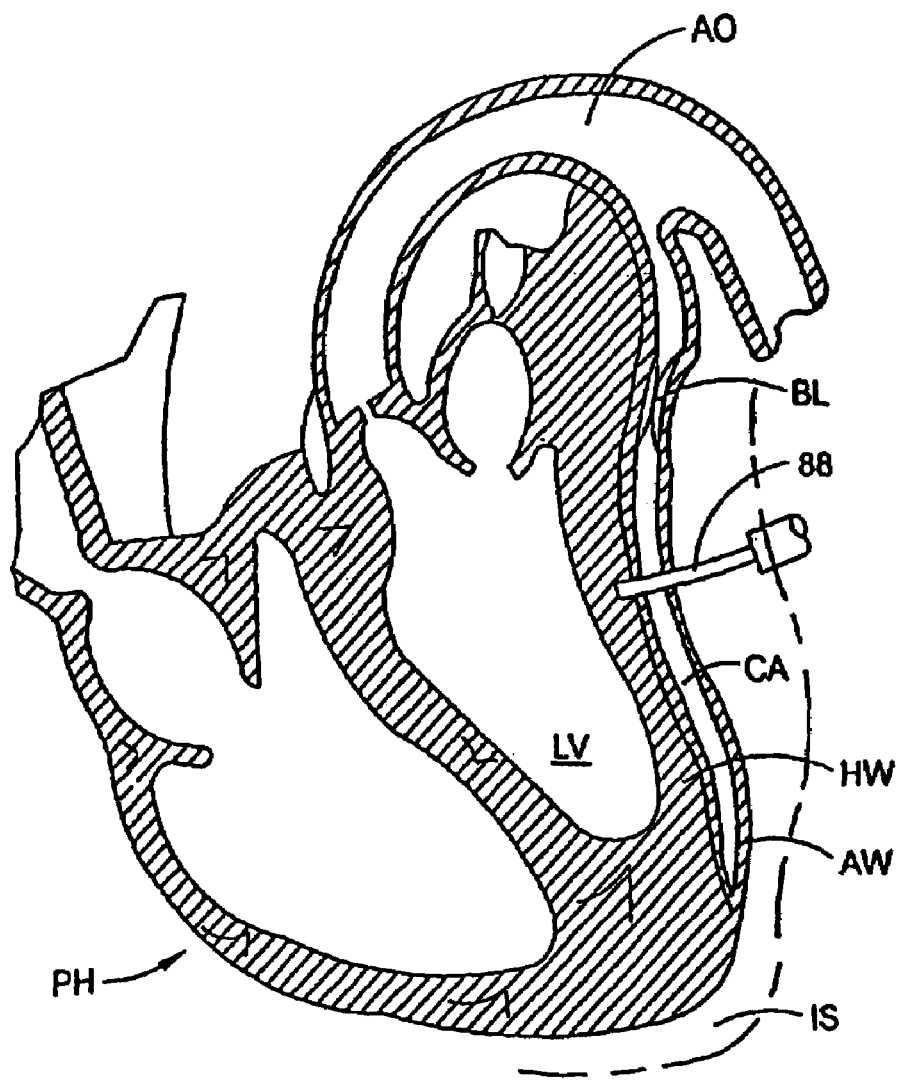
FIGS. 10A–10C are schematic cross-sectional views of a human heart, showing successive steps in a transmyocardial coronary artery bypass operation utilizing a penetrating rod for implanting a conduit.
Figure 10B:
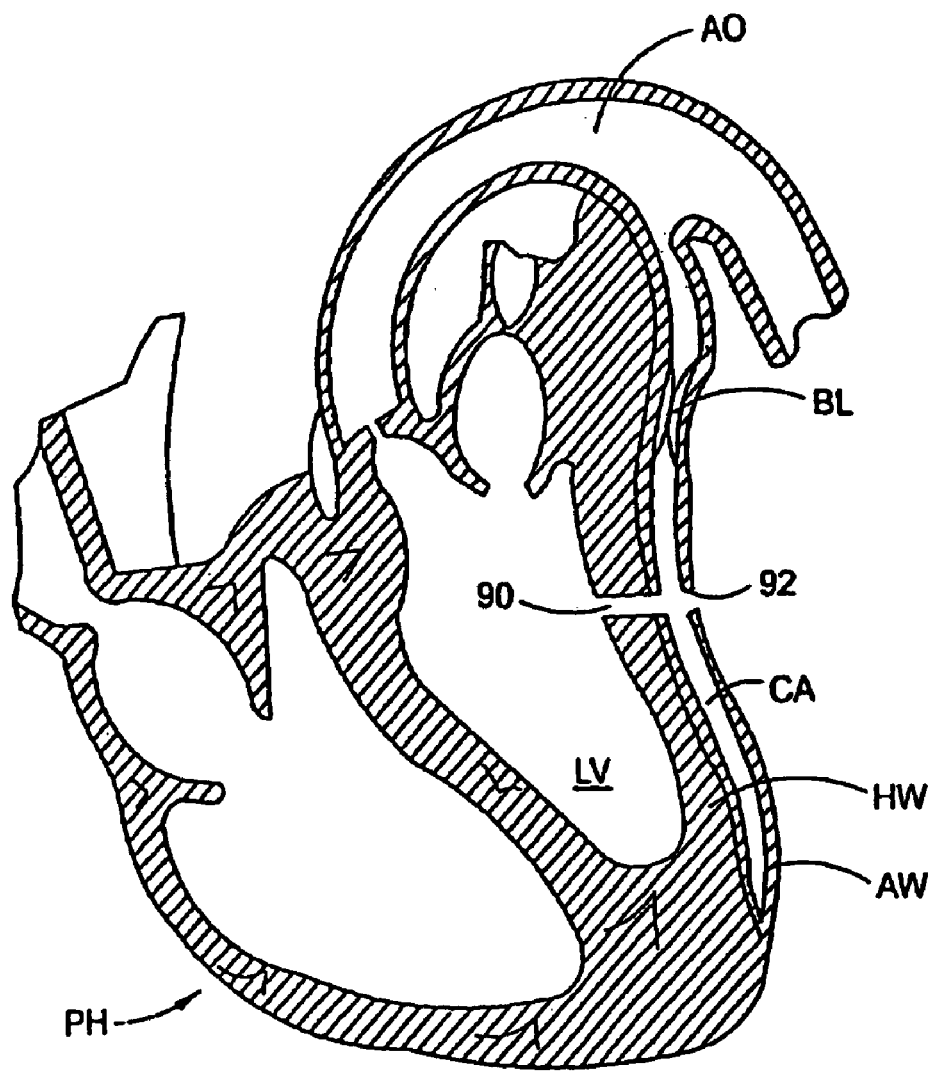
Figure 10C:
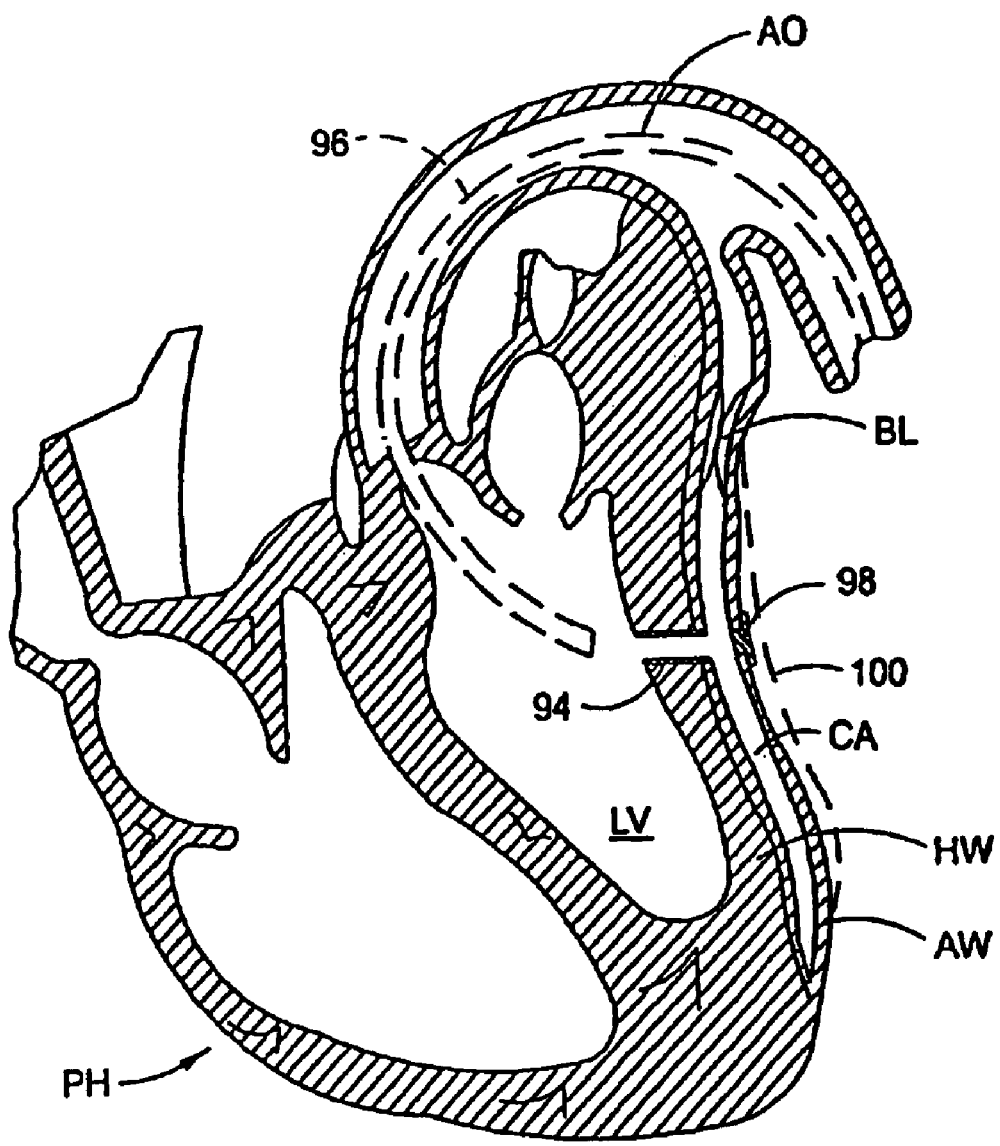

As illustrated in FIGS. 10A–10C, a transmyocardial coronary artery bypass may be performed from outside the patient's vascular system. An incising instrument 88 such as a laser or a drill is inserted pericardioscopically or through an open incision into the intrapericardial space IS and is operated to bore a passageway 90 in the heart wall or myocardium HW via the coronary artery CA, as shown in FIG. 10A. Passageway 90 (FIG. 10B) extends through heart wall HW and posterior wall PW of coronary artery CA and is aligned with an aperture 92 formed in anterior wall AW of coronary artery CA by the incising instrument 88.

Upon the formation of passageway 90, a stent 94 (FIG. 10C) is inserted in a collapsed configuration into the passageway and then expanded. Stent 94 may be inserted from outside the patient's vascular system, either through an open incision in the patient's chest or through a pericardioscopic cannula or port. Alternatively, stent 94 may be placed via a catheter 96 inserted through the vascular system including the aorta AO and the left ventricle LV. As in all cases of stent implantation described herein, stent 94 serves to maintain passageway 90 in an open state, i.e., prevents the closure of passageway 90 by muscular contraction forces during systole and, in the longer term, by natural healing processes of the myocardium.

After the formation of passageway 90 and after the installation of stent 94 via an extravascular operation, aperture 92 is closed, via sutures (not shown) and/or via a plug 98 (FIG. 10C) or patch which is stitched or laser bonded to anterior wall AW of coronary artery CA. If stent 94 is placed via an intravascular operation, aperture 92 is preferably closed prior to the disposition of the stent inside passageway 90. A brace 100 in the form of a patch is optionally placed over plug 98 and fastened to heart PH via sutures, glue or welding to support the plug against possible dislodgment under blood pressure forces.

Figure 11:
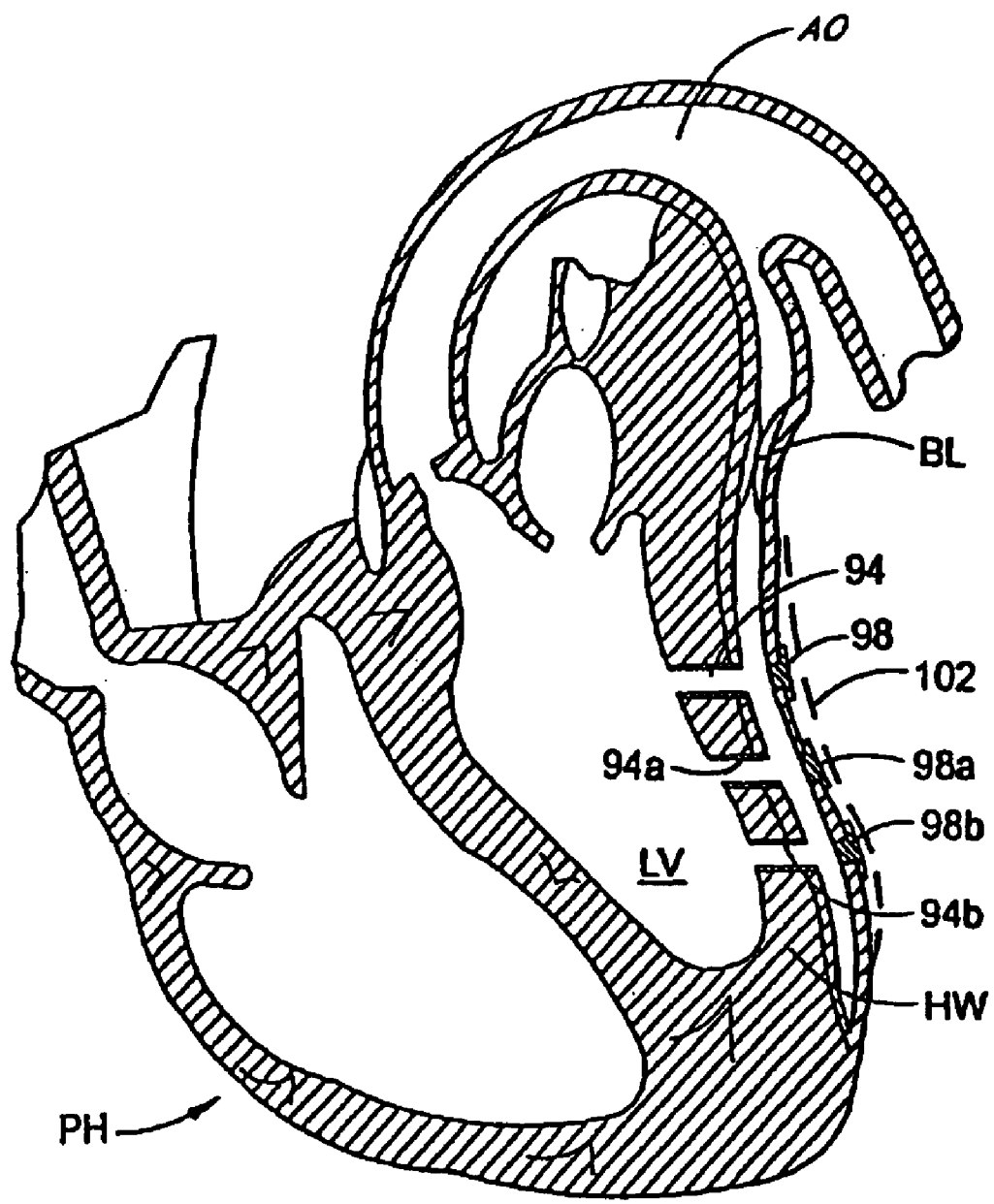
FIG. 11 is a schematic cross-sectional view similar to FIG. 10C, showing three transmyocardial conduits or stents implanted pursuant to the procedure of FIGS. 10A–10C.

FIG. 11 illustrates a triple transmyocardial coronary artery bypass wherein a plurality of stents 94, 94a and 94b are placed in respective passageways (not separately designated) extending through heart wall or myocardium HW and posterior wall PW of coronary artery CA. The passageways are formed and the stents 94, 94a and 94b inserted as described hereinabove with reference to FIGS. 10A–10C. Plugs 98, 98a and 98b are positioned in respective apertures (not separately designated) which are formed, as discussed above, in alignment with the passageways of stents 94, 94a and 94b. A brace 102 in the form of a patch is optionally placed over plugs 98, 98a and 98b and fastened to heart PH via sutures, glue or laser welding.

Figure 12:
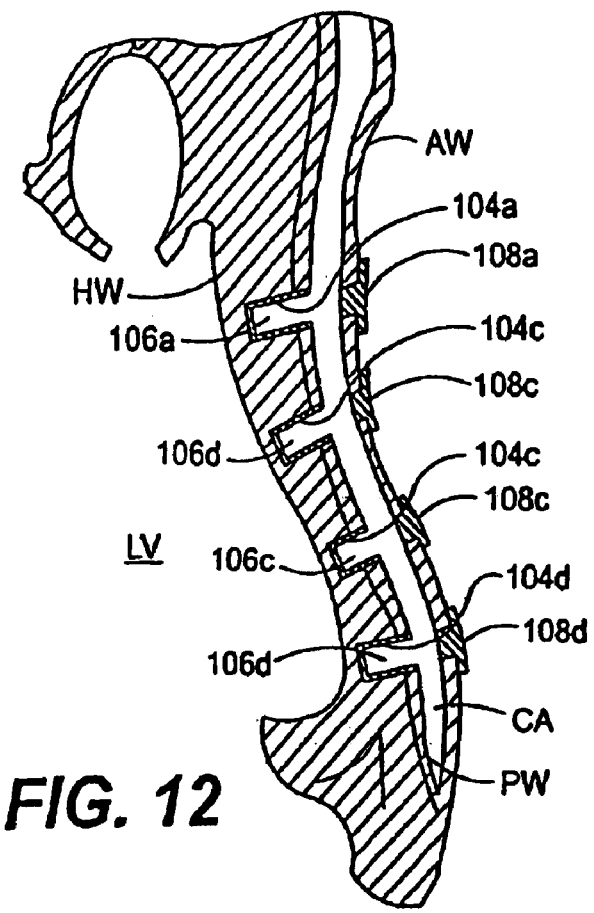
FIG. 12 is a schematic partial cross-sectional view of an artificial myocardial revascularization showing a plurality of partial conduits or stents extending from a coronary artery partially into the myocardium.
Figure 13:
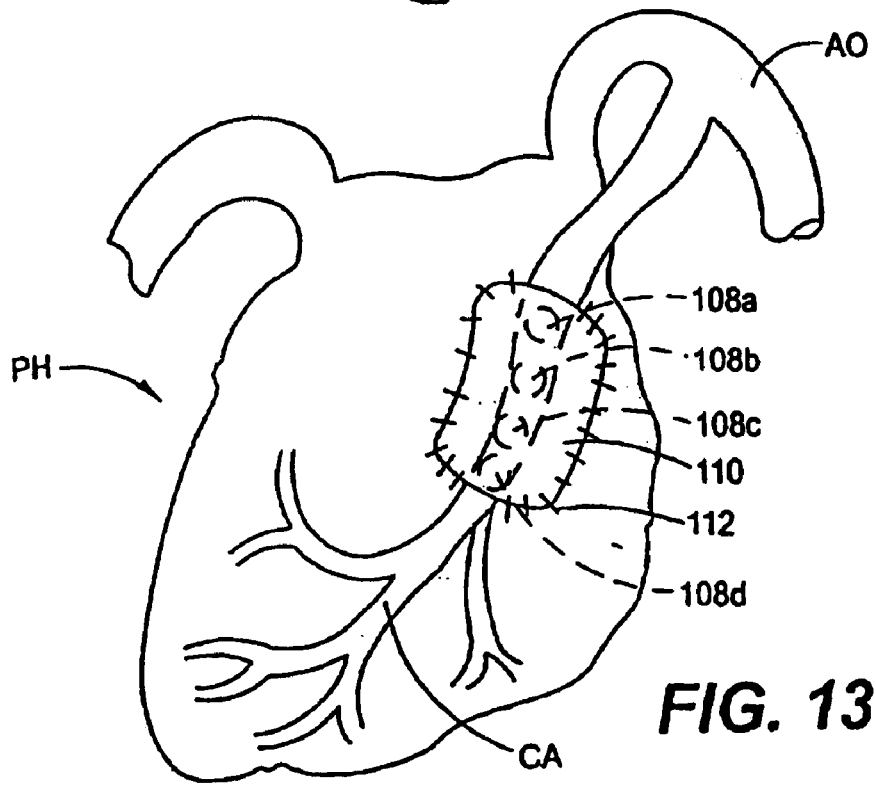
FIG. 13 is a schematic front elevational view of a human heart, showing an improvement in the myocardial revascularization of FIG. 12.

FIG. 12 depicts a modification of the transmyocardial coronary artery bypass of FIG. 11, wherein passageways 104a, 104b, 104c and 104d are formed by the extravascular technique discussed above with reference to FIGS. 10A–10C but which extend through posterior coronary artery wall PW and only part of the heart wall or myocardium HW from coronary artery CA. Stents 106a, 106b, 106c and 106d are inserted into respective passageways 104a, 104b, 104c and 104d via an extravascular operation. Thereafter, plugs 108a, 108b, 108c and 108d are inserted into or over respective apertures in anterior coronary artery wall AW aligned with passageways 104a, 104b, 104c and 104d and stents 106a, 106b, 106c and 106d. As illustrated in FIG. 13, a patch 110 may be placed over coronary artery CA and particularly over plugs 108a, 108b, 108c, 108d and attached via sutures 112 to heart PH to brace the plugs against dislodgment under systolic and diastolic blood pressures.

Figure 14A:
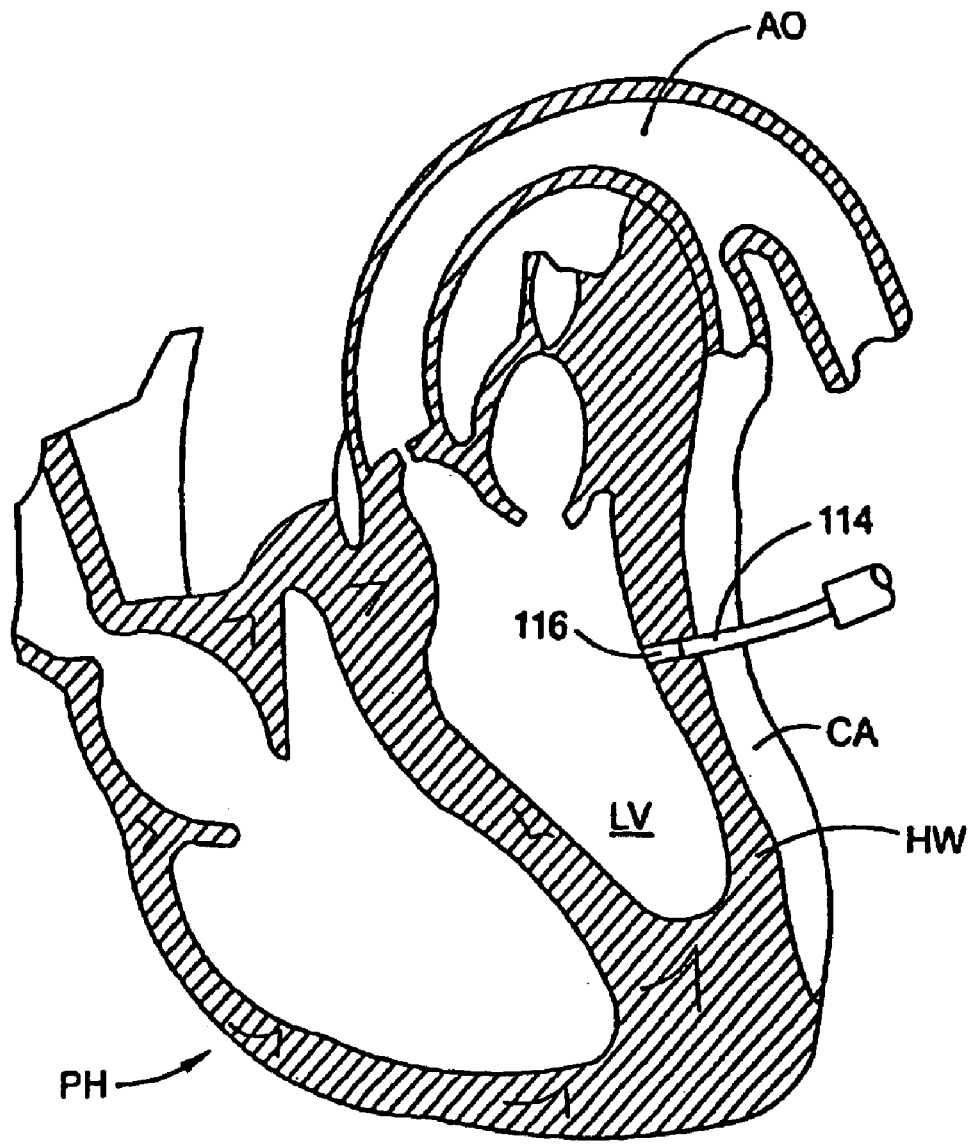
FIGS. 14A and 14B are schematic cross-sectional views of a human heart, showing successive steps in an artificial myocardial revascularization procedure, resulting in a plurality of conduits or stents extending from a left ventricle of the heart at least partially into the myocardium.
Figure 14B:
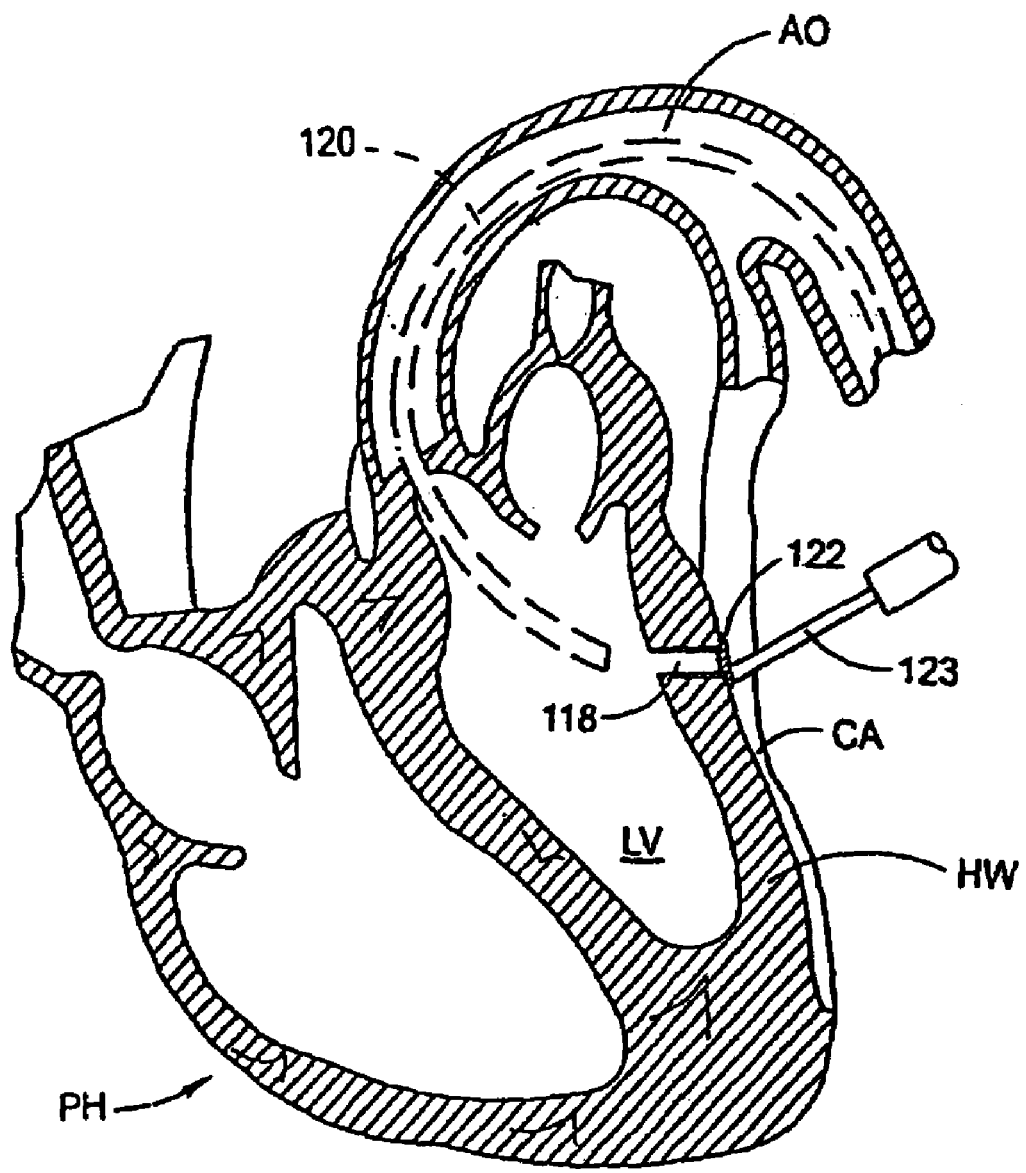

FIGS. 14A and 14B depict steps in a transmyocardial revascularization procedure. An incising instrument 114 such as a laser fiber or a drill is inserted in an extravascular procedure through an open chest incision or a pericardioscopic cannula or port and is used to form a channel or passageway 116 in heart wall or myocardium HW through the epicardium (not shown). A stent 118 is inserted into channel 116 in a collapsed configuration via an intravascularly deployed catheter 120 or in an extravascular operation. A plug 122 is inserted into an outer end of channel 116 to close off that outer end. Plug 122 may be attached to the epicardium of heart PH via a laser instrument 123 or via sutures (not shown). Several channels 116, 116a and 116b may be formed and provided with respective stents 118, 118a and 118b and respective plugs 122, 122a and 122b, as illustrated in FIG. 15. A patch 124 may be placed over plug 122 or plugs 122, 122a and 122b and attached via sutures 126 to heart wall HW.

Myocardial Plugs

The various conduits or stents disclosed herein may be provided with a layer of polymeric material carrying a biochemical composition, e.g., angiogenesis factor or the nucleic acid instructions therefor, for generating, stimulating, and enhancing blood vessel formation. As illustrated in FIG. 16, plugs 128 may be inserted into a patient's heart wall or myocardium HW from inside the left ventricle LV or right ventricle RV via an intravascularly deployed catheter (not shown). Alternatively, the plugs may be inserted into the heart wall or myocardium HW from outside of the heart in an open incision or pericardioscopic operation (not shown). In either case, the plugs carry angiogenesis factor, or the nucleic acid instructions therefor, for generating, stimulating, and enhancing vascular generation and growth. The angiogenesis factor is gradually released from the plugs, or stents, in time release fashion, to optimize the stimulation of vascular growth.

FIG. 16A is a schematic partial cross-sectional view of a triangular-shaped conduit comprising a plug 940 or stent or the like and having, for example, multiple factors applied thereto such as growth factors, genes, drugs, etc. The rate at which an applied factor is released may be controlled through appropriate configuration of the plug 940, e.g., by controlling its porosity.

Figure 16B:
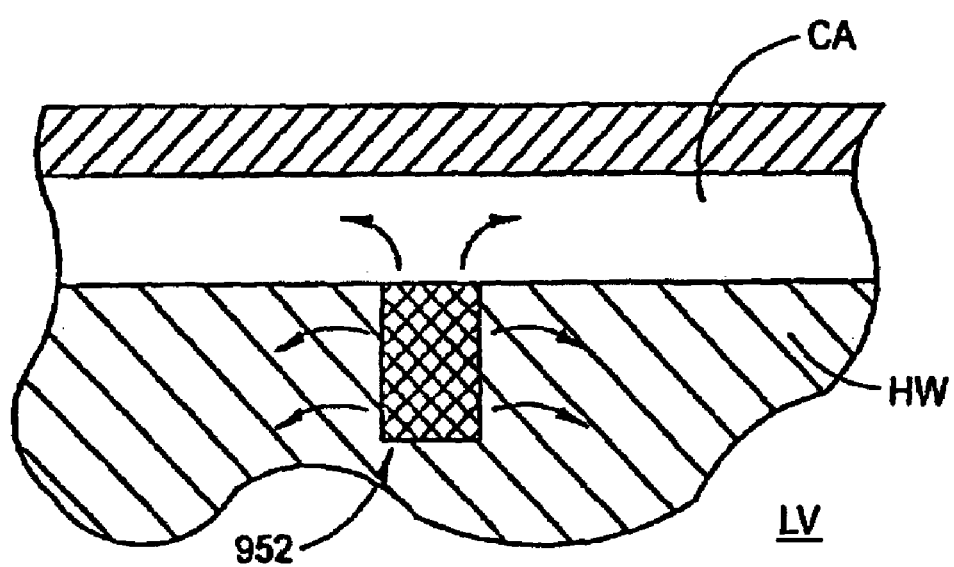
FIG. 16B is a side view of a biodegradable conduit or stent positioned within the myocardium, with the coronary artery and myocardium shown cut-away.

If desired, the stent or conduit of the present invention can be formed of biodegradable or bioabsorbable materials and/or used to deliver drugs directly into the myocardium and the coronary circulation. Such a stent 952 is illustrated in FIG. 16B. The biodegradable stent 952 can extend only partially through the heart wall HW as illustrated in FIG. 16B, but can also extend entirely through from the left ventricle LV to the coronary artery CA. Once positioned in the heart wall HW, the stent 952 degrades, dissolves or is absorbed over time to release drugs, genes, angiogenesis or growth factors, or other pharmaceutical compounds directly into the heart wall HW and the coronary artery CA, as shown by the arrows in FIG. 16B. Bioabsorbable materials include, but are not limited to, polymers of the linear aliphatic polyester and glycolide families, such as polylactide and polyglycolide.

Figure 16C:
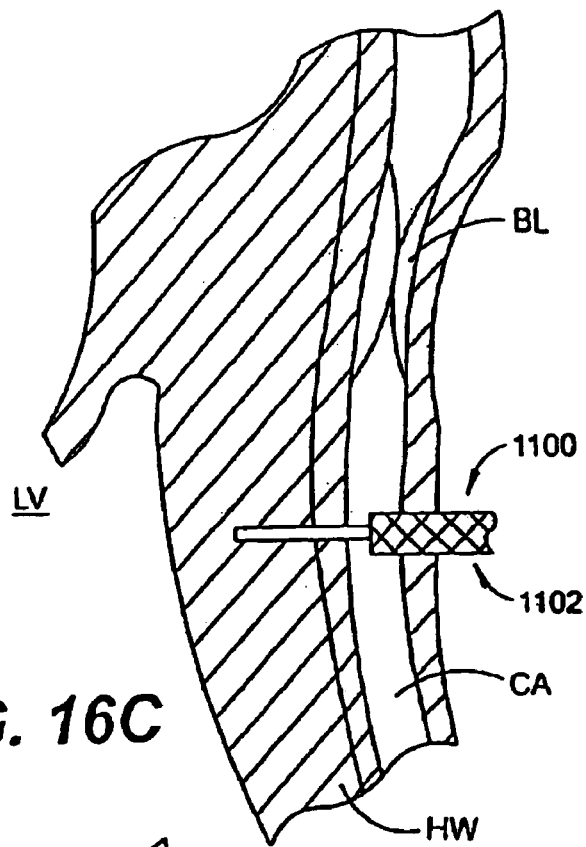
FIGS. 16C–16F are schematic, cross-sectional views of the external insertion of an absorbable intramyocardial plug in the myocardium.
Figure 16D:
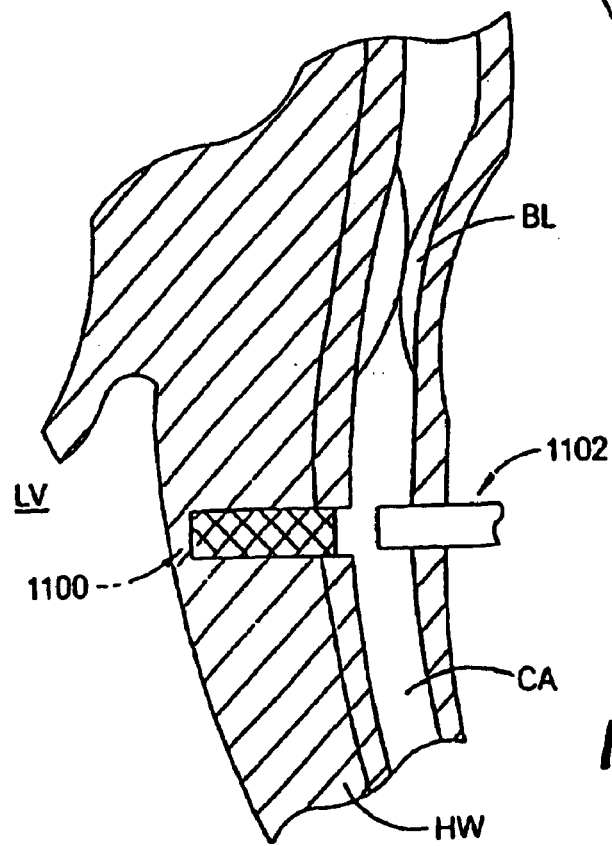
Figure 16E:
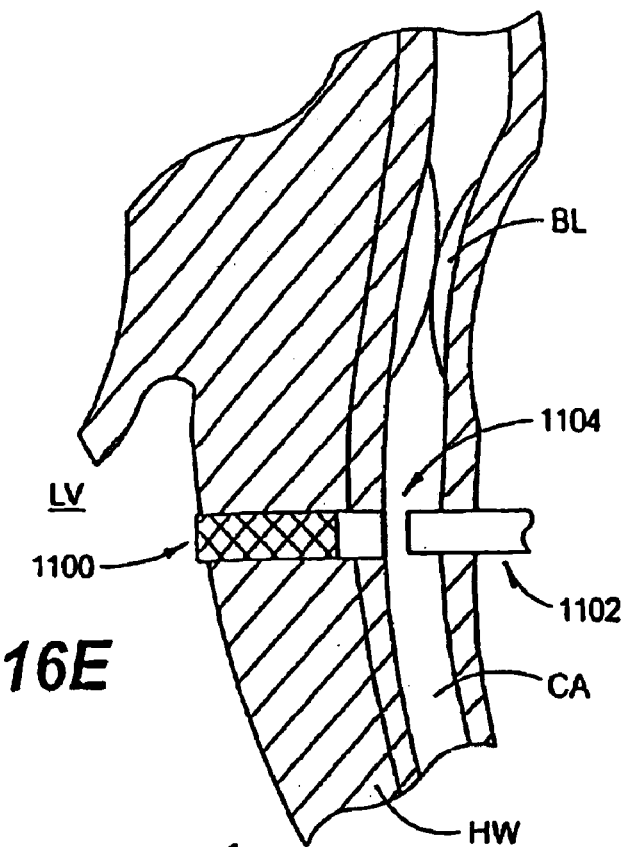
Figure 16F:
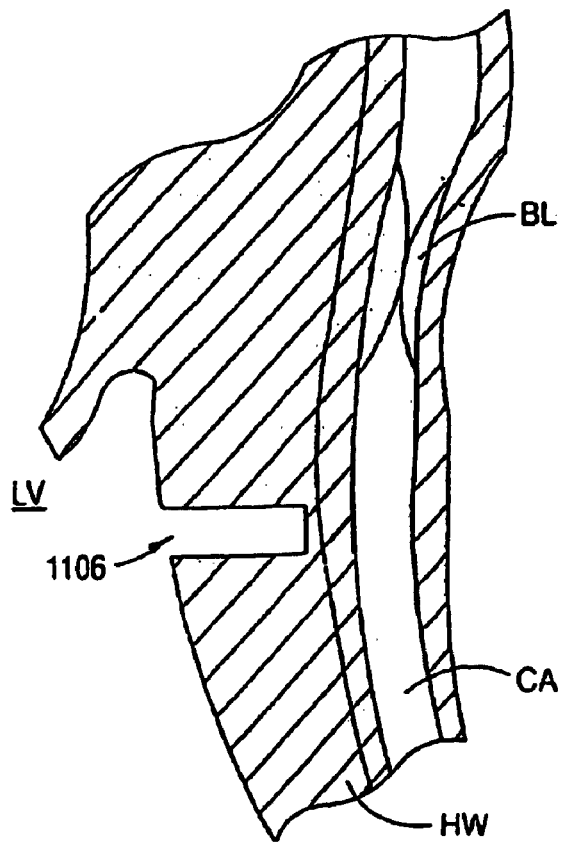

Such a stent is also illustrated in FIGS. 16C–16F. FIG. 16C illustrates the external insertion of a solid, but absorbable stent or plug 1100. A delivery device 1102, such as a thoroscope bearing the intramyocardial plug 1100 is inserted into the heart wall HW at a site distal to the blockage BL in the coronary artery CA as shown in FIG. 16D. The insertion site in the heart wall HW is permanently closed using sutures 1104, a plug, laser coagulation or similar means, as shown in FIG. 16E. This allows for myocardial revascularization. As the plug 1100 is absorbed, blood flows from the coronary artery CA into the passageway formed by the absorbed plug 1100. This results in the ischemic myocardial area being revascularized. Alternatively, as illustrated in FIGS. 16E and 16F, the intramyocardial plug 1100 can be inserted through the heart wall HW such that it extends into the left ventricle LV. As the plug 100 is absorbed by the body, there remains a space or channel 1106 in the heart wall HW that perfuses with oxygenated blood from the left ventricle LV. This channel 1106 acts as do the channels formed in the heart during percutaneous transmyocardial revascularization (PTMR), allowing the heart muscle to be exposed to additional oxygenated blood.

Figure 16G:
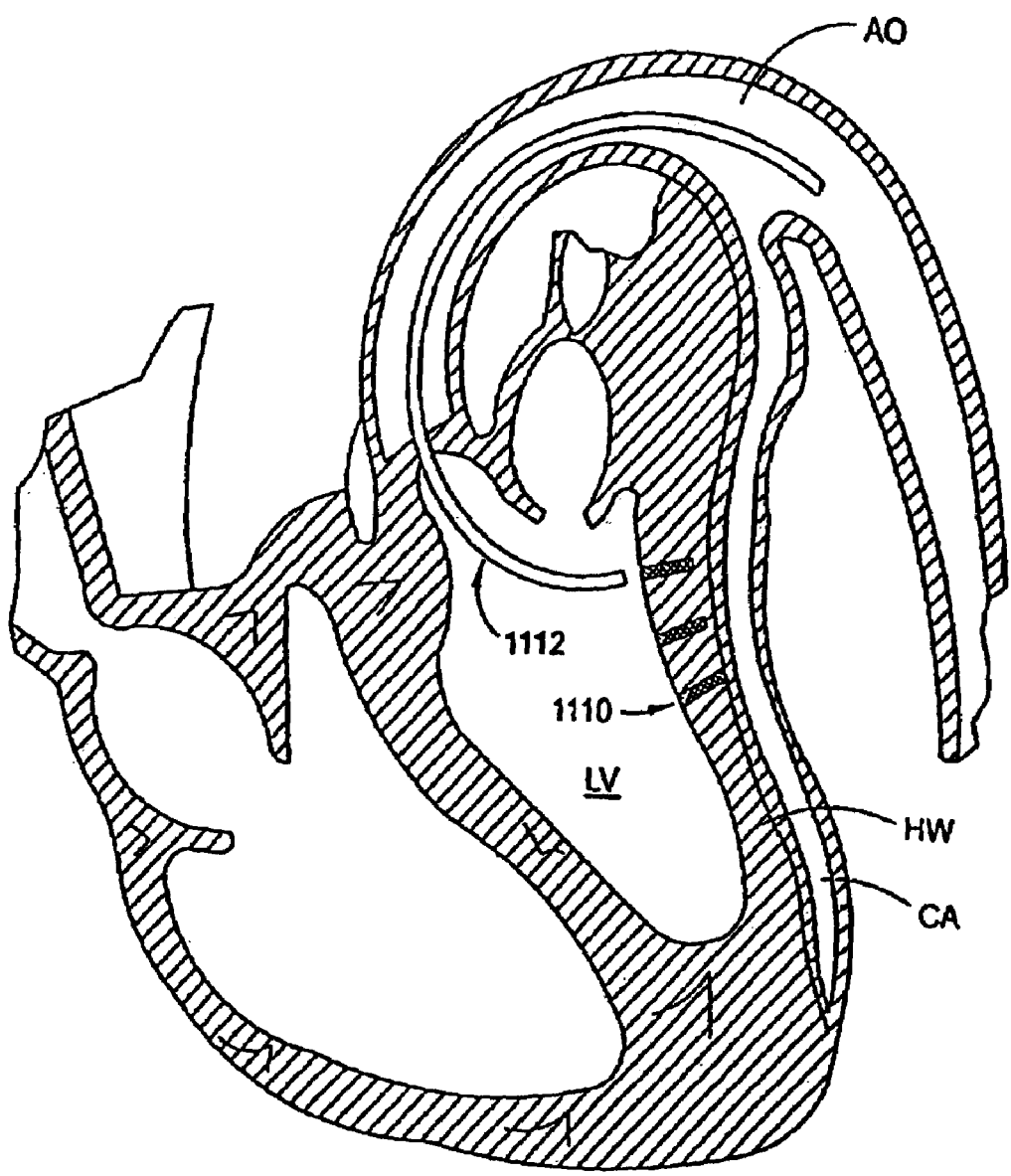
FIGS. 16G–16I are schematic, cross-sectional views of the insertion of absorbable intramyocardial plugs in the myocardium via the left ventricle.
Figure 16H:
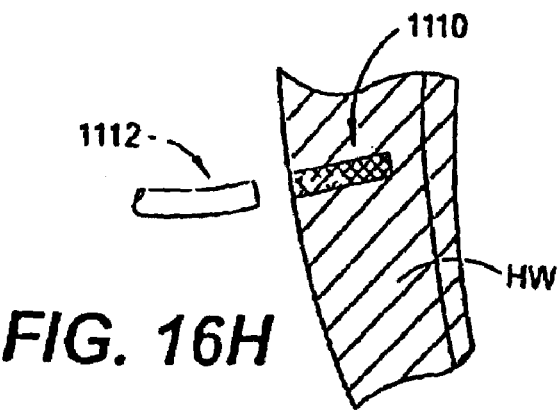
Figure 16I:
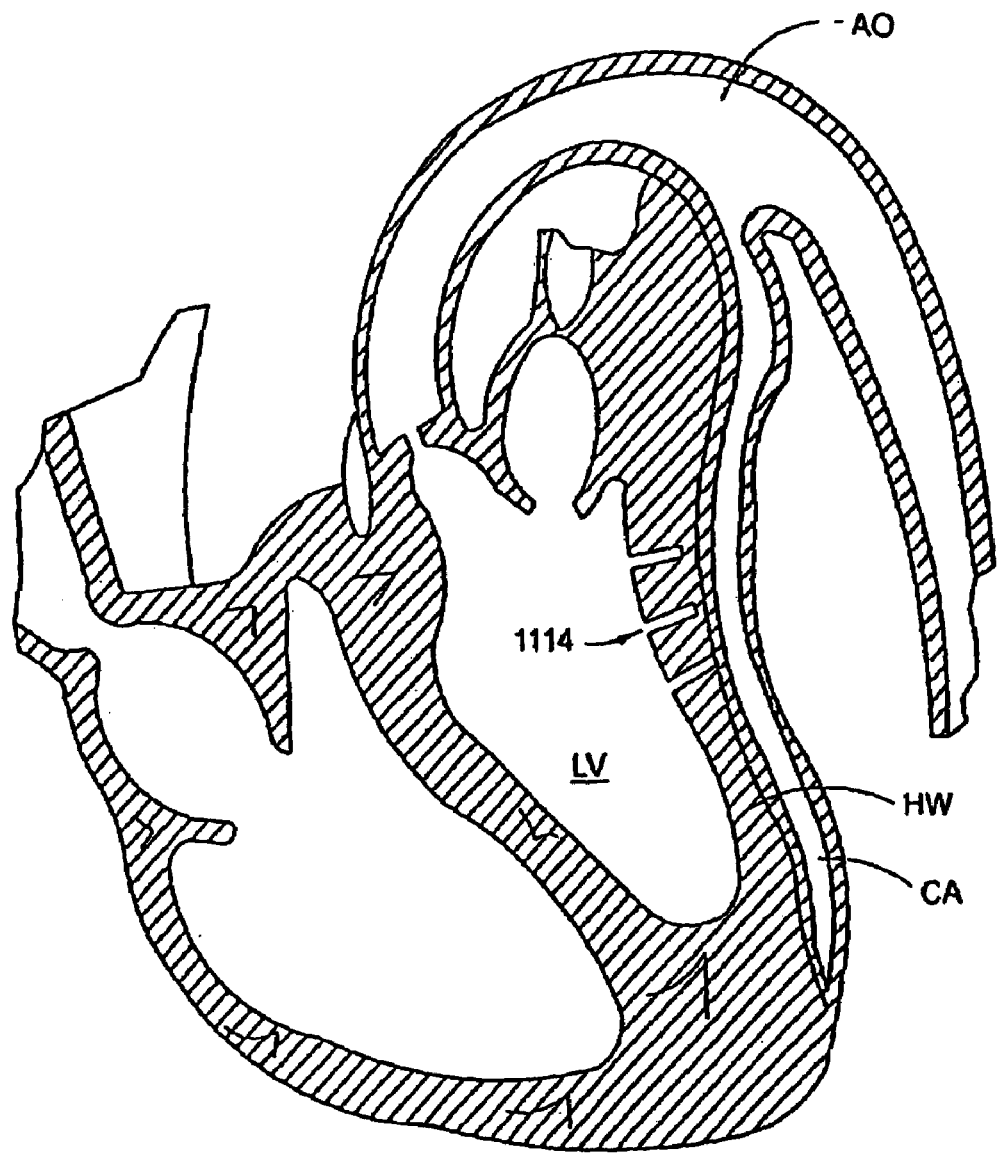

FIGS. 16G–16I illustrate an alternative means for delivering an absorbable plug 1110 into the heart wall HW. FIG. 16G illustrates the delivery of multiple plugs 1110 using a catheter 1112 threaded through the patient's vasculature and into the left ventricle LV of the heart. The plug 1110 is inserted into the myocardial wall as shown is FIG. 16H. The plug 1110 is absorbed over time, leaving an opening or channel 1114 in the heart wall HW (FIG. 16I) that perfuses with oxygenated blood from the left ventricle LV. This channel 1114 acts as do the channels formed in the heart during percutaneous transmyocardial revascularization (PTMR), allowing the heart muscle to be exposed to additional oxygenated blood.

Figure 16J:
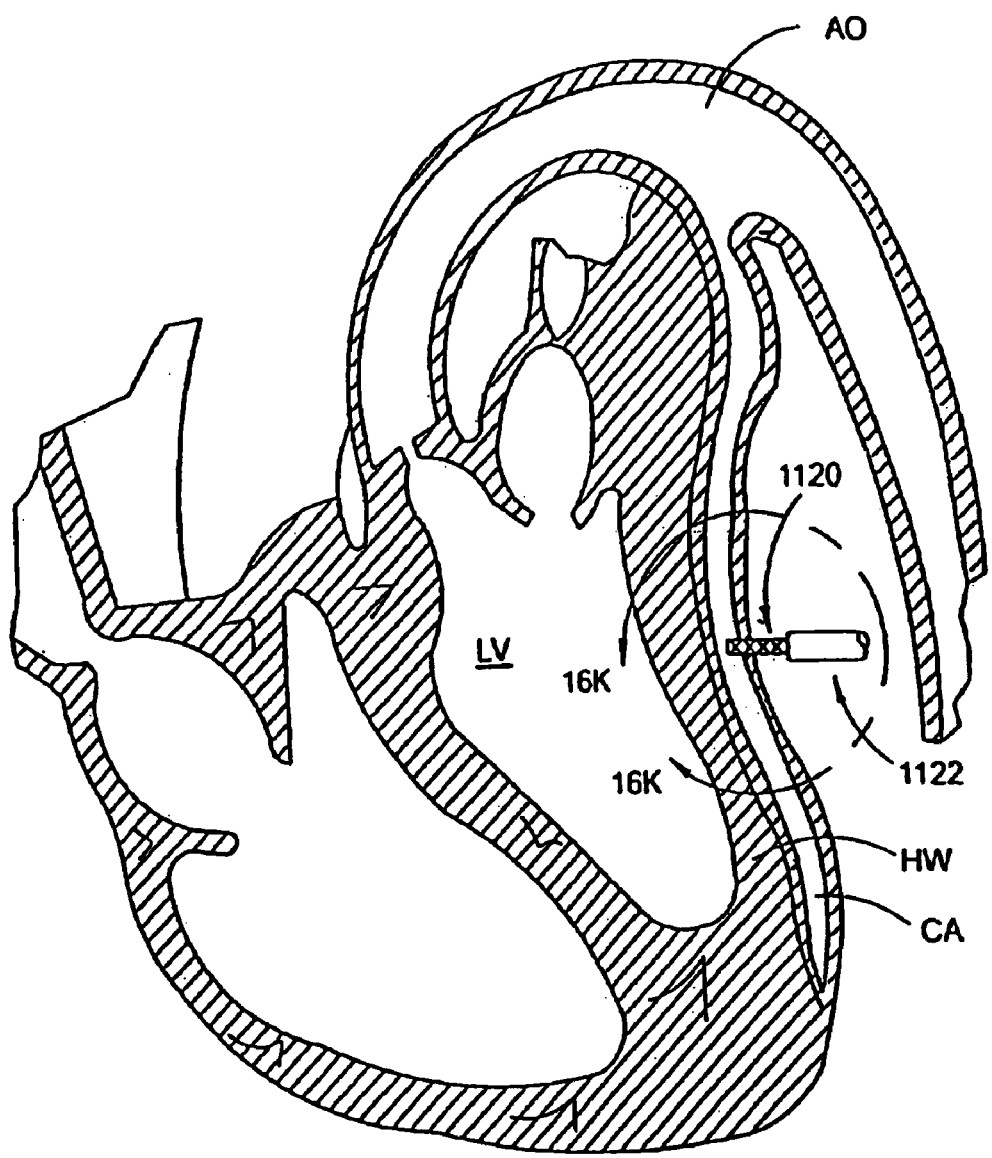
FIGS. 16J–16N are schematic, cross-sectional views of the external insertion of absorbable intramyocardial plugs used to form a conduit or shunt through the myocardium from the left ventricle to the coronary artery.
Figure 16K:
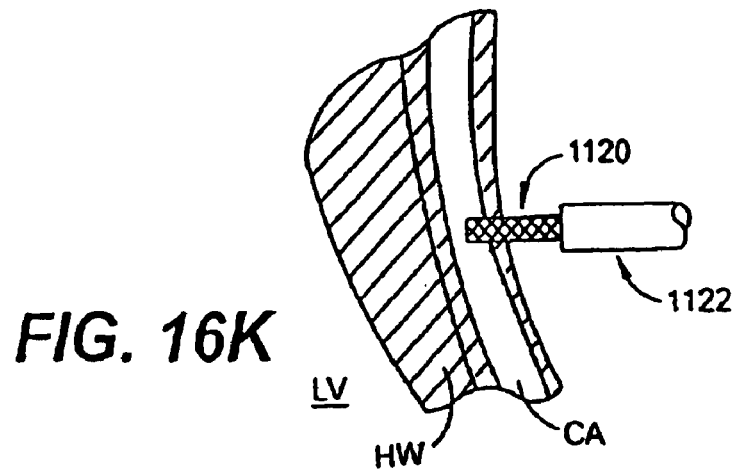
Figure 16L:
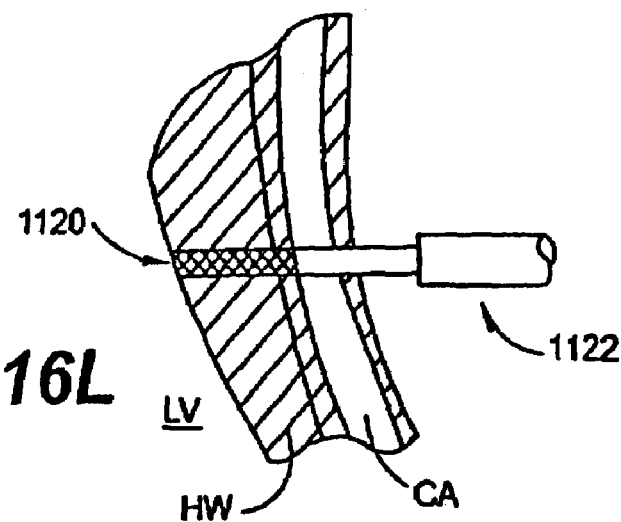
Figure 16M:
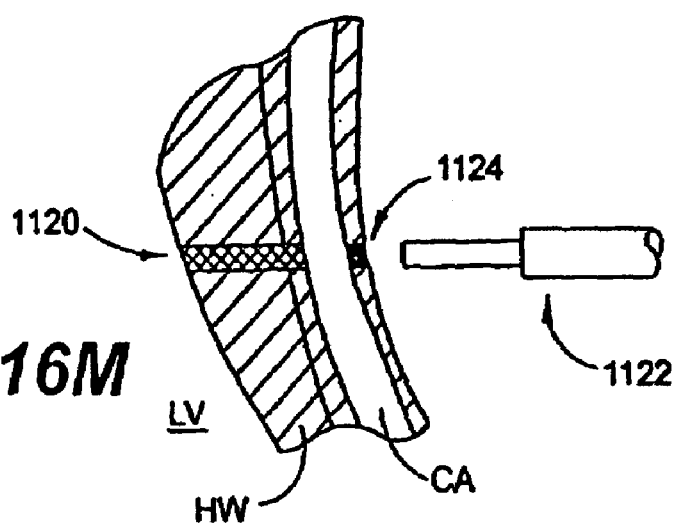
Figure 16N:
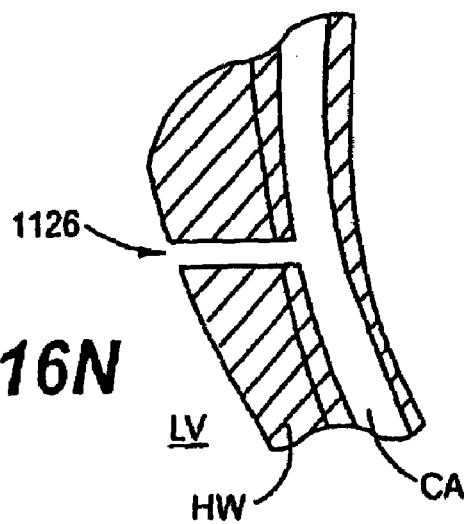

Turning now to FIGS. 16J–16N, there is shown the insertion of an absorbable intramyocardial plug 1120 that achieves the same result as a stent. The plug 1120 is inserted through the posterior wall of the coronary artery CA, either externally as described below, or internally using a delivery catheter threaded through the aorta AO and the coronary artery CA. External insertion is illustrated in FIGS. 16J–M. In FIG. 16J, there is illustrated a thoroscope 1122 having the absorbable plug 1120 at its distal end inserted into the chest of the patient, until it reaches the heart. The plug 1120 is inserted through the posterior wall of the coronary artery CA and into the heart wall HW (FIGS. 16K and 16L). As the delivery device 1122 is removed, the hole in the anterior wall of the coronary artery CA is closed, using sutures 1124, staples, laser coagulation, plugs such as GELFOAM, adhesives such as cyanoacrylate, or similar closure means, as illustrated in FIG. 16M. As the plug 1120 is absorbed, a shunt 1126 is formed between the left ventricle LV and the coronary artery CA, which allows for the passage of blood (FIG. 16N).

Figure 16O:
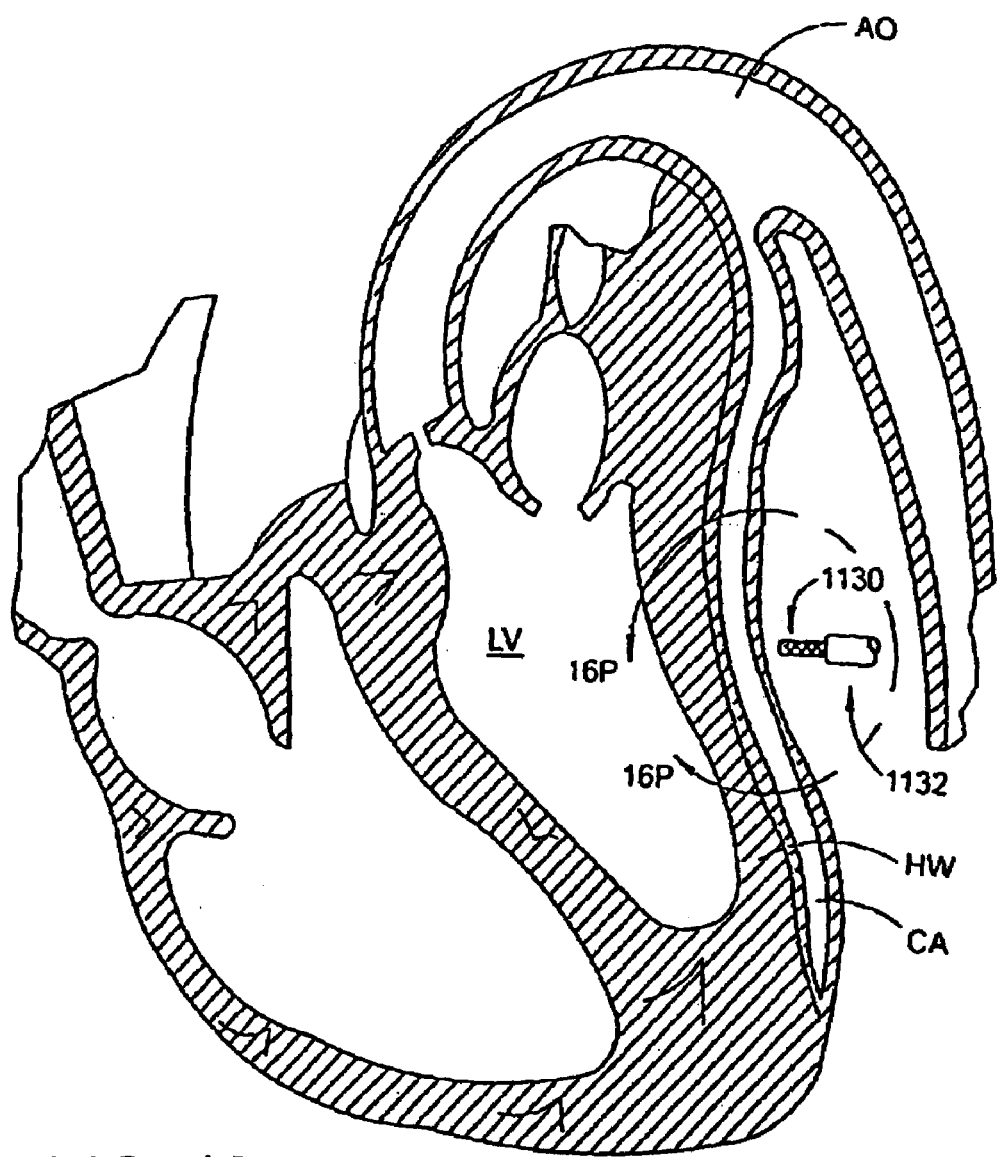
FIGS. 16O–16S are schematic, cross-sectional views of the external insertion of absorbable intramyocardial plugs in the myocardium.
Figure 16P:
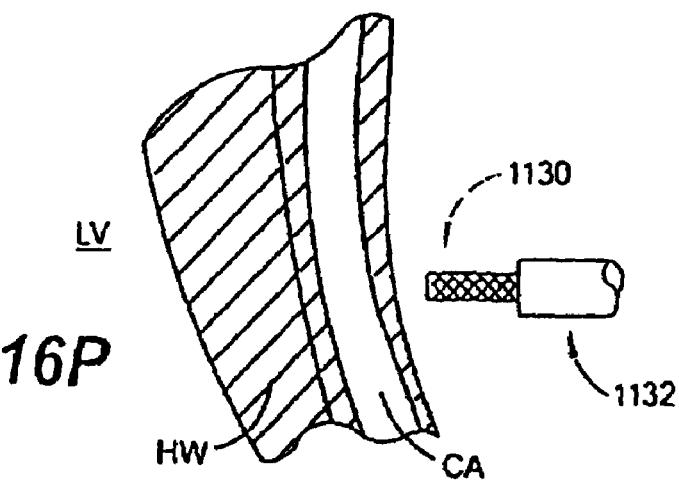
Figure 16Q:
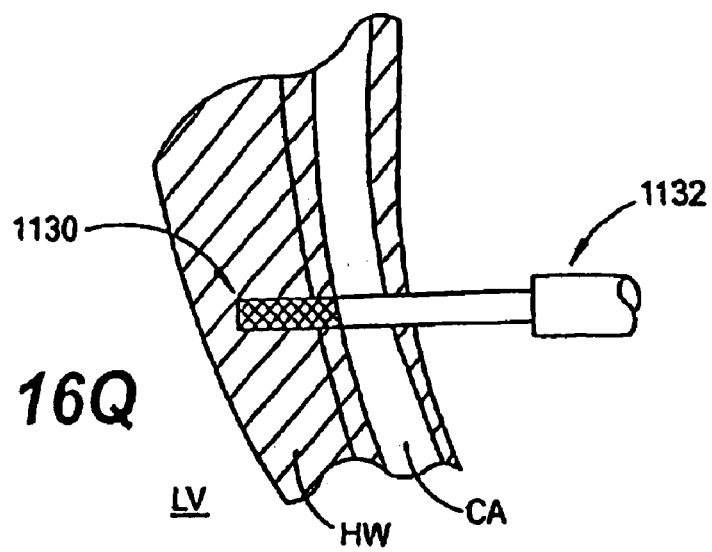
Figure 16R:
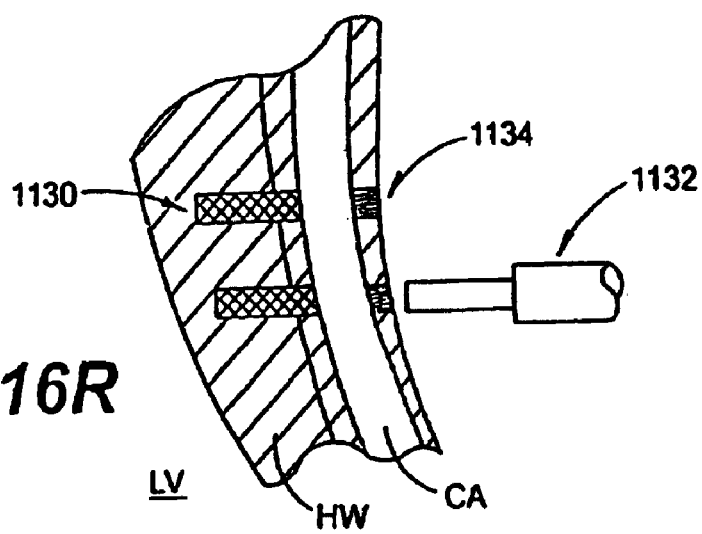
Figure 16S:
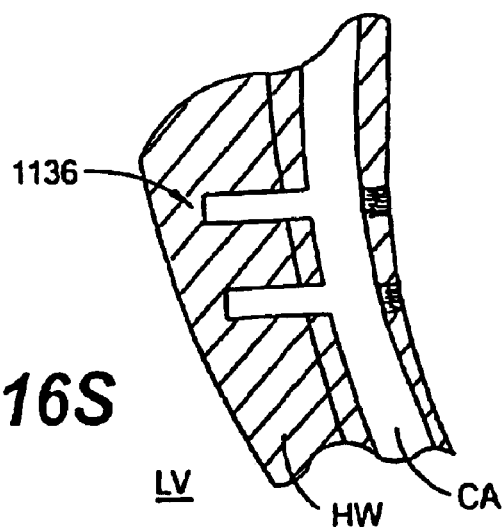

FIGS. 16O–16S illustrate the insertion of absorbable intramyocardial plugs 1130 which result in the perfusion of the heart wall HW with blood flowing through the coronary artery CA. In FIG. 16O, there is illustrated a thoroscope 1132 having the absorbable plug 1130 at its distal end being inserted into the chest of the patient, until it reaches the heart. The plug 1130 is inserted through the posterior wall of the coronary artery CA, and only partially through the heart wall HW such that it stops before reaching the left ventricle LV of the heart (FIG. 16Q). As the delivery device 1132 is removed, the hole in the anterior wall of the coronary artery CA is closed, using sutures 1134, staples laser coagulation, plugs, such as GELFOAM, adhesives such as cyanoacrylate or similar closure means, as illustrated in FIG. 16R. The plug 1130 is absorbed over time, leaving an opening or channel 1136 in the heart wall HW (FIG. 16S) that perfuses with oxygenated blood from the coronary artery CA. The channel 1130 acts as do the channels formed in the heart during percutaneous transmyocardial revascularization (PTMR), allowing the heart muscle to be exposed to additional oxygenated blood.

It is to be appreciated that the drawings herein are schematic. The stents and shunt portions in the forms of stents described herein may have a conventional wire infrastructure not shown in the drawings. Alternatively, the stents may be made of an elastic material having an internal spring constant permitting the stent to be temporarily collapsed and then returned to an opened configuration.

Intravascular or extravascular incising instruments disclosed herein for use in forming passageways or channels in the myocardium may be contact lasers or rotating or reciprocating drills. Other drilling or cutting instruments suitable for forming channels or tunnels may be used alternatively or additionally. Such instruments may take the form of ultrasonic cavitation devices, chemical devices for dissolving tissues, or heat treatment (electrocautery) devices.

Although suturing, gluing and laser welding are discussed herein for attaching plugs and reinforcement patches or braces to the cardiac tissues, equivalent alternatives to these techniques include stapling and tacking. Also, apertures in the epicardium or coronary artery may be closed without plugs or patches, for example, by the direct application of sutures or staples or by coagulation (electrical, thermal or laser).

It is to be understood that stents are preferred for maintaining open blood flow passageways in or through the myocardium. However, in some cases, stents may be omitted, for example, in the embodiments of FIGS. 10C, 11, 12, 14A and 14B and 15, depending on the needs of the patient.

Generally, stent 36 (FIG. 3), upstream portion 56 (FIGS. 6A, 6B) when in the form of a stent, stent 70 (FIG. 8), plugs 98, 98a, 98b (FIG. 11), stents 106a–106d (FIG. 12), and plugs 122, 122a, 122b (FIG. 15) have lengths which are predetermined by measuring the thickness of the myocardium. Procedures for such measurements are described in U.S. Pat. Nos. 5,429,144 and 5,662,124, the disclosures of which are hereby incorporated by reference in their entirety.

Self-Inserting Conduits

As is well known, the coronary artery CA branches off the aorta AO and is positioned along the external surface of the heart wall HW. Oxygenated blood flows from the heart PH to the aorta AO, into the coronary artery CA, and on to the rest of the body. In some individuals, plaque builds up within the coronary artery CA, blocking the free flow of blood and causing complications ranging from mild angina to heart attack and death.

In view of restoring the flow of oxygenated blood through the coronary artery CA, embodiments are disclosed which provide for the shunting of blood directly from the heart to a site in the coronary artery CA which is distal to the blockage BL. In a similar manner to that described above, a single rod-like conduit may utilize posterior heart wall access in order to be inserted through the walls of the coronary artery CA and the heart wall HW, and from there into the left ventricle LV of the heart PH which lies beneath the coronary artery CA. The hollow conduit is positioned such that the openings on either end of the conduit are within the coronary artery CA and the left ventricle LV. Blood flows through the opening in the left ventricle LV, through the hollow conduit and out of the opening positioned in the coronary artery CA distal to the site of the blockage BL. Thus, the self-inserting conduit is preferably rigid or at least semi-rigid in order to provide the ability to pierce through the heart wall or other tissue of the patient and to install the conduit as described above. In this case, the conduit is preferably a delivery rod in that it provides for its own delivery.

Figure 17:
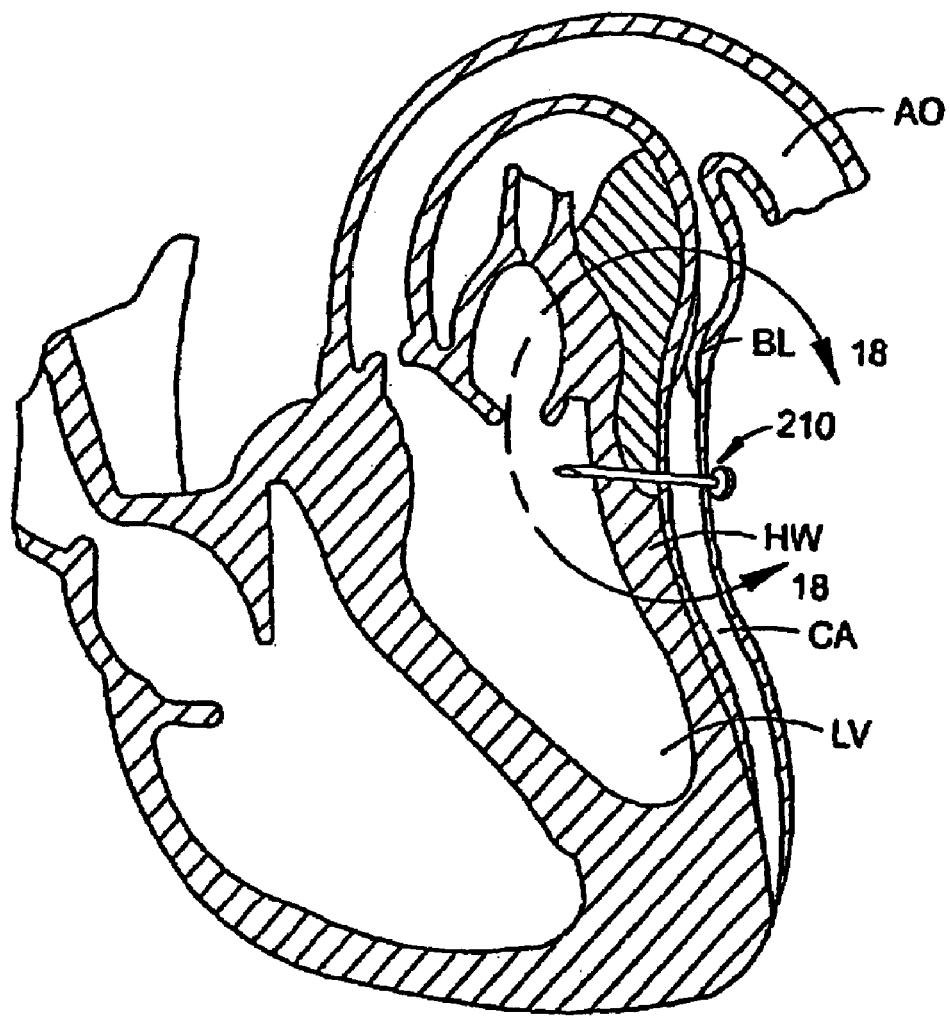
FIG. 17 is a small scale cross-sectional view of a heart with a blockage in the coronary artery and illustrating a self-inserting conduit.

Referring to FIG. 17, there is shown a cross-sectional view of a typical heart PH, aorta AO, and the coronary artery CA having a blockage BL therein. The coronary artery CA lies along the external surface of the wall of the heart HW. As is well known, the coronary artery CA supplies oxygenated blood pumped from the left ventricle of the heart LV and through the aorta AO to the heart muscle or heart wall HW.

FIG. 17 also illustrates in schematic fashion a bypass device 210 implanted distal to the blockage BL in the coronary artery CA. It should be noted that only the presently preferred embodiments of the bypass devices are described herein and only then in accordance with certain figures. However, arteries and vessels other than the coronary artery CA may be treated. As used herein, the term "vessel" shall be deemed to embrace any body organ, vessel, space or vasculature, including artificial members or prior implants, which contains or can contain bodily fluid. In addition, other types of blockages or vascular defects can be treated, including, for example, vascular bypass in other areas to alleviate problems such as aneurysms, deep vein thrombosis, or other types of calcified or stenosed vessels. Embodiments described herein may be used to bypass obstructed bile ducts in the liver, or to direct the blood supply away from tumors in an effort to destroy them. Access devices using configurations other than conduit devices as herein described, may also be implemented. Thus, the following description should not be construed to be limiting in any way.

Figure 18:
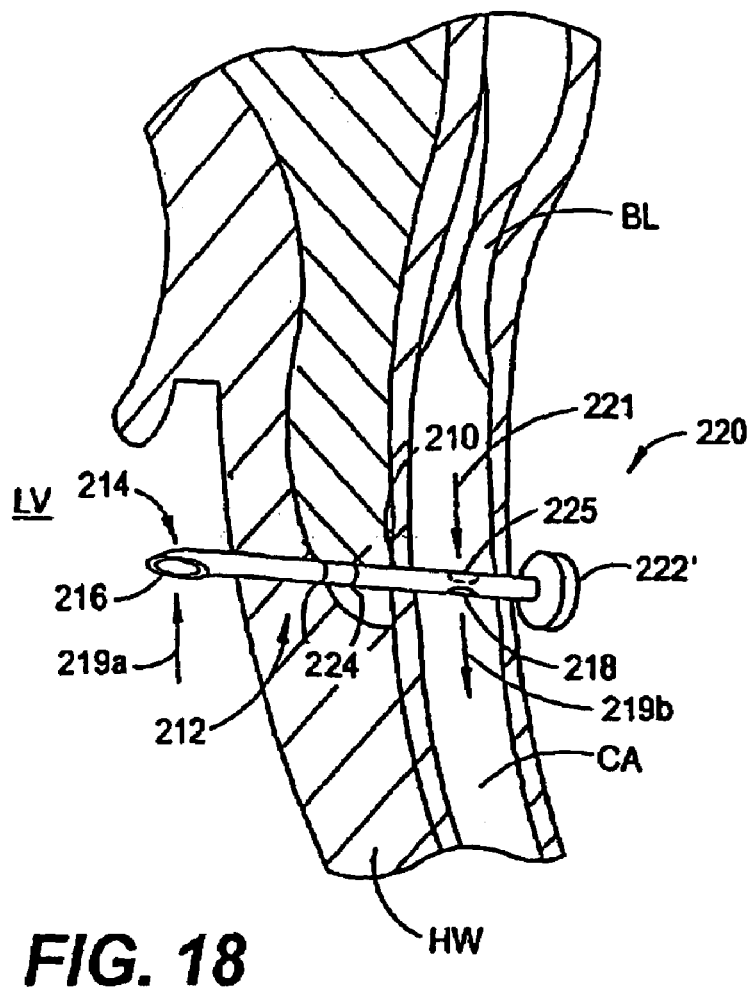
FIG. 18 is a close-up perspective view of one embodiment of the device of FIG. 17 shown implanted in the myocardium, with the coronary artery, myocardium and left ventricle of the heart shown cut-away.

Referring to FIG. 18, there is shown in greater detail one preferred embodiment of the bypass apparatus 210 of the present invention. The apparatus 210 is preferably formed of a biocompatible material, such as metal or a polymer. The apparatus 210 is shown piercing the coronary artery CA distal to the site of the blockage BL. The details of this conduit device 210 are described below. In connection with the somewhat schematic representation of FIG. 18, it will be noted that the device 210 pierces completely through the coronary artery CA, with the central portion 212 of the device 210 positioned within the myocardium HW and the distal portion 214 of the device 210 implanted in the left ventricle of the heart LV.

Each shunt device 210 (FIG. 18) is comprised of a central portion 212 formed by a hollow lumen having respective aperture or openings 216, 218 on each end. One opening 216 receives blood from the left ventricle LV and shunts it through the lumen and out the other opening 218 which is positioned in the coronary artery CA. The conduit 210 therefore allows oxygenated blood to flow directly from the left ventricle LV and into the coronary artery CA, as indicated by the arrows 219a and 219b in FIG. 18.

The distal end of the conduit 214 may be blunt (FIG. 20B) or tapered if desired (FIG. 18) to aid in the insertion of the device 210 through the coronary artery CA, the heart wall HW and the left ventricle LV. The proximal end 220 of the conduit 210 is preferably provided with a head portion 222 that is larger than the diameter of the lumen (FIG. 18), to help anchor the conduit 210 in place and prevent it from migrating or passing completely through the coronary artery CA. This head portion 222 also acts to seal the puncture in the coronary artery CA formed by the distal tip 214 of the conduit 210. The blood therefore flows through the conduit 210 and downstream within the coronary artery CA and not out through the puncture opening. If desired, the head portion 222 of the device 210 may be sutured into the surrounding tissue to prevent the device 210 from migrating from its proper position. Additional anchoring in the form of sutures or other means 224 is also preferably provided along the central portion 212 of the conduit 210. Anchoring the device 210 into the myocardium HW prevents migration of the conduit 210 from its proper position.

Figure 18A:
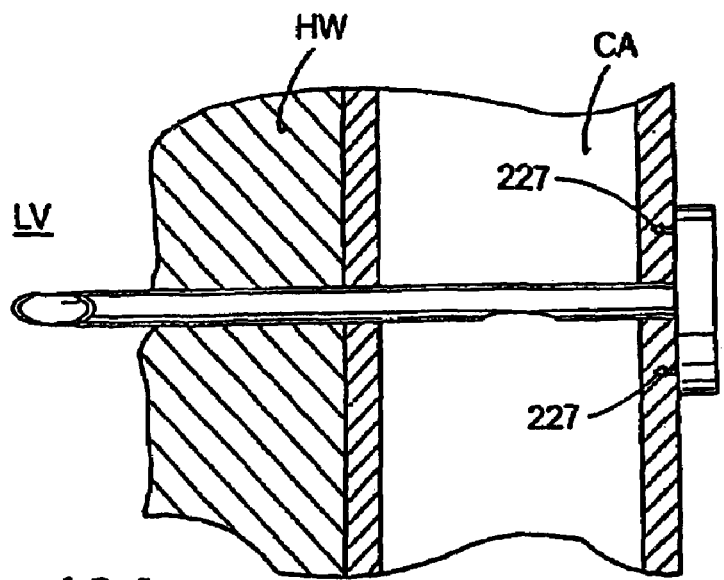
FIG. 18A is a schematic partial cross-sectional view of a self-inserting conduit, having dual prongs in the head or flange thereof to prevent rotation.

As illustrated in FIG. 18, the conduit 210 may also include a second opening 225 at its proximal end 220 opposite from the first opening 218. This second opening 225 allows for the perfusion of blood from the coronary artery CA as shown by the arrow 221 in FIG. 18, i.e., if the blockage BL does not completely block the coronary artery CA, blood may perfuse past the blockage BL and through the second opening 225. FIG. 18A illustrates a self-inserting conduit having a flange or head with dual prongs 227 to prevent rotation of the conduit in the coronary, to ensure proper blood flow through the opening 218.

In installing the device of this embodiment, the surgeon may make a small incision of a keyhole type in order to gain access to the blocked vessel. Visual access may be obtained through thoroscopy or similar endoscopic procedure. Such access is very minimally invasive. Once the area of blockage is located (through fluoroscopy, etc.), the conduit 210 is implanted in the body in the manner described above. The conduit device 210 is preferably introduced by way of an automatic gun or needle in order to reduce procedure time and avoid bleeding, but the conduit 210 may be implanted in other ways as well.

Figure 19A:
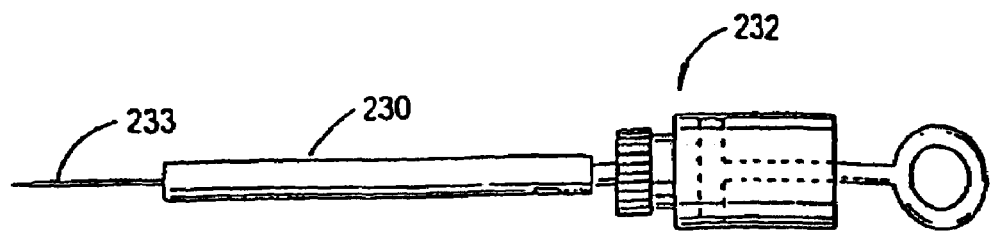
FIGS. 19A–C illustrate a method for implanting the conduit device of FIG. 17.
Figure 19B:
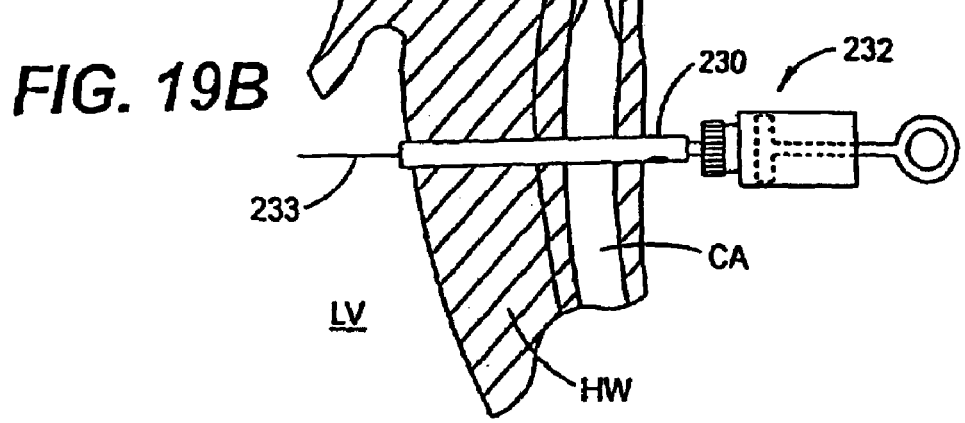
Figure 19C:
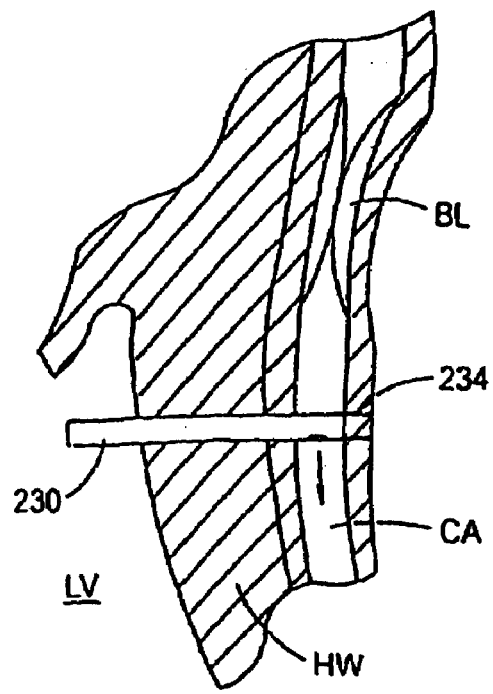

One method for implanting the device is illustrated in FIGS. 19A–C. The conduit 230 is first mounted over a needle 232 (FIG. 19A), and the needle 232 is used to puncture the coronary artery CA, heart wall HW and left ventricle LV (FIG. 19B). The distal end of the needle 232 is indicated by reference numeral 233. The needle 232 is then removed (FIG. 19C) and the anterior hole in the coronary artery CA is closed using sutures 234 or other suitable methods.

Figure 20A:
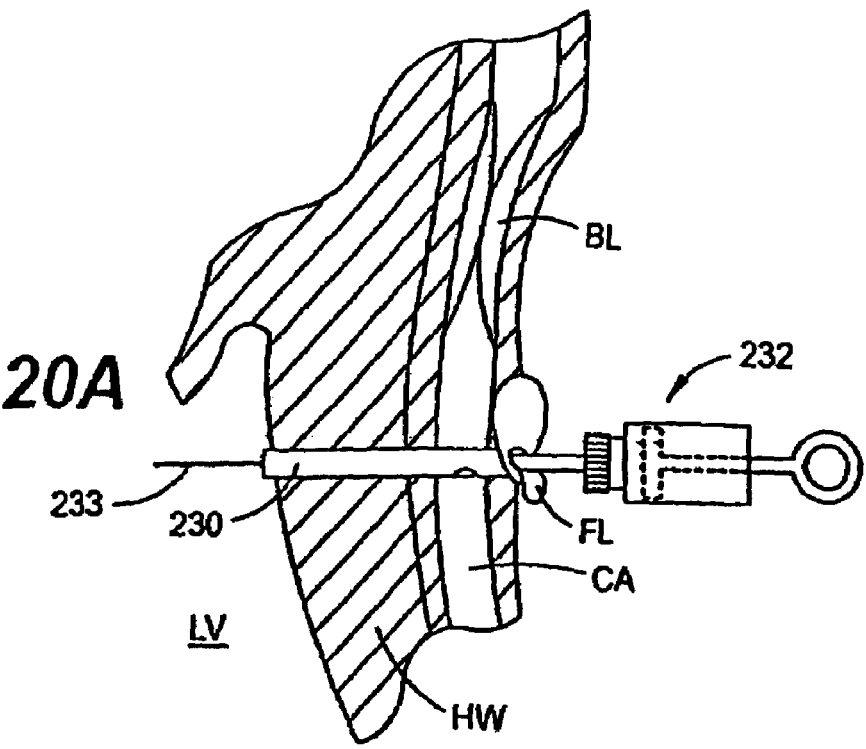
FIGS. 20A–B illustrate an alternate method for implanting the conduit device of FIG. 17.
Figure 20B:
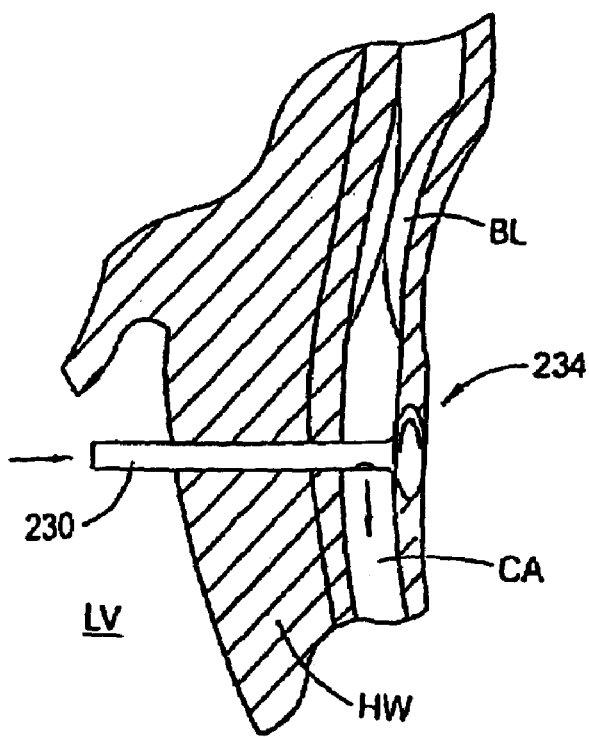

In an alternate method illustrated in FIGS. 20A and 20B, a flap FL is first cut in the wall of the coronary artery CA and the needle 232 bearing the conduit 230 is inserted through the flap FL and through the other side of the coronary artery CA, through the heart wall HW, and into the left ventricle LV. The needle 232 is withdrawn, leaving the conduit 230 in place. The flap FL is then closed using sutures 234 or other suitable means.

The conduit 230 is preferably anchored in place in the heart wall HW as described above to prevent migration and to ensure that the free flow of blood from the left ventricle LV to the coronary artery CA is maintained.

Coronary Bypass

Figure 21:
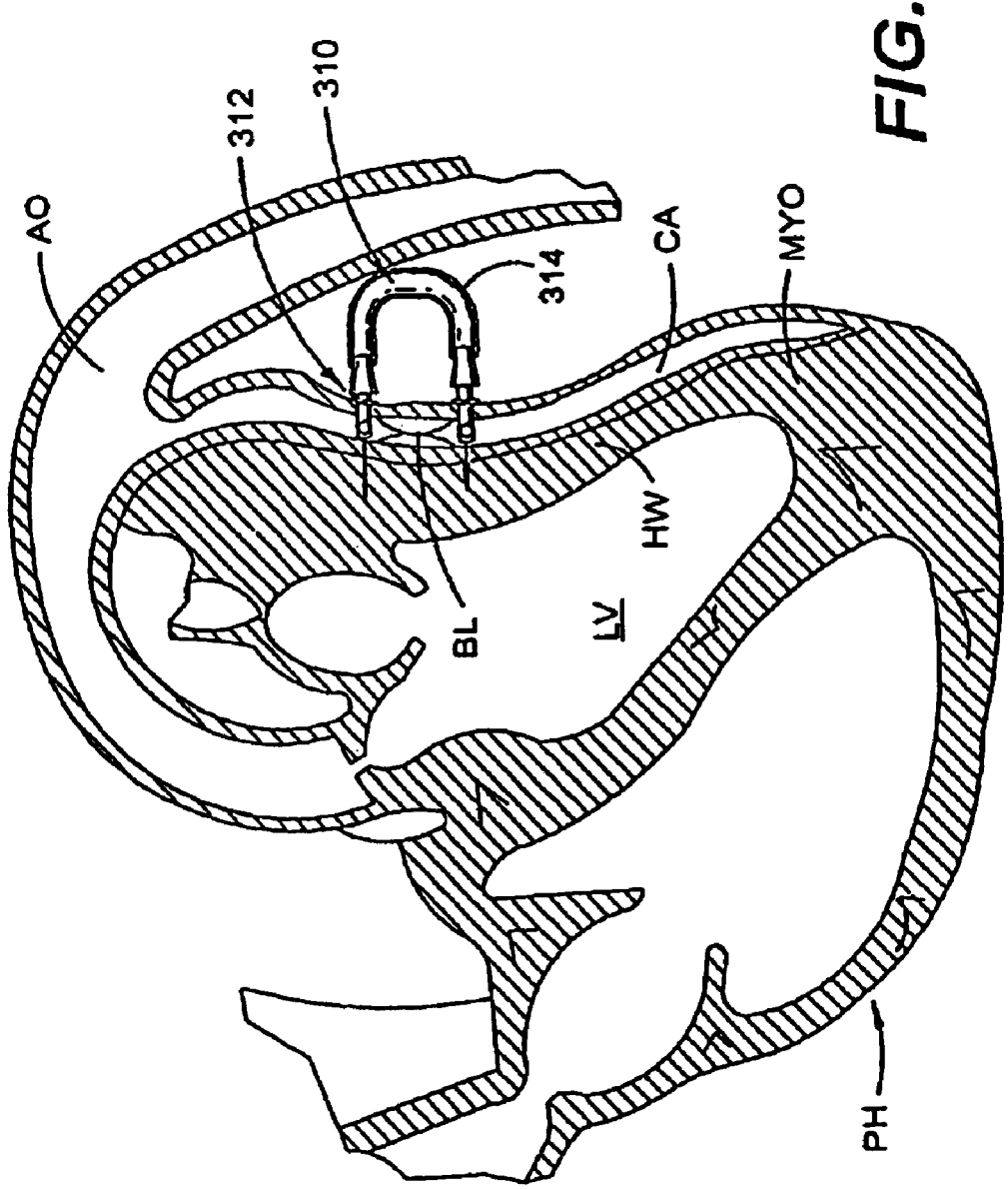
FIG. 21 is a small scale cross-sectional view of a heart with a blockage in the coronary artery, and further illustrating another embodiment of the bypass device of this embodiment.

Referring to FIG. 21, there is shown a cross-sectional view of a typical heart anatomy including the aorta AO with a blockage BL or stenosis in the coronary artery CA which is positioned along the external surface of the heart wall HW. As is well known, the coronary artery CA supplies blood pumped from the left ventricle LV to the aorta AO and into the heart muscles or myocardium HW.

FIG. 21 also illustrates in schematic fashion a bypass device 310 mounted both proximally and distally of the blockage BL by means of conduit combination access/shunt devices 312 and bypass conduit 314, described in more detail below.

Figure 22:
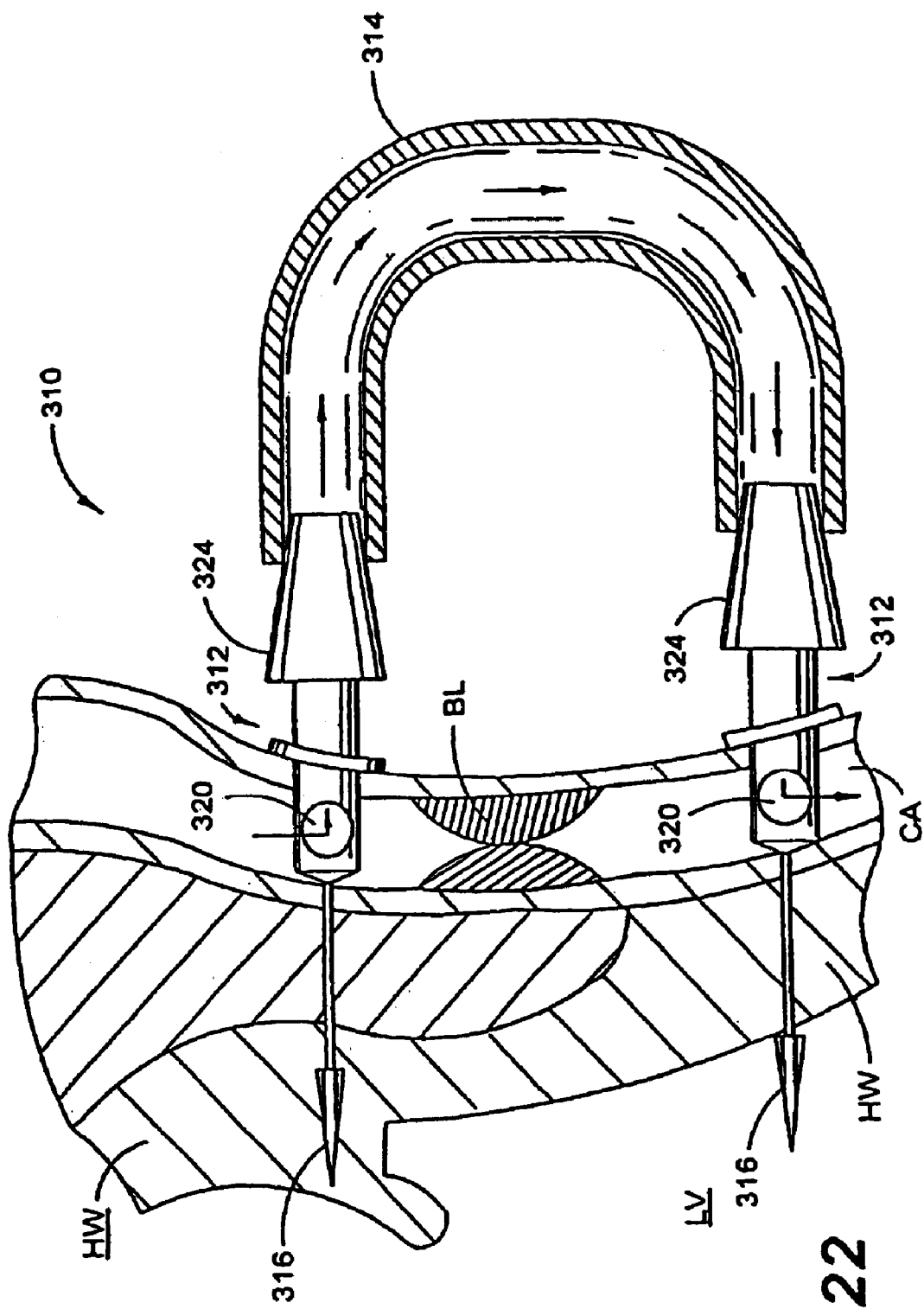
FIG. 22 is a close-up cross-sectional view of the blockage in the coronary artery and illustrating in greater detail the bypass device of the present invention.

Referring to FIG. 22, there is shown in greater detail one preferred embodiment of the bypass apparatus 310. The apparatus 310 is preferably formed of a biocompatible material, such as metal or a polymer. A pair of combination access/shunt devices 312 is shown proximally and distally of the blockage BL. The details of these conduit devices 312 are described below and shown in connection with FIGS. 24 and 25. In connection with FIG. 22, it will be noted that each access/shunt device 312 pierces completely through the coronary artery CA on the outside, leaving the conduit portion 316 of the device 312 implanted in the wall of the heart wall HW. The conduit portion 316 pierces not only through the coronary artery CA, but also into the tissue to provide anchoring and stabilization of the artery. The conduit portion 316 can be embedded in a tissue or passed completely through the tissue and into the left ventricle LV as shown in the portion of the device distal to the blockage BL.

Figure 22A:
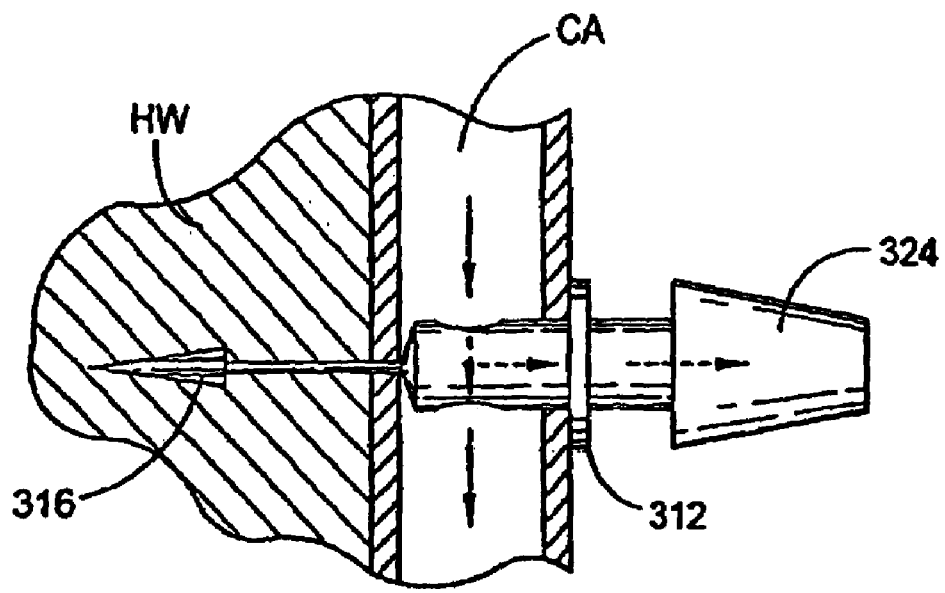
FIGS. 22A–22B are schematic partial cross-sectional views of conduits similar to that described in FIG. 22 illustrating alternative blood flow embodiments.
Figure 22B:
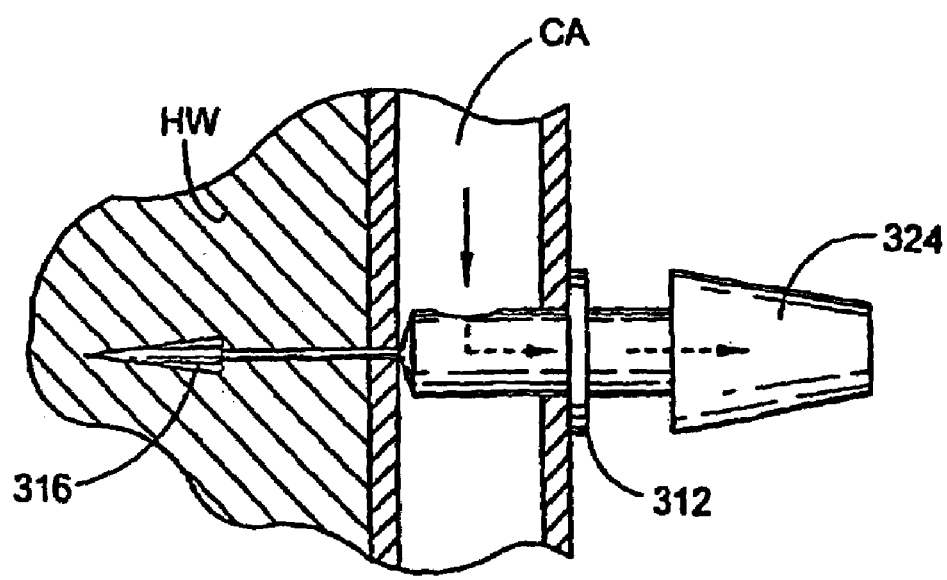

FIGS. 22A–22B illustrate two alternative embodiments for conduits of the nature described above. In FIG. 22A, the conduit is preferably placed proximally in the coronary artery CA to preferably allow some of the proximal flow in the coronary artery CA through the conduit and past the blockage BL to a downstream location in the coronary artery CA. This embodiment is preferably utilized in connection with blockages which are not complete, and yet advantageously also allows for bypass flow as described above. The conduit of FIG. 22B, however, does not allow any proximal flow through the coronary and all flow is diverted through the bypass.

Each access/shunt device 312 (e.g., see also FIG. 24) is comprised of a shunt portion 318 having an aperture 320 which, in the case of the proximal device, receives blood from the coronary artery CA and shunts it into a diversion tube 322 mounted proximally with respect to the conduit portion 316 and the aperture 320. The diversion tube 322 is in fluid communication with the aperture 320 to allow blood flow from the coronary artery CA into the aperture 320 and into the diversion tube 322 as indicated by the arrows in FIG. 22. Mounted proximally with respect to the diversion tube 322 is a connector piece 324 which is also in fluid communication therewith. The combination access/shunt device 312 which is distal of the blockage BL may be constructed in a similar fashion or may have another configuration in which blood flows in the direction opposite that indicated by the arrows in FIG. 22. The bypass conduit 314, which is hollow, is mounted on the two connector portions 324 of the devices 312, as shown in FIG. 22, to allow blood to bypass the blockage BL. The conduit 314 may be constructed from a vein or artery graft taken from the patient or a donor, an artificial vein graft, or any other biocompatible tubing including one made from a metal or polymer. All these connections are fluid-tight, as described below in more detail, to avoid hemorrhaging. FIG. 22 illustrates the conduit portion 314 somewhat exploded away from the connector portions 324 in order to illustrate the manner in which the complete bypass system can be assembled.

Figure 23:
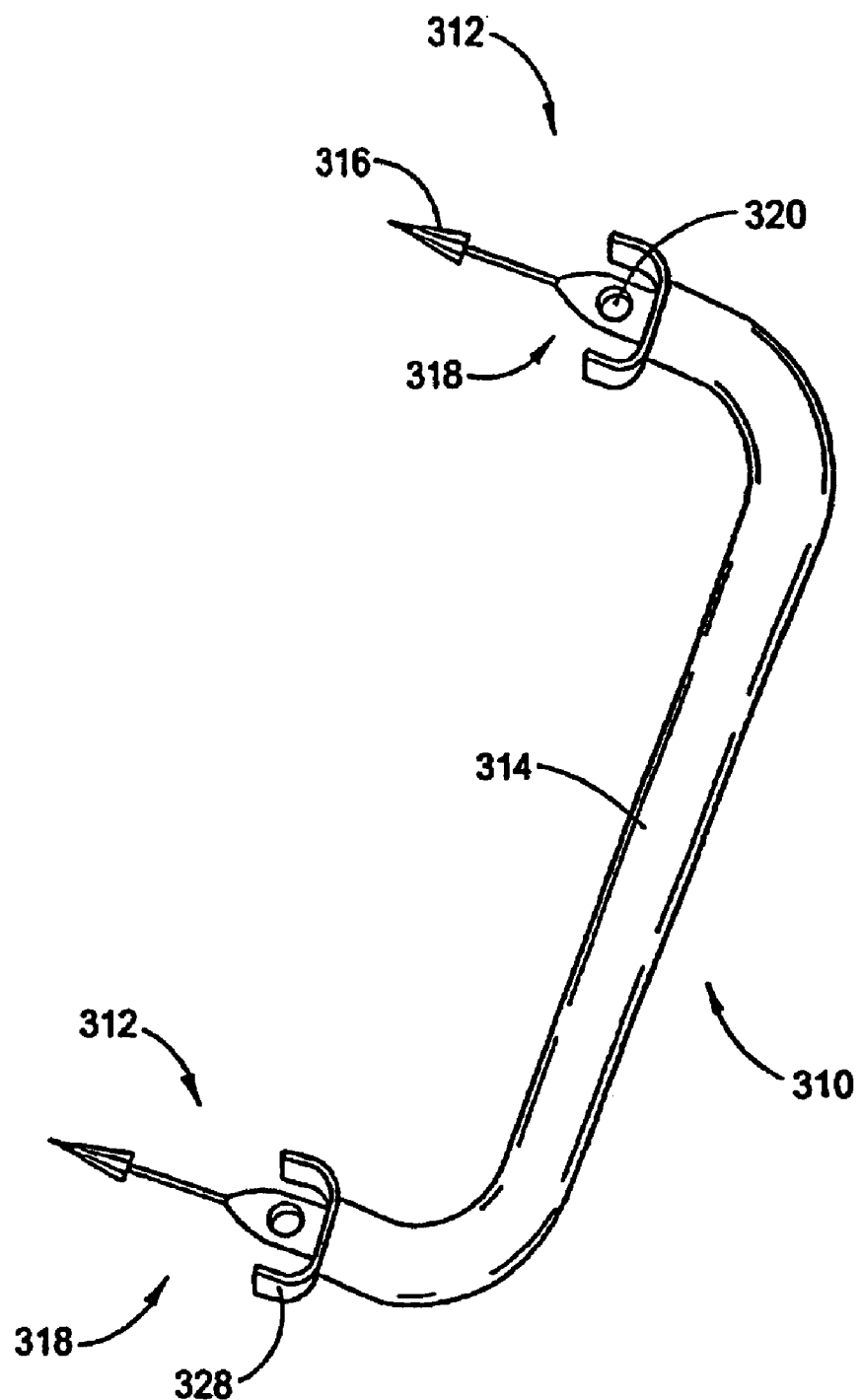
FIG. 23 is a perspective view of the bypass device and conduit.

FIG. 23 illustrates the conduit portion 314 of the bypass system 310 completely press-fit or snapped-down over the connector portions 324 (not shown in FIG. 23), as is the case in the final installation of the system.

Figure 24:
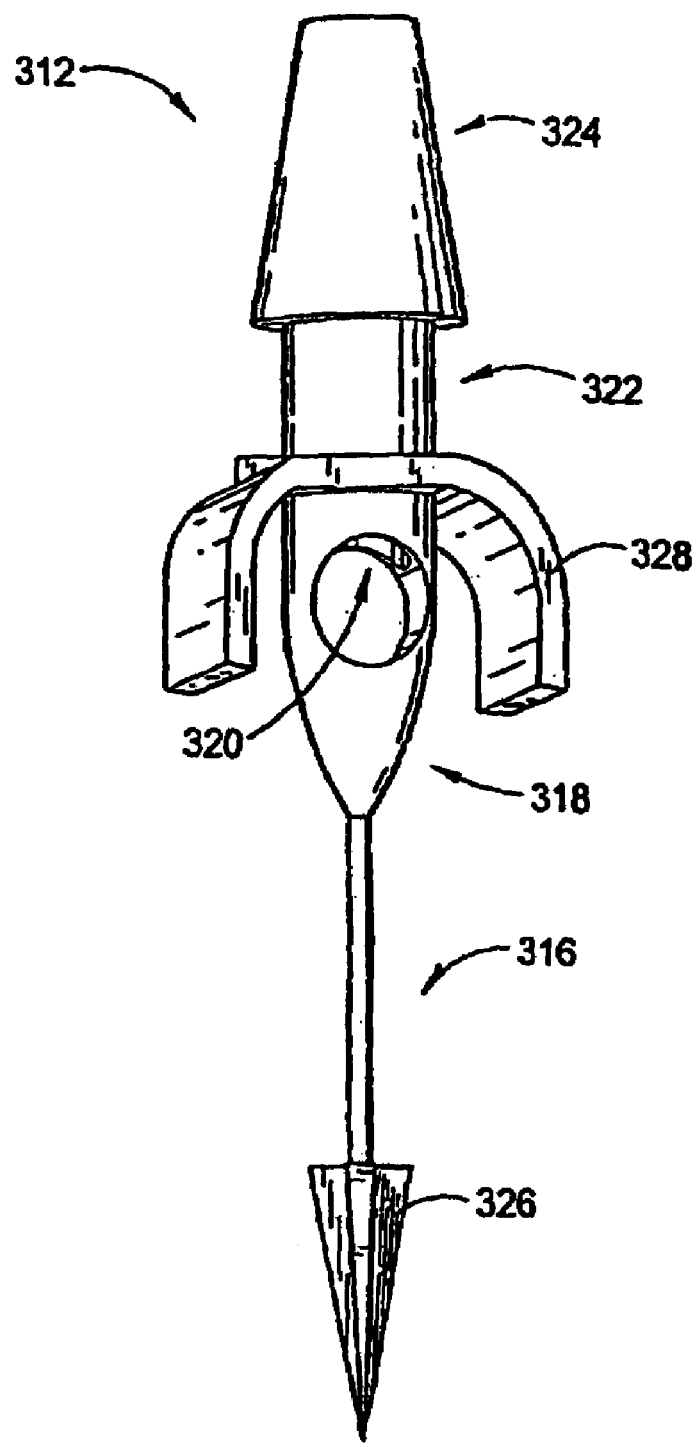
FIG. 24 is a close-up view of a combination access/shunt conduit device having a distal tip.

FIG. 24 illustrates the combination access/shunt device 312 in greater detail. The distal conduit portion 316, as described above, provides access to the coronary artery CA by piercing completely through and into the surrounding tissue. A barbed distal portion 326 having one or more barbs provides anchoring for the entire device. The proximal shunt portion 318 which resides in the vessel comprises the aperture 320 to allow blood to flow therein and from there, at a right angle, into the diversion tube 322 mounted proximally with respect to the aperture 320, as indicated by the arrow in FIG. 24. The proximal shunt portion 318 may be tapered if desired to aid in the insertion of the device 312 through the coronary artery CA and into the heart wall HW. Mounted on top of the diversion tube 322 is a connector tube 324 for receiving the bypass conduit 314 as described above. It will be noted that the connector tube 324 is frusto-conical in order to provide a fluid-tight press-fit for the bypass.

In a preferred embodiment, a biocompatible fabric or mesh (not shown) is incorporated into the structure of the device. This fabric or mesh helps to seal the vessel to prevent bleeding and provides a structure which allows endothelial cells to infiltrate the device 312 and incorporate it into the surrounding tissues.

Likewise, FIG. 24 illustrates an inverted U-shaped saddle portion 328 of the device 312 which serves a dual purpose. This saddle portion 328 fits over the artery when the combination access/shunt device 312 is installed therein, thereby stabilizing the artery. In addition, this saddle device 328 acts as a flange for self-sealing the puncture in the coronary artery CA formed by the barbed distal tip 326. In addition, the collar or saddle that may help contain the artery and mitigate any possible migration problems. Thus, blood flows through the diversion tube 322 and not out through the puncture opening. If desired, a loop may be added to the saddle portion 328 to allow the device to be sutured into the myocardium HW to prevent the device from migrating from its proper position.

Figure 25:
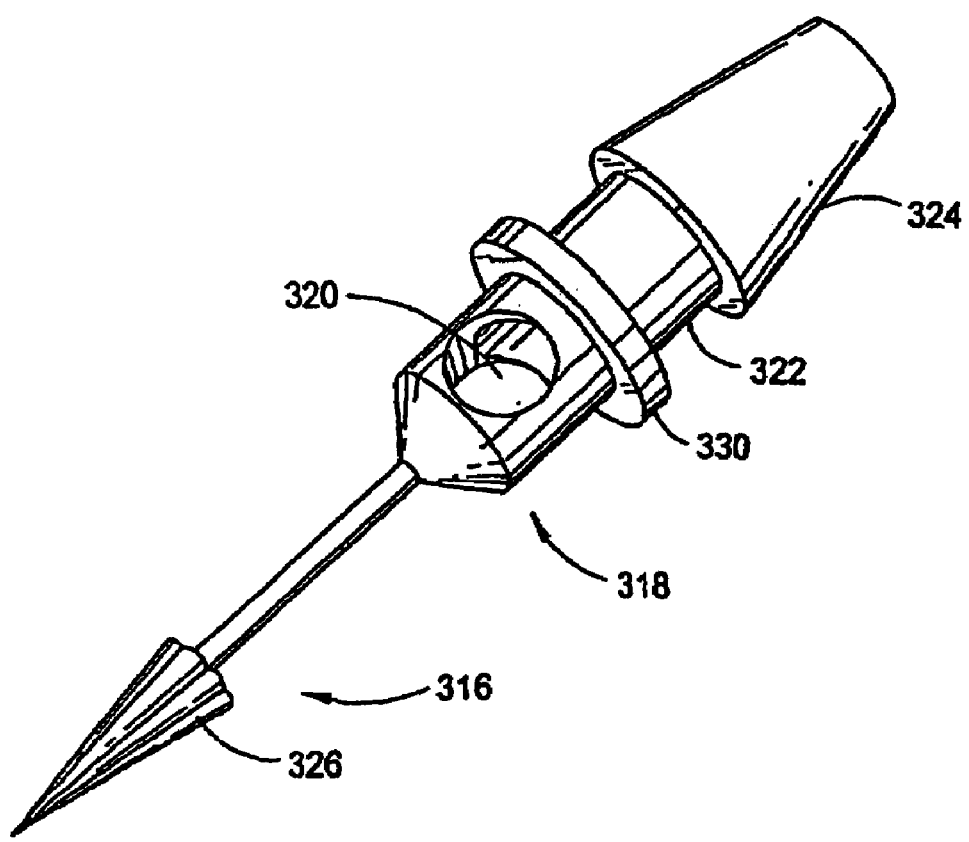
FIG. 25 is a perspective view of an alternative embodiment of a combination access/shunt device conduit.

FIG. 25 is an alternative embodiment of the conduit access/shunt device of FIG. 24 in which a planar flange 330 serves to stabilize the artery and to self-seal the puncture therein.

Figure 27:
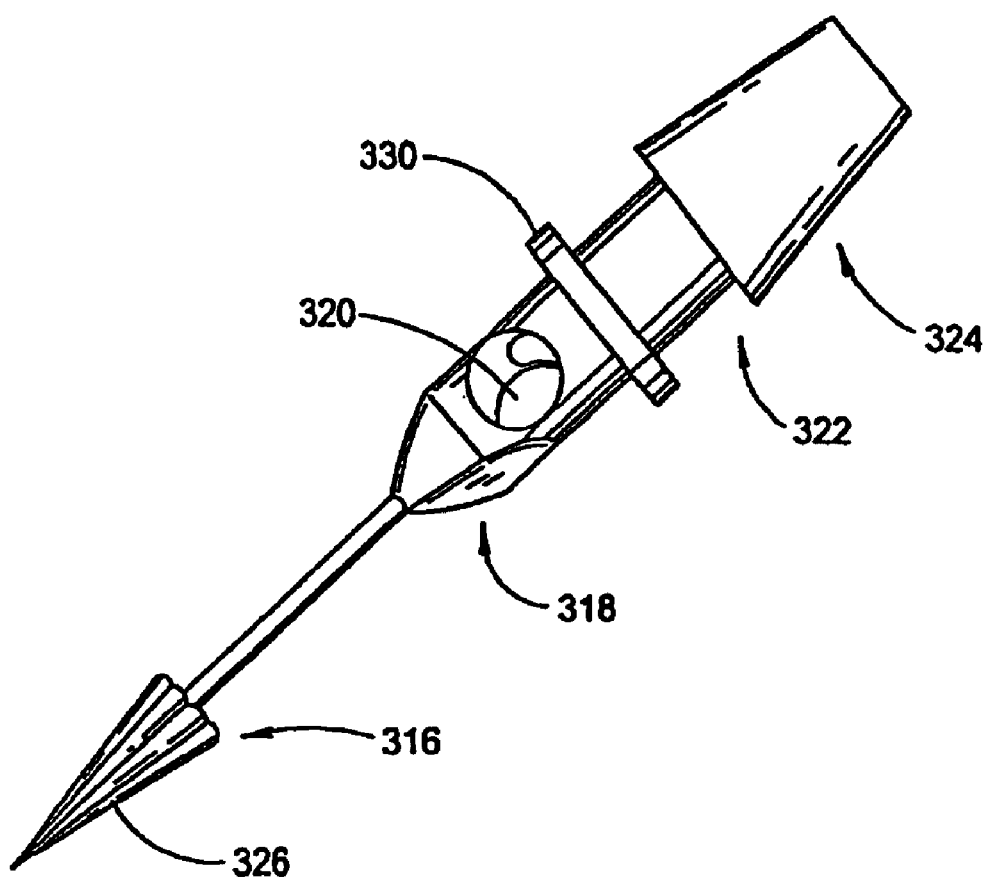
FIG. 27 is a perspective view of a third combination access/shunt embodiment which has a tapered configuration.
Figure 28:
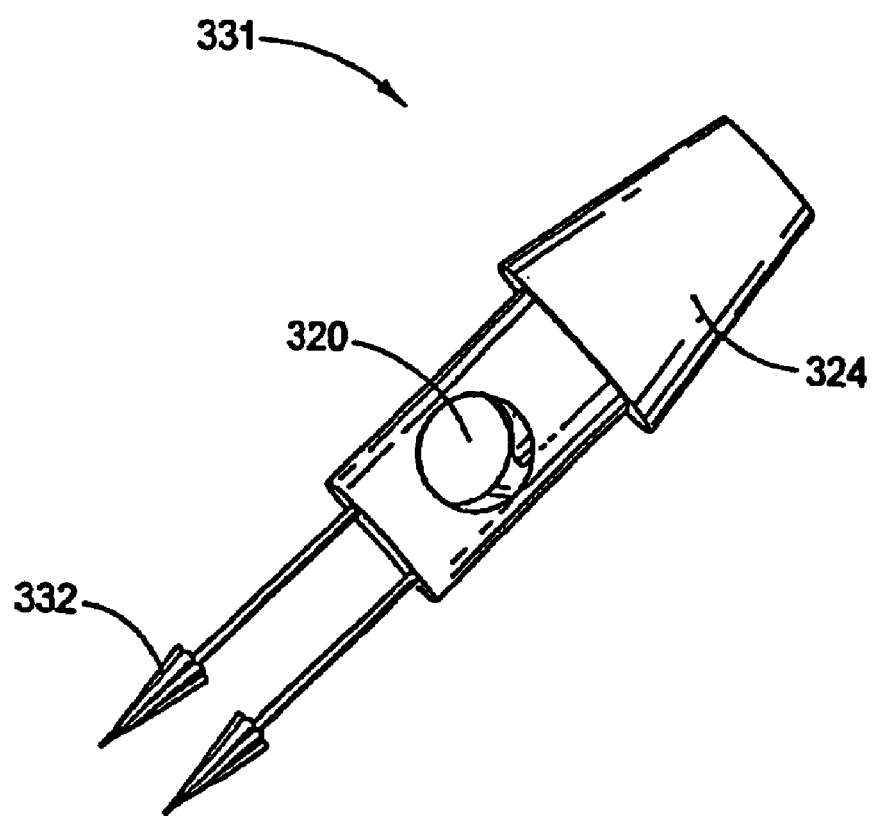
FIG. 28 is a perspective view of a fourth combination access/shunt embodiment with dual distal tips.

FIGS. 27 and 28 show views of two additional embodiments for device 312. FIG. 27 shows device 312 having a tapered configuration to aid in the insertion of the device 312. FIG. 28 shows a device 331 having dual distal tips to prevent rotation of the device when installed in the tissues of the patient.

In installing the device 310, the surgeon may make a small incision of a keyhole type in order to gain access to the blocked vessel. Visual access may be obtained through thoracoscopy or similar endoscopic procedure. Such access is very minimally invasive. Once the area of blockage is located (through fluoroscopy, etc.), one or both of the combination access/shunt devices 312 are installed in the artery in the manner described above. The conduit devices 312 would preferably be introduced by way of an automatic gun which would implant both conduit devices 312 and the conduit 314 at the same time in order to reduce procedure time and avoid bleeding. Alternatively, the conduits 312 could be introduced individually, provided that bleeding is controlled.

The device 310 can be sutured in place to provide for permanent bypass; alternatively, the device can be implanted temporarily to maintain the flow of blood through the coronary artery CA during bypass surgery. The device 310 is implanted as described above. A vein graft is sutured in place, with one end anastomosed to the aorta, and the other end to the coronary artery CA at a site distal to the blockage. The device 310 provides blood flow from the aorta to the coronary artery CA at a site distal to the blockage BL during the anastomosis. Once blood flow has been established through the vein graft, the bypass device may be removed.

Figure 29:
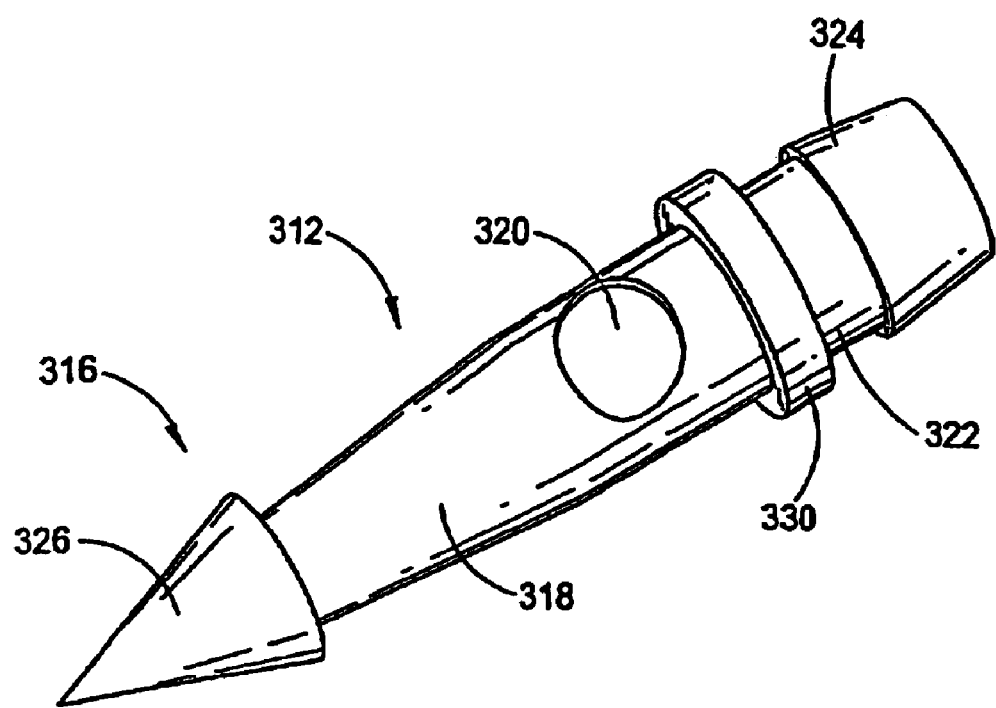
FIG. 29 is a perspective view of a conduit or shunt device according to a fifth embodiment of a combination access/shunt.

FIG. 29 illustrates a further embodiment of the combination access/shunt device 312. The distal conduit portion 316, as described above, provides access to the coronary artery CA by piercing completely therethrough and into the surrounding tissue. The barbed distal portion 326 having one or more barbs provides anchoring for the entire device. The proximal shunt portion 318 which resides in the vessel comprises an aperture 320 to allow blood to flow therein and from there, at a right angle, into the diversion tube 322 mounted proximally with respect to the aperture 320. The proximal shunt portion 318 may be tapered if desired to aid in the insertion of the device 312 through the coronary artery CA and into the heart wall HW. Mounted on top of the diversion tube 322 is a connector tube 324 for receiving a bypass conduit as described above. It will be noted that the connector tube 324 can be frusto-conical in order to provide a fluid-tight press-fit for the bypass. In a preferred embodiment, a biocompatible fabric or mesh (not shown) is incorporated into the structure of the device. This fabric or mesh helps to seal the vessel to prevent bleeding and provides a structure that allows endothelial cells to infiltrate the device 312 and incorporate it into the surrounding tissues. A planar flange 330 serves to stabilize the artery and to self-seal the puncture therein.

Figure 30:
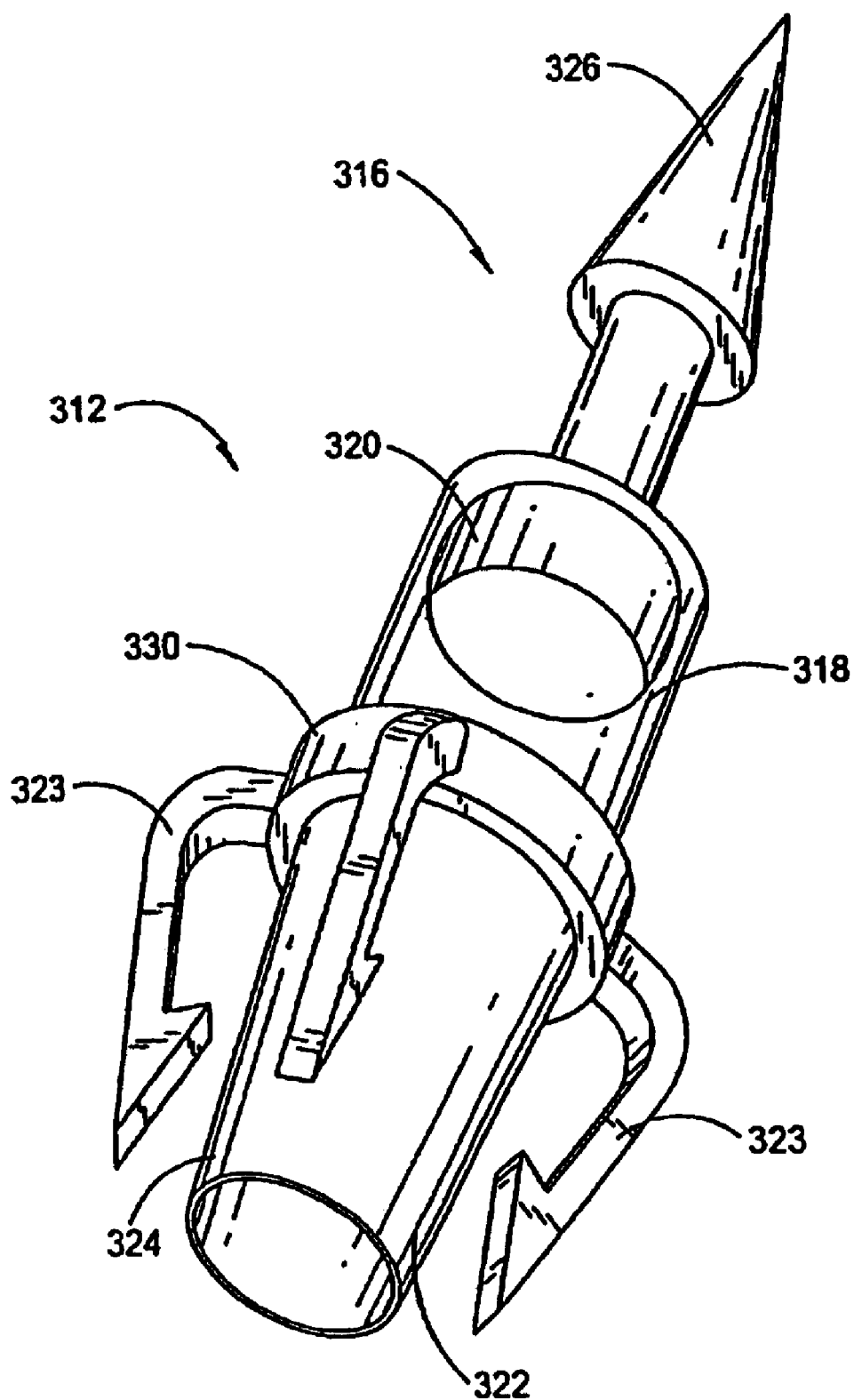
FIG. 30 is a perspective view of a conduit or shunt device according to a sixth embodiment of a combination access/shunt.

FIG. 30 illustrates a further embodiment of the combination access/shunt device 312. The distal conduit portion 316, as similar to that described above with respect to other embodiments, and has a barbed distal portion 326 having one or more barbs for anchoring the device. The proximal shunt portion 318 which resides in the vessel comprises an aperture 320 to allow blood to flow into the diversion tube 322. The proximal shunt portion 318 may be tapered. The top of the diversion tube 322 forms a tapered connector portion 324 for receiving a bypass conduit as described above. It will be noted that the connector portion 324 can be frusto-conical. In a preferred embodiment, a biocompatible fabric or mesh (not shown) is incorporated into the structure of the device, as above. A planar flange 330 serves to stabilize the artery and to self-seal the puncture therein. Attached to the planar flange and distributed thereabout are one or more retaining members 323, which can comprise detents at the end thereof for engaging the bypass conduit. The detents can be in the form of hooks, clasps, split rings, pads, or the like in order to mechanically retain the bypass conduit onto the connector portion 324 of the diversion tube 322.

Figure 31:
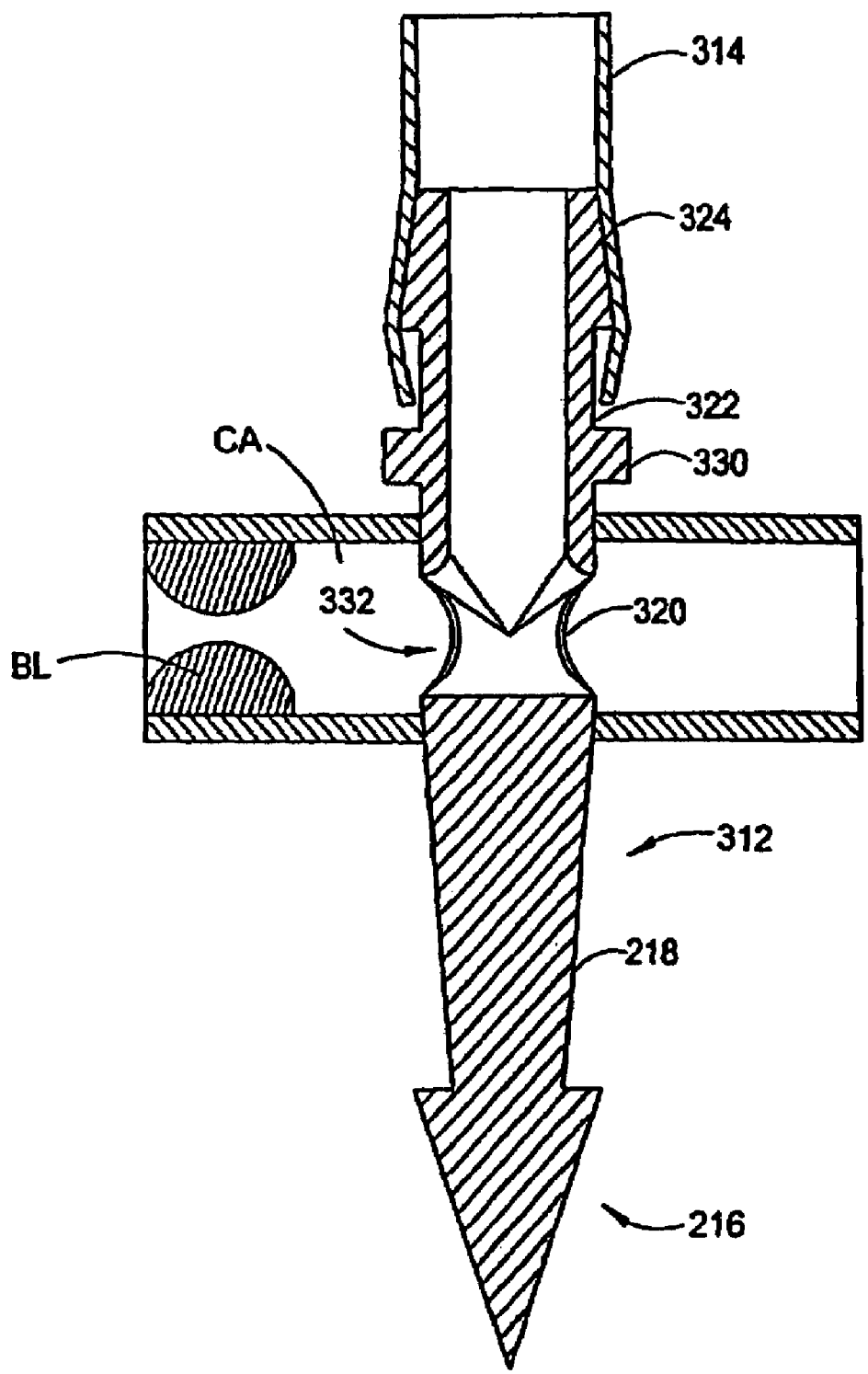
FIG. 31 shows the shunt device of FIG. 29 in cross-section.
Figure 32:
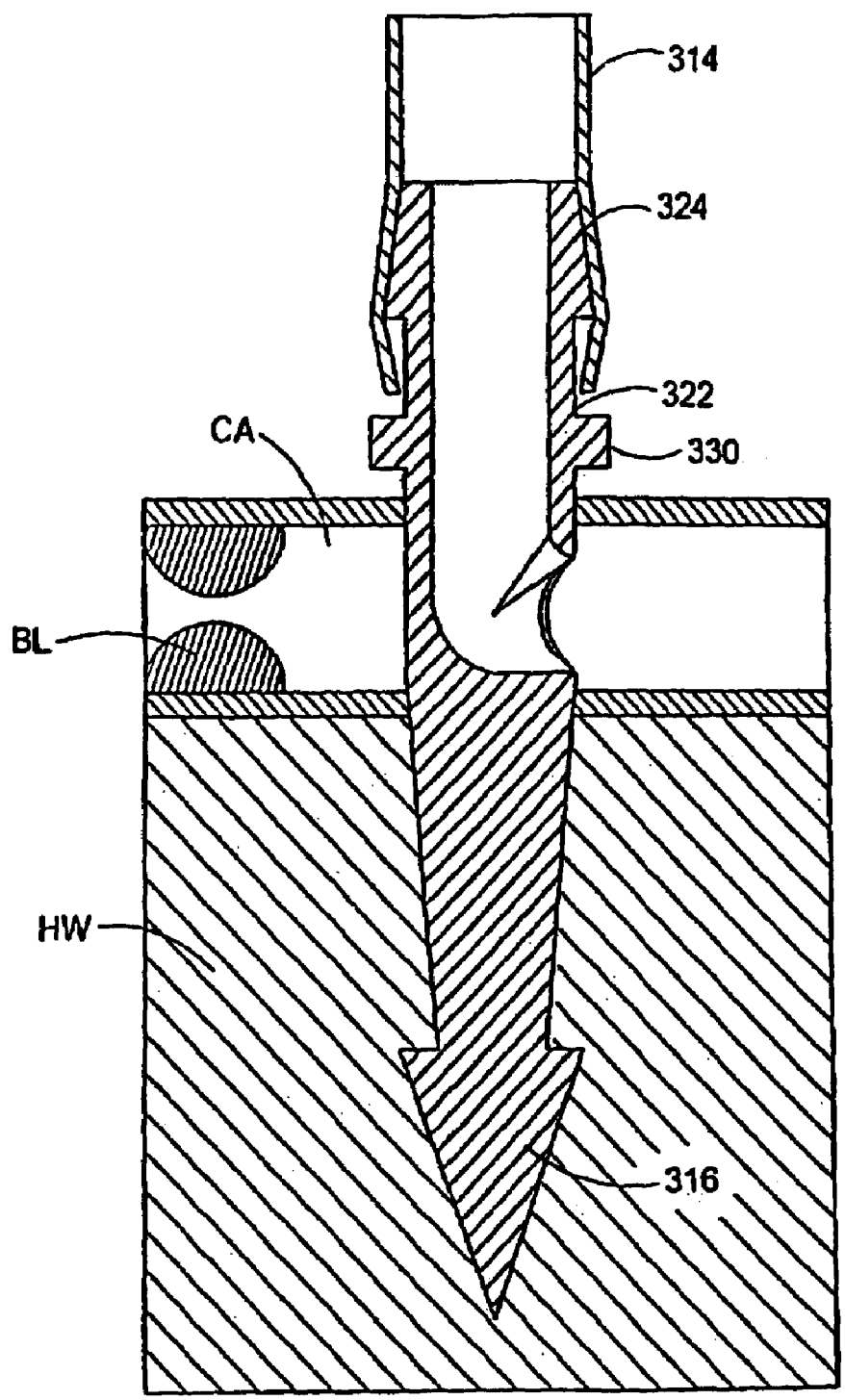
FIG. 32 is a close-up cross-sectional view of a coronary artery blockage and the myocardium of a patient and the shunt device according to FIG. 29.

Referring now to FIG. 31, the shunt device 312 of FIG. 29 is depicted in cross-section, where like features are referred to by the same reference numerals. The view depicts the device 312 inserted into an artery, such as the coronary artery CA of a patient, and further depicts a blockage BL therein. A bypass conduit, for example, a vein or artery graft 314, is secured to the connector tube 324 of the diversion tube 322 above the flange 330. Optionally, an access port or hole may be placed along the shunt body opposite the aperture 320 at portion 332 to increase total flow and to maintain blood perfusion through the vessel bypassed. It also should be noted that although the figure depicts the device 312 inserted perpendicular to the artery CA, the geometry of the device 312 allows it to be inserted at an angle without affecting its performance. This feature advantageously allows for more flexible application of the device during surgery, where perpendicular access to a vessel is not always available or convenient. FIG. 32 presents a view similar to that of FIG. 31, showing the barb 326 of the conduit device implanted in the myocardium HW of a patient for perfusing the coronary artery CA.

Figure 33:
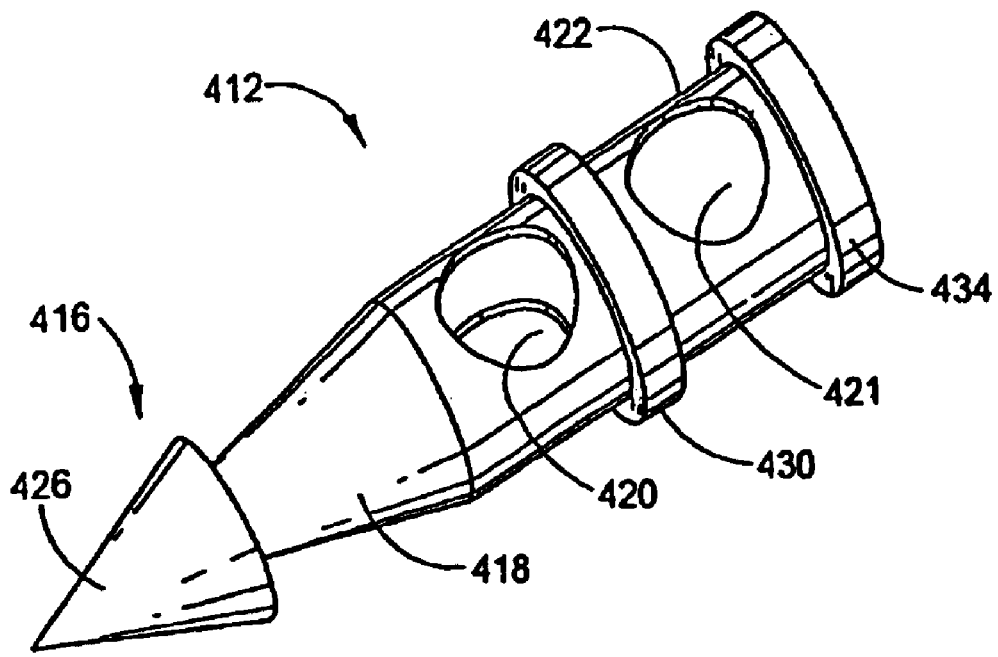
FIG. 33 is a perspective view of a side-by-side bypass device.
Figure 33A:
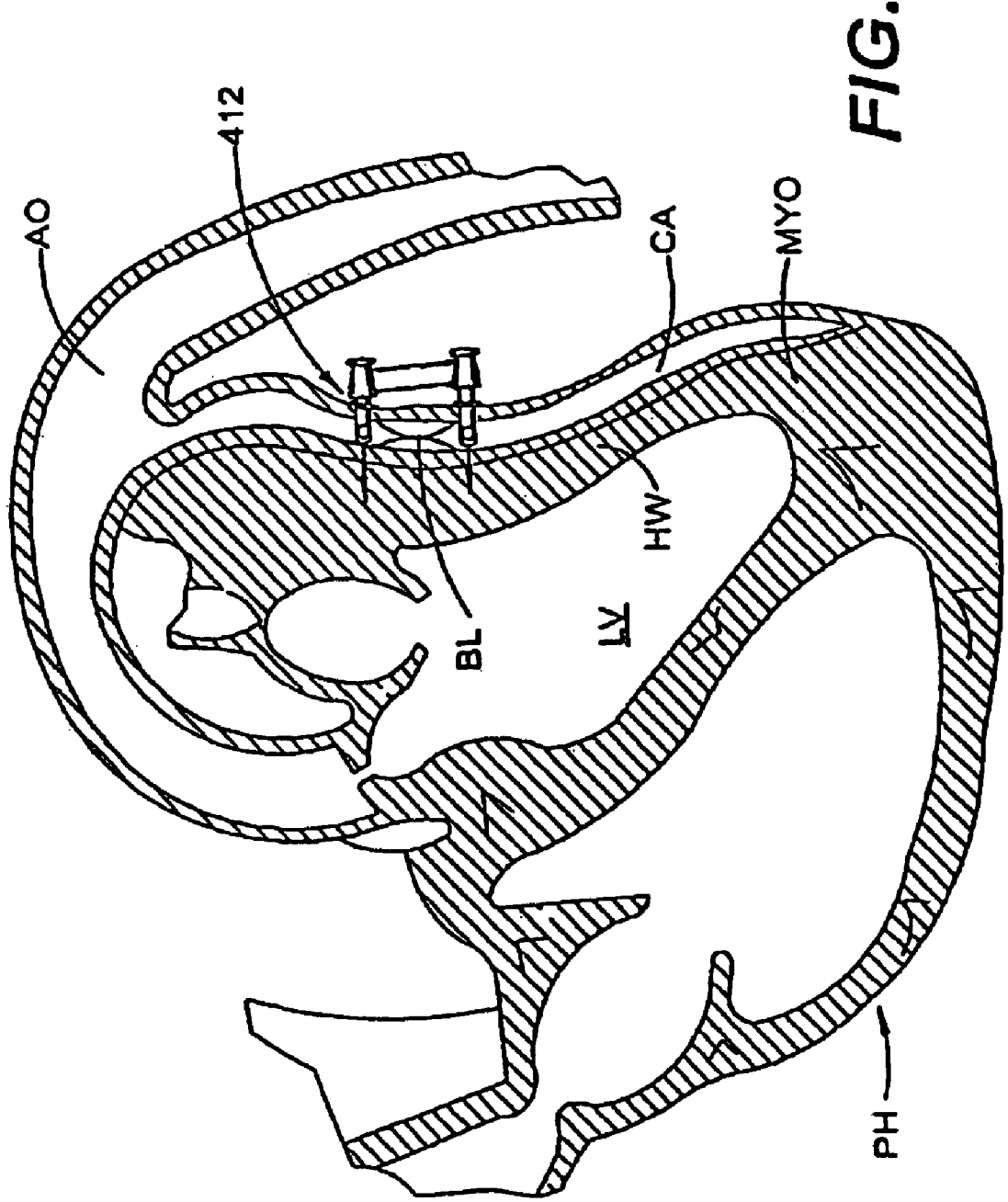
FIG. 33A is a schematic cross-sectional view illustrating the coronary bypass system which is more parallel to the coronary artery.

A side-by-side bypass device 412 is depicted in FIG. 33, and FIG. 33A illustrates in schematic fashion the bypass achieved with the conduit of FIG. 33. In this case, the bypass conduit runs more parallel to the coronary artery CA and therefore utilizes less space within the intrapericardial space. In this device, the distal conduit portion 416 is similar to that described above with respect to other embodiments, and has a barbed distal portion 426 having one or more barbs for anchoring the device. The proximal shunt portion 418 which resides in a vessel comprises an aperture 420 to allow blood to flow into the diversion tube 422. The aperture 420 passes through the shunt portion 418, and allows communication with the diversion tube to either side of the shunt portion 418. The proximal shunt portion 418 may be tapered. The top of the diversion tube 422 forms a connector portion with a second aperture 421 for communicating with a bypass conduit, such as an artery or vein graft. As above, a biocompatible fabric or mesh (not shown) can be incorporated into the structure of the device. A planar flange 430 serves to stabilize the artery and to self-seal the puncture therein. Similarly, a flange 434 is provided at the end of the diversion tube 422 to self-seal the puncture in the artery or vein graft.

Figure 34:
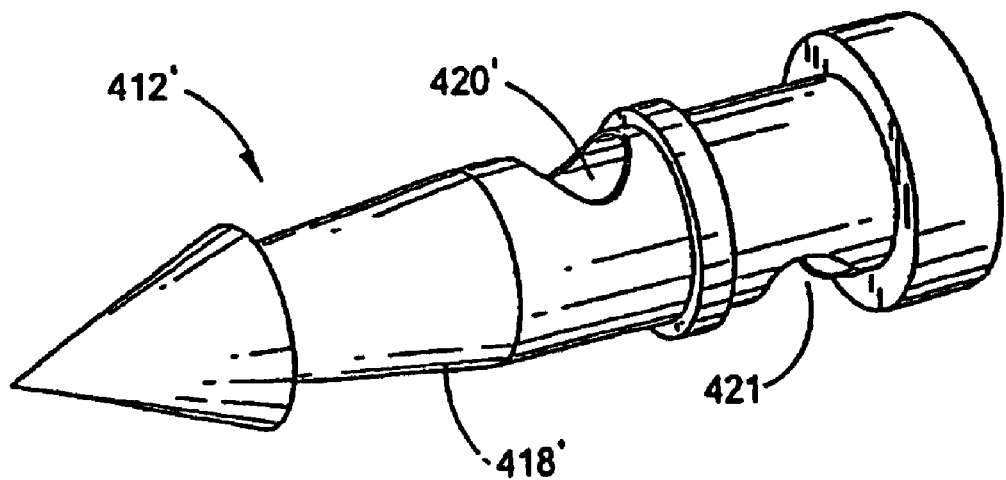
FIG. 34 is a perspective view of another side-by-side bypass embodiment.

FIG. 34 depicts an alternative embodiment 412' similar to the device of FIG. 33. The device of FIG. 34 has an aperture 420', which extends through only one side of the shunt portion 418'. It should be understood that the apertures of this and the preceding embodiment may be selectively placed and sized according to the desired application, the orientation of the blood vessels employed, and the location of anatomical features, blockages, etc.

Figure 35:
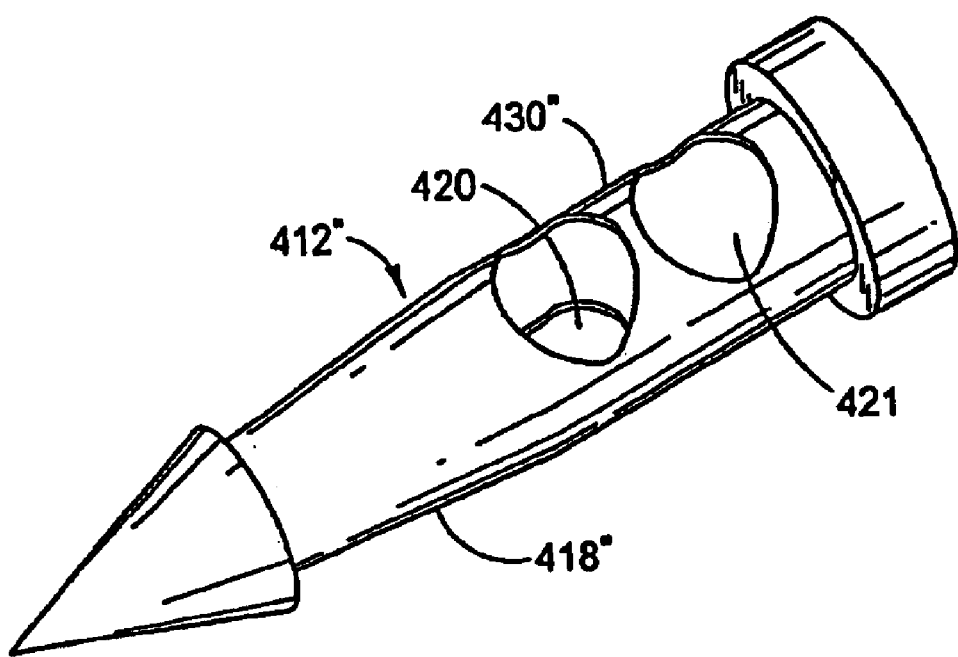
FIG. 35 is a perspective view of a third side-by-side bypass embodiment.

FIG. 35 depicts a further alternative embodiment 412" that is similar to the embodiment depicted in FIGS. 33 and 34 except that there is no flange between the apertures 420 and 421, but rather a smooth transition area 430". The shunt body 418" is shown to have a gentle taper.

Figure 37:
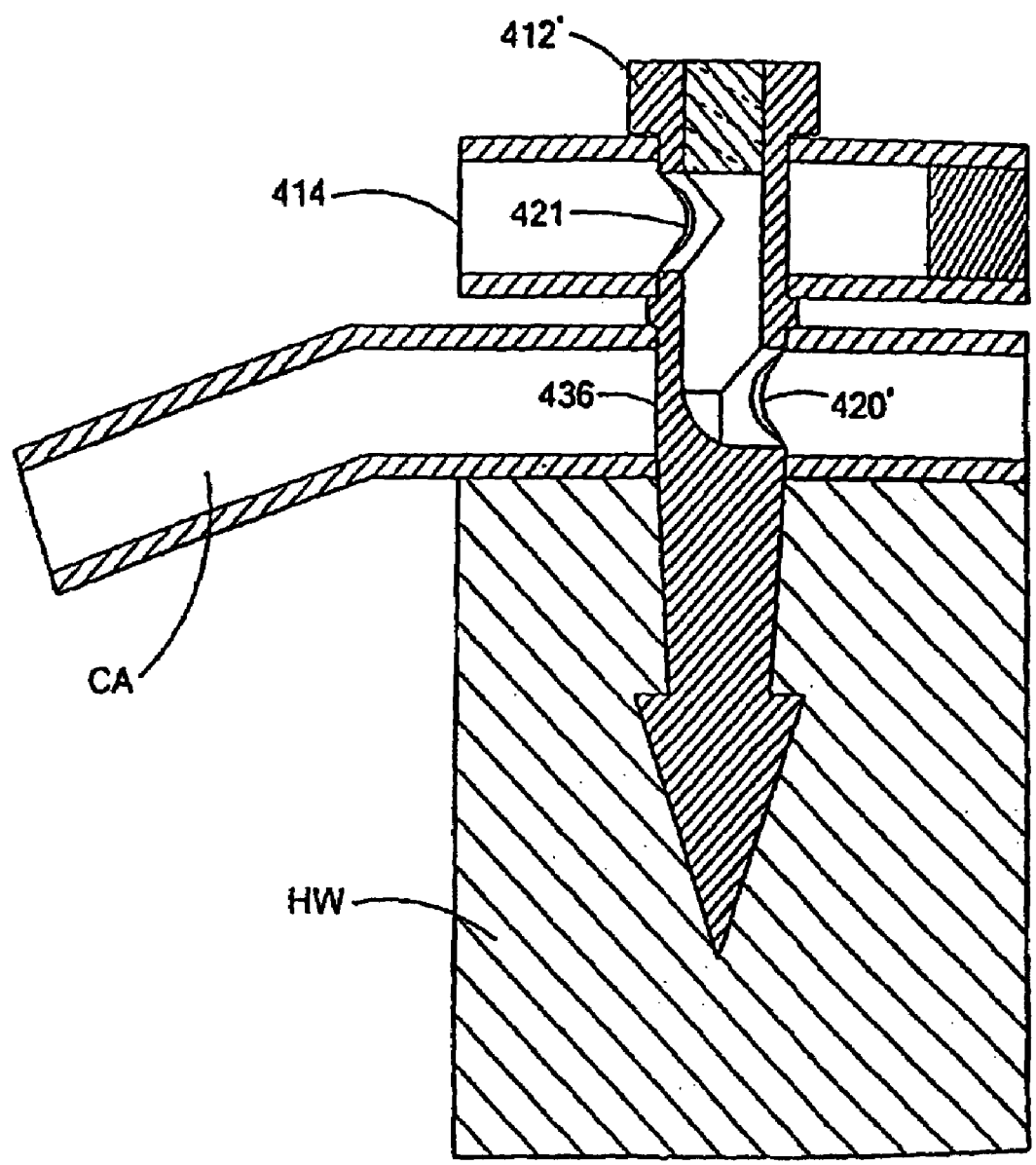
FIG. 37 is a close-up cross-sectional view of a coronary artery and the myocardium of a patient and the shunt device according to FIG. 34.

FIG. 37 is a cutaway schematic representation of the shunt device 412' depicted in FIG. 34 mounted within the patient, with the conduit end resident within the myocardium HW. The coronary artery CA and the bypass graft 414 are shown to be placed in fluid communication by the apertures 420', 421 in the shunt 412'. This illustration is illustrative of all side-by-side instant anastomosis devices described herein.

Further, it should be noted that a hole may be located at position 436 to allow additional perfusion of the coronary artery CA, and that the aperture 420' could pass through both sides, as in devices 412 and 412". Further, it should be noted that the device could be mounted at an angle, as discussed hereinabove.

Figure 38:
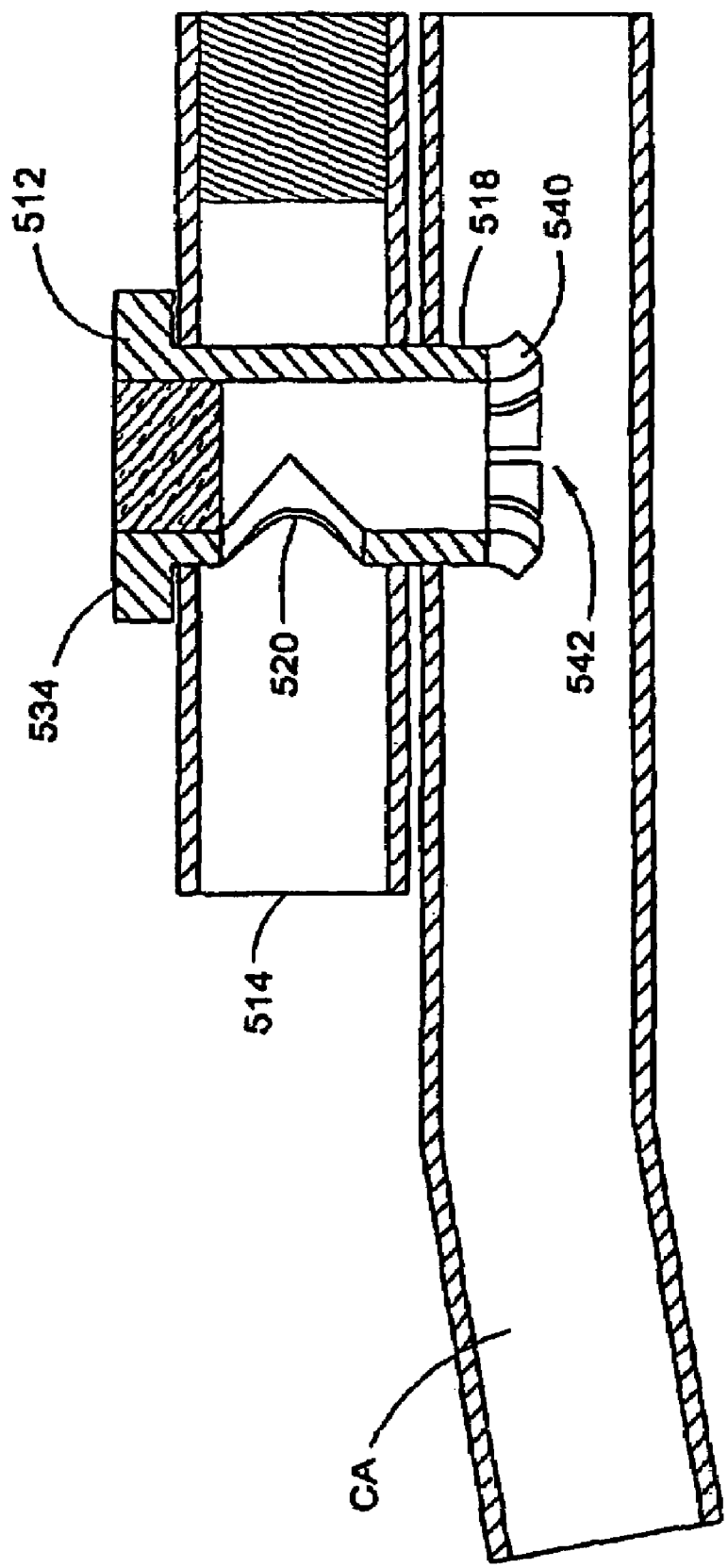
FIG. 38 is a close-up cross-sectional view of a coronary artery of a patient and the shunt device according to FIG. 36.

FIG. 38 is a cutaway schematic representation of a "rivet" type shunt device 512 mounted within the patient, with the retention members 540 deployed. A flange 534 seals the incision and maintains a bearing surface against the bypass graft 514, which could be venous or arterial. An aperture 520 opens a channel into the hollow stent body 518, which terminates in an open end 542. In this illustrative arrangement, the open end 542 is resident within the coronary artery CA.

For illustrative purposes, it has been found that an anastomosis shunt device of the type depicted in FIG. 29 can be dimensioned to have a height of 12.5 mm, with a body width of about 2 mm, a flange diameter of about 2.8 mm, and an inside diameter of the diversion tube of about 1.4 mm. The conduit can be dimensioned to be about 3 mm in height tapering to a width of about 2.1 mm. The aperture can be dimensioned to be about 1.4 mm in diameter, and can have an edge radius about the periphery of about 0.10 mm all around. An anastomosis shunt device of the type depicted in FIG. 33 can be dimensioned to have a height of 12.65 mm, with a body width of about 2.8 mm, a flange diameter of about 3.4 mm, and an inside diameter of the diversion tube of about 2.0 mm. The conduit can be dimensioned to be about 3 mm in height tapering to a width of about 2.6 mm. The apertures can be dimensioned to be about 2.0 mm in diameter, and can have an edge radius about the periphery of about 0.10 mm all around.

Anastomosis Devices and Methods

It will be noted in connection with the coronary bypass devices, systems, and methods described above that various connections from one conduit to another are necessary. The term "anastomosis" refers to the joining of two conduits or two vessels in a similar fashion; although, in the context of the present application, that term should not be limited to a particular medical definition or practice, but refers broadly to the connection of various conduits in connection with bypass systems. Thus, as described above, prefit connections from one conduit onto a hub of another conduit are possible, although other anastomosis configurations are described below.

Figure 39A:
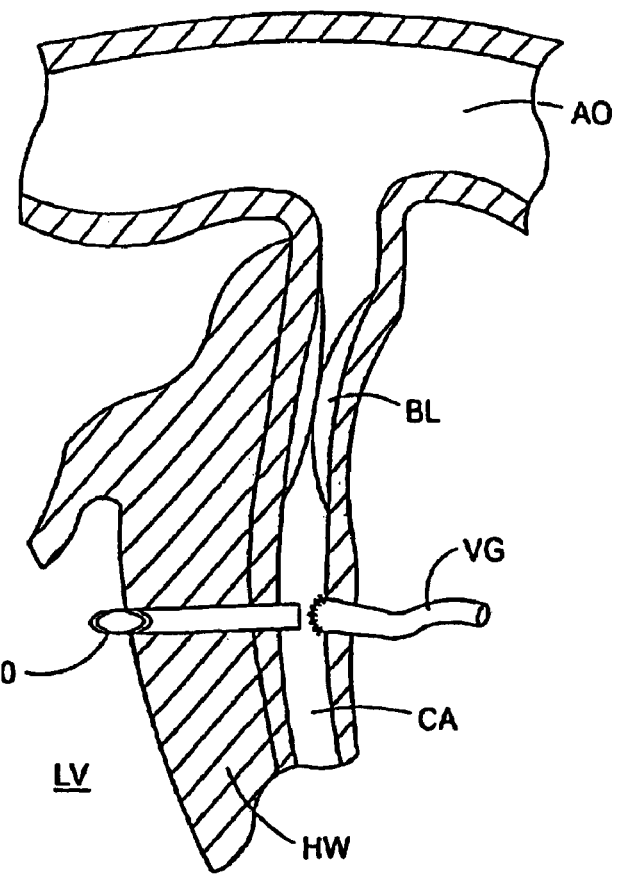
FIGS. 39A–B illustrate the temporary use of a stent during a coronary bypass procedure.
Figure 39B:
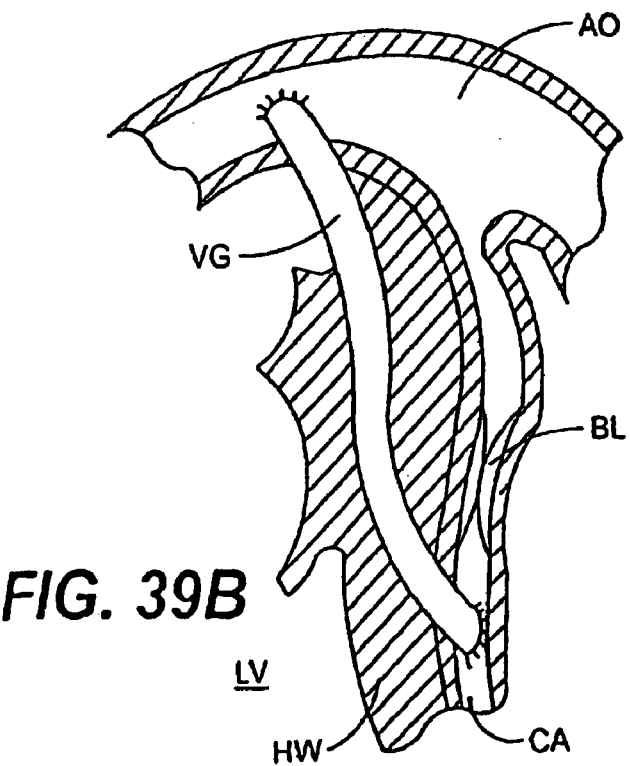

As shown in FIGS. 39A and 39B, a conduit 600 can be used to provide temporary blood flow during therapeutic procedures. For example, in typical coronary artery bypass surgery, a section of vein VG taken from the leg of the patient is attached at one end to the aorta AO and at the other end to a point distal to the blockage in the coronary artery CA. This surgery requires the delicate procedure of joining the vein graft VG to the aorta AO and to the coronary artery CA. This joining of the blood vessels is known as anastomosis. Normally, the patient is placed on a heart-lung machine to keep the blood oxygenated and flowing during this procedure, and the blood is diverted from the coronary artery CA to allow the physician to complete the anastomosis.

In one embodiment of the present invention, the conduit 600 is used to maintain blood flow through the coronary artery CA during bypass surgery (FIG. 39A). The vein graft VG is loaded on top of the stent 600 prior to implantation. The conduit 600 is implanted as described above, at the point of the vein graft VG anastomosis. The vein graft VG is sutured to the aorta and to the CA at a point distal to the blockage BL. If desired, the sutures can be preloaded onto the graft VG to facilitate the anastomosis. Once the vein graft VG has been attached, the conduit 600 is removed, and blood flow occurs from the aorta AO, through the vein graft VG, and down the coronary artery CA. The conduit 600 can be sutured in place during the anastomosis procedure for permanent attachment, if desired.

Figure 40:
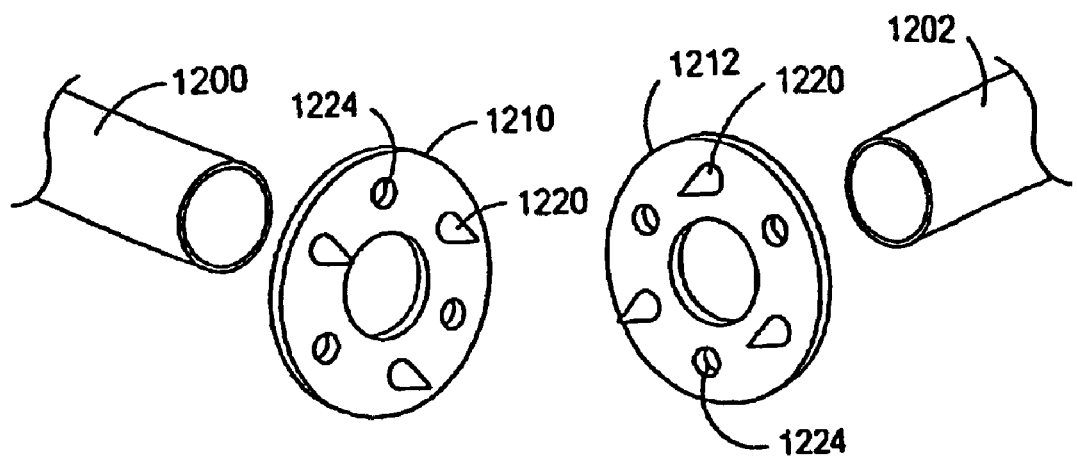
FIGS. 40 and 40A–40Q show a variety of members for securing segments of tissue to each other, as well as conduit members.
Figure 40A:
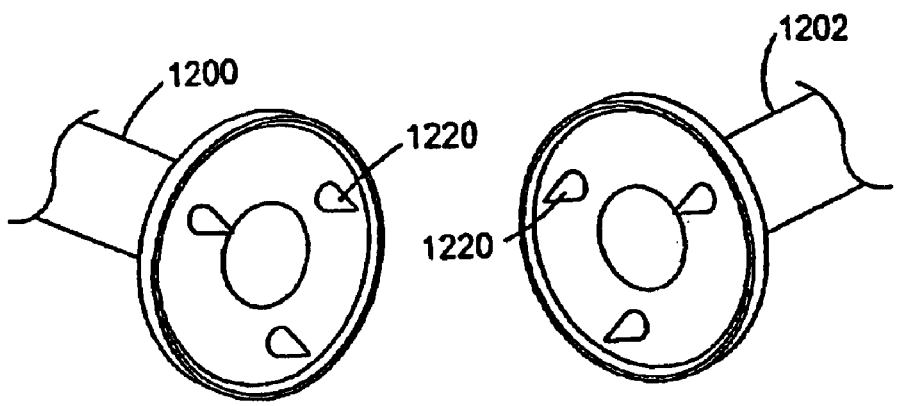
Figure 40B:
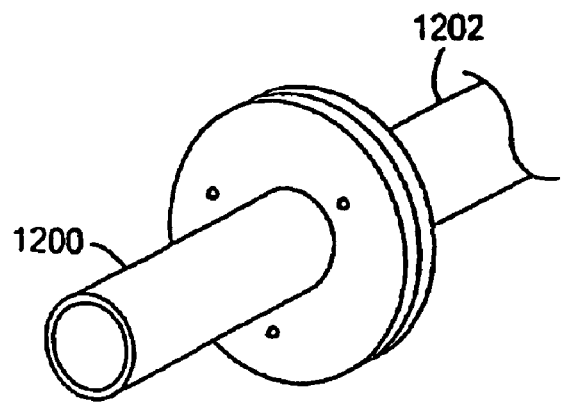
Figure 40F:
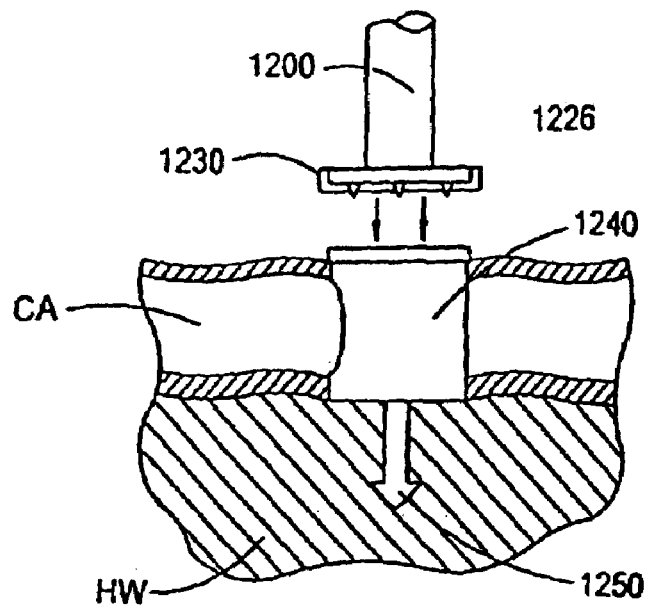
Figure 40G:
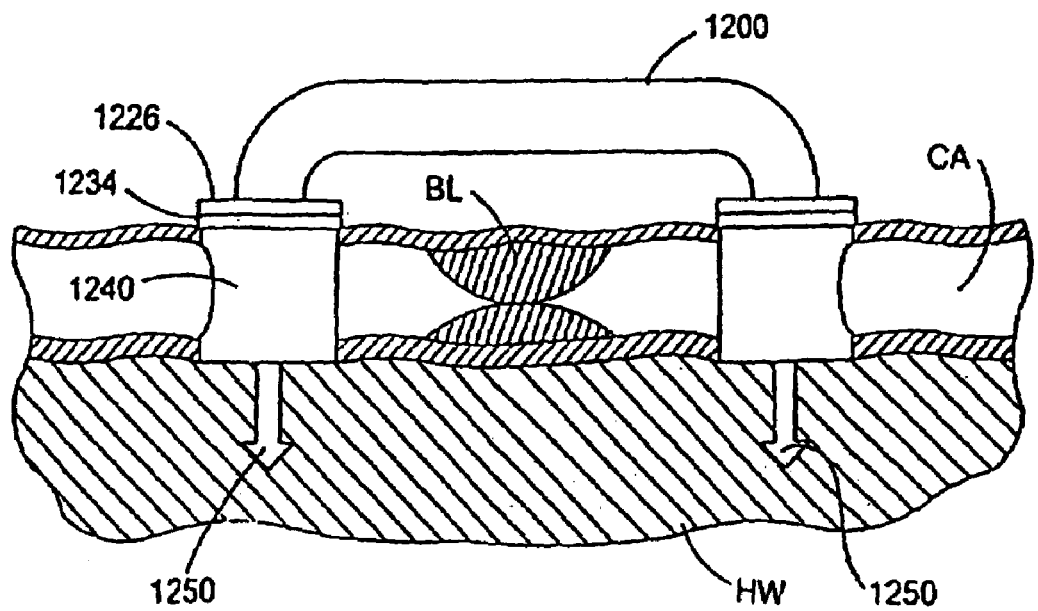

Other embodiments for connecting vessels or segments of vessels together are shown in FIGS. 40–40G. FIG. 40 illustrates two vessels 1200 and 1202 to be connected to respective disc members 1210 and 1212. Each of the disc members 1210 and 1212 includes a plurality of prongs 1220 which are configured to mate with opposing holes 1224. After the disc members 1210, 1212 are secured to the vessels 1200 and 1202 (FIG. 40A), the vessels 1200 and 1202 may be effectively joined by snapping or locking the disc members together. As illustrated in FIG. 40B, this may be done by aligning the prongs 1220 with the holes 1224, so that the prongs pass through and are accepted by the holes.

A technique for securing the vessels 1200 and 1202 to the disc members is illustrated in FIGS. 40C–40G. FIG. 40C shows the vessel 1200 (e.g., a left internal mammary artery or "LIMA") being brought into proximity with a disc member 1226, which, as shown in FIG. 40D, is brought over the vessel 1200, so that a portion 1230 of the vessel 1200 extends beyond the disc member 1226. As shown in FIG. 40E, the portion 1230 may then be advantageously everted over the disc member 1226, so that the prongs 1220 of the disc member 1226 pierce through the vessel portion 1230. As illustrated in FIGS. 40F and 40G, the disc member 1226 may then be mated with another disc member 1234 having a plurality of holes 1224 therein. The disc member 1234 may advantageously be part of a larger integrally formed conduit device 1240 for redirecting the flow of blood around a blockage BL (not shown in FIG. 40F) within the coronary artery CA. A spike 1250 may be used to secure the conduit device 1240 within the heart wall HW. Although the disc member 1226 is shown as having several prongs 1220 that mate with respective holes 1224 in another disc member 1234, it will be understood that disc members having alternate holes and prongs (like those in FIGS. 40–40B) may be used.

Figure 40H:
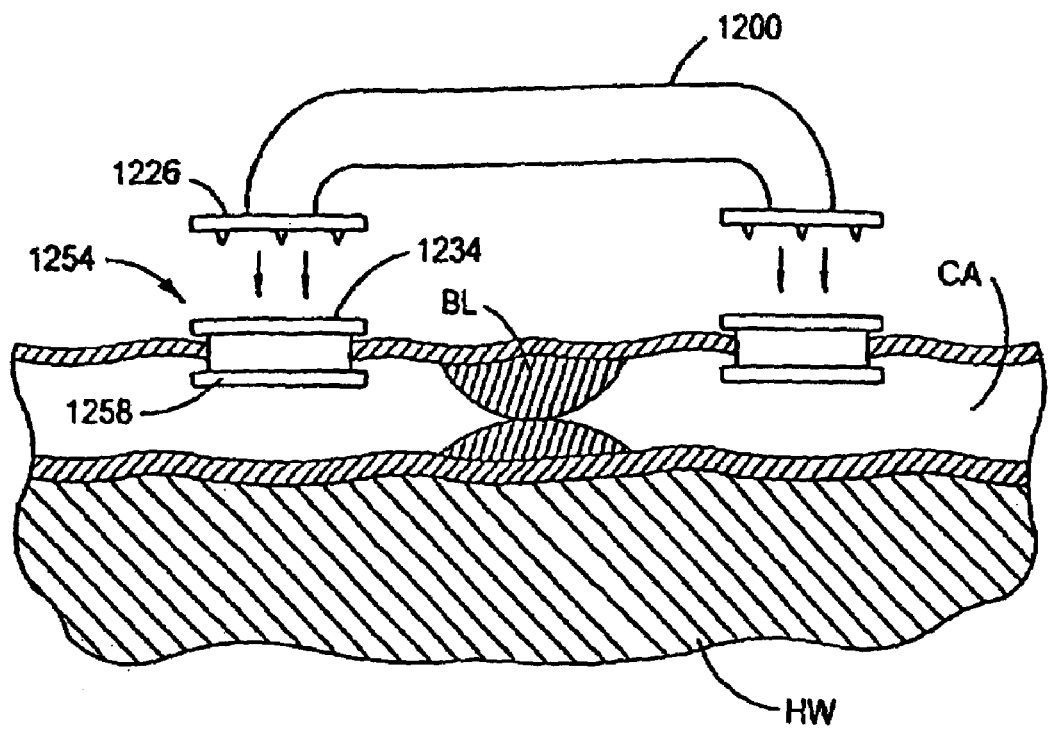
Figure 40I:
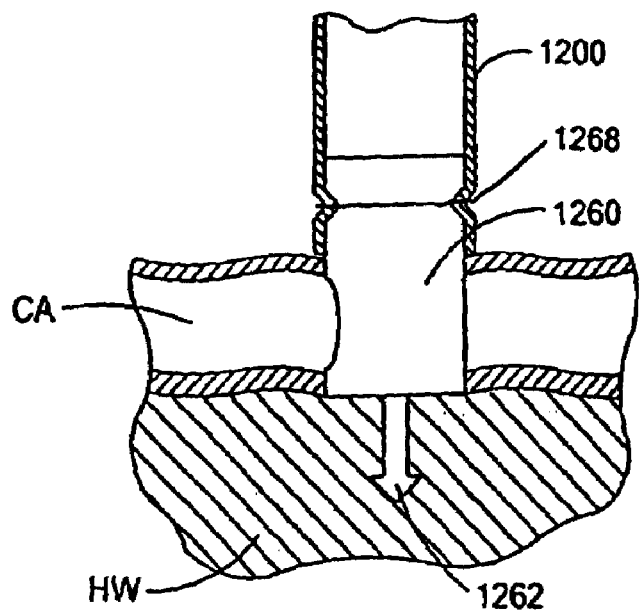
Figure 40J:
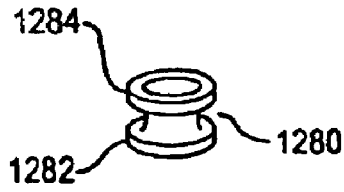
Figure 40K:
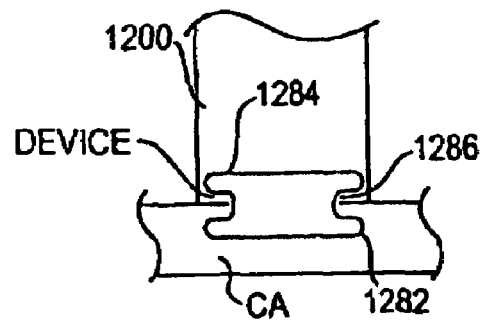

Another conduit device 1254 is shown in FIG. 40H, in which the device 1254 includes a disc member 1234 that mates with another disc member 1226. The conduit device 1254 is held snugly within the coronary artery CA by a rim element 1258 of the device 1254. In FIG. 40I a conduit device 1260 is shown that includes a spike 1262 for securing the device 1260 into the heart wall HW. A vessel 1200 fits around a cylindrical portion 1264 of the conduit device 1260 and is held around the cylindrical portion 1264 by friction or with a ligature 1268.

FIG. 40 J shows a conduit member 1280 having a pair of rings 1282 and 1284. As shown in FIG. 40 K, one of the rings 1282 fits snugly inside and against the wall of the coronary artery CA, while the other ring 1284 sits above and on top of the coronary artery CA. A vessel 1200 fits over the ring 1284 and may be held in place with a suture 1286.

Figure 40L:
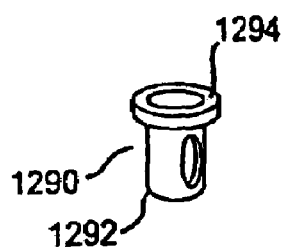
Figure 40M:
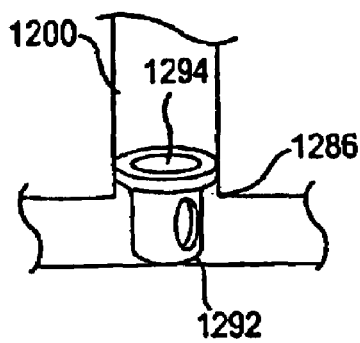

FIG. 40L shows another conduit member 1290, a base 1292 of which rests on the coronary artery CA, as illustrated in FIG. 40M. A suture 1286 may be used to secure the vessel 1200 to a ring 1294 of the conduit member 1290.

Figure 40N:
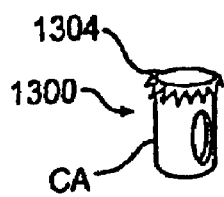

FIG. 40N shows another conduit member 1300 which functions similar to its counterpart in FIG. 40L, except that instead of a ring 1294, a plurality of teeth 1304 are used for holding the conduit member 1300 in place. Specifically, a vessel is brought over the conduit member so that the vessel slides beyond the teeth 1304. As the vessel 1200 is then retracted, the teeth 1304 engage the vessel 1200, thereby securing the vessel 1200 to the conduit member 1300, as shown in FIG. O.

Figure 40O:
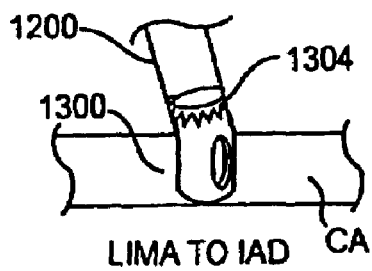
Figure 40P:
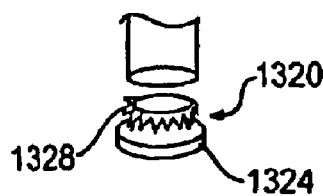
Figure 40Q:
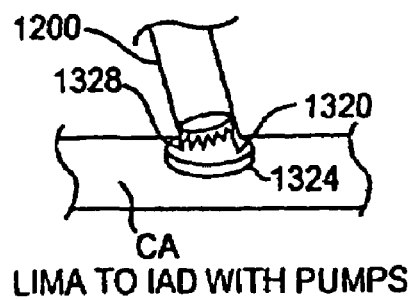

Another conduit member 1320 is shown in FIG. P. The member 1320 includes a ring 1324 and a plurality of teeth 1328. When in use, the ring 1324 contacts the inside of the coronary artery CA, whereas the teeth 1328 engage the vessel 1200 in a manner analogous to the embodiment of FIGS. 40N–O.

Conduits with Flow Resistance

One of the advantages of certain embodiments of the present conduits is that they can be designed to optimize fluid or blood flow through them. That is, the design or configuration of a conduit may be such that it automatically achieves flow control without microvalves, check valves, or other moving devices. (See, for example, the conduits of FIGS. 6A–H and 8–8P.) Such moving or articulating devices may be complicated or expensive to manufacture, particularly on the small scales required in this context. Thus, in one embodiment, flow control is achieved by maximizing flow through the conduit in one direction (preferably from the left ventricle to the coronary artery), but minimizing flow through the conduit in the opposite direction. Since flow rate through the conduit is a function of friction or drag, turbulence, and other fluid dynamic parameters, it may be convenient to discuss flow rate through the conduit in terms of resistance of the conduit to such flow. In other words, in one embodiment, it is advantageous to have a low conduit resistance in the forward direction (from the left ventricle to the coronary artery), but a higher resistance in the opposite direction. In that sense, the conduit acts as a type of choke device having a higher reversed flow resistance or diastolic resistance than the forward flow or systolic resistance.

Experimentation has shown, however, that the above characteristics may not necessarily produce optimized flow rate in the coronary artery. Thus, it should be remembered that flow rate through the conduit should be controlled such that it enhances total coronary flow rate, which total coronary flow rate is essential for perfusion of the heart tissues. Thus, experimentation has shown that the degree of proximal occlusion may have an effect on total coronary flow rate. It has been determined that, where a proximal occlusion is only partial, the total flow rate in the distal coronary artery may increase with greater systolic resistance in the conduit. This may be due, at least in part, to the back pressure which the flow through the conduit sees as a result of the partial occlusion. Thus, optimization under these circumstances must take into consideration the degree of proximal occlusion. In this regard, it has been determined that total coronary flow rate is increased with increasing systolic resistance through the conduit. Preferably, diastolic resistance remains high. For example, it has been found that with mild systolic resistance, an increase in coronary flow rate was achieved with approximately zero negative diastolic flow.

Figure 41:
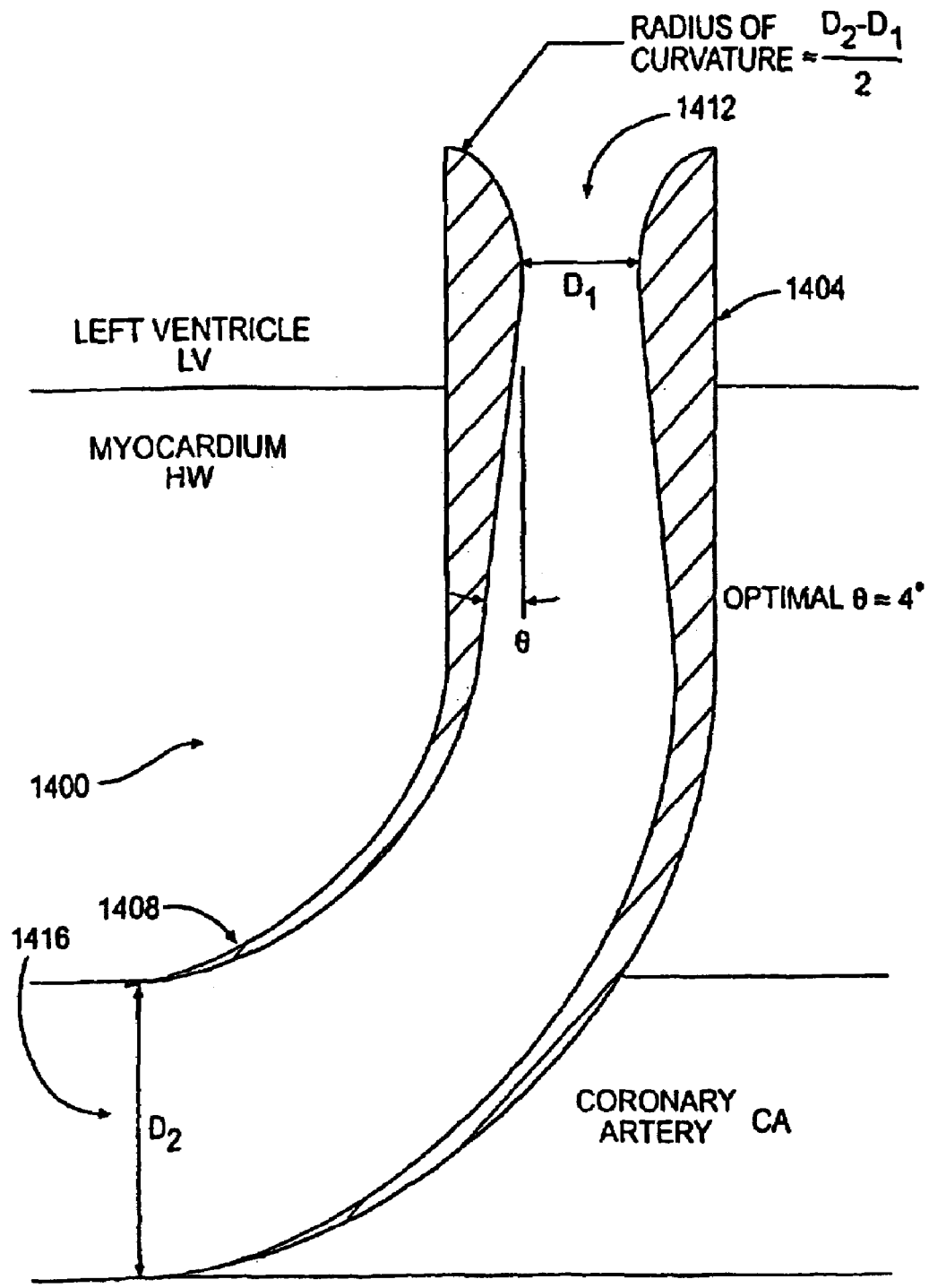
FIG. 41 shows a conduit of variable wall thickness.
Figure 41A:
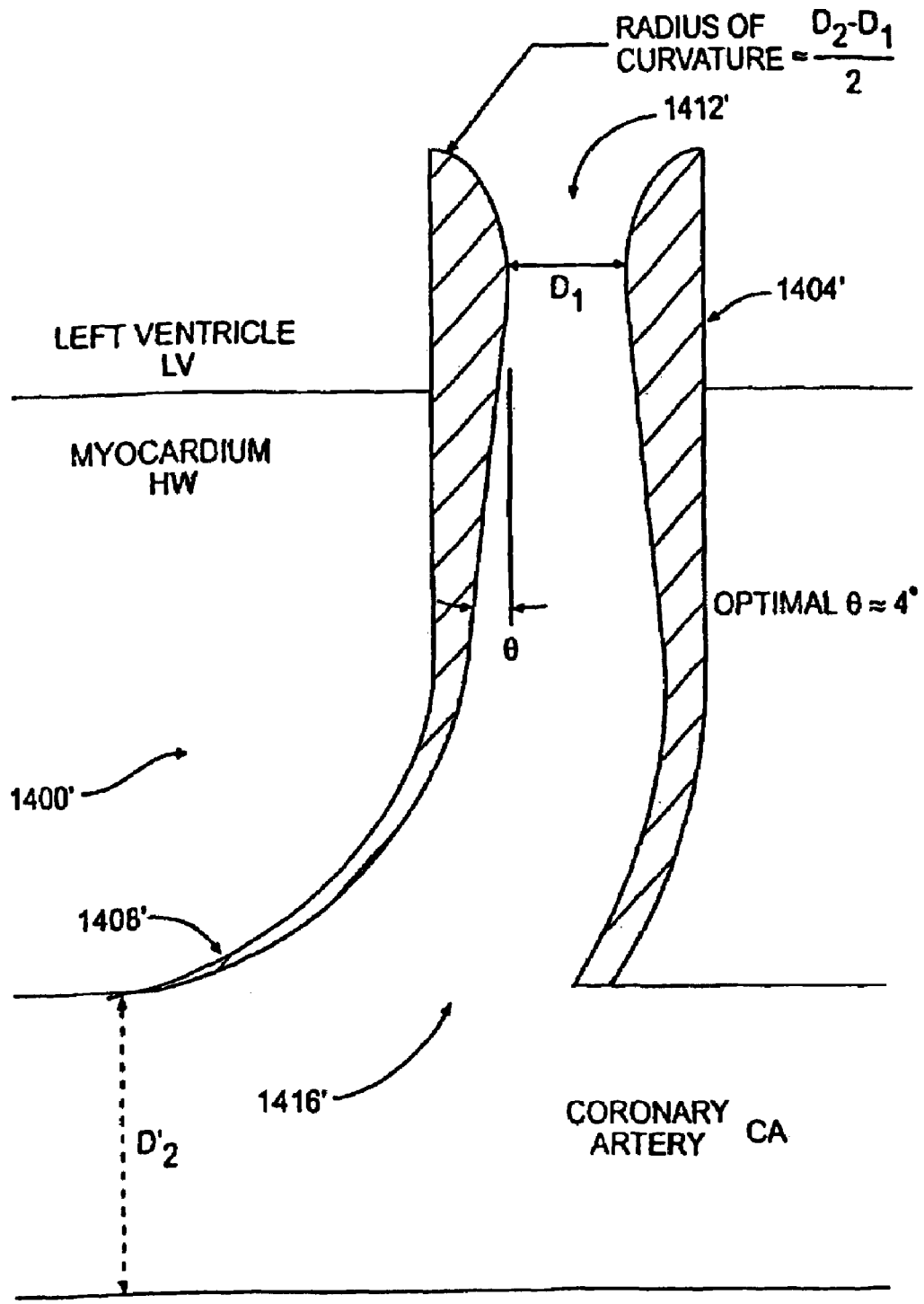
FIGS. 41A–41G show a variety of cross-sectional views of a conduit having varying wall thicknesses.
Figure 41B:
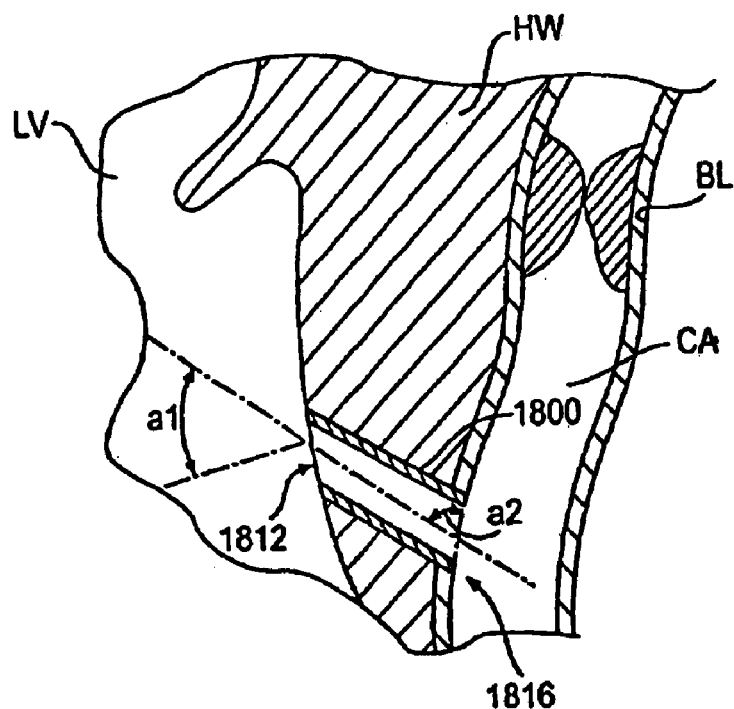
Figure 41C:
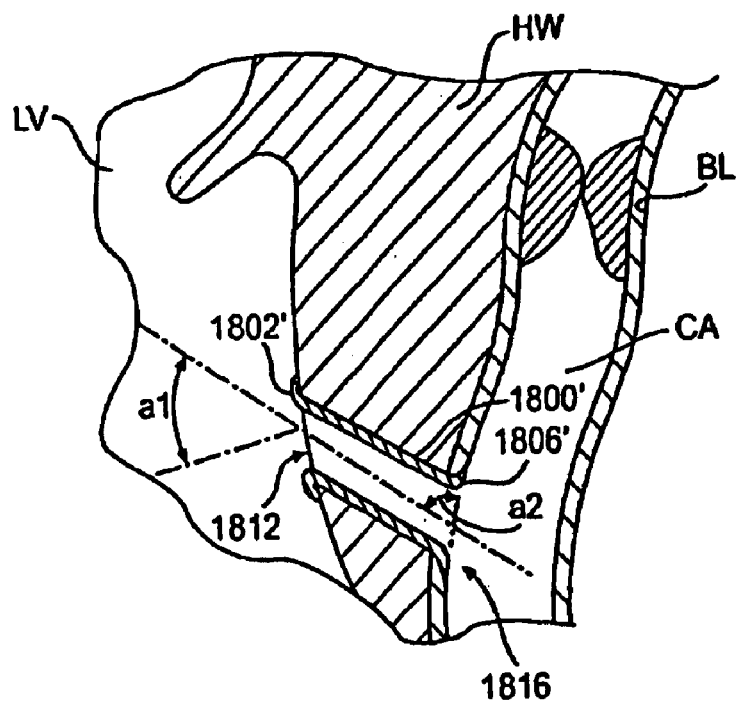
Figure 41D:
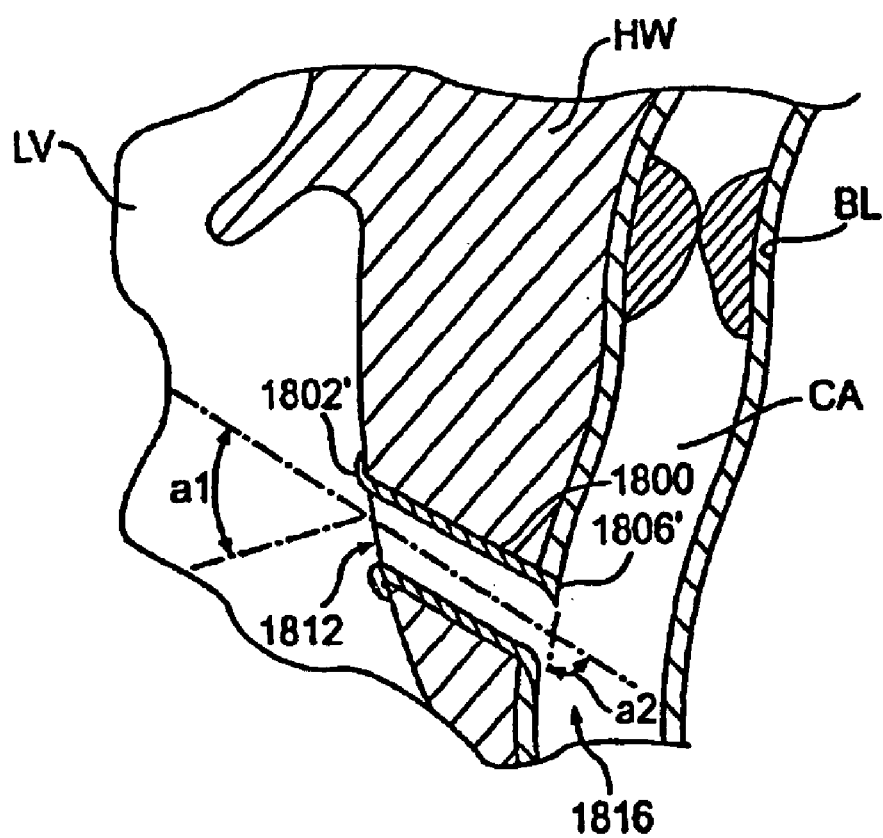
Figure 41E:
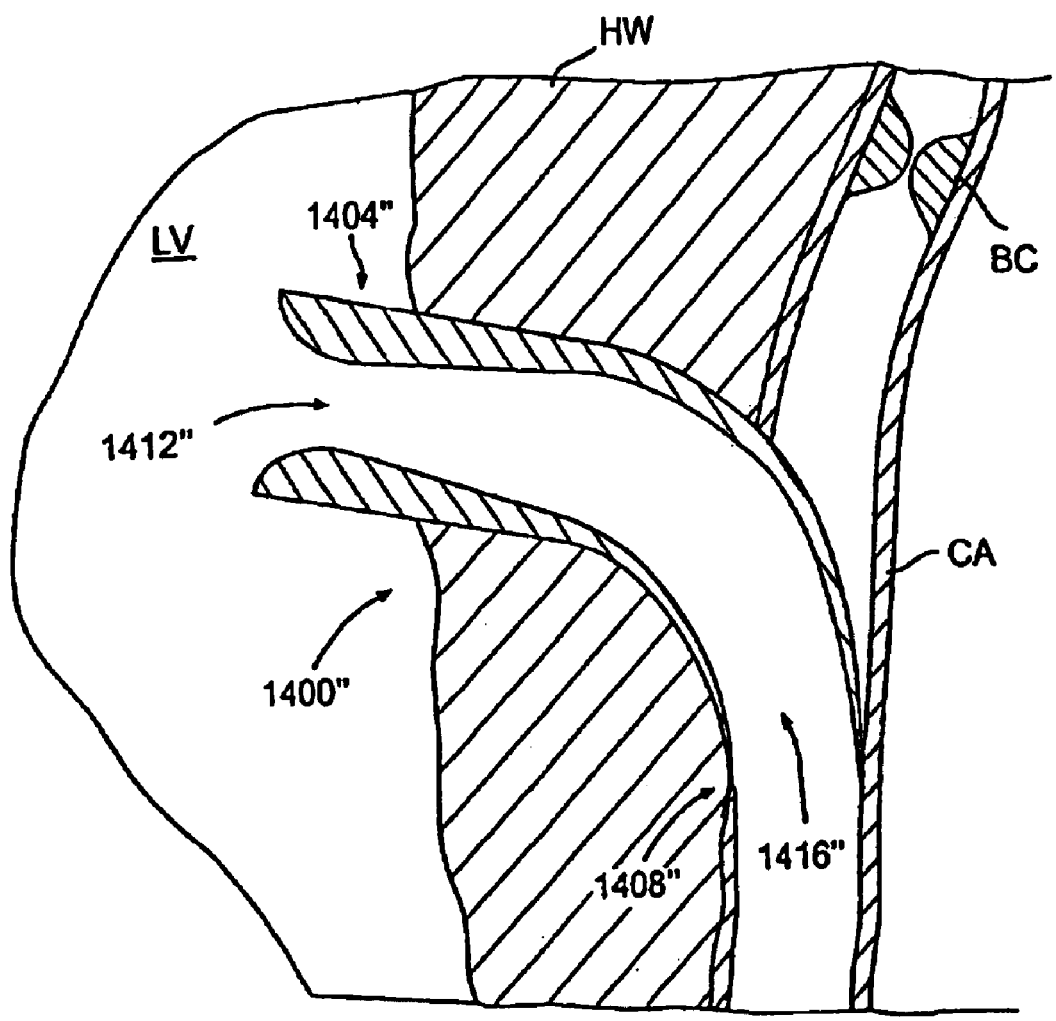
Figure 41F:
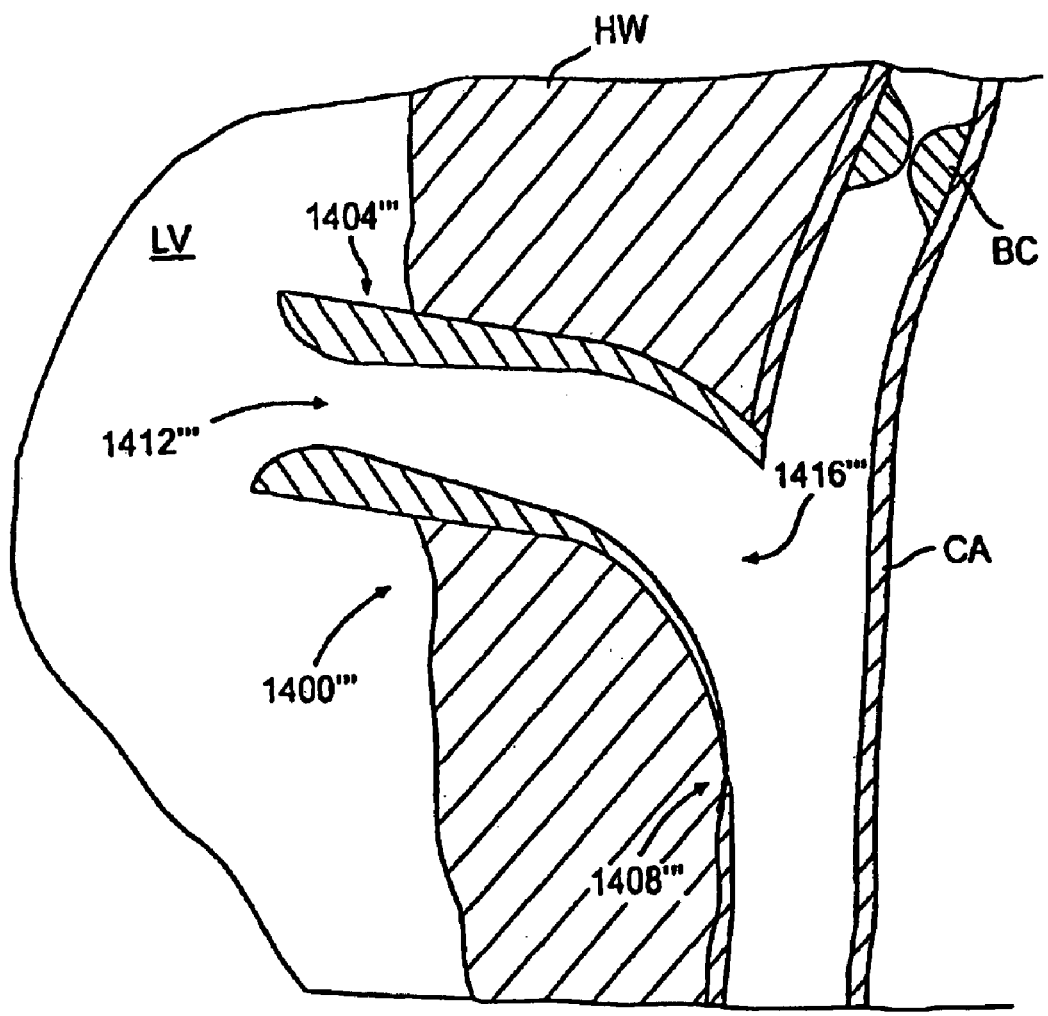
Figure 41G:
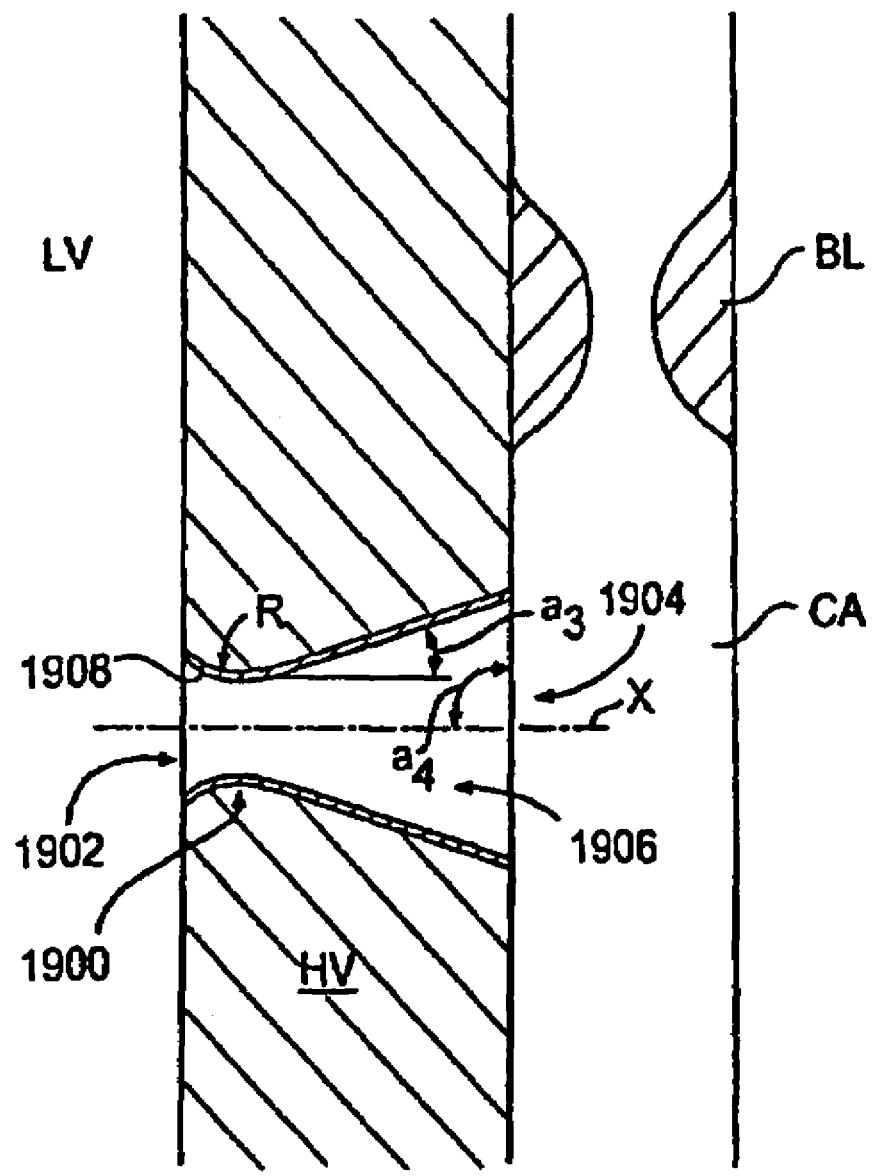

Thus, referring to FIG. 41, there is shown in schematic, cross-sectional view a conduit 1400 which has been designed to achieve flow optimization under certain circumstances, and which acts as an asymmetrical flow resistor. In this case, the conduit 1400 is generally curved with varying wall thickness, and has a proximal end 1404 which extends into the left ventricle LV and a distal end 1408 which curves so that its exit is approximately transverse to the direction of flow in the distal portion of the coronary artery CA. In this context, the term "distal" is used with respect to direction of flow and represents a location downstream from a given point in the flow path. It will be observed that the proximal portion of the conduit 1400 shown in FIG. 41 extends into the left ventricle LV to take into consideration the changing wall thickness of the myocardium. Thus, the proximal portion of the conduit 1400 may extend into the ventricle LV roughly 5%–30% to accommodate for such changing wall thicknesses. Thus, during systole, the myocardium HW contracts and goes into tension, thus increasing the thickness of the myocardium. The conduit 1400 of FIG. 41 is designed to accommodate such a thickening such that its entrance 1412 will be approximately flush with the internal surface of the myocardium HW during systole.

It will also be observed at the proximal end 1404 of the conduit 1400 that the entrance 1412 is shaped so as to have a high radius of curvature, which is approximately ½ of the difference between the diameter at the exit 1416 and the diameter of the conduit 1400 at the entrance 1412. This curvature tends to reduce flow losses (or in other words, decreases resistance to flow) at the entrance 1412, thereby maximizing flow through the conduit during systole. At the same time, it will be observed that the decreased diameter at the entrance 1412 increases the resistance to reverse diastolic flow at that location, thus tending to decrease negative flow through the conduit 1400 or flow from the coronary artery CA back into the ventricle LV. Thus, the proximal portion of the conduit 1400 is designed so as to achieve an abrupt expansion resulting in large exit losses and consequently high resistance to diastolic flow.

At the distal end 1408, on the other hand, flow losses are minimized, so as to minimize flow resistance. Such exit losses are essentially zero because the exit diameter of the conduit 1400 proximates or matches the diameter of the coronary artery CA. Moreover, during diastolic flow, there will be an "entrance" losses at the exit of the conduit 1400, thus increasing the resistance to such negative flow. Moreover, the curved configuration of the distal end 1408 of the conduit 1400 minimizes flow loss during diastole which results from proximal flow through a partial occlusion. In other words, the distal end 1408 of the conduit 1400 can be constructed so as to allow a proximal flow passing a partial occlusion and contributing to the flow through the conduit 1400 to produce an advantageous total coronary flow rate. Such distal designs for the conduit 1400 are described elsewhere herein and are compatible with the conduit of FIG. 41. Moreover, the conduit 1400 can be constructed from a rigid or flexible material, it may be a solid wall or lattice structure (e.g., stent-like) as described below.

Thus, the conduit 1400 of FIG. 41 can be designed so as to optimize total flow rate by designing a certain flow resistance through the conduit 1400 in accordance with the conditions indicated by the patient. In this embodiment, the wall thickness of the conduit 1400 varies by a taper (θ) of approximately 4°, thus producing the differences in entrance and exit diameters. This degree of taper tends to minimize losses in a gradual conical expansion region.

Figure 42:
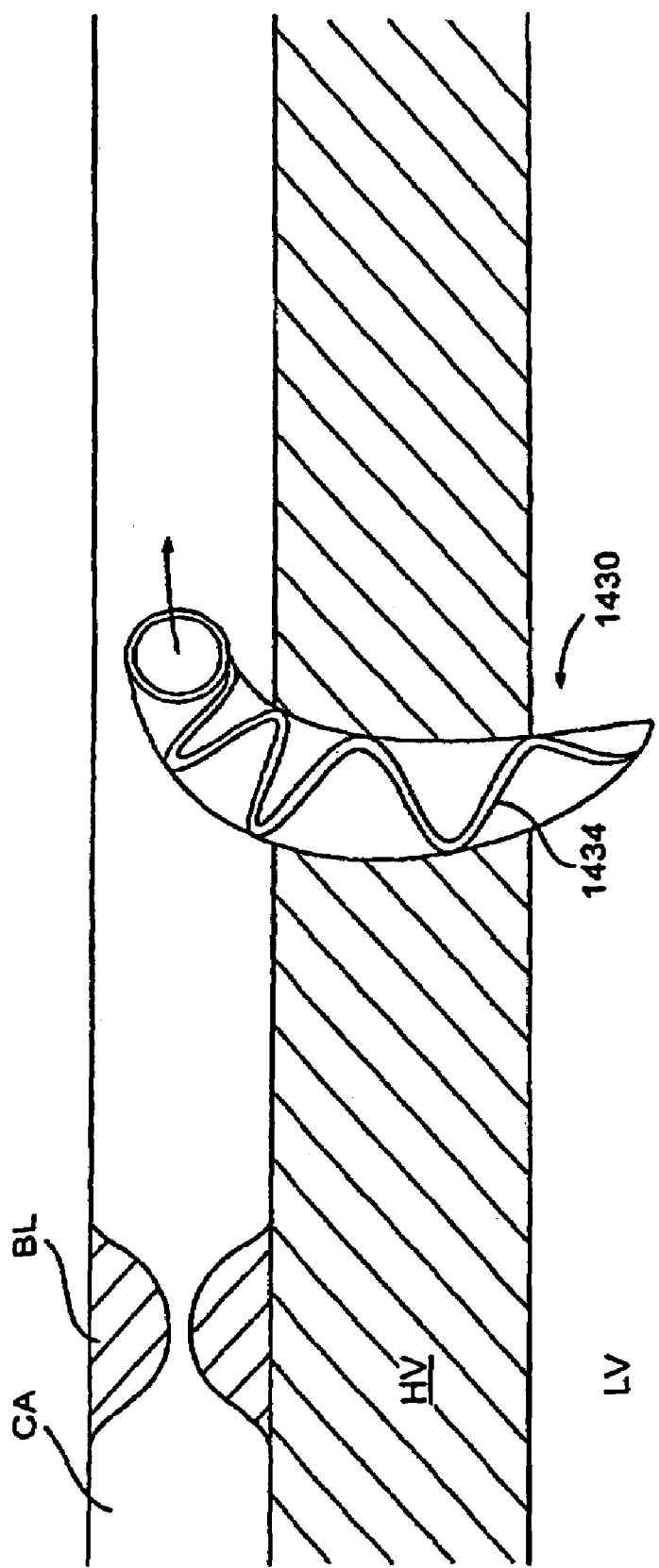
FIGS. 42, 43, 44A–44C, and 45 show conduits designed to take advantage of flow resistance to facilitate flow control.

Referring to FIGS. 42–45, it can be seen that other conduit configurations can result in advantageous flow resistance. These conduit designs may or may not embody the design characteristics of the conduit 1400 of FIG. 41. For example, shown in FIG. 42 is a schematic view of a curved conduit 1430, similar to that of FIG. 41, except having a spiral flow path 1434 therethrough. This spiral flow path 1434 increases the resistance to negative or diastolic flow. By the same token, during systole, the pressures available are sufficient to overcome the resistance presented by the spiral flow path 1434. In this case, the conduit 1430 may be of solid configuration and having a spiral flow path cut or bored therethrough. On the other hand, the conduit 1430 may be manufactured in a spiral fashion comprising a hollow flow path through the spiral.

Figure 43:
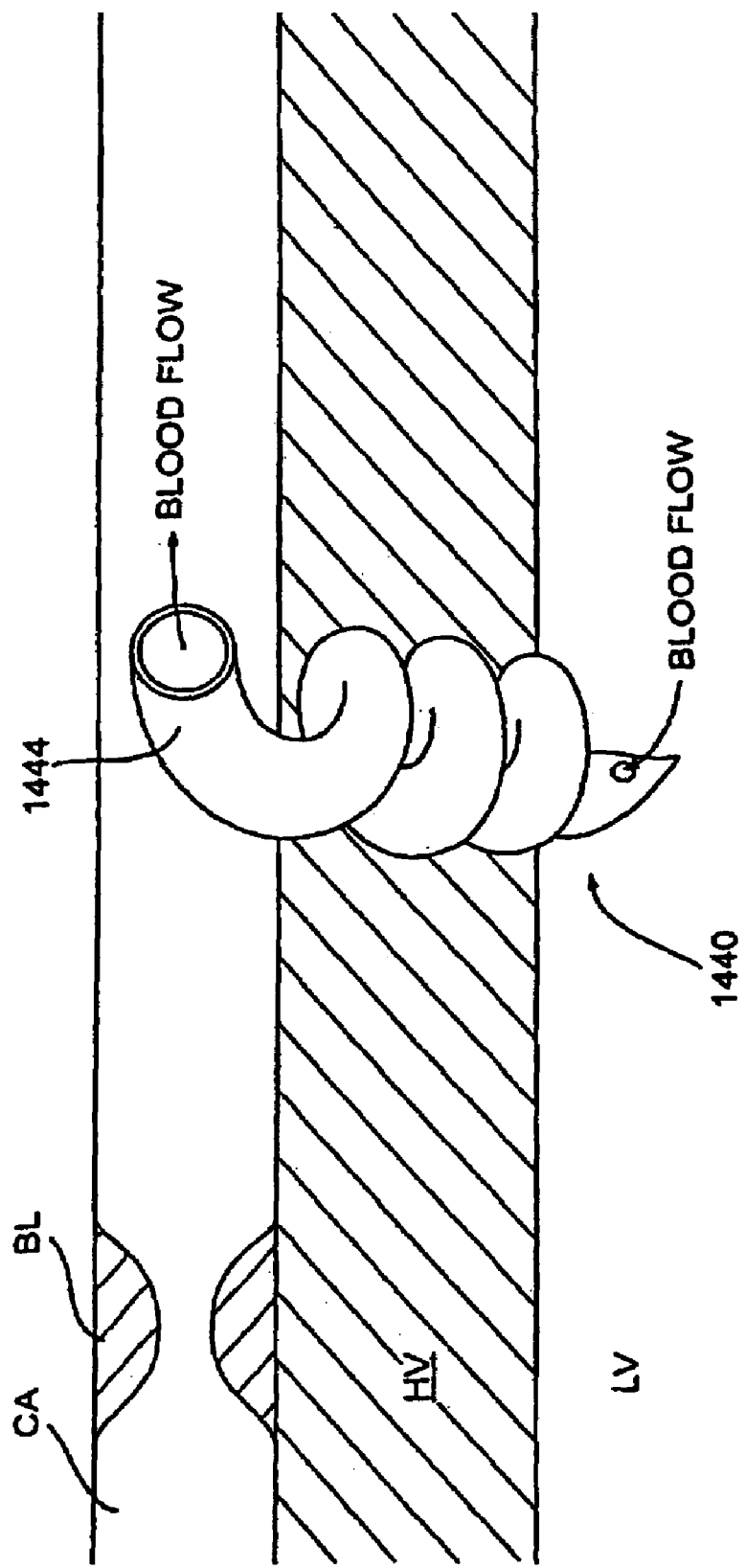

Similarly, as shown in FIG. 43, there is shown a conduit 1440 with a helical flow path 1444. Again, this conduit 1440 takes advantage of the increased flow resistance in the negative or reverse flow direction during diastole. The side walls of these conduits may be straight or tapered, as shown in FIG. 41, to further effect the degree of resistance. Thus, not only does the blood flow see a larger pressure differential between the vessel and the ventricle, but it may also see an increasing pressure due to a gradually tapered, smaller diameter blood flow path in the reverse direction. Again, however, this design may be reversed (in order to increase forward resistance) where only a partial occlusion is presented.

Figure 44A:
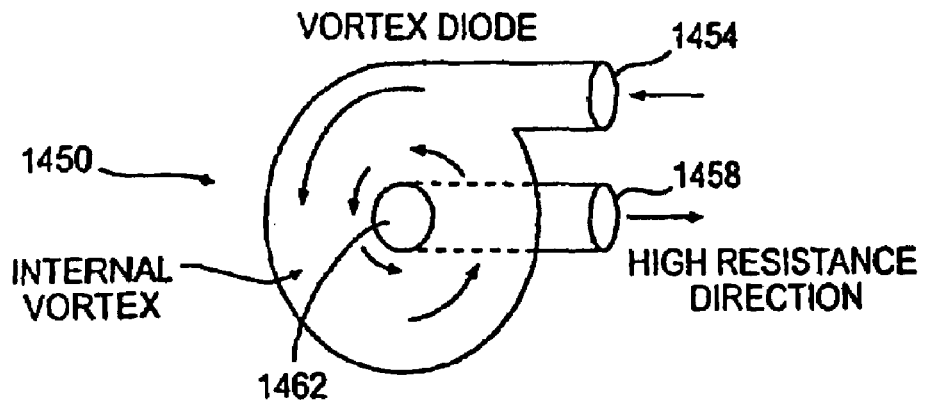
Figure 44B:
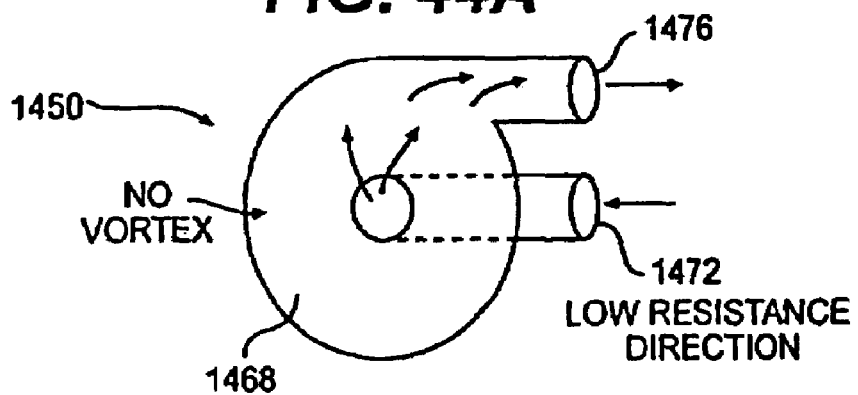
Figure 44C:
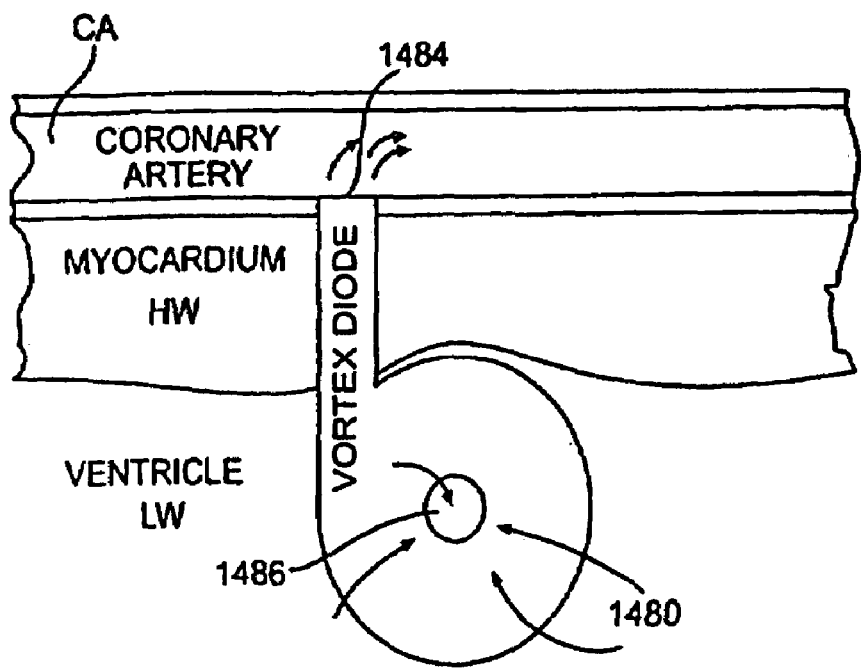

FIGS. 44A–44C utilize an alternate method of flow resistance which comprises a type of fluidic vortex diode. Referring to FIG. 44A, there is shown a conduit 1450 having an entrance 1454 and an exit 1458. It will be appreciated that the entrance 1454 and exit 1458 can be positioned in the ventricle LV and coronary artery CA, respectively, and that this illustration is only schematic with respect to the placement of the conduit 1450 in the heart tissues of the patient. Furthermore, as discussed above, the entrance 1454 and exit 1458 may be placed in the ventricle LV and coronary artery CA, respectively, or vice versa, depending upon patient indications and the desired flow optimization. Thus, it is convenient with respect to FIGS. 44A and 44B to discuss them in terms of a high resistance direction (shown in FIG. 44A) and a low resistance direction (shown in FIG. 44B). Both such flow resistances are achieved in a single device by providing a chamber or housing (preferably circular) with a tangential flow port and a central axial flow port. If the direction of flow is such that fluid enters the tangential flow port and exits the axial flow port, as shown in FIG. 44A, a vortex 1462 is created in the circular chamber. This vortex 1462 greatly impedes the flow of fluid through the device and provides for a high resistance fluid flow conduit. The fluid dynamics behind this result are such that the rotation of the fluid in the chamber generates centrifugal forces that cause the fluid to push outward toward the periphery of the chamber. Since fluid is entering the chamber at the periphery where the resulting centrifugal forces react, the outward push of the rotating fluid impedes the flow.

When the flow direction is reversed, such as that shown in FIG. 44B, fluid flows into the chamber 1468 from the central axial flow port 1472 and from there to the tangential flow port 1476. However, no vortex is created. Thus, the resistance of conduit 1450 to the flow of fluid in this direction is relatively low.

A conduit 1480 utilizing this type of vortex diode device is shown in FIG. 44C. Thus, in this embodiment, the tangential flow port 1484 is placed in the coronary artery CA such that a high resistance to reverse flow is generated. On the other hand, the entrance 1486 to the axial flow port is placed in the ventricle LV so that blood flow into the conduit 1480 sees low resistance.

Figure 45:
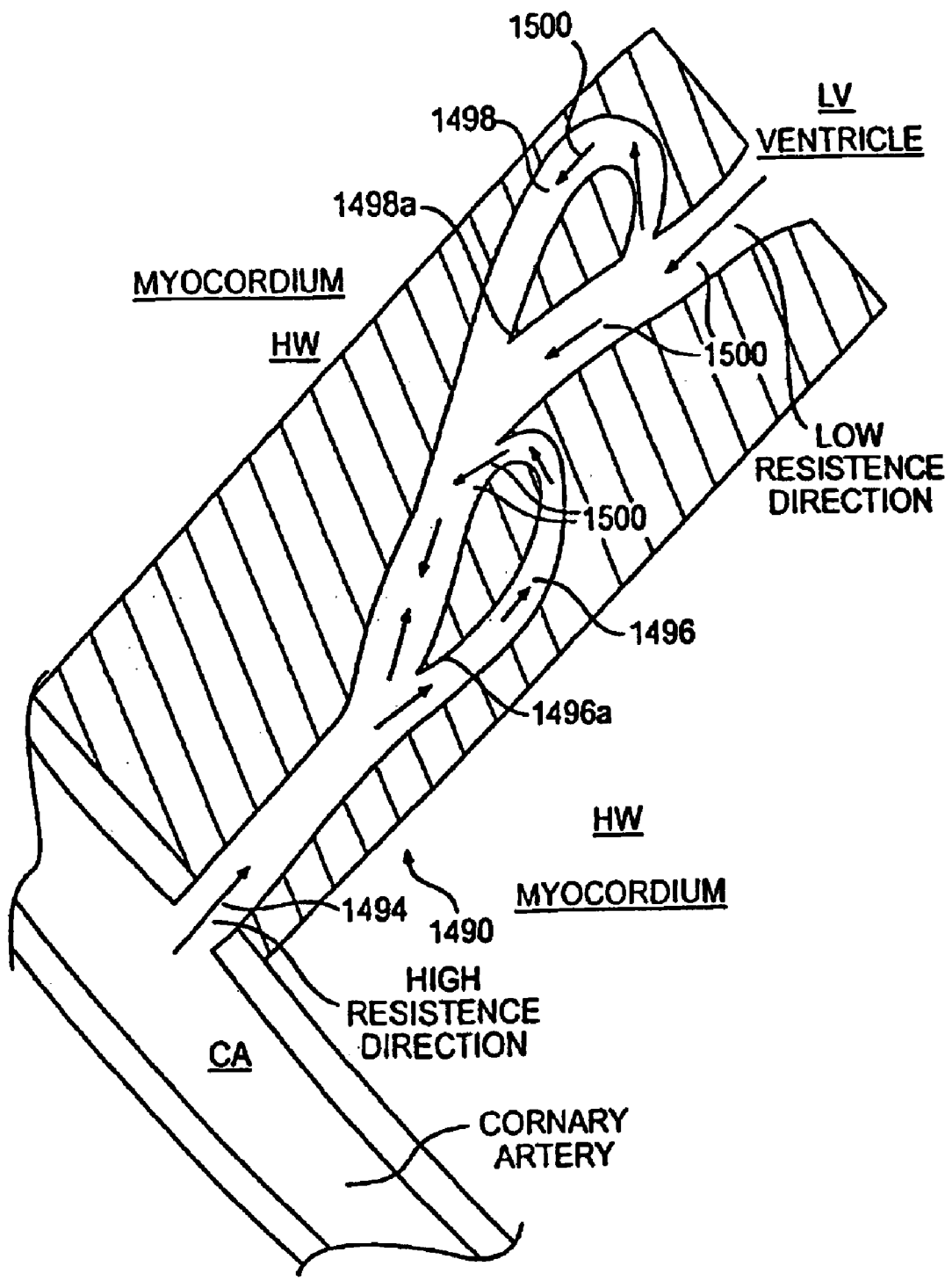

FIG. 45 illustrates an alternate embodiment of a conduit 1490 utilizing flow resistance. In this case, the conduit 1490 is in the nature of a tesla valvular conduit. The geometry of the flow path in this device is such that flow entering the conduit 1490 from one direction 1494, which is generally likely to occur during diastole, is bifurcated at several locations with part of the flow being conducted into passages 1496, 1498 that redirect portions of the flow back into the main flow stream 1494 in a direction 1500 that is essentially reversed to the direction 1494 of the main flow stream. This reversed direction 1500 flow impedes the main flow stream 1494 and sets up a high resistance to fluid flow. On the other hand, when fluid enters in the opposite direction 1502, such as is likely to occur during systole, no such bifurcation and no resulting flow impedance occurs. Thus, as shown in FIG. 45, the higher resistance flow direction is from the coronary artery CA toward the ventricle LV. Flow in that direction 1494 experiences at least two bifurcations 1496a, 1498a with resulting reverse flow 1500 to impede diastolic blood flow. On the other hand, flow 1502 from the ventricle LV toward the coronary CA does not experience any bifurcations, thus resulting in lower flow resistance.

Conduits with Proximal Extensions

As discussed above, flow resistance in the direction of ventricle LV to coronary artery CA can be reduced by an increased exit diameter at the conduit distal portion which opens into the coronary artery CA. At this location, a conduit exit diameter which approximates or matches the diameter of the coronary will result in decreased flow losses and minimize flow resistance. Due to the curvature of the conduit, the flow at the conduit exit is approximately parallel to the axial flow in the coronary. Thus, this distal conduit portion may serve not only as an advantageous controller of the flow, but the extension nature of the distal portion can also serve to anchor or support the conduit in its position. Furthermore, as noted above, this distal portion of the conduit can be designed to allow proximal flow past a partial occlusion, past the distal portion of the conduit, and into the lower coronary regions for profusion of the heart.

Figure 46:
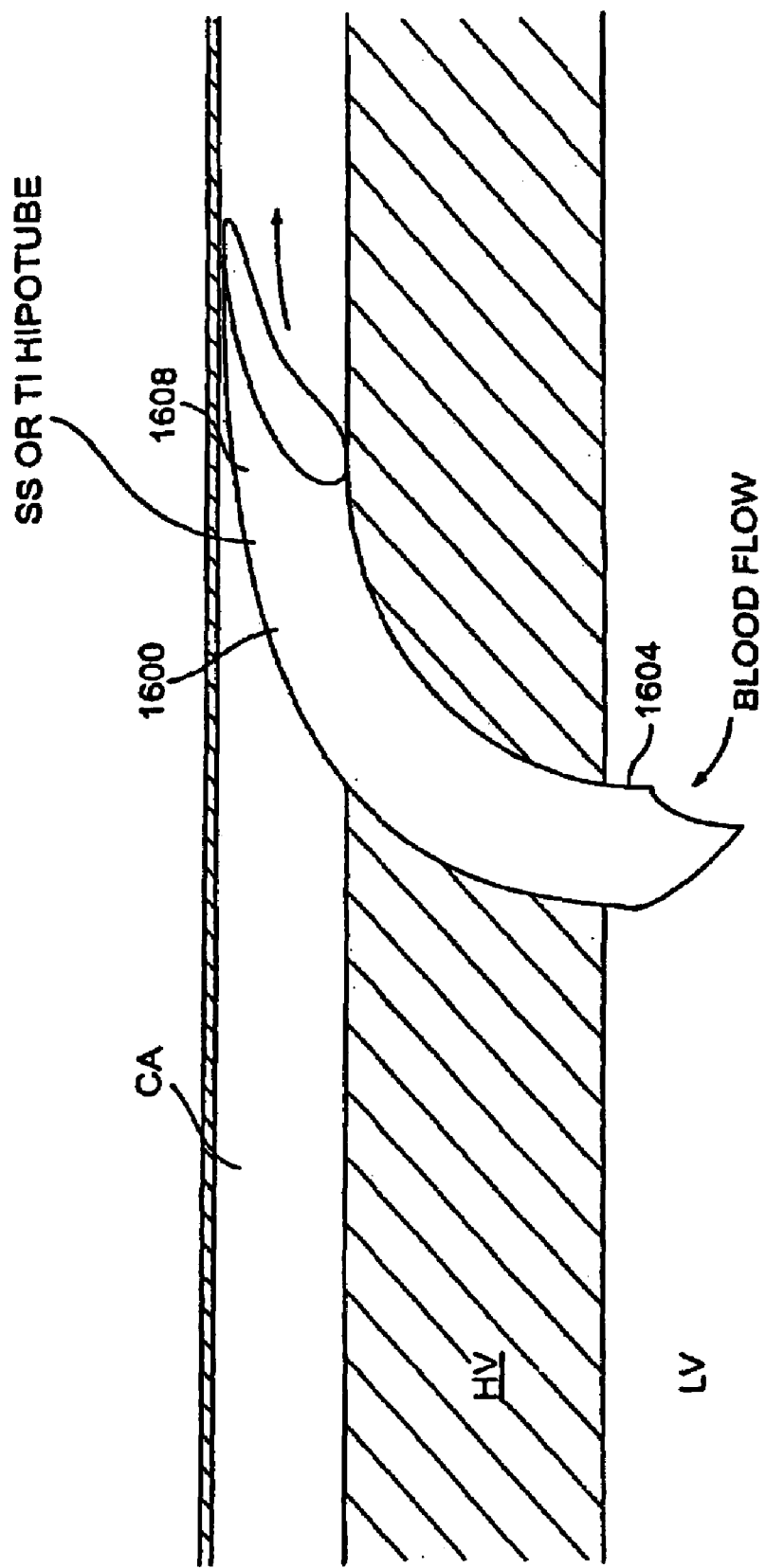

Thus, referring to FIG. 46, there is shown a schematic, partial cross-sectional view of a curved conduit 1600 having an extension portion 1604 at its proximal end (to take into consideration changes in myocardial thickness) and a distal extension 1608 at the conduit distal end extending into the coronary artery CA. Besides minimizing flow losses and anchoring the conduit 1600 in place, this distal extension 1608 also reduces trauma to the coronary artery CA by directing flow downstream in a substantially parallel direction.

Figure 47A:
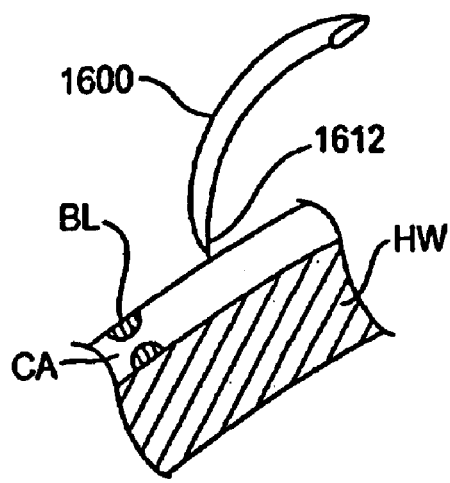
Figure 47B:
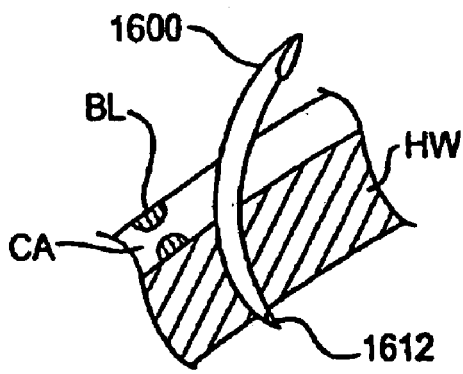
Figure 47C:
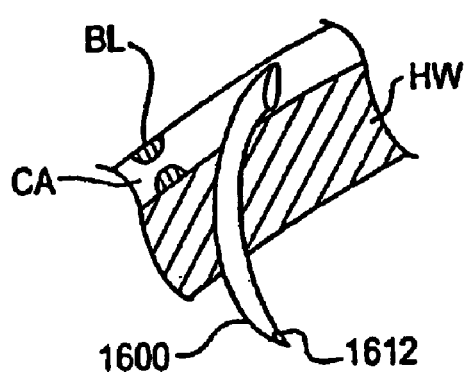
Figure 47D:
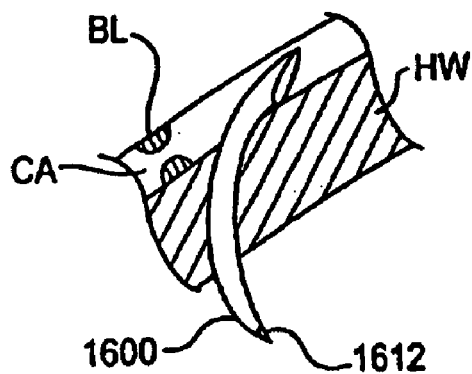

The conduit 1600 of FIG. 46 may be installed in one embodiment, in accordance with FIGS. 47A–D. Thus, with reference to FIG. 47A, the curved tubular conduit 1600 may have a sharpened or pointed proximal tip 1612 to allow it to penetrate the heart tissues, including at least the coronary artery CA and the myocardium HW so that the proximal end extends into the ventricle LV, as shown in FIG. 47B. The curved conduit 1600 is advanced in a rotational or curved fashion, as shown in FIG. 47C, so that it extends well into the ventricle LV. In fact, the conduit 1600 can be of such a length and constructed from a material to allow it to bend and curve into the coronary artery CA in a downstream fashion, as shown in FIG. 47C. Thus, the curved conduit 1600 actually is placed so as to bypass its final destination to allow it to be curved and then inserted in a downstream fashion as shown in FIG. 47D.

Figure 48:
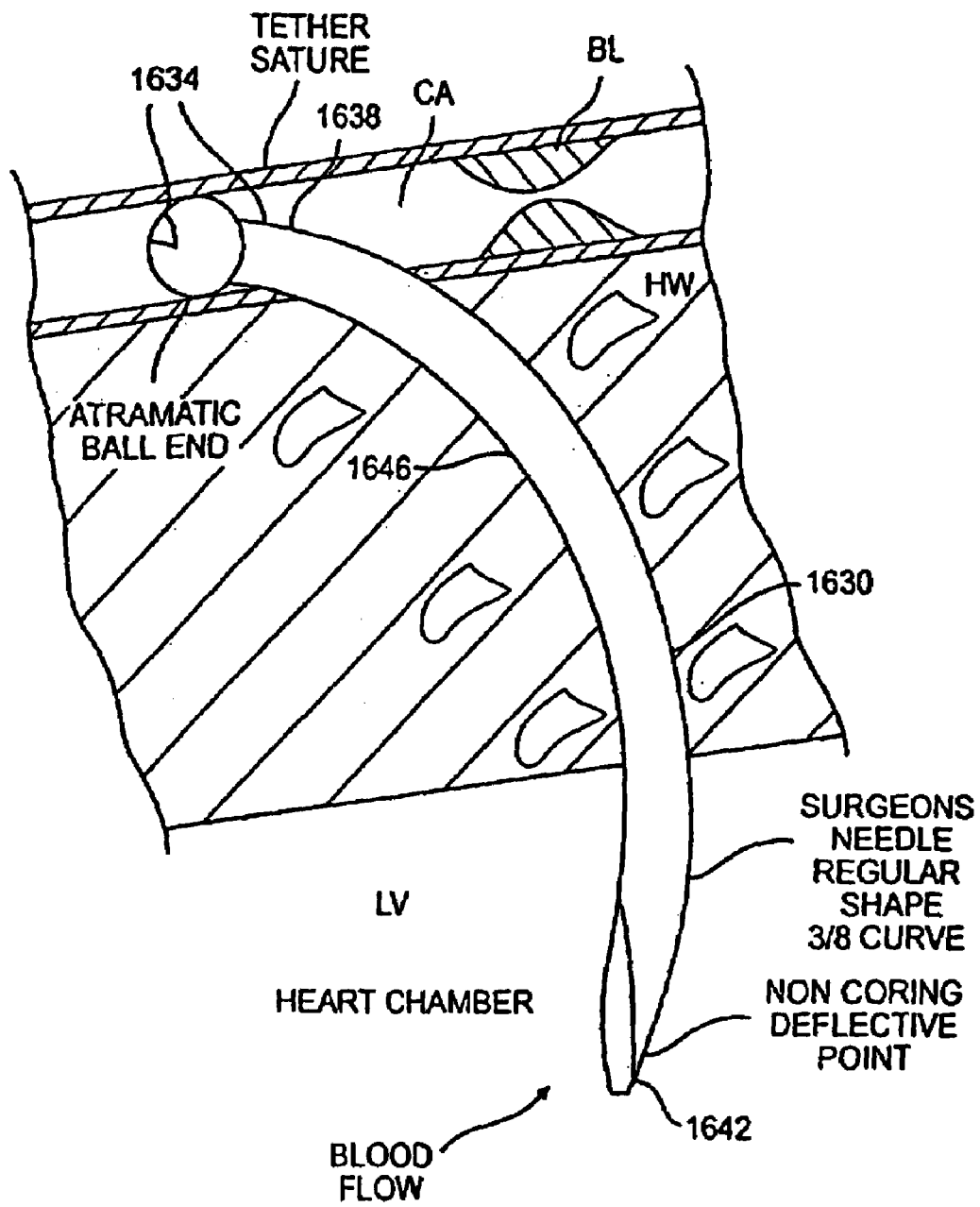

An alternate embodiment of the conduit 1600 of FIG. 46 is shown in FIG. 48. In this case, the hollow, curved, tubular conduit 1630 is provided with an atraumatic ball configuration 1634 at the distal end of the conduit 1630. This configuration allows for reduced flow losses at the exit, while at the same time providing a proximal extension which secures the conduit 1630 in place without damaging the sensitive linings of the vessel. Alternatively, the neck of the conduit 1630 just proximal the end having the atraumatic ball 1634 provides a location for an anchoring suture or tether 1638, as shown in FIG. 48. The proximal end of the conduit 1630 can be provided with a non-coring, deflective point 1642, and the tubular section 1646 can be constructed from a surgeon's needle having a ⅜ inch radius of curvature. As with all the conduits depicted herein, they can be installed in a variety of vascular or surgical procedures, depending upon patient indications. Thus, the conduit 1630 of FIG. 48 may be implanted in the manner illustrated in FIGS. 47A–47D. Alternatively, it may be inserted by means of a curved trocar or stylet, or may even travel over a thin guidewire. The conduit 1630 may be constructed from a rigid or semi-rigid material, it may have solid walls or a lattice stent-like construction as discussed below.

Figure 48A:
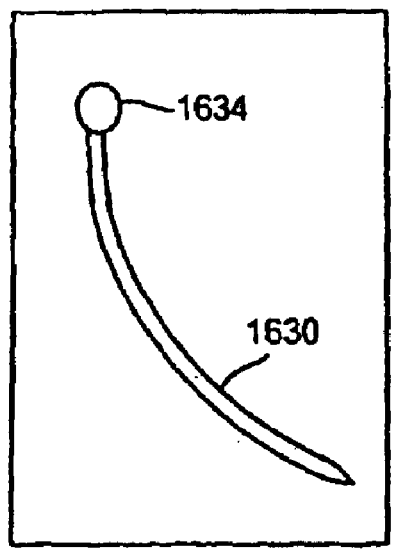
Figure 48B:
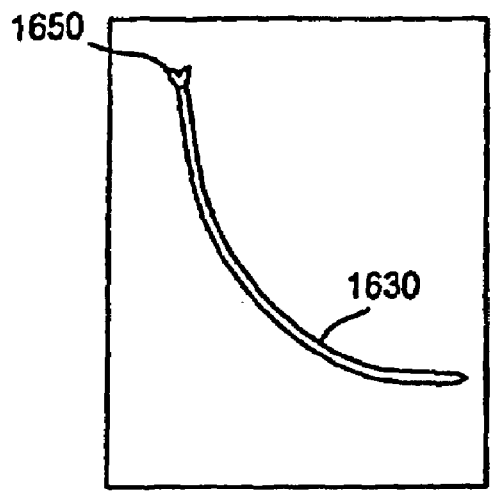
Figure 48C:
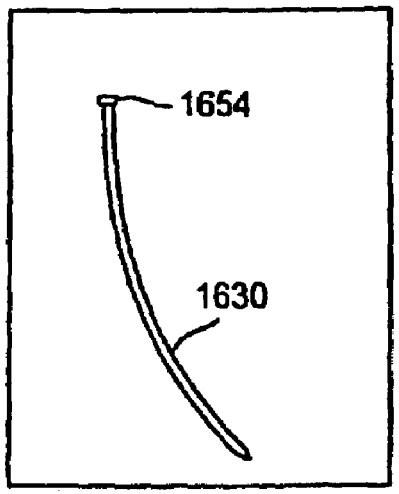

FIG. 48A illustrates the conduit 1630 of FIG. 48 in its uninstalled condition. FIGS. 48B–C illustrate alternate embodiments in which the atraumatic ball end at the distal end of the conduit 1630 is replaced with a partial ball 1650 or semi-spherical section, shown in FIG. 48B, or a flange-type structure 1654 as shown in FIG. 48C.

Another embodiment of a conduit 1670 having a proximal extension is shown in FIG. 49. In this case, the proximal portion 1674 of the conduit 1670 and the main body 1678 portion thereof which extends to the myocardium HW are relatively stiff or rigid regions. These portions of the conduit 1670 can be constructed from a smooth material, such as a metallic stainless steel or nitinol hypotube. Thus, a laminar flow pattern is generated in the conduit 1670 in these regions.

On the other hand, as the flow approaches the artery CA, the conduit 1670 can be constructed from a combination of laser cut hypotube and elastomer to provide a flexible distal portion which extends proximally into the coronary artery CA. In the embodiment of FIG. 49, the curved section of the conduit 1670 is stent-like or is of a lattice construction. It can be manufactured by laser cutting of a nitinol hypotube with elastomeric sections joining the lattice portions. The proximal extension 1674 may comprise at least a unitary arm with a circular flow exit 1682, as illustrated in FIG. 49.

Figure 50A:
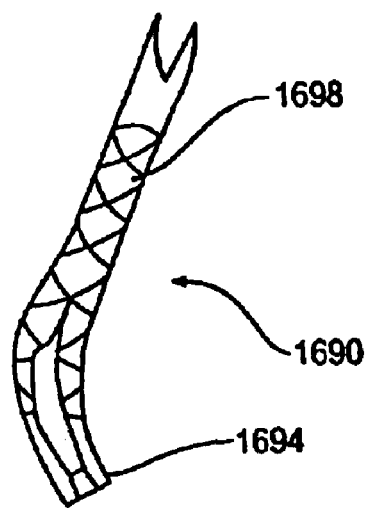
FIGS. 50A–50C and 51A–51D show a variety of conduits of a lattice construction.
Figure 50B:
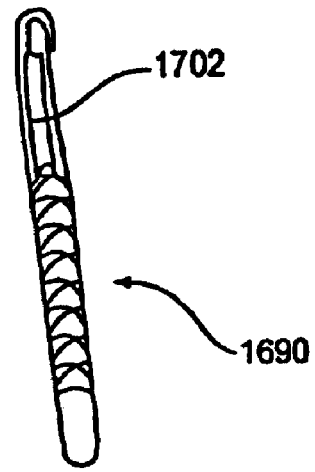
Figure 50C:
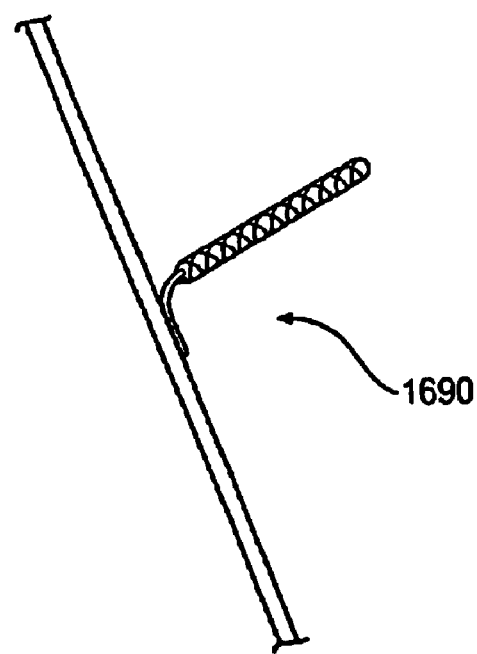
Figure 51A:
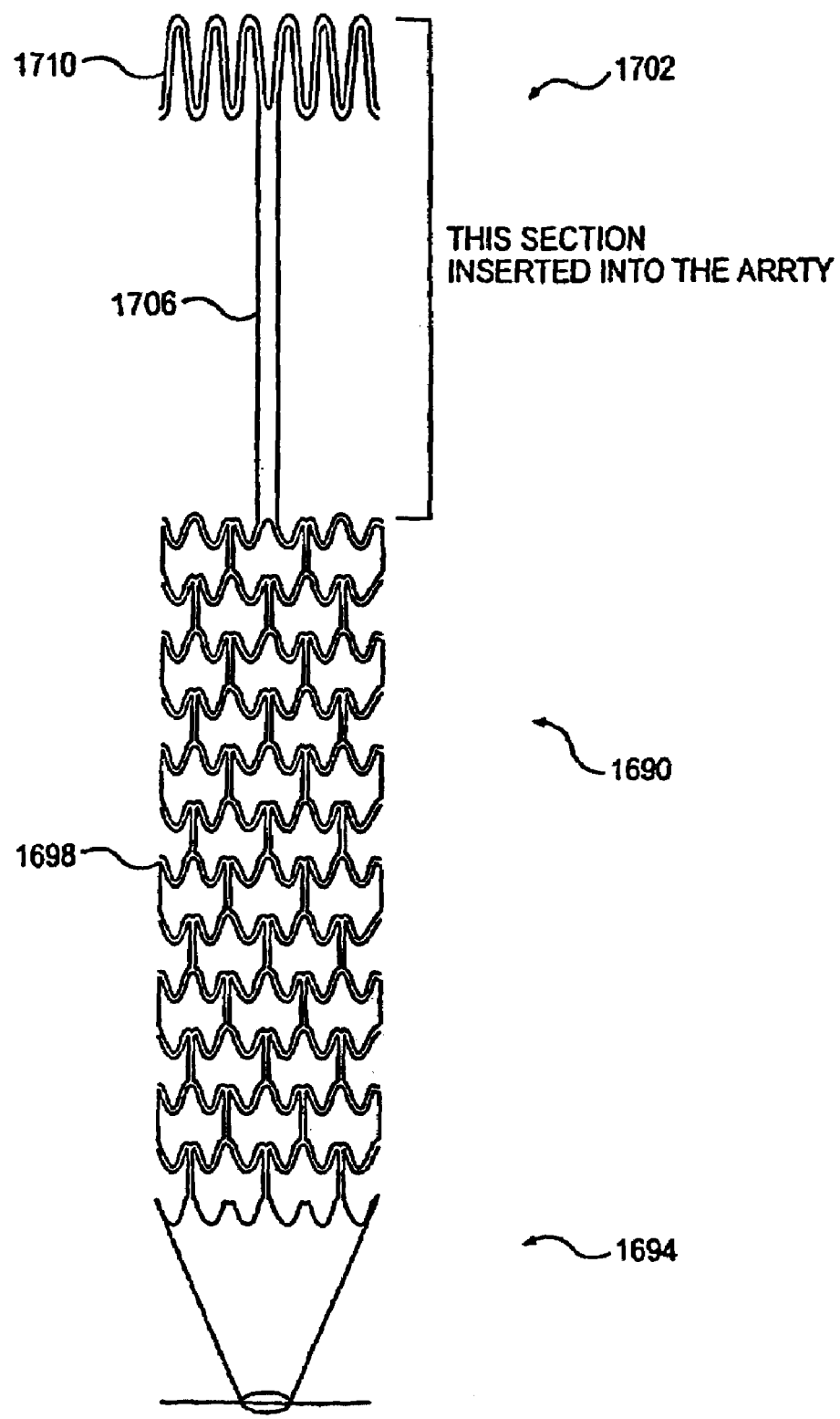
Figure 51B:
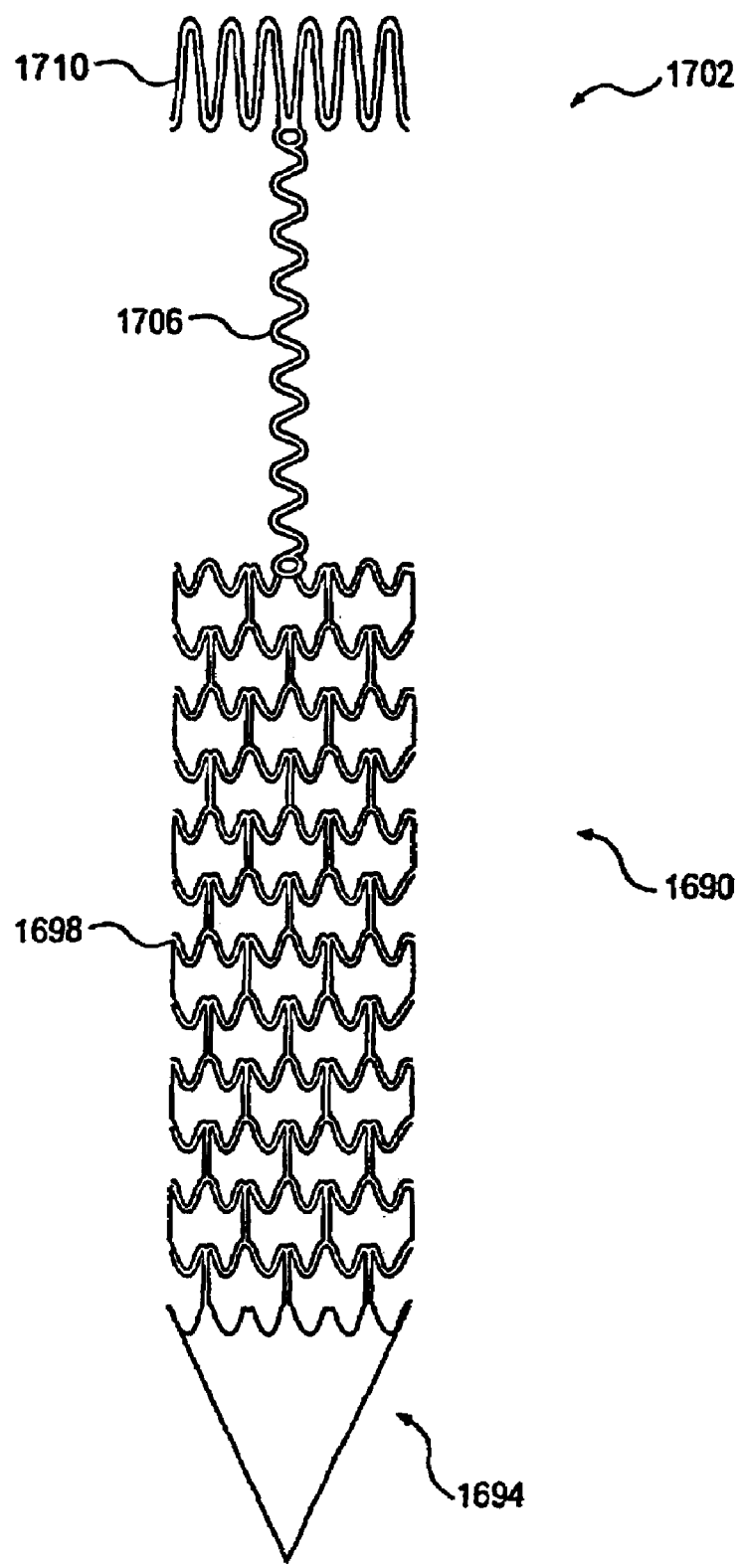
Figure 51C:
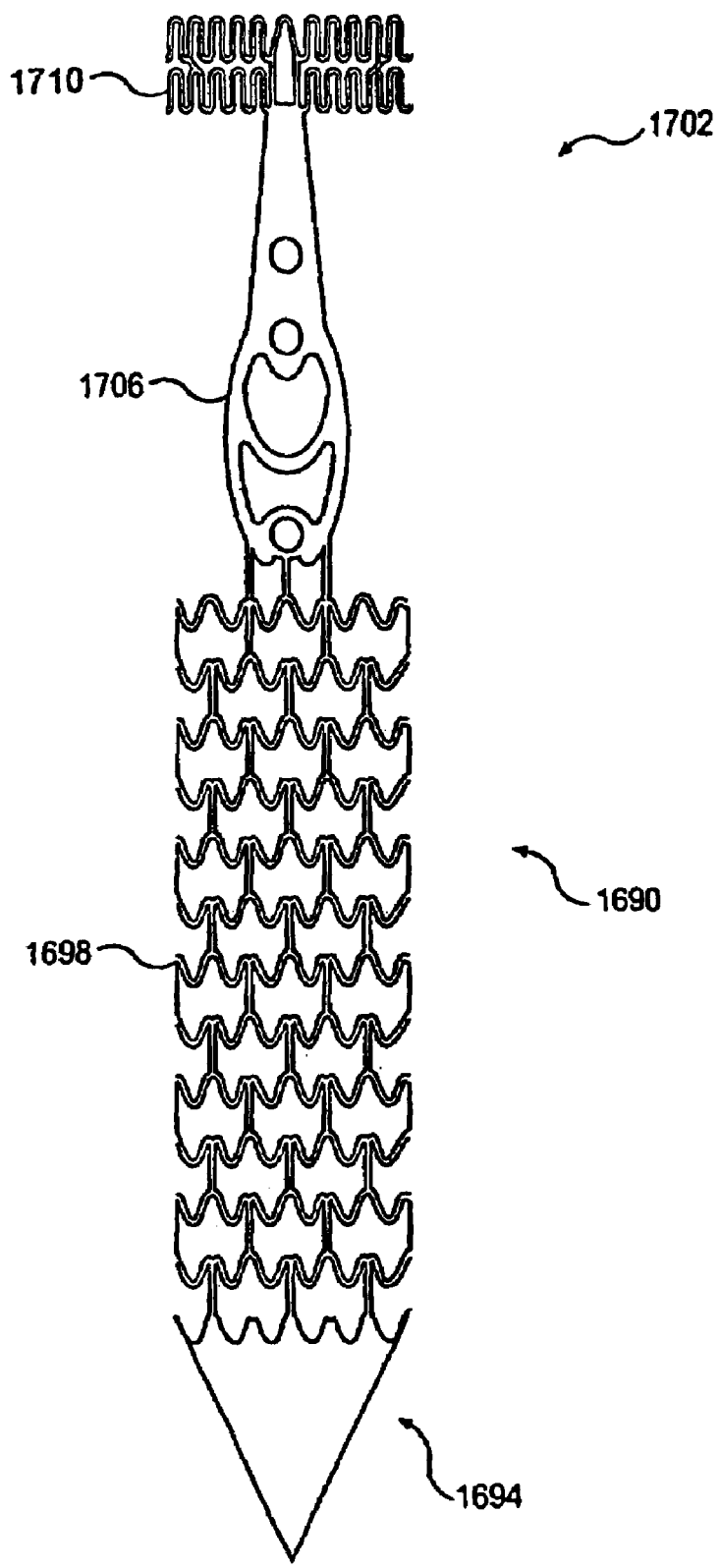
Figure 51D:
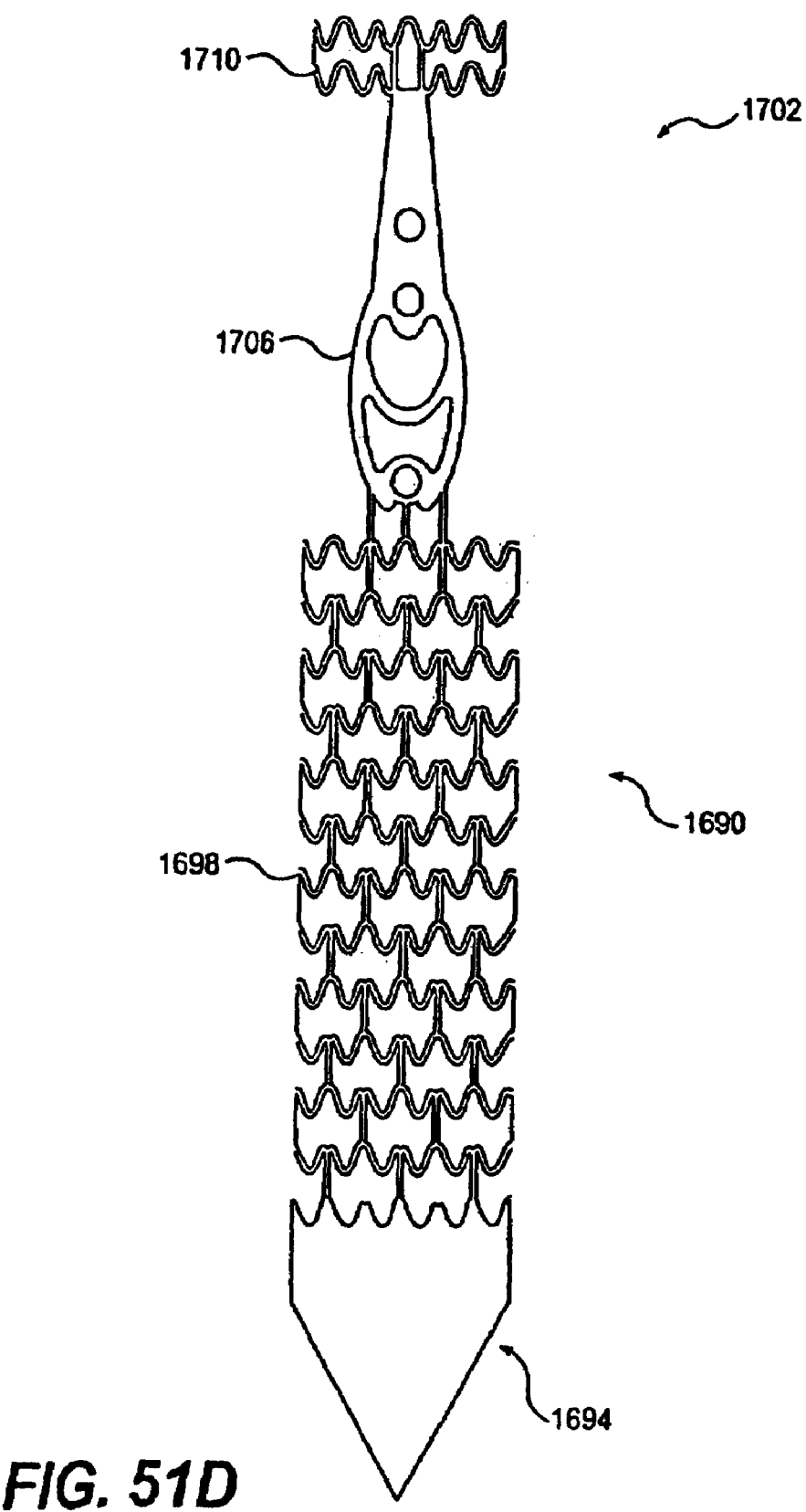

Alternatively, as shown in FIGS. 50A–50C, the conduit of FIG. 49 can be constructed so that it is substantially entirely of a lattice construction or stent-like. In this case, the term stent-like is used to refer to coronary stents which are often implanted following angioplasty, and is thus in an illustrated manner only and not to be restrictive in any sense of the term. Thus, as shown in FIG. 50A, there is a conduit 1690 having a solid or smooth proximal end 1694 which extends into the ventricle LV and a main body section 1698 which is of a lattice-type construction. This section likewise can be constructed from the laser cutting or other cutting of a nitinol hypotube or other material. FIG. 50B illustrates the conduit 1690 of FIG. 50A prior to having its distal portion 1702 bent so as to extend into the distal regions of the coronary artery CA. FIG. 50C, on the other hand, illustrates the conduit 1690 of FIG. 50A as installed in the heart tissues with the distal portion 1702 curved so as to align with the coronary artery CA.

The lattice construction of the conduit 1690 of FIGS. 50A–C may be constructed from a variety of materials. FIGS. 51A–51D illustrate various constructions for the conduit 1690 in FIG. 50, which includes a single arm with an opening at its end. In each case, the conduit 1690 is comprised essentially of a tapered or pointed proximal section 1694 which extends into the ventricle LV, a main body 1698 of a lattice construction, and an extension arm 1706 and distal anchor 1710 which extends into the coronary artery CA. The distal extension arm 1706 and exit portion can take on a variety of shapes as shown in FIGS. 51A–51D. These conduits 1690 can be constructed, preferably, from a nitinol tubing of approximately 0.060 inches in outer diameter with an inner diameter of approximately 0.048 inches. Another advantage of these conduits 1690 is their flexibility in the main body region 1698 in response to changes in myocardial thickness. Also, due to the lattice construction at the distal end, proximal flow through the coronary CA is not impeded.

Figure 52:
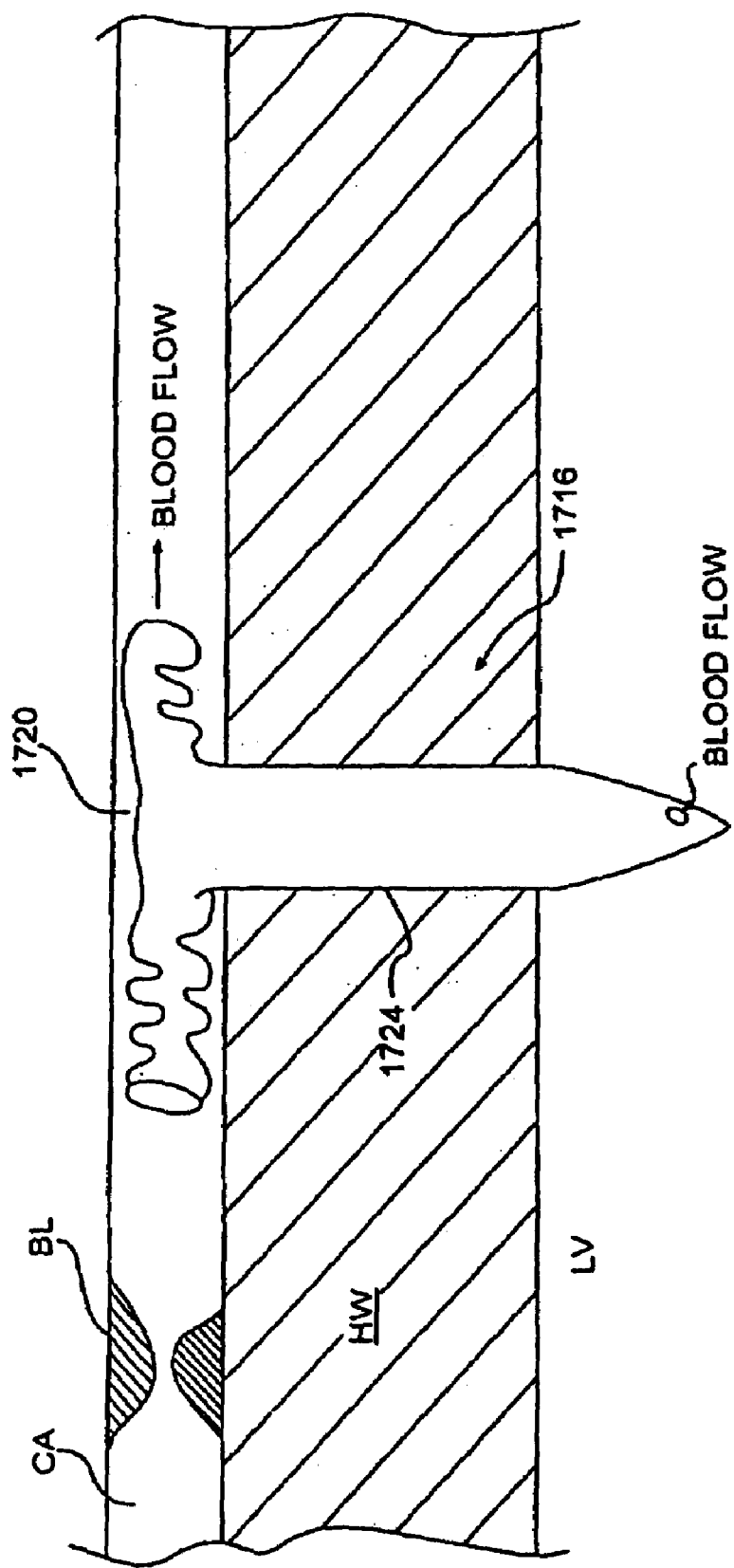
FIG. 52 shows a conduit having a T-like distal portion.

FIG. 52 illustrates an alternate embodiment 1716 with a distal extension 1720 extending both distally in the coronary artery CA as well as proximally. Thus, the distal portion 1720 of the conduit 1716 has a T-like configuration. As shown in FIG. 52, this T-like distal portion 1720 of the conduit 1716 may have a lattice construction such as the conduit 1690 shown in FIGS. 50 and 51. The main body 1724 of the conduit 1716 of FIG. 52 may be a smooth tubular structure, or may be of a lattice construction as shown in FIGS. 50 and 51.

Figure 53:
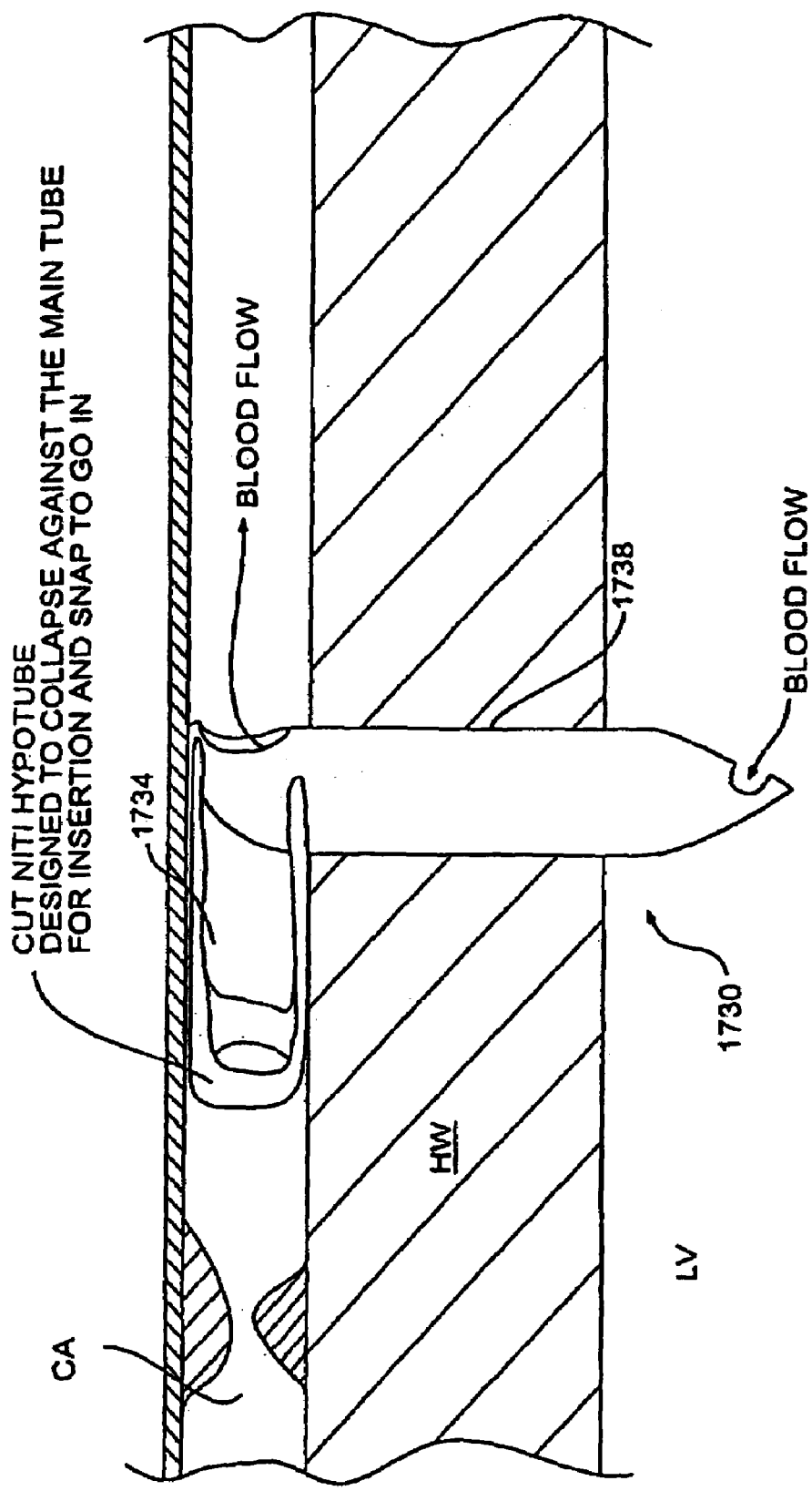
FIG. 53 shows a conduit that has an articulating distal portion.

The conduit 1730 of FIG. 53 has an articulating distal portion 1734 which may fold down either in a manner so as to either extend distally with respect to the coronary artery CA or proximally, as shown in FIG. 53. In this case, the distal extension 1734 of the conduit 1730 is preferably of a lattice construction made from a nitinol hypotube as discussed above. This distal portion 1734 is designed to collapse against the main body 1738 of the conduit 1730 for insertion and then extend to an approximately 90° position, as shown in FIG. 53, within the coronary lumen after insertion. Thus, the distal portion 1734 of the conduit 1730 serves as an articulating or anchor arm for positioning the device within the heart tissues.

Figure 54:
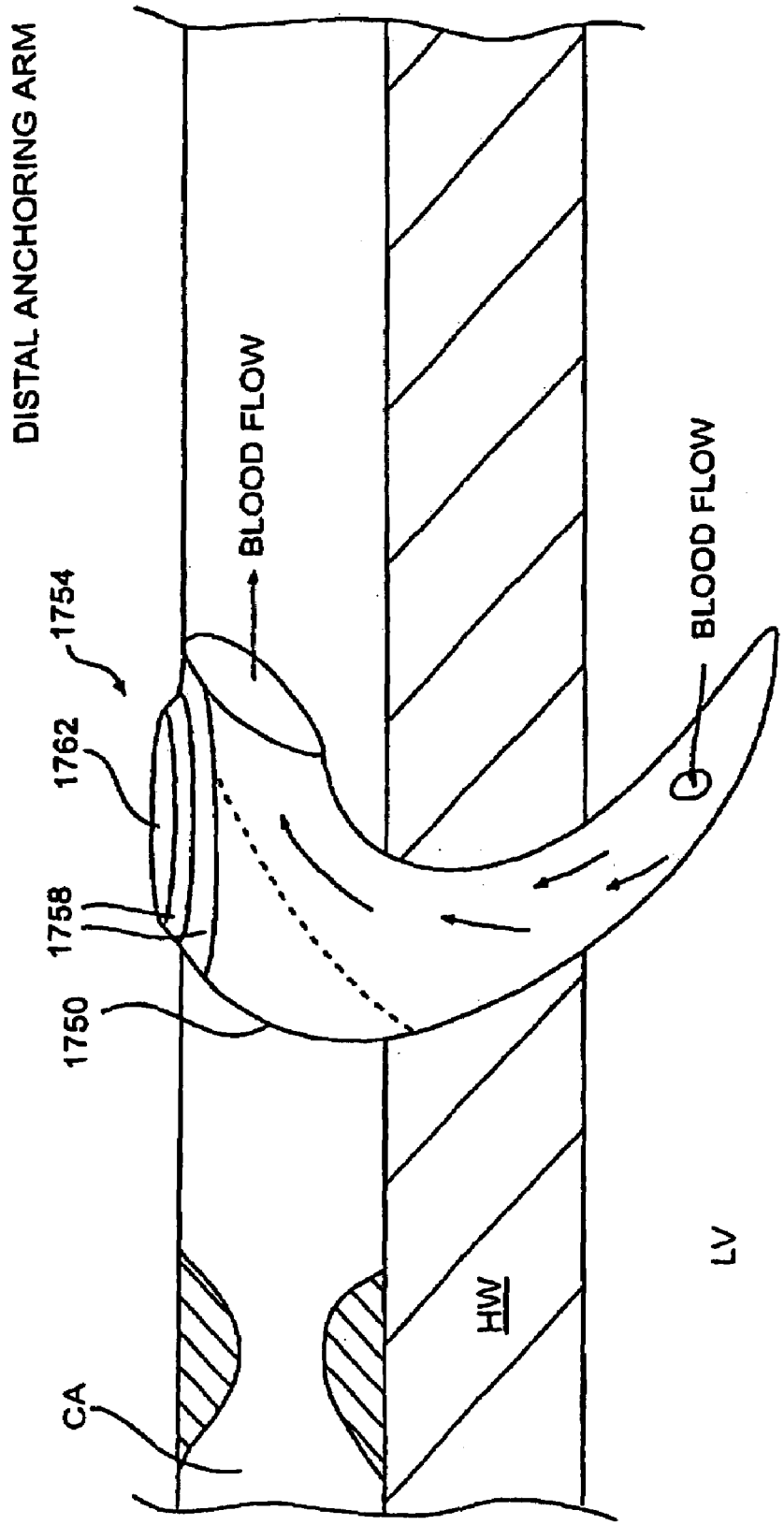
FIG. 54 shows a conduit that has an elastomeric distal anchoring arm.

FIG. 54 illustrates an alternate embodiment 1750 having an elastomeric distal anchoring arm 1754 for the conduit 1750. In this case, the distal portion of the conduit 1750 is provided with a sealing portion 1758 and a shoulder portion 1762. Both of these may preferably be constructed from elastomeric material or some other soft material. The sealing portion 1758 extends through a hole in the coronary artery CA which is used to implant the conduit 1750 of FIG. 54. The shoulder portion 1762 supports the sealing portion 1758 and seals the opening against the coronary wall. The distal portion of the conduit 1750 itself may be constructed from a metallic or other flexible material such that the bias or bending characteristic of the conduit 1750 causes it to push slightly at the distal end against the coronary wall, thus providing the seal.

The bypass devices and methods herein provide significant improvements in the treatment of vascular blockages. It should be understood that while various anatomical features have been discussed herein for ease of reference, the anastomosis devices described herein can also be used in connection with vessels other than coronary artery, etc. Thus, it is intended that the present invention is applicable to a wide range of uses where vascular anastomosis is indicated. It is further intended that the present invention may applicable during a wide variety of surgical techniques, from conventional sternotomy or "open chest" procedures, to minimally-invasive direct coronary artery bypass (MIDCAB) and even vascular approaches.

Accordingly, it is to be understood that the drawings and descriptions herein are proffered by way of example to facilitate comprehension of the invention and should not be construed to limit the scope thereof.

What is claimed is:

1. A method of providing direct blood flow between a heart chamber and a coronary vessel, the method comprising the steps of:
   inserting an instrument through an anterior wall of the coronary vessel;
   further inserting the instrument through a posterior wall of the coronary vessel and a heart wall between the heart chamber and the coronary vessel to form a passageway in the heart wall; and
   radially expanding an implant within the passageway.

2. The method of claim 1, further comprising advancing the implant past the posterior wall of the coronary vessel and into the passageway.

3. The method of claim 2, further comprising advancing the implant past the anterior wall of the coronary vessel.

4. The method of claim 1, further comprising inserting the implant in the passageway via a catheter.

5. The method of claim 4, further comprising advancing the catheter to the passageway via the heart chamber.

6. The method of claim 1, wherein expanding the implant includes expanding an implant carrying a substance for delivery to the heart wall.

7. The method of claim 6, wherein the substance is chosen from angiogenesis factors and nucleic acid instructions for angiogensis factors.

8. The method of claim 6, wherein the substance is for at least one of generating, stimulating, and enhancing blood vessel formation.

9. The method of claim 1, wherein the implant includes a stent.

10. The method of claim 1, wherein expanding the implant includes expanding the implant from a collapsed configuration.

11. The method of claim 1, wherein the passageway in the heart wall is formed via one of lasing, drilling, and boring.

12. The method of claim 1, wherein inserting the instrument includes inserting an incising instrument.

13. The method of claim 1, further comprising removing the instrument from the heart wall prior to expanding the implant in the passageway.

14. The method of claim 1, wherein the implant does not extend substantially along an axial direction of the vessel.

* * * * *